US011441136B2

(12) United States Patent
Oestergaard et al.

(10) Patent No.: US 11,441,136 B2
(45) **Date of Patent: *Sep. 13, 2022**

(54) DNASE VARIANTS

(71) Applicant: Novozymes A/S, Bagsvaerd (DK)

(72) Inventors: Lars Henrik Oestergaard, Charlottelund (DK); Lars Giger, Valby (DK); Annette Helle Johansen, Bronshoj (DK); Lars Beier, Soborg (DK); Jurgen Carsten Franz Knotzel, Copenhagen (DK); Gernot J. Abel, Copenhagen (DK); Klaus Gori, Dyssegaard (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/757,557

(22) PCT Filed: Oct. 26, 2018

(86) PCT No.: PCT/EP2018/079441

§ 371 (c)(1),
(2) Date: Apr. 20, 2020

(87) PCT Pub. No.: WO2019/081724

PCT Pub. Date: May 2, 2019

(65) Prior Publication Data

US 2020/0325461 A1 Oct. 15, 2020

(30) Foreign Application Priority Data

Oct. 27, 2017 (EP) .................................... 17198946
Nov. 30, 2017 (EP) .................................... 17204656

(51) Int. Cl.
*C12N 9/22* (2006.01)

(52) U.S. Cl.
CPC .................................... *C12N 9/22* (2013.01)

(58) Field of Classification Search
CPC .......................... C12N 9/22; C12Y 301/21001
See application file for complete search history.

(56) References Cited

U.S. PATENT DOCUMENTS 10,774,293 B2 * 9/2020 Beier ................. C11D 3/38654
10,781,408 B2 * 9/2020 Oestergaard ............. C11D 3/30
10,800,997 B2 * 10/2020 Beier .................. C11D 11/0017
2019/0211284 A1 * 7/2019 Beier ................. C11D 3/38654

FOREIGN PATENT DOCUMENTS

WO 2017/059802 A1 4/2017
WO 2017/162836 A1 9/2017

OTHER PUBLICATIONS

Wen et al., 2017, Uniprot Acces No. A0A1S1FRN2.

* cited by examiner

*Primary Examiner* — Karen Cochrane Carlson
(74) *Attorney, Agent, or Firm* — Yoshimi Barron

(57) ABSTRACT

The present invention relates to polypeptide variants and methods for obtaining variants. The present invention also relates to polynucleotides encoding the variants; nucleic acid constructs, vectors, and host cells comprising the polynucleotides; and methods of using the variants.

10 Claims, No Drawings

Specification includes a Sequence Listing.

SEQUENCE LISTING

```
<160> NUMBER OF SEQ ID NOS: 28

<210> SEQ ID NO 1
<211> LENGTH: 182
<212> TYPE: PRT
<213> ORGANISM: Bacillus cibi

<400> SEQUENCE: 1

Thr Pro Pro Gly Thr Pro Ser Lys Ser Ala Ala Gln Ser Gln Leu Asn
1               5                   10                  15

Ala Leu Thr Val Lys Thr Glu Gly Ser Met Ser Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ser
    130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
            180


<210> SEQ ID NO 2
<211> LENGTH: 182
<212> TYPE: PRT
<213> ORGANISM: Bacillus horikoshii

<400> SEQUENCE: 2

Leu Pro Pro Gly Thr Pro Thr Lys Ser Glu Ala Gln Asn Gln Leu Asn
1               5                   10                  15

Ser Leu Thr Val Lys Ser Glu Gly Ser Met Thr Gly Tyr Ser Arg Asp
            20                  25                  30

Leu Phe Pro His Trp Ser Gly Gln Gly Asn Gly Cys Asp Thr Arg Gln
```

```
        35                  40                  45

Ile Val Leu Gln Arg Asp Ala Asp Tyr Tyr Thr Gly Thr Cys Pro Thr
    50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ser Leu Gln Thr Met
                165                 170                 175

Leu Asn Gly Cys Ala Tyr
            180


<210> SEQ ID NO 3
<211> LENGTH: 182
<212> TYPE: PRT
<213> ORGANISM: Bacillus species

<400> SEQUENCE: 3

Leu Pro Pro Gly Thr Pro Ser Lys Ser Glu Ala Gln Ser Gln Leu Asn
1               5                   10                  15

Ala Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Ala Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180


<210> SEQ ID NO 4
<211> LENGTH: 182
<212> TYPE: PRT
<213> ORGANISM: Bacillus horikoshii
```

-continued

<400> SEQUENCE: 4

```
Leu Pro Pro Gly Thr Pro Ser Lys Ser Glu Ala Gln Ser Gln Leu Asn
1               5                   10                  15

Ser Leu Thr Val Lys Ser Glu Asp Pro Met Thr Gly Tyr Ser Arg Asp
            20                  25                  30

His Phe Pro His Trp Ser Gly Gln Gly Asn Gly Cys Asp Thr Arg Gln
        35                  40                  45

Ile Val Leu Gln Arg Asp Ala Asp Tyr Tyr Ser Gly Asn Cys Pro Val
    50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Val Val Pro Leu Ala Glu Ala Trp
                85                  90                  95

Arg Ser Gly Ala Ser Ser Trp Thr Thr Glu Gln Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ala Leu Gln Thr Met
                165                 170                 175

Leu Asn Gly Cys Val Tyr
            180
```

<210> SEQ ID NO 5
<211> LENGTH: 182
<212> TYPE: PRT
<213> ORGANISM: Bacillus horikoshii

<400> SEQUENCE: 5

```
Leu Pro Pro Gly Thr Pro Ser Lys Ser Glu Ala Gln Ser Gln Leu Asn
1               5                   10                  15

Ser Leu Thr Val Lys Thr Glu Asp Pro Met Thr Gly Tyr Ser Arg Asp
            20                  25                  30

Leu Phe Pro His Trp Ser Gly Gln Gly Ser Gly Cys Asp Thr Arg Gln
        35                  40                  45

Ile Val Leu Gln Arg Asp Ala Asp Tyr Phe Thr Gly Thr Cys Pro Thr
    50                  55                  60

Thr Ser Gly Lys Trp Tyr Ser Tyr Phe Asp Gly Val Ile Val Tyr Ser
65                  70                  75                  80

Pro Ser Glu Ile Asp Val Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Thr Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ser Leu Gln Thr Met
                165                 170                 175
```

```
Leu Asn Gly Cys Ala Tyr
            180


<210> SEQ ID NO 6
<211> LENGTH: 182
<212> TYPE: PRT
<213> ORGANISM: Bacillus species

<400> SEQUENCE: 6

Leu Pro Pro Gly Thr Pro Ser Lys Ser Glu Ala Gln Ser Gln Leu Asn
1               5                   10                  15

Ala Leu Thr Val Lys Ala Glu Asp Pro Met Thr Gly Tyr Ser Arg Asn
            20                  25                  30

Leu Phe Pro His Trp Asn Ser Gln Gly Asn Gly Cys Asn Thr Arg Gln
        35                  40                  45

Leu Val Leu Gln Arg Asp Ala Asp Tyr Tyr Ser Gly Asn Cys Pro Val
    50                  55                  60

Thr Ser Gly Arg Trp Tyr Ser Tyr Phe Asp Gly Val Val Val Thr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Lys Glu Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
                165                 170                 175

Leu Asn Thr Cys Ser Tyr
            180


<210> SEQ ID NO 7
<211> LENGTH: 182
<212> TYPE: PRT
<213> ORGANISM: Bacillus species

<400> SEQUENCE: 7

Leu Pro Pro Gly Thr Pro Ser Lys Ser Gln Ala Gln Ser Gln Leu Asn
1               5                   10                  15

Ala Leu Thr Val Lys Ala Glu Asp Pro Met Thr Gly Tyr Ser Arg Asn
            20                  25                  30

Leu Phe Pro His Trp Ser Ser Gln Gly Asn Gly Cys Asn Thr Arg Gln
        35                  40                  45

Leu Val Leu Gln Arg Asp Ala Asp Tyr Tyr Ser Gly Asn Cys Pro Val
    50                  55                  60

Thr Ser Gly Arg Trp Tyr Ser Tyr Phe Asp Gly Val Val Val Thr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Glu Phe Ala
            100                 105                 110

Asn Asp Leu Asn Gly Pro Gln Leu Ile Ala Val Thr Ala Ser Val Asn
        115                 120                 125
```

```
Arg Ser Lys Gly Asp Gln Asp Pro Ser Thr Trp Gln Pro Pro Arg Val
    130                 135                 140

Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
                165                 170                 175

Leu Asn Thr Cys Ser Tyr
            180


<210> SEQ ID NO 8
<211> LENGTH: 182
<212> TYPE: PRT
<213> ORGANISM: Bacillus species

<400> SEQUENCE: 8

Leu Pro Pro Gly Thr Pro Ser Lys Ser Glu Ala Gln Ser Gln Leu Thr
1               5                   10                  15

Ser Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Asn Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Ala Glu Gln Arg Arg Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Thr
    130                 135                 140

Gly Ala Arg Cys Ala Tyr Ala Lys Trp Trp Ile Asn Thr Lys Tyr Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180


<210> SEQ ID NO 9
<211> LENGTH: 185
<212> TYPE: PRT
<213> ORGANISM: Bacillus species

<400> SEQUENCE: 9

Ala Ser Ala Phe Pro Pro Gly Thr Pro Ser Lys Ser Thr Ala Gln Ser
1               5                   10                  15

Gln Leu Asn Ser Leu Pro Val Lys Ser Glu Gly Ser Met Asn Gly Tyr
            20                  25                  30

Ser Arg Asp Lys Phe Pro His Trp Ile Ser Gln Gly Asp Gly Cys Asp
        35                  40                  45

Thr Arg Gln Leu Val Leu Lys Arg Asp Gly Asp Tyr Tyr Ser Gly Ser
    50                  55                  60

Cys Pro Val Thr Ser Gly Lys Trp Tyr Ser Tyr Tyr Asp Gly Ile Thr
65                  70                  75                  80
```

-continued

```
Val Tyr Ser Pro Ser Glu Ile Asp Ile Asp His Ile Val Pro Leu Ala
                85                  90                  95

Glu Ala Trp Arg Ser Gly Ala Ser Gly Trp Thr Thr Glu Lys Arg Gln
            100                 105                 110

Ser Phe Ala Asn Asp Leu Asn Gly Pro Gln Leu Ile Ala Val Thr Ala
        115                 120                 125

Ser Val Asn Arg Ser Lys Gly Asp Gln Asp Pro Ser Thr Trp Gln Pro
    130                 135                 140

Pro Arg Ser Gly Ser His Cys Ala Tyr Ala Lys Met Trp Val Asn Thr
145                 150                 155                 160

Lys Tyr Arg Trp Gly Leu His Leu Gln Ser Ala Glu Lys Ser Ala Leu
                165                 170                 175

Gln Ser Met Leu Asn Ala Cys Ser Tyr
            180                 185


<210> SEQ ID NO 10
<211> LENGTH: 185
<212> TYPE: PRT
<213> ORGANISM: Bacillus horneckiae

<400> SEQUENCE: 10

Ala Ser Ala Phe Pro Pro Gly Thr Pro Ser Lys Ser Thr Ala Gln Ser
1               5                   10                  15

Gln Leu Asn Ser Leu Thr Val Lys Ser Glu Gly Ser Met Thr Gly Tyr
            20                  25                  30

Ser Arg Asp Lys Phe Pro His Trp Ile Ser Gln Gly Asp Gly Cys Asp
        35                  40                  45

Thr Arg Gln Leu Val Leu Lys Arg Asp Gly Asp Tyr Tyr Ser Gly Asn
    50                  55                  60

Cys Pro Val Thr Ser Gly Lys Trp Tyr Ser Tyr Tyr Asp Gly Ile Thr
65                  70                  75                  80

Val Tyr Ser Pro Ser Glu Ile Asp Ile Asp His Ile Val Pro Leu Ala
                85                  90                  95

Glu Ala Trp Arg Ser Gly Ala Ser Gly Trp Thr Thr Glu Lys Arg Gln
            100                 105                 110

Ser Phe Ala Asn Asp Leu Asn Gly Pro Gln Leu Ile Ala Val Thr Ala
        115                 120                 125

Ser Val Asn Arg Ser Lys Gly Asp Gln Asp Pro Ser Thr Trp Gln Pro
    130                 135                 140

Pro Arg Ser Gly Ser His Cys Ala Tyr Ala Lys Met Trp Val Asn Thr
145                 150                 155                 160

Lys Tyr Arg Trp Gly Leu His Val Gln Ser Ala Glu Lys Ser Ala Leu
                165                 170                 175

Gln Ser Met Leu Asn Ala Cys Ser Tyr
            180                 185


<210> SEQ ID NO 11
<211> LENGTH: 182
<212> TYPE: PRT
<213> ORGANISM: Bacillus species

<400> SEQUENCE: 11

Phe Pro Pro Glu Ile Pro Ser Lys Ser Thr Ala Gln Ser Gln Leu Asn
1               5                   10                  15

Ser Leu Thr Val Lys Ser Glu Asp Ala Met Thr Gly Tyr Ser Arg Asp
            20                  25                  30
```

```
Lys Phe Pro His Trp Ile Ser Gln Gly Asp Gly Cys Asp Thr Arg Gln
        35                  40                  45

Met Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ser
    130                 135                 140

Gly Ala Arg Cys Ala Tyr Ala Lys Met Trp Val Asn Thr Lys Tyr Arg
145                 150                 155                 160

Trp Gly Leu His Leu Gln Ser Ala Glu Lys Ser Gly Leu Glu Ser Met
                165                 170                 175

Leu Asn Thr Cys Ser Tyr
            180


<210> SEQ ID NO 12
<211> LENGTH: 182
<212> TYPE: PRT
<213> ORGANISM: Bacillus species

<400> SEQUENCE: 12

Leu Pro Pro Asp Leu Pro Ser Lys Ser Thr Thr Gln Ala Gln Leu Asn
1               5                   10                  15

Ser Leu Asn Val Lys Asn Glu Glu Ser Met Ser Gly Tyr Ser Arg Glu
            20                  25                  30

Lys Phe Pro His Trp Ile Ser Gln Gly Asp Gly Cys Asp Thr Arg Gln
        35                  40                  45

Val Ile Leu Lys Arg Asp Ala Asp Asn Tyr Ser Gly Asn Cys Pro Val
    50                  55                  60

Thr Ser Gly Lys Trp Tyr Ser Tyr Tyr Asp Gly Ile Thr Phe Asn Asp
65                  70                  75                  80

Pro Ser Gln Leu Asp Ile Asp His Val Val Pro Leu Ala Glu Ala Trp
                85                  90                  95

Arg Ser Gly Ala Ser Ser Trp Ser Thr Ala Lys Arg Glu Asp Phe Ala
            100                 105                 110

Asn Asp Leu Asn Gly Pro Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Asn Cys Ala Tyr Ala Lys Met Trp Ile Asn Thr Lys Tyr Asn
145                 150                 155                 160

Trp Gly Leu His Leu Gln Ser Ser Glu Lys Thr Ala Leu Gln Gly Met
                165                 170                 175

Leu Asn Ser Cys Ser Tyr
            180


<210> SEQ ID NO 13
<211> LENGTH: 182
<212> TYPE: PRT
<213> ORGANISM: Bacillus species
```

<400> SEQUENCE: 13

Phe Pro Pro Gly Thr Pro Ser Lys Ser Thr Ala Gln Ser Gln Leu Asn
1 5 10 15

Ser Leu Thr Val Lys Ser Glu Gly Ser Met Thr Gly Tyr Ser Arg Asp
20 25 30

Lys Phe Pro His Trp Ile Gly Gln Gly Ser Gly Cys Asp Thr Arg Gln
35 40 45

Leu Val Leu Gln Arg Asp Ala Asp Tyr Tyr Ser Gly Ser Cys Pro Val
50 55 60

Thr Ser Gly Lys Trp Tyr Ser Tyr Tyr Asp Gly Val Thr Phe Tyr Asp
65 70 75 80

Pro Ser Asp Leu Asp Ile Asp His Val Val Pro Leu Ala Glu Ala Trp
85 90 95

Arg Ser Gly Ala Ser Ser Trp Ser Thr Gln Lys Arg Lys Asp Phe Ala
100 105 110

Asn Asp Leu Ser Gly Pro Gln Leu Ile Ala Val Ser Ala Ser Ser Asn
115 120 125

Arg Ser Lys Gly Asp Gln Asp Pro Ser Thr Trp Gln Pro Thr Arg Ser
130 135 140

Gly Ala Ala Cys Gly Tyr Ser Lys Trp Trp Ile Ser Thr Lys His Lys
145 150 155 160

Trp Gly Leu Ser Leu Gln Ser Ser Glu Lys Asn Ala Leu Gln Gly Met
165 170 175

Leu Asn Ser Cys Val Tyr
180

<210> SEQ ID NO 14
<211> LENGTH: 182
<212> TYPE: PRT
<213> ORGANISM: Bacillus idriensis

<400> SEQUENCE: 14

Leu Pro Pro Gly Thr Pro Ser Lys Ser Thr Ala Gln Ser Gln Leu Asn
1 5 10 15

Ala Leu Thr Val Gln Thr Glu Gly Ser Met Thr Gly Tyr Ser Arg Asp
20 25 30

Lys Phe Pro His Trp Ile Ser Gln Gly Asn Gly Cys Asp Thr Arg Gln
35 40 45

Val Val Leu Gln Arg Asp Ala Asp Tyr Tyr Ser Gly Thr Cys Pro Val
50 55 60

Thr Ser Gly Lys Trp Tyr Ser Tyr Tyr Asp Gly Val Thr Leu Tyr Asn
65 70 75 80

Pro Ser Asp Leu Asp Ile Asp His Val Val Ala Leu Ala Glu Ala Trp
85 90 95

Arg Ser Gly Ala Ser Ser Trp Thr Thr Asp Lys Arg Glu Asp Phe Ala
100 105 110

Asn Asp Leu Ser Gly Thr Gln Leu Ile Ala Val Ser Ala Ser Thr Asn
115 120 125

Arg Ser Lys Gly Asp Gln Asp Pro Ser Thr Trp Gln Pro Pro Arg Ser
130 135 140

Gly Ala Ala Cys Gly Tyr Ala Lys Trp Trp Ile Ser Thr Lys Tyr Lys
145 150 155 160

Trp Asn Leu Asn Leu Gln Ser Ser Glu Lys Thr Ala Leu Gln Ser Met
165 170 175

```
Leu Asn Ser Cys Ser Tyr
            180


<210> SEQ ID NO 15
<211> LENGTH: 182
<212> TYPE: PRT
<213> ORGANISM: Bacillus algicola

<400> SEQUENCE: 15

Phe Pro Pro Gly Thr Pro Ser Lys Ser Glu Ala Gln Ser Gln Leu Asn
1               5                   10                  15

Ser Leu Thr Val Gln Ser Glu Gly Ser Met Ser Gly Tyr Ser Arg Asp
            20                  25                  30

Lys Phe Pro His Trp Ile Gly Gln Gly Asn Gly Cys Asp Thr Arg Gln
        35                  40                  45

Leu Val Leu Gln Arg Asp Ala Asp Tyr Tyr Ser Gly Asp Cys Pro Val
    50                  55                  60

Thr Ser Gly Lys Trp Tyr Ser Tyr Phe Asp Gly Val Thr Val Tyr Asp
65                  70                  75                  80

Pro Ser Asp Leu Asp Ile Asp His Met Val Pro Met Ala Glu Ala Trp
                85                  90                  95

Arg Ser Gly Ala Ser Ser Trp Ser Thr Gln Lys Arg Glu Asp Phe Ala
            100                 105                 110

Asn Asp Leu Ser Gly Pro His Leu Ile Ala Val Thr Ala Ser Ser Asn
        115                 120                 125

Arg Ser Lys Gly Asp Gln Asp Pro Ser Thr Trp Lys Pro Thr Arg Tyr
    130                 135                 140

Gly Ala His Cys Gly Tyr Ala Lys Trp Trp Ile Asn Thr Lys Tyr Val
145                 150                 155                 160

Tyr Asp Leu Thr Leu Gln Ser Ser Glu Lys Thr Glu Leu Gln Ser Met
                165                 170                 175

Leu Asn Thr Cys Ser Tyr
            180


<210> SEQ ID NO 16
<211> LENGTH: 182
<212> TYPE: PRT
<213> ORGANISM: Artificial sequence
<220> FEATURE:
<223> OTHER INFORMATION: Synthetic construct

<400> SEQUENCE: 16

Leu Pro Pro Asn Ile Pro Ser Lys Ala Asp Ala Leu Thr Lys Leu Asn
1               5                   10                  15

Ala Leu Thr Val Gln Thr Glu Gly Pro Met Thr Gly Tyr Ser Arg Asp
            20                  25                  30

Leu Phe Pro His Trp Ser Ser Gln Gly Asn Gly Cys Asn Thr Arg His
        35                  40                  45

Val Val Leu Lys Arg Asp Ala Asp Ser Val Val Asp Thr Cys Pro Val
    50                  55                  60

Thr Thr Gly Arg Trp Tyr Ser Tyr Tyr Asp Gly Leu Val Phe Thr Ser
65                  70                  75                  80

Ala Ser Asp Ile Asp Ile Asp His Val Val Pro Leu Ala Glu Ala Trp
                85                  90                  95

Arg Ser Gly Ala Ser Ser Trp Thr Ser Thr Lys Arg Gln Ser Phe Ala
            100                 105                 110
```

```
Asn Asp Leu Asn Gly Pro Gln Leu Ile Ala Val Ser Ala Thr Ser Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Met Trp Val Glu Thr Lys Ser Arg
145                 150                 155                 160

Trp Gly Leu Thr Leu Gln Ser Ser Glu Lys Ala Ala Leu Gln Thr Ala
                165                 170                 175

Ile Asn Ala Cys Ser Tyr
            180


<210> SEQ ID NO 17
<211> LENGTH: 182
<212> TYPE: PRT
<213> ORGANISM: Bacillus vietnamensis

<400> SEQUENCE: 17

Phe Pro Pro Gly Thr Pro Ser Lys Ser Thr Ala Gln Ser Gln Leu Asn
1               5                   10                  15

Ala Leu Thr Val Lys Ser Glu Ser Ser Met Thr Gly Tyr Ser Arg Asp
            20                  25                  30

Lys Phe Pro His Trp Ile Gly Gln Arg Asn Gly Cys Asp Thr Arg Gln
        35                  40                  45

Leu Val Leu Gln Arg Asp Ala Asp Ser Tyr Ser Gly Ser Cys Pro Val
    50                  55                  60

Thr Ser Gly Ser Trp Tyr Ser Tyr Tyr Asp Gly Val Thr Phe Thr Asp
65                  70                  75                  80

Pro Ser Asp Leu Asp Ile Asp His Val Val Pro Leu Ala Glu Ala Trp
                85                  90                  95

Arg Ser Gly Ala Ser Ser Trp Thr Thr Ala Lys Arg Glu Asp Phe Ala
            100                 105                 110

Asn Asp Leu Ser Gly Pro Gln Leu Ile Ala Val Ser Ala Ser Ser Asn
        115                 120                 125

Arg Ser Lys Gly Asp Gln Asp Pro Ser Thr Trp Gln Pro Pro Arg Ser
    130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ile Tyr
            180


<210> SEQ ID NO 18
<211> LENGTH: 182
<212> TYPE: PRT
<213> ORGANISM: Bacillus hwajinpoensis

<400> SEQUENCE: 18

Ile Pro Pro Gly Thr Pro Ser Lys Ser Ala Ala Gln Ser Gln Leu Asp
1               5                   10                  15

Ser Leu Ala Val Gln Ser Glu Gly Ser Met Ser Gly Tyr Ser Arg Asp
            20                  25                  30

Lys Phe Pro His Trp Ile Gly Gln Gly Asn Gly Cys Asp Thr Arg Gln
        35                  40                  45

Leu Val Leu Gln Arg Asp Ala Asp Tyr Tyr Ser Gly Asp Cys Pro Val
    50                  55                  60
```

-continued

```
Thr Ser Gly Lys Trp Tyr Ser Tyr Phe Asp Gly Val Gln Val Tyr Asp
65                  70                  75                  80

Pro Ser Tyr Leu Asp Ile Asp His Met Val Pro Leu Ala Glu Ala Trp
                85                  90                  95

Arg Ser Gly Ala Ser Ser Trp Ser Thr Gln Lys Arg Glu Asp Phe Ala
            100                 105                 110

Asn Asp Leu Asp Gly Pro His Leu Ile Ala Val Thr Ala Ser Ser Asn
        115                 120                 125

Arg Ser Lys Gly Asp Gln Asp Pro Ser Thr Trp Lys Pro Thr Arg Tyr
    130                 135                 140

Ser Ala His Cys Gly Tyr Ala Lys Trp Trp Ile Asn Thr Lys Tyr Val
145                 150                 155                 160

Tyr Asp Leu Asn Leu Gln Ser Ser Glu Lys Ser Ala Leu Gln Ser Met
                165                 170                 175

Leu Asn Thr Cys Ser Tyr
            180


<210> SEQ ID NO 19
<211> LENGTH: 182
<212> TYPE: PRT
<213> ORGANISM: Paenibacillus mucilaginosus

<400> SEQUENCE: 19

Leu Pro Pro Gly Thr Pro Ser Lys Ser Thr Ala Gln Ser Gln Leu Asn
1               5                   10                  15

Ser Leu Thr Val Lys Ser Glu Ser Thr Met Thr Gly Tyr Ser Arg Asp
            20                  25                  30

Lys Phe Pro His Trp Thr Ser Gln Gly Gly Gly Cys Asp Thr Arg Gln
        35                  40                  45

Val Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Gln Asn Phe Ala
            100                 105                 110

Asn Asp Leu Gly Gly Pro Gln Leu Ile Ala Val Thr Ala Ser Ser Asn
        115                 120                 125

Arg Ala Lys Gly Asp Gln Asp Pro Ser Thr Trp Lys Pro Thr Arg Ser
    130                 135                 140

Gly Ala His Cys Ala Tyr Ala Lys Trp Trp Ile Asn Thr Lys Tyr Arg
145                 150                 155                 160

Trp Gly Leu His Leu Gln Ser Ser Glu Lys Thr Ala Leu Gln Ser Met
                165                 170                 175

Leu Asn Thr Cys Ser Tyr
            180


<210> SEQ ID NO 20
<211> LENGTH: 182
<212> TYPE: PRT
<213> ORGANISM: Bacillus indicus

<400> SEQUENCE: 20

Thr Pro Pro Gly Thr Pro Ser Lys Ser Thr Ala Gln Thr Gln Leu Asn
1               5                   10                  15
```

```
Ala Leu Thr Val Lys Thr Glu Gly Ser Met Thr Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Val Thr Phe Tyr Asp
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ala
    130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
            180


<210> SEQ ID NO 21
<211> LENGTH: 182
<212> TYPE: PRT
<213> ORGANISM: Bacillus marisflavi

<400> SEQUENCE: 21

Thr Pro Pro Val Thr Pro Ser Lys Ala Thr Ser Gln Ser Gln Leu Asn
1               5                   10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Lys Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Lys Cys Gly Tyr Ala Lys Trp Trp Ile Ser Thr Lys Ser Lys
145                 150                 155                 160

Trp Asn Leu Ser Leu Gln Ser Ser Glu Lys Thr Ala Leu Gln Gly Met
                165                 170                 175

Leu Asn Ser Cys Val Tyr
            180


<210> SEQ ID NO 22
```

<211> LENGTH: 184
<212> TYPE: PRT
<213> ORGANISM: Bacillus luciferensis

<400> SEQUENCE: 22

```
Ala Ser Leu Pro Pro Gly Ile Pro Ser Leu Ser Thr Ala Gln Ser Gln
1               5                   10                  15

Leu Asn Ser Leu Thr Val Lys Ser Glu Gly Ser Leu Thr Gly Tyr Ser
            20                  25                  30

Arg Asp Val Phe Pro His Trp Ile Ser Gln Gly Ser Gly Cys Asp Thr
        35                  40                  45

Arg Gln Val Val Leu Lys Arg Asp Ala Asp Tyr Tyr Ser Gly Asn Cys
    50                  55                  60

Pro Val Thr Ser Gly Lys Trp Tyr Ser Tyr Tyr Asp Gly Val Thr Val
65                  70                  75                  80

Tyr Ser Pro Ser Glu Ile Asp Ile Asp His Val Val Pro Leu Ala Glu
                85                  90                  95

Ala Trp Arg Ser Gly Ala Ser Ser Trp Thr Thr Glu Lys Arg Gln Asn
            100                 105                 110

Phe Ala Asn Asp Leu Asn Gly Pro Gln Leu Ile Ala Val Thr Ala Ser
        115                 120                 125

Ser Asn Arg Ser Lys Gly Asp Gln Asp Pro Ser Thr Trp Gln Pro Thr
    130                 135                 140

Arg Thr Gly Ala Arg Cys Ala Tyr Ala Lys Met Trp Ile Asn Thr Lys
145                 150                 155                 160

Tyr Arg Trp Gly Leu His Leu Gln Ser Ser Glu Lys Ser Ala Leu Gln
                165                 170                 175

Ser Met Leu Asn Thr Cys Ser Tyr
            180
```

<210> SEQ ID NO 23
<211> LENGTH: 182
<212> TYPE: PRT
<213> ORGANISM: Bacillus marisflavi

<400> SEQUENCE: 23

```
Thr Pro Pro Val Thr Pro Ser Lys Glu Thr Ser Gln Ser Gln Leu Asn
1               5                   10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Lys Phe Thr His
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Lys Cys Gly Tyr Ala Lys Trp Trp Ile Ser Thr Lys Ser Lys
145                 150                 155                 160
```

```
Trp Asn Leu Ser Leu Gln Ser Ser Glu Lys Thr Ala Leu Gln Gly Met
                165                 170                 175

Leu Asn Ser Cys Val Tyr
            180


<210> SEQ ID NO 24
<211> LENGTH: 182
<212> TYPE: PRT
<213> ORGANISM: Bacillus species

<400> SEQUENCE: 24

Leu Pro Ser Gly Ile Pro Ser Lys Ser Thr Ala Gln Ser Gln Leu Asn
1               5                   10                  15

Ser Leu Thr Val Lys Ser Glu Gly Ser Met Thr Gly Tyr Ser Arg Asp
            20                  25                  30

Lys Phe Pro His Trp Ile Ser Gln Gly Gly Gly Cys Asp Thr Arg Gln
        35                  40                  45

Val Val Leu Lys Arg Asp Ala Asp Tyr Tyr Ser Gly Asn Cys Pro Val
    50                  55                  60

Thr Ser Gly Lys Trp Tyr Ser Tyr Tyr Asp Gly Ile Ser Val Tyr Ser
65                  70                  75                  80

Pro Ser Glu Ile Asp Ile Asp His Val Val Pro Leu Ala Glu Ala Trp
                85                  90                  95

Arg Ser Gly Ala Ser Ser Trp Thr Thr Thr Lys Arg Gln Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Tyr
    130                 135                 140

Gly Ala Arg Cys Ala Tyr Ala Lys Met Trp Ile Asn Thr Lys Tyr Arg
145                 150                 155                 160

Trp Asp Leu Asn Leu Gln Ser Ser Glu Lys Ser Ser Leu Gln Ser Met
                165                 170                 175

Leu Asp Thr Cys Ser Tyr
            180


<210> SEQ ID NO 25
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp (D) or Met (M) or Leu (L)
<220> FEATURE:
<221> NAME/KEY: MISC_FEATURE
<222> LOCATION: (2)..(2)
<223> OTHER INFORMATION: Xaa = Ser (S) or Thr (T)
<220> FEATURE:
<221> NAME/KEY: MISC_FEATURE
<222> LOCATION: (7)..(7)
<223> OTHER INFORMATION: Xaa = Asp (D) or Asn (N)

<400> SEQUENCE: 25

Xaa Xaa Gly Tyr Ser Arg Xaa
1               5


<210> SEQ ID NO 26
<211> LENGTH: 8
```

<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa = any amino acid

<400> SEQUENCE: 26

```
Ala Ser Xaa Asn Arg Ser Lys Gly
1               5
```

<210> SEQ ID NO 27
<211> LENGTH: 182
<212> TYPE: PRT
<213> ORGANISM: Artificial sequence
<220> FEATURE:
<223> OTHER INFORMATION: Synthetic construct

<400> SEQUENCE: 27

```
Ile Pro Pro Gly Thr Pro Ser Lys Ser Ala Ala Gln Ser Gln Leu Asn
1               5                   10                  15

Ala Leu Thr Val Lys Pro Glu Gly Ser Met Ser Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Trp Tyr Ser Gly Asn Cys Pro Val
    50                  55                  60

Thr Ser Gly Ser Trp Tyr Ser Tyr Tyr Asp Gly Leu Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ser
    130                 135                 140

Gly Ala His Cys Gly Tyr Ser Lys Trp Trp Ile Ser Thr Lys Tyr Lys
145                 150                 155                 160

Trp Gly Leu Ser Leu Gln Leu Ser Glu Lys Thr Ala Leu Gln Asp Met
                165                 170                 175

Leu Asn Ser Cys Ser Tyr
            180
```

<210> SEQ ID NO 28
<211> LENGTH: 182
<212> TYPE: PRT
<213> ORGANISM: Artificial sequence
<220> FEATURE:
<223> OTHER INFORMATION: Synthetic construct

<400> SEQUENCE: 28

```
Ile Pro Pro Gly Thr Pro Ser Lys Ser Ala Ala Gln Tyr Gln Leu Asn
1               5                   10                  15

Ala Leu Thr Val Lys Pro Glu Gly Ser Met Leu Gly Tyr Ser Arg Asp
            20                  25                  30

Leu Phe Pro His Trp Ile Ser Gln Gly Gly Gly Cys Asp Thr Arg Gln
        35                  40                  45
```

-continued

```
Val Val Leu Lys Arg Asp Ala Asp Trp Tyr Val Gly Asn Cys Pro Val
    50                  55                  60

Thr Ser Gly Ser Trp Tyr Ser Tyr Tyr Asp Gly Leu Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Arg Asp Phe Ala
            100                 105                 110

Asn Asp Leu Asp Gly Pro Gln Leu Ile Ala Val Ser Ala Ser Val Asn
        115                 120                 125

Arg Ser Lys Gly Asp Gln Asp Pro Ser Thr Trp Gln Pro Pro Arg Pro
    130                 135                 140

Gly Ala His Cys Gly Tyr Ser Lys Trp Trp Ile Ser Thr Lys Tyr Lys
145                 150                 155                 160

Trp Gly Leu Ser Leu Gln Leu Ser Glu Lys Thr Ala Leu Gln Asp Met
                165                 170                 175

Leu Asn Ser Cys Ser Tyr
            180
```

DNASE VARIANTS

CROSS-REFERENCE TO RELATED APPLICATIONS

This application is a 35 U.S.C. 371 national application of international application no. PCT/EP2018/079441 filed Oct. 26, 2018 which claims priority or the benefit under 35 U.S.C. 119 of European application no. 17198946.0 and 17204656.7 filed Oct. 27, 2017 and Nov. 30, 2017, the contents of which are fully incorporated herein by reference.

REFERENCE TO A JOINT RESEARCH AGREEMENT

The embodiments claimed in the present application were made under a joint research agreement between The Procter & Gamble Company and Novozymes A/S.

REFERENCE TO A SEQUENCE LISTING

This application contains a Sequence Listing in computer readable form, which is incorporated herein by reference. The name of the file containing the Sequence Listing is SQ.txt, which was created on Mar. 16, 2021 and has 42.3 KB.

BACKGROUND OF THE INVENTION

Field of the Invention

The present invention relates to novel DNase variants exhibiting alterations relative to the parent DNase in one or more properties including: wash performance, detergent stability and/or storage stability. The variants of the invention are suitable for use in cleaning processes and detergent compositions, such as laundry compositions and dish wash compositions, including hand wash and automatic dish wash compositions. The present invention also relates to isolated DNA sequences encoding the variants, expression vectors, host cells, and methods for producing and using the DNase variants of the invention.

Description of the Related Art

Enzymes have been used in detergents for decades most commercially relevant are the proteases and amylases effectively removing protein and starch related soiling, respectively. However, most household care related soiling is a complex mixture of various organic matters. Hard surfaces and fabrics are exposed to skin debris e.g. dead cells, sweat and sebum, pollution as well as microorganisms from outside and from e.g. the body. Microorganisms may adhere to soil on laundry or surfaces and such adhered microorganisms may propagate and form biofilm. Biofilm is often embedded in a self-produced matrix of extracellular polymeric substance (EPS). Biofilm EPS is a polymeric conglomeration generally composed of extracellular DNA, proteins, and polysaccharides. House hold care related soling composes different organic stains such as of protein, starch, grease but also e.g. DNA. Consequently, stain removal requires different enzyme activity, which vary depending on the specific stain targeted.

To be useful in cleaning processes such as laundry an enzyme such a DNase need to be stable in detergent compositions and compatible with standard detergent components such as surfactants, builders, bleaches etc.

The present invention provides such enzymes which are suitable for use in detergents for e.g. improving laundry and washing/dish machine.

SUMMARY OF THE INVENTION

The present invention relates to DNase variants which are particularly useful in detergents and cleaning processes, such as laundry and dish wash.

One aspect of the invention relates to a DNase variant, which compared to a DNase with SEQ ID NO: 1, comprises two or more substitutions selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein the positions correspond to the positions of SEQ ID NO: 1 (numbering according to SEQ ID NO: 1), wherein the variant has a sequence identity to the polypeptide shown in SEQ ID NO: 1 or the polypeptide show in SEQ ID NO: 28 of at least 90%, and wherein the variant has DNase activity.

One aspect of the invention relates to a DNase variant, which compared to a DNase with SEQ ID NO: 1, comprises two or more of the following mutations T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D, G175E, wherein the positions correspond to the positions of SEQ ID NO: 1 (numbering according to SEQ ID NO: 1), wherein the variant has a sequence identity to the polypeptide shown in SEQ ID NO: 1 of at least 80% and the variant has DNase activity.

Another aspect of the invention relates to a method for obtaining a DNase variant, comprising;

a) introducing into a parent DNase two or more of the following mutations: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D, G175E, wherein the positions correspond to the positions of SEQ ID NO: 1 (numbering according to SEQ ID NO: 1) and wherein the variant has DNase activity, b) and recovering the variant.

A third aspect of the invention relates to the use of a DNase variant according to the invention for deep cleaning of an item, wherein the item is a textile or a hard surface.

Sequences

SEQ ID NO: 1 mature polypeptide obtained from *Bacillus cibi*

SEQ ID NO: 2 mature polypeptide obtained from *Bacillus horikoshii*

SEQ ID NO: 3 mature polypeptide obtained from *Bacillus* sp-62520

SEQ ID NO: 4 mature polypeptide obtained from *Bacillus horikoshii*

SEQ ID NO: 5 mature polypeptide obtained from *Bacillus horikoshii*

SEQ ID NO: 6 mature polypeptide obtained from *Bacillus* sp-16840

SEQ ID NO: 7 mature polypeptide obtained from *Bacillus* sp-16840

SEQ ID NO: 8 mature polypeptide obtained from *Bacillus* sp-62668

SEQ ID NO: 9 mature polypeptide obtained from *Bacillus* sp-13395

SEQ ID NO: 10 mature polypeptide obtained from *Bacillus horneckiae*

SEQ ID NO: 11 mature polypeptide obtained from *Bacillus* sp-11238

SEQ ID NO: 12 mature polypeptide obtained from *Bacillus* sp-62451

SEQ ID NO: 13 mature polypeptide obtained from *Bacillus* sp-18318

SEQ ID NO: 14 mature polypeptide obtained from *Bacillus idriensis*

SEQ ID NO: 15 is the mature polypeptide obtained from *Bacillus algicola*

SEQ ID NO: 16 mature polypeptide obtained from environmental sample J

SEQ ID NO: 17 mature polypeptide obtained from *Bacillus vietnamensis*

SEQ ID NO: 18 mature polypeptide obtained from *Bacillus hwajinpoensis*

SEQ ID NO: 19 mature polypeptide obtained from *Paenibacillus mucilaginosus*

SEQ ID NO: 20 mature polypeptide obtained from *Bacillus indicus*

SEQ ID NO: 21 Mature polypeptide obtained from *Bacillus marisflavi*

SEQ ID NO: 22 mature polypeptide obtained from *Bacillus luciferensis*

SEQ ID NO: 23 mature polypeptide obtained from *Bacillus marisflavi*

SEQ ID NO: 24 mature polypeptide obtained from *Bacillus* sp. SA2-6

SEQ ID NO: 25 motif [D/M/1_][S/T]GYSR[D/N]

SEQ ID NO: 26 motif ASXNRSKG

SEQ ID NO: 27 DNase variant

SEQ ID NO: 28 DNase variant

Definitions

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the DNase variant enzyme used in the composition. In some aspects, granular compositions are in "compact" form, while in other aspects, the liquid compositions are in a "concentrated" form.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "biofilm" means any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp.

The term "cDNA" means a DNA molecule that can be prepared by reverse transcription from a mature, spliced, mRNA molecule obtained from a prokaryotic or eukaryotic cell. A cDNA lacks intron sequences that may be present in the corresponding genomic DNA. The initial, primary RNA transcript is a precursor to mRNA that is processed through a series of steps, including splicing, before appearing as mature spliced mRNA.

The term "Glade" means a group of polypeptides clustered together based on homologous features traced to a common ancestor. Polypeptide clades can be visualized as phylogenetic trees and a Glade is a group of polypeptides that consists of a common ancestor and all its lineal descendants. Polypeptides forming a group e.g. a Glade as shown in a phylogenetic tree may often share common properties and are also functionally more closely related than other polypeptides not in the Glade.

The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for introducing specific restriction sites facilitating ligation of the control sequences with the coding region of the polynucleotide encoding a variant.

By the term "deep cleaning" is meant disruption or removal of components of organic matter, e.g. biofilm and EPS, such as polysaccharides, proteins, DNA, soil or other components present in the organic matter.

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, soap bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. The terms "detergent composition" and "detergent formulation" are used in reference to mixtures which are intended for use in a wash medium for the cleaning of soiled objects. In some aspects, the term is used in reference to laundering fabrics and/or garments (e.g., "laundry detergents"). In alternative aspects, the term refers to other detergents, such as those used to clean dishes, cutlery, etc. (e.g., "dishwashing detergents"). It is not intended that the present invention be limited to any particular detergent formulation or composition. The term "detergent composition" is not intended to be limited to compositions that contain surfactants. It is intended that in addition to the variants according to the invention, the term encompasses detergents that may contain, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "DNase", "DNase variants" or "DNase parent" means a polypeptide with DNase activity that catalyzes the hydrolytic cleavage of phosphodiester linkages in DNA, thus degrading DNA. DNases belong to the esterases (EC-number 3.1), a subgroup of the hydrolases. The DNases are classified e.g. in E.C. 3.1.11, E.C. 3.1.12, E.C. 3.1.15, E.C. 3.1.16, E.C. 3.1.21, E.C 3.1.22, E.C 3.1.23, E.C 3.1.24 and E.C.3.1.25 as well as EC 3.1.21.X, where X=1, 2, 3, 4, 5, 6, 7, 8 or 9. The term "DNase" and the expression "a polypeptide with DNase activity" may be used interchangeably throughout the application. For purposes of the present invention, DNase activity is determined according to the procedure described in the Assay I. In some aspects, the DNase variants of the present invention have improved DNase activity compared to the parent DNase. In some aspects, the DNase variants of the present invention have at least 100%, e.g., at least 110%, at least 120%, at least 130%, at least 140%, at least 150%, at least 160%, at least 170%, at least 180%, at least 190%, or at least 200% DNase activity compared to the polypeptide shown in SEQ ID NO: 1 or such as from 100% to 200% DNase activity compared to the polypeptide shown in SEQ ID NO: 1.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a DNase variant refers to the quantity of DNase variant described hereinbefore that achieves a desired level of enzymatic activity, e.g., in a defined detergent composition.

The term "expression" includes any step involved in the production of the variant including, but not limited to, transcription, post-transcriptional modification, translation, post-translational modification, and secretion.

The term "expression vector" means a linear or circular DNA molecule that comprises a polynucleotide encoding a variant and is operably linked to additional nucleotides that provide for its expression.

The term "fabric" encompasses any textile material. Thus, it is intended that the term encompass garments, as well as fabrics, yarns, fibers, non-woven materials, natural materials, synthetic materials, and any other textile material.

The term "high detergent concentration" system includes detergents wherein greater than about 2000 ppm of detergent components is present in the wash water. European detergents are generally considered to be high detergent concentration systems.

The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

The term "improved property" means a characteristic associated with a variant that is improved compared to the parent and/or compared to a DNase with SEQ ID NO: 1, or compared to a DNase having the identical amino acid sequence of said variant but not having the alterations at two or more of said specified positions. Such improved properties include, but are not limited to, stability, such as detergent stability, wash performance e.g. deep cleaning effect and the deep-cleaning effect may include but is not limited to de-gluing effect. Improved property also includes improved stability in presence of certain enzymes e.g. proteases (protease stability) or substances e.g. stability in presence of sulfite e.g. sulfite stability.

The term "improved DNase activity" is defined herein as an altered DNase activity e.g. by increased catalyse of hydrolytic cleavage of phosphodiester linkages in the DNA i.e. the DNase variant displaying an alteration of the activity relative (or compared) to the activity of the parent DNase, such as compared to a DNase with SEQ ID NO: 1 or compared to a DNase having the identical amino acid sequence of said variant but not having the alterations at one or more of said specified positions.

The term "low detergent concentration" system includes detergents where less than about 800 ppm of detergent components is present in the wash water. Asian, e.g., Japanese detergents are typically considered low detergent concentration systems.

The term "improved wash performance" includes but is not limited to the term "deep cleaning effect". Improved performance e.g. deep cleaning performance of a DNase variant according to the invention is measured compared to the DNase parent e.g. the DNase shown in SEQ ID NO: 1 or compared to a DNase having the identical amino acid sequence of said variant but not having the alterations at one or more of said specified positions. The improved performance e.g. deep cleaning performance may be expressed as a Remission value of the stained swatches. After washing and rinsing the swatches are spread out flat and allowed to air dry at room temperature overnight. All washed swatches are evaluated the day after the wash. Light reflectance evaluations of the swatches are done using a Macbeth Color Eye 7000 reflectance spectrophotometer with very small aperture. The measurements are made without UV in the incident light and remission at 460 nm is extracted. Positive responses indicate that soil are removed including soil stuck to the fabric due to e.g. a biofilm or EPS sticky layer.

The term "isolated polynucleotide" means a polynucleotide that is modified by the hand of man. In some aspects, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

The term "mature polypeptide" means a polypeptide in its final form following translation and any post-translational modifications, such as N-terminal processing, C-terminal truncation, glycosylation, phosphorylation, etc. In some aspects, the mature polypeptide is amino acids 1 to 182 of SEQ ID NO: 1. The N-terminals of the mature polypeptide used according to the present invention were experimentally confirmed based on EDMAN N-terminal sequencing data and Intact MS data. It is known in the art that a host cell may produce a mixture of two of more different mature polypeptides (i.e., with a different C-terminal and/or N-terminal amino acid) expressed by the same polynucleotide.

The term "mature polypeptide coding sequence" means a polynucleotide that encodes a mature polypeptide having DNase activity.

The term "medium detergent concentration" system includes detergents wherein between about 800 ppm and about 2000 ppm of detergent components is present in the wash water. North American detergents are generally considered to be medium detergent concentration systems.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

The term "non-fabric detergent compositions" include non-textile surface detergent compositions, including but not limited to compositions for hard surface cleaning, such as dishwashing detergent compositions including manual dish wash compositions, oral compositions, denture compositions, and personal cleansing compositions.

The term "operably linked" means a configuration in which a control sequence is placed at an appropriate position relative to the coding sequence of a polynucleotide such that the control sequence directs the expression of the coding sequence.

The term "parent" DNase, DNase parent or precursor DNase may be used interchangeably. In context of the present invention "parent DNase" is to be understood as a DNase into which at least one alteration is made in the amino acid sequence to produce a DNase variant having an amino acid sequence which is less than 100% identical to the DNase sequence into which the alteration was made i.e. the parent DNase. Thus, the parent is a DNase having identical amino acid sequence compared to the variant but not having the alterations at one or more (or two or more) of the specified positions. It will be understood, that in the present context the expression "having identical amino acid sequence" relates to 100% sequence identity. In a particular aspect the DNase parent is a DNase having at least 60%, at least 61%, at least 62%, at least 63%, at least 64%, at least 65%, at least 66%, at least 67%, at least 68%, at least 69%, at least 70%, at least 72%, at least 73%, at least 74%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6 or 100% identity to a polypeptide shown in SEQ ID NO: 1.

The term "relevant washing conditions" is used herein to indicate the conditions, particularly washing temperature, time, washing mechanics, detergent concentration, type of detergent and water hardness, actually used in households in a detergent market segment.

The term "stability" includes storage stability and stability during use, e.g. during a wash process and reflects the stability of the DNase variant according to the invention as a function of time e.g. how much activity is retained when the DNase variant is kept in solution in particular in a detergent solution. The stability is influenced by many factors e.g. pH, temperature, detergent composition e.g. amount of builder, surfactants etc. The DNase stability may be measured as described in example 2-6. The term "improved stability" or "increased stability" is defined herein as a variant DNase displaying an increased stability in solutions, relative to the stability of the parent DNase and/or relative to SEQ ID NO: 1. "Improved stability" and "increased stability" includes detergent stability. The term "detergent stability" or "improved detergent stability may be improved stability of the DNase activity compared to the DNase parent. The DNase stability is measured as described in example 2-6.

The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well-known recombinant methods or by classical purification methods.

The term "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "transcription promoter" is used for a promoter which is a region of DNA that facilitates the transcription of a particular gene. Transcription promoters are typically located near the genes they regulate, on the same strand and upstream (towards the 5' region of the sense strand).

The term "transcription terminator" is used for a section of the genetic sequence that marks the end of gene or operon on genomic DNA for transcription.

The term "variant" means a polypeptide having DNase activity and which comprises a substitution at one or more (e.g., several) positions. A substitution means replacement of the amino acid occupying a position with a different amino acid, a deletion means removal of an amino acid occupying a position and an insertion means adding amino acids e.g. 1 to 10 amino acids, preferably 1-3 amino acids adjacent to an amino acid occupying a position. The variants of the present invention have at least 20%, e.g., at least 40%, at least 50%, at least 60%, at least 70%, at least 80%, at least 90%, at least 95%, or at least 100% of the DNase activity of the mature polypeptide shown in SEQ ID NO: 1. The term "DNase variant" means a polypeptide having DNase activity and comprise an alteration, i.e., a substitution, insertion, and/or deletion at one or more (or one or several) positions compared to the parent DNase e.g. compared to SEQ ID NO: 1.

The term "water hardness" or "degree of hardness" or "dH" or "° dH" as used herein refers to German degrees of hardness. One degree is defined as 10 milligrams of calcium oxide per liter of water.

The term "wild-type DNase" means a DNase expressed by a naturally occurring organism, such as a fungal, bacterium, archaea, yeast, plant or animal found in nature.

Conventions for Designation of Variants

For purposes of the present invention, the polypeptide disclosed in SEQ ID NO: 1 is used to determine the corresponding amino acid residue in another DNase. The amino acid sequence of another DNase is aligned with the polypeptide disclosed in SEQ ID NO: 1, and based on the alignment, the amino acid position number corresponding to any amino acid residue in the polypeptide disclosed in SEQ ID NO: 1 is determined using e.g. the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another DNase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When another enzyme has diverged from the polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP super families of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

As different amino acids may be present at a given position depending on the selected parent for the variants the amino acid positions are indicated with $\#_1$, $\#_2$, etc. in the definitions below. In describing the variants of the present invention, the nomenclature described below is adapted for ease of reference. The accepted IUPAC single letter or three letters amino acid abbreviations are employed.

Substitutions:

For an amino acid substitution, the following nomenclature is used: Original amino acid, position, substituted amino acid. Accordingly, the substitution of valine at position $\#_1$ with alanine is designated as "Val $\#_1$Ala" or "V $\#_1$A". Multiple mutations are separated by addition marks ("+") or by commas (,), e.g., "Val $\#_1$Ala+"Pro $\#_2$Gly" or V $\#_1$A, P $\#_2$G, representing substitutions at positions $\#_1$ and $\#_2$ of valine (V) and proline (P) with alanine (A) and glycine (G), respectively. If more than one amino acid may be substituted in a given position these are listed in brackets, such as [X] or {X}. Thus, if both Trp and Lys may be substituted instead of the amino acid occupying at position $\#_1$ this is indicated as X $\#_1$ {W, K}, X $\#_1$ [W, K] or X $\#_1$[W/K], where the X indicate the amino acid residue present at the position of the parent DNase e.g. such as a DNase shown in SEQ ID NO: 1 or a DNase having at least 60% identity hereto. In some cases, the variants may be represented as $\#_1$ {W, K} or X $\#_2$P indicating that the amino acids to be substituted vary depending on the parent. For convenience, as SEQ ID NO: 1 is used for numbering the substitutions, the amino acid in the corresponding position in SEQ ID NO: 1 is indicated, e.g. T1A. However, it will be clear to the skilled artisan that a DNase variant comprising T1A is not limited to parent DNases having threonine at a position corresponding to position 1 of SEQ ID NO: 1. In a parent DNase having e.g. asparagine in position 1, the skilled person would translate the mutation specified as T1A to N1A. In the event the parent DNase has alanine in position 1, the skilled person would recognize that the parent DNase is not changed at this position. The same applies for deletions and insertions described below.

Deletions:

For an amino acid deletion, the following nomenclature is used: Original amino acid, position, *. Accordingly, the deletion of valine at position $\#_1$ is designated as "Val $\#_1$*" or "V $\#_1$*". Multiple deletions are separated by addition marks ("+") or commas, e.g., "Val $\#_1$*+Pro $\#_2$*" or "V $\#_1$*, P $\#_2$*".

Insertions:

The insertion of an additional amino acid residue such as e.g. a lysine after Val $\#_1$ may be indicated by: Val $\#_1$ValLys or V $\#_1$VK. Alternatively, insertion of an additional amino acid residue such as lysine after V $\#_1$ may be indicated by: *$\#_1$aK. When more than one amino acid residue is inserted, such as e.g. a Lys, and Gly after $\#_1$ this may be indicated as: Val $\#_1$ValLysGly or V $\#_1$VKG. In such cases, the inserted amino acid residue(s) may also be numbered by the addition of lower case letters to the position number of the amino acid residue preceding the inserted amino acid residue(s), in this example: *$\#_1$aK *$\#_1$bG.

Multiple Alterations:

Variants comprising multiple alterations are separated by addition marks ("+") or by commas (,), e.g., "Val $\#_1$Trp+Pro $\#_2$Gly" or "V $\#_1$W, P $\#_2$G" representing a substitution of valine and proline at positions $\#_1$ and $\#_2$ with tryptophan and glycine, respectively as described above.

Different Alterations:

Where different alterations can be introduced at a position, the different alterations may be separated by a comma, e.g., "Val $\#_1$Trp, Lys" or V $\#_1$W, K representing a substitution of valine at position $\#_1$ with tryptophan or lysine. Thus, "Val $\#_1$Trp, Lys+Pro $\#_2$Asp" designates the following variants: "Val $\#_1$Trp+Pro $\#_2$Asp", "Val $\#_1$Lys+Pro $\#_2$Asp" or V $\#_1$W, K+P $\#_2$D. The term "substitution set" is in the context of the present invention a variant comprising more than one mutation compared to the parent or reference enzyme e.g. the substitution set T1I+S13Y (compared to SEQ ID NO: 1) is a variant of SEQ ID NO: 1 comprising the two mutations T1I+S13Y compared to SEQ ID NO: 1.

Specific for Nomenclature of Clades

For purposes of the present invention, the nomenclature [IV] or [I/V] means that the amino acid at this position may be isoleucine (Ile, I) or valine (Val, V). Likewise, the nomenclature [LVI] and [L/V/I] means that the amino acid at this position may be a leucine (Leu, L), valine (Val, V) or isoleucine (Ile, I), and so forth for other combinations as described herein. Unless otherwise limited further, the amino acid X is defined such that it may be any of the 20 naturally-occurring amino acids.

DETAILED DESCRIPTION OF THE INVENTION

The present invention provides novel DNases preferably obtained from *Bacillus*, in particular, *Bacillus cibi*. The DNases of the invention comprise at least 60% sequence identity to a polypeptide with SEQ ID NO: 1 and comprise an alteration of at least two amino acid positions compared to the DNase with SEQ ID NO: 1. In some aspects, a DNase variant of the invention comprise an amino acid sequence comprising at least two substitutions of an amino acid made at positions equivalent to the positions in SEQ ID NO: 1. The present invention also relates to methods for of producing DNase variants. The DNase variants of the present invention have at least one improved property compared to the parent DNase or compared to SEQ ID NO: 1. Properties includes but are not limited to: stability such as; stability in detergents, storage stability, in wash stability and thermo stability, wash performance in particular deep-cleaning performance, increased expression level and malodor reduction.

DNase Variants

Some aspects of the invention relate to DNase variants of SEQ ID NO: 1 or variants of a DNase having at least 60% identity hereto and to methods for production of a DNase variant of SEQ ID NO: 1 or a DNase having at least 60% identity hereto.

The present invention relates to a DNase comprising an alteration at two or more positions selected from the list consisting of positions 1, 13, 22, 25, 27, 39, 42, 57, 59, 76, 109, 116, 127, 144, 147, 167 and 175, wherein each position corresponds to the position of the polypeptide of SEQ ID NO: 1, wherein the variant has DNase activity.

In some aspects the variant has a sequence identity of at least 60%, at least 65%, at least 70%, at least 75%, at least 80%, at least 85%, at least 90%, at least 95%, such as at least 96%, at least 97%, at least 98%, or at least 99%, but less than 100%, to the amino acid sequence of the mature parent DNase e.g. the DNase shown in SEQ ID NO: 1.

In some aspects the variant has DNase activity, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1.

In some preferred aspects the alteration is a substitution and the DNase variant of the invention comprises two or more substitutions (compared to SEQ ID NO: 1), wherein the substitutions are selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein the variant has DNase activity and wherein each position corresponds to the position of the polypeptide shown in SEQ ID NO: 1 (numbering according to SEQ ID NO: 1).

In some aspects, the number of substitutions in the variants of the present invention is 2-20, e.g., 2-10 and 2-5, such as 2, 3, 4, 5, 6, 7, 8, 9, 10, 11, 12, 13, 14, 15, 16, 17, 18, 19 or 20 substitutions. In one aspect the total number of substitutions compared to SEQ ID NO: 1 is 3-20, e.g. at least 5 to 20, at least 10 to 20 or such as at least 15 to 20 substitutions compared to the DNase comprising the amino acid sequence shown in SEQ ID NO: 1.

The invention further relates to variants of a DNase parent polypeptide comprising SEQ ID NO: 1 wherein the variant comprises an alteration compared to SEQ ID NO: 1 in at least two positions selected from the positions: 1, 13, 22, 25, 27, 39, 42, 57, 59, 76, 109, 116, 127, 144, 147, 167 and 175, corresponding to the positions of SEQ ID NO: 1, wherein the variant has an amino acid sequence which is at least 60%, at least 70%, at least 80%, at least 90% or at least 95% identical to SEQ ID NO: 1, wherein the variant has DNase activity and wherein the variant has at least one improved property compared to the DNase of SEQ ID NO: 1.

In one aspect the invention relates to a DNase variant comprising a substitution at the positions corresponding to position 1 and 13 of SEQ ID NO: 1, wherein the variant has DNase activity.

In one aspect the invention relates to a DNase variant comprising a substitution at the positions corresponding to position 1 and 22 of SEQ ID NO: 1, wherein the variant has DNase activity.

In one aspect the invention relates to a DNase variant comprising a substitution at the positions corresponding to position 1 and 25 of SEQ ID NO: 1, wherein the variant has DNase activity.

In one aspect the invention relates to a DNase variant comprising a substitution at the positions corresponding to position 1 and 27 of SEQ ID NO: 1, wherein the variant has DNase activity.

In one aspect the invention relates to a DNase variant comprising a substitution at the positions corresponding to position 1 and 39 of SEQ ID NO: 1, wherein the variant has DNase activity.

In one aspect the invention relates to a DNase variant comprising a substitution at the positions corresponding to position 1 and 42 of SEQ ID NO: 1, wherein the variant has DNase activity.

In one aspect the invention relates to a DNase variant comprising a substitution at the positions corresponding to position 1 and 57 of SEQ ID NO: 1, wherein the variant has DNase activity.

In one aspect the invention relates to a DNase variant comprising a substitution at the positions corresponding to position 1 and 59 of SEQ ID NO: 1, wherein the variant has DNase activity.

In one aspect the invention relates to a DNase variant comprising a substitution at the positions corresponding to position 1 and 76 of SEQ ID NO: 1, wherein the variant has DNase activity.

In one aspect the invention relates to a DNase variant comprising a substitution at the positions corresponding to position 1 and 109 of SEQ ID NO: 1, wherein the variant has DNase activity.

In one aspect the invention relates to a DNase variant comprising a substitution at the positions corresponding to position 1 and 116 of SEQ ID NO: 1, wherein the variant has DNase activity.

In one aspect the invention relates to a DNase variant comprising a substitution at the positions corresponding to position 1 and 127 of SEQ ID NO: 1, wherein the variant has DNase activity.

In one aspect the invention relates to a DNase variant comprising a substitution at the positions corresponding to position 1 and 144 of SEQ ID NO: 1, wherein the variant has DNase activity.

In one aspect the invention relates to a DNase variant comprising a substitution at the positions corresponding to position 1 and 147 of SEQ ID NO: 1, wherein the variant has DNase activity.

In one aspect the invention relates to a DNase variant comprising a substitution at the positions corresponding to position 1 and 167 of SEQ ID NO: 1, wherein the variant has DNase activity.

In one aspect the invention relates to a DNase variant comprising a substitution at the positions corresponding to position 1 and 175 of SEQ ID NO: 1, wherein the variant has DNase activity.

In one aspect the invention relates to a DNase variant comprising a substitution at the positions corresponding to position 13 and 22 of SEQ ID NO: 1, wherein the variant has DNase activity.

In one aspect the invention relates to a DNase variant comprising a substitution at the positions corresponding to position 13 and 25 of SEQ ID NO: 1, wherein the variant has DNase activity.

In one aspect the invention relates to a DNase variant comprising a substitution at the positions corresponding to position 13 and 27 of SEQ ID NO: 1, wherein the variant has DNase activity.

In one aspect the invention relates to a DNase variant comprising a substitution at the positions corresponding to position 13 and 39 of SEQ ID NO: 1, wherein the variant has DNase activity.

In one aspect the invention relates to a DNase variant comprising a substitution at the positions corresponding to position 13 and 42 of SEQ ID NO: 1, wherein the variant has DNase activity.

In one aspect the invention relates to a DNase variant comprising a substitution at the positions corresponding to position 13 and 57 of SEQ ID NO: 1, wherein the variant has DNase activity.

In one aspect the invention relates to a DNase variant comprising a substitution at the positions corresponding to position 13 and 59 of SEQ ID NO: 1, wherein the variant has DNase activity.

In one aspect the invention relates to a DNase variant comprising a substitution at the positions corresponding to position 13 and 76 of SEQ ID NO: 1, wherein the variant has DNase activity.

In one aspect the invention relates to a DNase variant comprising a substitution at the positions corresponding to position 13 and 109 of SEQ ID NO: 1, wherein the variant has DNase activity.

In one aspect the invention relates to a DNase variant comprising a substitution at the positions corresponding to position 13 and 116 of SEQ ID NO: 1, wherein the variant has DNase activity.

In one aspect the invention relates to a DNase variant comprising a substitution at the positions corresponding to position 13 and 127 of SEQ ID NO: 1, wherein the variant has DNase activity.

In one aspect the invention relates to a DNase variant comprising a substitution at the positions corresponding to position 13 and 144 of SEQ ID NO: 1, wherein the variant has DNase activity.

In one aspect the invention relates to a DNase variant comprising a substitution at the positions corresponding to position 13 and 147 of SEQ ID NO: 1, wherein the variant has DNase activity.

In one aspect the invention relates to a DNase variant comprising a substitution at the positions corresponding to position 13 and 167 of SEQ ID NO: 1, wherein the variant has DNase activity.

In one aspect the invention relates to a DNase variant comprising a substitution at the positions corresponding to position 13 and 175 of SEQ ID NO: 1, wherein the variant has DNase activity.

In one aspect the invention relates to a DNase variant comprising a substitution at the positions corresponding to position 22 and 25 of SEQ ID NO: 1, wherein the variant has DNase activity.

In one aspect the invention relates to a DNase variant comprising a substitution at the positions corresponding to position 22 and 27 of SEQ ID NO: 1, wherein the variant has DNase activity.

In one aspect the invention relates to a DNase variant comprising a substitution at the positions corresponding to position 22 and 39 of SEQ ID NO: 1, wherein the variant has DNase activity.

In one aspect the invention relates to a DNase variant comprising a substitution at the positions corresponding to position 22 and 42 of SEQ ID NO: 1, wherein the variant has DNase activity.

In one aspect the invention relates to a DNase variant comprising a substitution at the positions corresponding to position 22 and 57 of SEQ ID NO: 1, wherein the variant has DNase activity.

In one aspect the invention relates to a DNase variant comprising a substitution at the positions corresponding to position 22 and 59 of SEQ ID NO: 1, wherein the variant has DNase activity.

In one aspect the invention relates to a DNase variant comprising a substitution at the positions corresponding to position 22 and 76 of SEQ ID NO: 1, wherein the variant has DNase activity.

In one aspect the invention relates to a DNase variant comprising a substitution at the positions corresponding to position 22 and 109 of SEQ ID NO: 1, wherein the variant has DNase activity.

In one aspect the invention relates to a DNase variant comprising a substitution at the positions corresponding to position 22 and 116 of SEQ ID NO: 1, wherein the variant has DNase activity.

In one aspect the invention relates to a DNase variant comprising a substitution at the positions corresponding to position 22 and 127 of SEQ ID NO: 1, wherein the variant has DNase activity.

In one aspect the invention relates to a DNase variant comprising a substitution at the positions corresponding to position 22 and 144 of SEQ ID NO: 1, wherein the variant has DNase activity.

In one aspect the invention relates to a DNase variant comprising a substitution at the positions corresponding to position 22 and 147 of SEQ ID NO: 1, wherein the variant has DNase activity.

In one aspect the invention relates to a DNase variant comprising a substitution at the positions corresponding to position 22 and 167 of SEQ ID NO: 1, wherein the variant has DNase activity.

In one aspect the invention relates to a DNase variant comprising a substitution at the positions corresponding to position 22 and 175 of SEQ ID NO: 1, wherein the variant has DNase activity.

In one aspect the invention relates to a DNase variant comprising a substitution at the positions corresponding to position 25 and 27 of SEQ ID NO: 1, wherein the variant has DNase activity.

In one aspect the invention relates to a DNase variant comprising a substitution at the positions corresponding to position 25 and 39 of SEQ ID NO: 1, wherein the variant has DNase activity.

In one aspect the invention relates to a DNase variant comprising a substitution at the positions corresponding to position 25 and 42 of SEQ ID NO: 1, wherein the variant has DNase activity.

In one aspect the invention relates to a DNase variant comprising a substitution at the positions corresponding to position 25 and 57 of SEQ ID NO: 1, wherein the variant has DNase activity.

In one aspect the invention relates to a DNase variant comprising a substitution at the positions corresponding to position 25 and 59 of SEQ ID NO: 1, wherein the variant has DNase activity.

In one aspect the invention relates to a DNase variant comprising a substitution at the positions corresponding to position 25 and 76 of SEQ ID NO: 1, wherein the variant has DNase activity.

In one aspect the invention relates to a DNase variant comprising a substitution at the positions corresponding to position 25 and 109 of SEQ ID NO: 1, wherein the variant has DNase activity.

In one aspect the invention relates to a DNase variant comprising a substitution at the positions corresponding to position 25 and 116 of SEQ ID NO: 1, wherein the variant has DNase activity.

In one aspect the invention relates to a DNase variant comprising a substitution at the positions corresponding to position 25 and 127 of SEQ ID NO: 1, wherein the variant has DNase activity.

In one aspect the invention relates to a DNase variant comprising a substitution at the positions corresponding to position 25 and 144 of SEQ ID NO: 1, wherein the variant has DNase activity.

In one aspect the invention relates to a DNase variant comprising a substitution at the positions corresponding to position 25 and 147 of SEQ ID NO: 1, wherein the variant has DNase activity.

In one aspect the invention relates to a DNase variant comprising a substitution at the positions corresponding to position 25 and 167 of SEQ ID NO: 1, wherein the variant has DNase activity.

In one aspect the invention relates to a DNase variant comprising a substitution at the positions corresponding to position 25 and 175 of SEQ ID NO: 1, wherein the variant has DNase activity.

In one aspect the invention relates to a DNase variant comprising a substitution at the positions corresponding to position 27 and 39 of SEQ ID NO: 1, wherein the variant has DNase activity.

In one aspect the invention relates to a DNase variant comprising a substitution at the positions corresponding to position 27 and 42 of SEQ ID NO: 1, wherein the variant has DNase activity.

In one aspect the invention relates to a DNase variant comprising a substitution at the positions corresponding to position 27 and 57 of SEQ ID NO: 1, wherein the variant has DNase activity.

In one aspect the invention relates to a DNase variant comprising a substitution at the positions corresponding to position 27 and 59 of SEQ ID NO: 1, wherein the variant has DNase activity.

In one aspect the invention relates to a DNase variant comprising a substitution at the positions corresponding to position 27 and 76 of SEQ ID NO: 1, wherein the variant has DNase activity.

In one aspect the invention relates to a DNase variant comprising a substitution at the positions corresponding to position 27 and 109 of SEQ ID NO: 1, wherein the variant has DNase activity.

In one aspect the invention relates to a DNase variant comprising a substitution at the positions corresponding to position 27 and 116 of SEQ ID NO: 1, wherein the variant has DNase activity.

In one aspect the invention relates to a DNase variant comprising a substitution at the positions corresponding to position 27 and 127 of SEQ ID NO: 1, wherein the variant has DNase activity.

In one aspect the invention relates to a DNase variant comprising a substitution at the positions corresponding to position 27 and 144 of SEQ ID NO: 1, wherein the variant has DNase activity.

In one aspect the invention relates to a DNase variant comprising a substitution at the positions corresponding to position 27 and 147 of SEQ ID NO: 1, wherein the variant has DNase activity.

In one aspect the invention relates to a DNase variant comprising a substitution at the positions corresponding to position 27 and 167 of SEQ ID NO: 1, wherein the variant has DNase activity.

In one aspect the invention relates to a DNase variant comprising a substitution at the positions corresponding to position 27 and 175 of SEQ ID NO: 1, wherein the variant has DNase activity.

In one aspect the invention relates to a DNase variant comprising a substitution at the positions corresponding to position 39 and 42 of SEQ ID NO: 1, wherein the variant has DNase activity.

In one aspect the invention relates to a DNase variant comprising a substitution at the positions corresponding to position 39 and 57 of SEQ ID NO: 1, wherein the variant has DNase activity.

In one aspect the invention relates to a DNase variant comprising a substitution at the positions corresponding to position 39 and 59 of SEQ ID NO: 1, wherein the variant has DNase activity.

In one aspect the invention relates to a DNase variant comprising a substitution at the positions corresponding to position 39 and 76 of SEQ ID NO: 1, wherein the variant has DNase activity.

In one aspect the invention relates to a DNase variant comprising a substitution at the positions corresponding to position 39 and 109 of SEQ ID NO: 1, wherein the variant has DNase activity.

In one aspect the invention relates to a DNase variant comprising a substitution at the positions corresponding to position 39 and 116 of SEQ ID NO: 1, wherein the variant has DNase activity.

In one aspect the invention relates to a DNase variant comprising a substitution at the positions corresponding to position 39 and 127 of SEQ ID NO: 1, wherein the variant has DNase activity.

In one aspect the invention relates to a DNase variant comprising a substitution at the positions corresponding to position 39 and 144 of SEQ ID NO: 1, wherein the variant has DNase activity.

In one aspect the invention relates to a DNase variant comprising a substitution at the positions corresponding to position 39 and 147 of SEQ ID NO: 1, wherein the variant has DNase activity.

In one aspect the invention relates to a DNase variant comprising a substitution at the positions corresponding to position 39 and 167 of SEQ ID NO: 1, wherein the variant has DNase activity.

In one aspect the invention relates to a DNase variant comprising a substitution at the positions corresponding to position 39 and 175 of SEQ ID NO: 1, wherein the variant has DNase activity.

In one aspect the invention relates to a DNase variant comprising a substitution at the positions corresponding to position 42 and 57 of SEQ ID NO: 1, wherein the variant has DNase activity.

In one aspect the invention relates to a DNase variant comprising a substitution at the positions corresponding to position 42 and 59 of SEQ ID NO: 1, wherein the variant has DNase activity.

In one aspect the invention relates to a DNase variant comprising a substitution at the positions corresponding to position 42 and 76 of SEQ ID NO: 1, wherein the variant has DNase activity.

In one aspect the invention relates to a DNase variant comprising a substitution at the positions corresponding to position 42 and 76 of SEQ ID NO: 1, wherein the variant has DNase activity.

In one aspect the invention relates to a DNase variant comprising a substitution at the positions corresponding to position 42 and 116 of SEQ ID NO: 1, wherein the variant has DNase activity.

In one aspect the invention relates to a DNase variant comprising a substitution at the positions corresponding to position 42 and 127 of SEQ ID NO: 1, wherein the variant has DNase activity.

In one aspect the invention relates to a DNase variant comprising a substitution at the positions corresponding to position 42 and 144 of SEQ ID NO: 1, wherein the variant has DNase activity.

In one aspect the invention relates to a DNase variant comprising a substitution at the positions corresponding to position 42 and 147 of SEQ ID NO: 1, wherein the variant has DNase activity.

In one aspect the invention relates to a DNase variant comprising a substitution at the positions corresponding to position 42 and 167 of SEQ ID NO: 1, wherein the variant has DNase activity.

In one aspect the invention relates to a DNase variant comprising a substitution at the positions corresponding to position 42 and 175 of SEQ ID NO: 1, wherein the variant has DNase activity.

In one aspect the invention relates to a DNase variant comprising a substitution at the positions corresponding to position 57 and 59 of SEQ ID NO: 1, wherein the variant has DNase activity.

In one aspect the invention relates to a DNase variant comprising a substitution at the positions corresponding to position 57 and 76 of SEQ ID NO: 1, wherein the variant has DNase activity.

In one aspect the invention relates to a DNase variant comprising a substitution at the positions corresponding to position 57 and 109 of SEQ ID NO: 1, wherein the variant has DNase activity.

In one aspect the invention relates to a DNase variant comprising a substitution at the positions corresponding to position 57 and 116 of SEQ ID NO: 1, wherein the variant has DNase activity.

In one aspect the invention relates to a DNase variant comprising a substitution at the positions corresponding to position 57 and 127 of SEQ ID NO: 1, wherein the variant has DNase activity.

In one aspect the invention relates to a DNase variant comprising a substitution at the positions corresponding to position 57 and 144 of SEQ ID NO: 1, wherein the variant has DNase activity.

In one aspect the invention relates to a DNase variant comprising a substitution at the positions corresponding to position 57 and 147 of SEQ ID NO: 1, wherein the variant has DNase activity.

In one aspect the invention relates to a DNase variant comprising a substitution at the positions corresponding to position 57 and 167 of SEQ ID NO: 1, wherein the variant has DNase activity.

In one aspect the invention relates to a DNase variant comprising a substitution at the positions corresponding to position 57 and 175 of SEQ ID NO: 1, wherein the variant has DNase activity.

In one aspect the invention relates to a DNase variant comprising a substitution at the positions corresponding to position 59 and 76 of SEQ ID NO: 1, wherein the variant has DNase activity.

In one aspect the invention relates to a DNase variant comprising a substitution at the positions corresponding to position 59 and 109 of SEQ ID NO: 1, wherein the variant has DNase activity.

In one aspect the invention relates to a DNase variant comprising a substitution at the positions corresponding to position 59 and 116 of SEQ ID NO: 1, wherein the variant has DNase activity.

In one aspect the invention relates to a DNase variant comprising a substitution at the positions corresponding to position 59 and 127 of SEQ ID NO: 1, wherein the variant has DNase activity.

In one aspect the invention relates to a DNase variant comprising a substitution at the positions corresponding to position 59 and 144 of SEQ ID NO: 1, wherein the variant has DNase activity.

In one aspect the invention relates to a DNase variant comprising a substitution at the positions corresponding to position 59 and 147 of SEQ ID NO: 1, wherein the variant has DNase activity.

In one aspect the invention relates to a DNase variant comprising a substitution at the positions corresponding to position 59 and 167 of SEQ ID NO: 1, wherein the variant has DNase activity.

In one aspect the invention relates to a DNase variant comprising a substitution at the positions corresponding to position 59 and 175 of SEQ ID NO: 1, wherein the variant has DNase activity.

In one aspect the invention relates to a DNase variant comprising a substitution at the positions corresponding to position 76 and 109 of SEQ ID NO: 1, wherein the variant has DNase activity.

In one aspect the invention relates to a DNase variant comprising a substitution at the positions corresponding to position 76 and 116 of SEQ ID NO: 1, wherein the variant has DNase activity.

In one aspect the invention relates to a DNase variant comprising a substitution at the positions corresponding to position 76 and 127 of SEQ ID NO: 1, wherein the variant has DNase activity.

In one aspect the invention relates to a DNase variant comprising a substitution at the positions corresponding to position 76 and 144 of SEQ ID NO: 1, wherein the variant has DNase activity.

In one aspect the invention relates to a DNase variant comprising a substitution at the positions corresponding to position 76 and 147 of SEQ ID NO: 1, wherein the variant has DNase activity.

In one aspect the invention relates to a DNase variant comprising a substitution at the positions corresponding to position 76 and 167 of SEQ ID NO: 1, wherein the variant has DNase activity.

In one aspect the invention relates to a DNase variant comprising a substitution at the positions corresponding to position 76 and 175 of SEQ ID NO: 1, wherein the variant has DNase activity.

In one aspect the invention relates to a DNase variant comprising a substitution at the positions corresponding to position 109 and 116 of SEQ ID NO: 1, wherein the variant has DNase activity.

In one aspect the invention relates to a DNase variant comprising a substitution at the positions corresponding to position 109 and 127 of SEQ ID NO: 1, wherein the variant has DNase activity.

In one aspect the invention relates to a DNase variant comprising a substitution at the positions corresponding to position 109 and 144 of SEQ ID NO: 1, wherein the variant has DNase activity.

In one aspect the invention relates to a DNase variant comprising a substitution at the positions corresponding to position 109 and 147 of SEQ ID NO: 1, wherein the variant has DNase activity.

In one aspect the invention relates to a DNase variant comprising a substitution at the positions corresponding to position 109 and 167 of SEQ ID NO: 1, wherein the variant has DNase activity.

In one aspect the invention relates to a DNase variant comprising a substitution at the positions corresponding to position 109 and 175 of SEQ ID NO: 1, wherein the variant has DNase activity.

In one aspect the invention relates to a DNase variant comprising a substitution at the positions corresponding to position 116 and 127 of SEQ ID NO: 1, wherein the variant has DNase activity.

In one aspect the invention relates to a DNase variant comprising a substitution at the positions corresponding to position 116 and 144 of SEQ ID NO: 1, wherein the variant has DNase activity.

In one aspect the invention relates to a DNase variant comprising a substitution at the positions corresponding to position 116 and 147 of SEQ ID NO: 1, wherein the variant has DNase activity.

In one aspect the invention relates to a DNase variant comprising a substitution at the positions corresponding to position 116 and 167 of SEQ ID NO: 1, wherein the variant has DNase activity.

In one aspect the invention relates to a DNase variant comprising a substitution at the positions corresponding to position 116 and 175 of SEQ ID NO: 1, wherein the variant has DNase activity.

In one aspect the invention relates to a DNase variant comprising a substitution at the positions corresponding to position 144 and 147 of SEQ ID NO: 1, wherein the variant has DNase activity.

In one aspect the invention relates to a DNase variant comprising a substitution at the positions corresponding to position 144 and 167 of SEQ ID NO: 1, wherein the variant has DNase activity.

In one aspect the invention relates to a DNase variant comprising a substitution at the positions corresponding to position 144 and 175 of SEQ ID NO: 1, wherein the variant has DNase activity.

In one aspect the invention relates to a DNase variant comprising a substitution at the positions corresponding to position 147 and 167 of SEQ ID NO: 1, wherein the variant has DNase activity.

In one aspect the invention relates to a DNase variant comprising a substitution at the positions corresponding to position 147 and 175 of SEQ ID NO: 1, wherein the variant has DNase activity.

In one aspect the invention relates to a DNase variant comprising a substitution at the positions corresponding to position 167 and 175 of SEQ ID NO: 1, wherein the variant has DNase activity.

The invention further relates to DNase variants comprising a combination of substitutions as set out below.

In one aspect the invention relates to a DNase variant comprising the substitutions T1I+S13Y wherein the positions correspond to the positions of SEQ ID NO: 1 and wherein the variant has DNase activity.

In one aspect the invention relates to a DNase variant comprising the substitutions T1I+T22P wherein the positions correspond to the positions of SEQ ID NO: 1 and wherein the variant has DNase activity.

In one aspect the invention relates to a DNase variant comprising the substitutions T1I+S39P wherein the positions correspond to the positions of SEQ ID NO: 1 and wherein the variant has DNase activity.

In one aspect the invention relates to a DNase variant comprising the substitutions T1I+S42G wherein the positions correspond to the positions of SEQ ID NO: 1 and wherein the variant has DNase activity.

In one aspect the invention relates to a DNase variant comprising the substitutions T1I+S42A wherein the positions correspond to the positions of SEQ ID NO: 1 and wherein the variant has DNase activity.

In one aspect the invention relates to a DNase variant comprising the substitutions T1I+S42T wherein the positions correspond to the positions of SEQ ID NO: 1 and wherein the variant has DNase activity.

In one aspect the invention relates to a DNase variant comprising the substitutions T1I+S57W wherein the positions correspond to the positions of SEQ ID NO: 1 and wherein the variant has DNase activity.

In one aspect the invention relates to a DNase variant comprising the substitutions T1I+S57Y wherein the positions correspond to the positions of SEQ ID NO: 1 and wherein the variant has DNase activity.

In one aspect the invention relates to a DNase variant comprising the substitutions T1I+S57F wherein the positions correspond to the positions of SEQ ID NO: 1 and wherein the variant has DNase activity.

In one aspect the invention relates to a DNase variant comprising the substitutions T1I+S59V wherein the positions correspond to the positions of SEQ ID NO: 1 and wherein the variant has DNase activity.

In one aspect the invention relates to a DNase variant comprising the substitutions T1I+S591 wherein the positions correspond to the positions of SEQ ID NO: 1 and wherein the variant has DNase activity.

In one aspect the invention relates to a DNase variant comprising the substitutions T1I+S59L wherein the positions correspond to the positions of SEQ ID NO: 1 and wherein the variant has DNase activity.

In one aspect the invention relates to a DNase variant comprising the substitutions T1I+V76L wherein the positions correspond to the positions of SEQ ID NO: 1 and wherein the variant has DNase activity.

In one aspect the invention relates to a DNase variant comprising the substitutions T1I+V761 wherein the positions correspond to the positions of SEQ ID NO: 1 and wherein the variant has DNase activity.

In one aspect the invention relates to a DNase variant comprising the substitutions T1I+Q109R wherein the positions correspond to the positions of SEQ ID NO: 1 and wherein the variant has DNase activity.

In one aspect the invention relates to a DNase variant comprising the substitutions T1I+S116D wherein the positions correspond to the positions of SEQ ID NO: 1 and wherein the variant has DNase activity.

In one aspect the invention relates to a DNase variant comprising the substitutions T1I+S116E wherein the positions correspond to the positions of SEQ ID NO: 1 and wherein the variant has DNase activity.

In one aspect the invention relates to a DNase variant comprising the substitutions T1I+T127V wherein the positions correspond to the positions of SEQ ID NO: 1 and wherein the variant has DNase activity.

In one aspect the invention relates to a DNase variant comprising the substitutions T1I+T127I wherein the positions correspond to the positions of SEQ ID NO: 1 and wherein the variant has DNase activity.

In one aspect the invention relates to a DNase variant comprising the substitutions T1I+T127L wherein the positions correspond to the positions of SEQ ID NO: 1 and wherein the variant has DNase activity.

In one aspect the invention relates to a DNase variant comprising the substitutions T1I+S144P wherein the positions correspond to the positions of SEQ ID NO: 1 and wherein the variant has DNase activity.

In one aspect the invention relates to a DNase variant comprising the substitutions T1I+A147H wherein the positions correspond to the positions of SEQ ID NO: 1 and wherein the variant has DNase activity.

In one aspect the invention relates to a DNase variant comprising the substitutions T1I+S167L wherein the positions correspond to the positions of SEQ ID NO: 1 and wherein the variant has DNase activity.

In one aspect the invention relates to a DNase variant comprising the substitutions T1I+S1671 wherein the positions correspond to the positions of SEQ ID NO: 1 and wherein the variant has DNase activity.

In one aspect the invention relates to a DNase variant comprising the substitutions T1I+S167V wherein the positions correspond to the positions of SEQ ID NO: 1 and wherein the variant has DNase activity.

In one aspect the invention relates to a DNase variant comprising the substitutions T1I+G175D wherein the positions correspond to the positions of SEQ ID NO: 1 and wherein the variant has DNase activity.

In one aspect the invention relates to a DNase variant comprising the substitutions T1I+G175E wherein the positions correspond to the positions of SEQ ID NO: 1 and wherein the variant has DNase activity.

In one aspect the invention relates to a DNase variant comprising the substitutions T1L+T22P wherein the positions correspond to the positions of SEQ ID NO: 1 and wherein the variant has DNase activity.

In one aspect the invention relates to a DNase variant comprising the substitutions T1L+S13Y wherein the positions correspond to the positions of SEQ ID NO: 1 and wherein the variant has DNase activity.

In one aspect the invention relates to a DNase variant comprising the substitutions T1L+T22P wherein the positions correspond to the positions of SEQ ID NO: 1 and wherein the variant has DNase activity.

In one aspect the invention relates to a DNase variant comprising the substitutions T1L+S25P wherein the positions correspond to the positions of SEQ ID NO: 1 and wherein the variant has DNase activity.

In one aspect the invention relates to a DNase variant comprising the substitutions T1L+S27L wherein the positions correspond to the positions of SEQ ID NO: 1 and wherein the variant has DNase activity.

In one aspect the invention relates to a DNase variant comprising the substitutions T1L+S39P wherein the positions correspond to the positions of SEQ ID NO: 1 and wherein the variant has DNase activity.

In one aspect the invention relates to a DNase variant comprising the substitutions T1L+S42G wherein the positions correspond to the positions of SEQ ID NO: 1 and wherein the variant has DNase activity.

In one aspect the invention relates to a DNase variant comprising the substitutions T1L+S42A wherein the positions correspond to the positions of SEQ ID NO: 1 and wherein the variant has DNase activity.

In one aspect the invention relates to a DNase variant comprising the substitutions T1L+S42T wherein the positions correspond to the positions of SEQ ID NO: 1 and wherein the variant has DNase activity.

In one aspect the invention relates to a DNase variant comprising the substitutions T1L+S57W wherein the positions correspond to the positions of SEQ ID NO: 1 and wherein the variant has DNase activity.

In one aspect the invention relates to a DNase variant comprising the substitutions T1L+S57Y wherein the positions correspond to the positions of SEQ ID NO: 1 and wherein the variant has DNase activity.

In one aspect the invention relates to a DNase variant comprising the substitutions T1L+S57F wherein the positions correspond to the positions of SEQ ID NO: 1 and wherein the variant has DNase activity.

In one aspect the invention relates to a DNase variant comprising the substitutions T1L+S59V wherein the positions correspond to the positions of SEQ ID NO: 1 and wherein the variant has DNase activity.

In one aspect the invention relates to a DNase variant comprising the substitutions T1L+S591 wherein the positions correspond to the positions of SEQ ID NO: 1 and wherein the variant has DNase activity.

In one aspect the invention relates to a DNase variant comprising the substitutions T1L+S59L wherein the positions correspond to the positions of SEQ ID NO: 1 and wherein the variant has DNase activity.

In one aspect the invention relates to a DNase variant comprising the substitutions T1L+V76L wherein the positions correspond to the positions of SEQ ID NO: 1 and wherein the variant has DNase activity.

In one aspect the invention relates to a DNase variant comprising the substitutions T1L+V761 wherein the positions correspond to the positions of SEQ ID NO: 1 and wherein the variant has DNase activity.

In one aspect the invention relates to a DNase variant comprising the substitutions T1L+Q109R wherein the positions correspond to the positions of SEQ ID NO: 1 and wherein the variant has DNase activity.

In one aspect the invention relates to a DNase variant comprising the substitutions T1L+S116D wherein the positions correspond to the positions of SEQ ID NO: 1 and wherein the variant has DNase activity.

In one aspect the invention relates to a DNase variant comprising the substitutions T1L+S116E wherein the positions correspond to the positions of SEQ ID NO: 1 and wherein the variant has DNase activity.

In one aspect the invention relates to a DNase variant comprising the substitutions T1L+T127V wherein the positions correspond to the positions of SEQ ID NO: 1 and wherein the variant has DNase activity.

In one aspect the invention relates to a DNase variant comprising the substitutions T1L+T127I wherein the positions correspond to the positions of SEQ ID NO: 1 and wherein the variant has DNase activity.

In one aspect the invention relates to a DNase variant comprising the substitutions T1L+T127L wherein the positions correspond to the positions of SEQ ID NO: 1 and wherein the variant has DNase activity.

In one aspect the invention relates to a DNase variant comprising the substitutions T1L+S144P wherein the positions correspond to the positions of SEQ ID NO: 1 and wherein the variant has DNase activity.

In one aspect the invention relates to a DNase variant comprising the substitutions T1L+A147H wherein the positions correspond to the positions of SEQ ID NO: 1 and wherein the variant has DNase activity.

In one aspect the invention relates to a DNase variant comprising the substitutions T1L+S167L wherein the positions correspond to the positions of SEQ ID NO: 1 and wherein the variant has DNase activity.

In one aspect the invention relates to a DNase variant comprising the substitutions T1L+S167I wherein the positions correspond to the positions of SEQ ID NO: 1 and wherein the variant has DNase activity.

In one aspect the invention relates to a DNase variant comprising the substitutions T1L+S167V wherein the positions correspond to the positions of SEQ ID NO: 1 and wherein the variant has DNase activity.

In one aspect the invention relates to a DNase variant comprising the substitutions T1L+G175D wherein the positions correspond to the positions of SEQ ID NO: 1 and wherein the variant has DNase activity.

In one aspect the invention relates to a DNase variant comprising the substitutions T1L+G175E wherein the positions correspond to the positions of SEQ ID NO: 1 and wherein the variant has DNase activity.

In one aspect the invention relates to a DNase variant comprising the substitutions T1V+S13Y wherein the positions correspond to the positions of SEQ ID NO: 1 and wherein the variant has DNase activity.

In one aspect the invention relates to a DNase variant comprising the substitutions T1V+T22P wherein the positions correspond to the positions of SEQ ID NO: 1 and wherein the variant has DNase activity.

In one aspect the invention relates to a DNase variant comprising the substitutions T1V+S25P wherein the positions correspond to the positions of SEQ ID NO: 1 and wherein the variant has DNase activity.

In one aspect the invention relates to a DNase variant comprising the substitutions T1V+S27L wherein the positions correspond to the positions of SEQ ID NO: 1 and wherein the variant has DNase activity.

In one aspect the invention relates to a DNase variant comprising the substitutions T1V+S39P wherein the positions correspond to the positions of SEQ ID NO: 1 and wherein the variant has DNase activity.

In one aspect the invention relates to a DNase variant comprising the substitutions T1V+S42G wherein the positions correspond to the positions of SEQ ID NO: 1 and wherein the variant has DNase activity.

In one aspect the invention relates to a DNase variant comprising the substitutions T1V+S42A wherein the positions correspond to the positions of SEQ ID NO: 1 and wherein the variant has DNase activity.

In one aspect the invention relates to a DNase variant comprising the substitutions T1V+S42T wherein the positions correspond to the positions of SEQ ID NO: 1 and wherein the variant has DNase activity.

In one aspect the invention relates to a DNase variant comprising the substitutions T1V+S57W wherein the positions correspond to the positions of SEQ ID NO: 1 and wherein the variant has DNase activity.

In one aspect the invention relates to a DNase variant comprising the substitutions T1V+S57Y wherein the positions correspond to the positions of SEQ ID NO: 1 and wherein the variant has DNase activity.

In one aspect the invention relates to a DNase variant comprising the substitutions T1V+S57F wherein the positions correspond to the positions of SEQ ID NO: 1 and wherein the variant has DNase activity.

In one aspect the invention relates to a DNase variant comprising the substitutions T1V+S59V wherein the positions correspond to the positions of SEQ ID NO: 1 and wherein the variant has DNase activity.

In one aspect the invention relates to a DNase variant comprising the substitutions T1V+S59I wherein the positions correspond to the positions of SEQ ID NO: 1 and wherein the variant has DNase activity.

In one aspect the invention relates to a DNase variant comprising the substitutions T1V+S59L wherein the positions correspond to the positions of SEQ ID NO: 1 and wherein the variant has DNase activity.

In one aspect the invention relates to a DNase variant comprising the substitutions T1V+V76L wherein the positions correspond to the positions of SEQ ID NO: 1 and wherein the variant has DNase activity.

In one aspect the invention relates to a DNase variant comprising the substitutions T1V+V76I wherein the positions correspond to the positions of SEQ ID NO: 1 and wherein the variant has DNase activity.

In one aspect the invention relates to a DNase variant comprising the substitutions T1V+Q109R wherein the positions correspond to the positions of SEQ ID NO: 1 and wherein the variant has DNase activity.

In one aspect the invention relates to a DNase variant comprising the substitutions T1V+S116D wherein the positions correspond to the positions of SEQ ID NO: 1 and wherein the variant has DNase activity.

In one aspect the invention relates to a DNase variant comprising the substitutions T1V+S116E wherein the positions correspond to the positions of SEQ ID NO: 1 and wherein the variant has DNase activity.

In one aspect the invention relates to a DNase variant comprising the substitutions T1V+T127V wherein the positions correspond to the positions of SEQ ID NO: 1 and wherein the variant has DNase activity.

In one aspect the invention relates to a DNase variant comprising the substitutions T1V+T127I wherein the positions correspond to the positions of SEQ ID NO: 1 and wherein the variant has DNase activity.

In one aspect the invention relates to a DNase variant comprising the substitutions T1V+T127L wherein the positions correspond to the positions of SEQ ID NO: 1 and wherein the variant has DNase activity.

In one aspect the invention relates to a DNase variant comprising the substitutions T1V+S144P wherein the positions correspond to the positions of SEQ ID NO: 1 and wherein the variant has DNase activity.

In one aspect the invention relates to a DNase variant comprising the substitutions T1V+A147H wherein the positions correspond to the positions of SEQ ID NO: 1 and wherein the variant has DNase activity.

In one aspect the invention relates to a DNase variant comprising the substitutions T1V+S167L wherein the positions correspond to the positions of SEQ ID NO: 1 and wherein the variant has DNase activity.

In one aspect the invention relates to a DNase variant comprising the substitutions T1V+S167I wherein the positions correspond to the positions of SEQ ID NO: 1 and wherein the variant has DNase activity.

In one aspect the invention relates to a DNase variant comprising the substitutions T1V+S167V wherein the positions correspond to the positions of SEQ ID NO: 1 and wherein the variant has DNase activity.

In one aspect the invention relates to a DNase variant comprising the substitutions T1V+G175D wherein the positions correspond to the positions of SEQ ID NO: 1 and wherein the variant has DNase activity.

In one aspect the invention relates to a DNase variant comprising the substitutions T1V+G175E wherein the positions correspond to the positions of SEQ ID NO: 1 and wherein the variant has DNase activity.

In one aspect the invention relates to a DNase variant comprising the substitutions S13Y+T22P wherein the positions correspond to the positions of SEQ ID NO: 1 and wherein the variant has DNase activity.

In one aspect the invention relates to a DNase variant comprising the substitutions S13Y+S25P wherein the positions correspond to the positions of SEQ ID NO: 1 and wherein the variant has DNase activity.

In one aspect the invention relates to a DNase variant comprising the substitutions S13Y+S27L wherein the positions correspond to the positions of SEQ ID NO: 1 and wherein the variant has DNase activity.

In one aspect the invention relates to a DNase variant comprising the substitutions S13Y+S39P wherein the positions correspond to the positions of SEQ ID NO: 1 and wherein the variant has DNase activity.

In one aspect the invention relates to a DNase variant comprising the substitutions S13Y+S42G wherein the positions correspond to the positions of SEQ ID NO: 1 and wherein the variant has DNase activity.

In one aspect the invention relates to a DNase variant comprising the substitutions S13Y+S42A wherein the positions correspond to the positions of SEQ ID NO: 1 and wherein the variant has DNase activity.

In one aspect the invention relates to a DNase variant comprising the substitutions S13Y+S42T wherein the positions correspond to the positions of SEQ ID NO: 1 and wherein the variant has DNase activity.

In one aspect the invention relates to a DNase variant comprising the substitutions S13Y+S57W wherein the positions correspond to the positions of SEQ ID NO: 1 and wherein the variant has DNase activity.

In one aspect the invention relates to a DNase variant comprising the substitutions S13Y+S57Y wherein the positions correspond to the positions of SEQ ID NO: 1 and wherein the variant has DNase activity.

In one aspect the invention relates to a DNase variant comprising the substitutions S13Y+S57F wherein the positions correspond to the positions of SEQ ID NO: 1 and wherein the variant has DNase activity.

In one aspect the invention relates to a DNase variant comprising the substitutions S13Y+S59V wherein the positions correspond to the positions of SEQ ID NO: 1 and wherein the variant has DNase activity.

In one aspect the invention relates to a DNase variant comprising the substitutions S13Y+S591 wherein the positions correspond to the positions of SEQ ID NO: 1 and wherein the variant has DNase activity.

In one aspect the invention relates to a DNase variant comprising the substitutions S13Y+S59L wherein the positions correspond to the positions of SEQ ID NO: 1 and wherein the variant has DNase activity.

In one aspect the invention relates to a DNase variant comprising the substitutions S13Y+V76L wherein the positions correspond to the positions of SEQ ID NO: 1 and wherein the variant has DNase activity.

In one aspect the invention relates to a DNase variant comprising the substitutions S13Y+V76I wherein the positions correspond to the positions of SEQ ID NO: 1 and wherein the variant has DNase activity.

In one aspect the invention relates to a DNase variant comprising the substitutions S13Y+Q109R wherein the positions correspond to the positions of SEQ ID NO: 1 and wherein the variant has DNase activity.

In one aspect the invention relates to a DNase variant comprising the substitutions S13Y+S116D wherein the positions correspond to the positions of SEQ ID NO: 1 and wherein the variant has DNase activity.

In one aspect the invention relates to a DNase variant comprising the substitutions S13Y+S116E wherein the positions correspond to the positions of SEQ ID NO: 1 and wherein the variant has DNase activity.

In one aspect the invention relates to a DNase variant comprising the substitutions S13Y+T127V wherein the positions correspond to the positions of SEQ ID NO: 1 and wherein the variant has DNase activity.

In one aspect the invention relates to a DNase variant comprising the substitutions S13Y+T127I wherein the positions correspond to the positions of SEQ ID NO: 1 and wherein the variant has DNase activity.

In one aspect the invention relates to a DNase variant comprising the substitutions S13Y+T127L wherein the positions correspond to the positions of SEQ ID NO: 1 and wherein the variant has DNase activity.

In one aspect the invention relates to a DNase variant comprising the substitutions S13Y+S144P wherein the positions correspond to the positions of SEQ ID NO: 1 and wherein the variant has DNase activity.

In one aspect the invention relates to a DNase variant comprising the substitutions S13Y+A147H wherein the positions correspond to the positions of SEQ ID NO: 1 and wherein the variant has DNase activity.

In one aspect the invention relates to a DNase variant comprising the substitutions S13Y+S167L wherein the positions correspond to the positions of SEQ ID NO: 1 and wherein the variant has DNase activity.

In one aspect the invention relates to a DNase variant comprising the substitutions S13Y+S1671 wherein the positions correspond to the positions of SEQ ID NO: 1 and wherein the variant has DNase activity.

In one aspect the invention relates to a DNase variant comprising the substitutions S13Y+S167V wherein the positions correspond to the positions of SEQ ID NO: 1 and wherein the variant has DNase activity.

In one aspect the invention relates to a DNase variant comprising the substitutions S13Y+G175D wherein the positions correspond to the positions of SEQ ID NO: 1 and wherein the variant has DNase activity.

In one aspect the invention relates to a DNase variant comprising the substitutions S13Y+G175E wherein the positions correspond to the positions of SEQ ID NO: 1 and wherein the variant has DNase activity.

In one aspect the invention relates to a DNase variant comprising the substitutions T22P+S25P wherein the positions correspond to the positions of SEQ ID NO: 1 and wherein the variant has DNase activity.

In one aspect the invention relates to a DNase variant comprising the substitutions T22P+S27L wherein the positions correspond to the positions of SEQ ID NO: 1 and wherein the variant has DNase activity.

In one aspect the invention relates to a DNase variant comprising the substitutions T22P+S39P wherein the positions correspond to the positions of SEQ ID NO: 1 and wherein the variant has DNase activity.

In one aspect the invention relates to a DNase variant comprising the substitutions T22P+S42G wherein the positions correspond to the positions of SEQ ID NO: 1 and wherein the variant has DNase activity.

In one aspect the invention relates to a DNase variant comprising the substitutions T22P+S42A wherein the positions correspond to the positions of SEQ ID NO: 1 and wherein the variant has DNase activity.

In one aspect the invention relates to a DNase variant comprising the substitutions T22P+S42T wherein the positions correspond to the positions of SEQ ID NO: 1 and wherein the variant has DNase activity.

In one aspect the invention relates to a DNase variant comprising the substitutions T22P+S57W wherein the positions correspond to the positions of SEQ ID NO: 1 and wherein the variant has DNase activity.

In one aspect the invention relates to a DNase variant comprising the substitutions T22P+S57Y wherein the positions correspond to the positions of SEQ ID NO: 1 and wherein the variant has DNase activity.

In one aspect the invention relates to a DNase variant comprising the substitutions T22P+S57F wherein the positions correspond to the positions of SEQ ID NO: 1 and wherein the variant has DNase activity.

In one aspect the invention relates to a DNase variant comprising the substitutions T22P+S59V wherein the positions correspond to the positions of SEQ ID NO: 1 and wherein the variant has DNase activity.

In one aspect the invention relates to a DNase variant comprising the substitutions T22P+S591 wherein the positions correspond to the positions of SEQ ID NO: 1 and wherein the variant has DNase activity.

In one aspect the invention relates to a DNase variant comprising the substitutions T22P+S59L wherein the positions correspond to the positions of SEQ ID NO: 1 and wherein the variant has DNase activity.

In one aspect the invention relates to a DNase variant comprising the substitutions T22P+V76L wherein the positions correspond to the positions of SEQ ID NO: 1 and wherein the variant has DNase activity.

In one aspect the invention relates to a DNase variant comprising the substitutions T22P+V761 wherein the positions correspond to the positions of SEQ ID NO: 1 and wherein the variant has DNase activity.

In one aspect the invention relates to a DNase variant comprising the substitutions T22P+Q109R wherein the positions correspond to the positions of SEQ ID NO: 1 and wherein the variant has DNase activity.

In one aspect the invention relates to a DNase variant comprising the substitutions T22P+S116D wherein the positions correspond to the positions of SEQ ID NO: 1 and wherein the variant has DNase activity.

In one aspect the invention relates to a DNase variant comprising the substitutions T22P+S116E wherein the positions correspond to the positions of SEQ ID NO: 1 and wherein the variant has DNase activity.

In one aspect the invention relates to a DNase variant comprising the substitutions T22P+T127V wherein the positions correspond to the positions of SEQ ID NO: 1 and wherein the variant has DNase activity.

In one aspect the invention relates to a DNase variant comprising the substitutions T22P+T1271 wherein the positions correspond to the positions of SEQ ID NO: 1 and wherein the variant has DNase activity.

In one aspect the invention relates to a DNase variant comprising the substitutions T22P+T127L wherein the positions correspond to the positions of SEQ ID NO: 1 and wherein the variant has DNase activity.

In one aspect the invention relates to a DNase variant comprising the substitutions T22P+S144P wherein the positions correspond to the positions of SEQ ID NO: 1 and wherein the variant has DNase activity.

In one aspect the invention relates to a DNase variant comprising the substitutions T22P+A147H wherein the positions correspond to the positions of SEQ ID NO: 1 and wherein the variant has DNase activity.

In one aspect the invention relates to a DNase variant comprising the substitutions T22P+S167L wherein the positions correspond to the positions of SEQ ID NO: 1 and wherein the variant has DNase activity.

In one aspect the invention relates to a DNase variant comprising the substitutions T22P+S167I wherein the positions correspond to the positions of SEQ ID NO: 1 and wherein the variant has DNase activity.

In one aspect the invention relates to a DNase variant comprising the substitutions T22P+S167V wherein the positions correspond to the positions of SEQ ID NO: 1 and wherein the variant has DNase activity.

In one aspect the invention relates to a DNase variant comprising the substitutions T22P+G175D wherein the positions correspond to the positions of SEQ ID NO: 1 and wherein the variant has DNase activity.

In one aspect the invention relates to a DNase variant comprising the substitutions T22P+G175E wherein the positions correspond to the positions of SEQ ID NO: 1 and wherein the variant has DNase activity.

In one aspect the invention relates to a DNase variant comprising the substitutions S25P+S27L wherein the positions correspond to the positions of SEQ ID NO: 1 and wherein the variant has DNase activity.

In one aspect the invention relates to a DNase variant comprising the substitutions S25P+S39P wherein the positions correspond to the positions of SEQ ID NO: 1 and wherein the variant has DNase activity.

In one aspect the invention relates to a DNase variant comprising the substitutions S25P+S42G wherein the positions correspond to the positions of SEQ ID NO: 1 and wherein the variant has DNase activity.

In one aspect the invention relates to a DNase variant comprising the substitutions S25P+S42A wherein the positions correspond to the positions of SEQ ID NO: 1 and wherein the variant has DNase activity.

In one aspect the invention relates to a DNase variant comprising the substitutions S25P+S42T wherein the positions correspond to the positions of SEQ ID NO: 1 and wherein the variant has DNase activity.

In one aspect the invention relates to a DNase variant comprising the substitutions S25P+S57W wherein the positions correspond to the positions of SEQ ID NO: 1 and wherein the variant has DNase activity.

In one aspect the invention relates to a DNase variant comprising the substitutions S25P+S57Y wherein the positions correspond to the positions of SEQ ID NO: 1 and wherein the variant has DNase activity.

In one aspect the invention relates to a DNase variant comprising the substitutions S25P+S57F wherein the positions correspond to the positions of SEQ ID NO: 1 and wherein the variant has DNase activity.

In one aspect the invention relates to a DNase variant comprising the substitutions S25P+S59V wherein the positions correspond to the positions of SEQ ID NO: 1 and wherein the variant has DNase activity.

In one aspect the invention relates to a DNase variant comprising the substitutions S25P+S59I wherein the positions correspond to the positions of SEQ ID NO: 1 and wherein the variant has DNase activity.

In one aspect the invention relates to a DNase variant comprising the substitutions S25P+S59L wherein the positions correspond to the positions of SEQ ID NO: 1 and wherein the variant has DNase activity.

In one aspect the invention relates to a DNase variant comprising the substitutions S25P+V76L wherein the positions correspond to the positions of SEQ ID NO: 1 and wherein the variant has DNase activity.

In one aspect the invention relates to a DNase variant comprising the substitutions S25P+V76I wherein the positions correspond to the positions of SEQ ID NO: 1 and wherein the variant has DNase activity.

In one aspect the invention relates to a DNase variant comprising the substitutions S25P+Q109R wherein the positions correspond to the positions of SEQ ID NO: 1 and wherein the variant has DNase activity.

In one aspect the invention relates to a DNase variant comprising the substitutions S25P+S116D wherein the positions correspond to the positions of SEQ ID NO: 1 and wherein the variant has DNase activity.

In one aspect the invention relates to a DNase variant comprising the substitutions S25P+S116E wherein the positions correspond to the positions of SEQ ID NO: 1 and wherein the variant has DNase activity.

In one aspect the invention relates to a DNase variant comprising the substitutions S25P+T127V wherein the positions correspond to the positions of SEQ ID NO: 1 and wherein the variant has DNase activity.

In one aspect the invention relates to a DNase variant comprising the substitutions S25P+T127I wherein the positions correspond to the positions of SEQ ID NO: 1 and wherein the variant has DNase activity.

In one aspect the invention relates to a DNase variant comprising the substitutions S25P+T127L wherein the positions correspond to the positions of SEQ ID NO: 1 and wherein the variant has DNase activity.

In one aspect the invention relates to a DNase variant comprising the substitutions S25P+S144P wherein the positions correspond to the positions of SEQ ID NO: 1 and wherein the variant has DNase activity.

In one aspect the invention relates to a DNase variant comprising the substitutions S25P+A147H wherein the positions correspond to the positions of SEQ ID NO: 1 and wherein the variant has DNase activity.

In one aspect the invention relates to a DNase variant comprising the substitutions S25P+S167L wherein the positions correspond to the positions of SEQ ID NO: 1 and wherein the variant has DNase activity.

In one aspect the invention relates to a DNase variant comprising the substitutions S25P+S167I wherein the positions correspond to the positions of SEQ ID NO: 1 and wherein the variant has DNase activity.

In one aspect the invention relates to a DNase variant comprising the substitutions S25P+S167V wherein the positions correspond to the positions of SEQ ID NO: 1 and wherein the variant has DNase activity.

In one aspect the invention relates to a DNase variant comprising the substitutions S25P+G175D wherein the positions correspond to the positions of SEQ ID NO: 1 and wherein the variant has DNase activity.

In one aspect the invention relates to a DNase variant comprising the substitutions S25P+G175E wherein the positions correspond to the positions of SEQ ID NO: 1 and wherein the variant has DNase activity.

In one aspect the invention relates to a DNase variant comprising the substitutions S39P+S42G wherein the positions correspond to the positions of SEQ ID NO: 1 and wherein the variant has DNase activity.

In one aspect the invention relates to a DNase variant comprising the substitutions S39P+S42A wherein the positions correspond to the positions of SEQ ID NO: 1 and wherein the variant has DNase activity.

In one aspect the invention relates to a DNase variant comprising the substitutions S39P+S42T wherein the positions correspond to the positions of SEQ ID NO: 1 and wherein the variant has DNase activity.

In one aspect the invention relates to a DNase variant comprising the substitutions S39P+S57W wherein the positions correspond to the positions of SEQ ID NO: 1 and wherein the variant has DNase activity.

In one aspect the invention relates to a DNase variant comprising the substitutions S39P+S57Y wherein the positions correspond to the positions of SEQ ID NO: 1 and wherein the variant has DNase activity.

In one aspect the invention relates to a DNase variant comprising the substitutions S39P+S57F wherein the positions correspond to the positions of SEQ ID NO: 1 and wherein the variant has DNase activity.

In one aspect the invention relates to a DNase variant comprising the substitutions S39P+S59V wherein the positions correspond to the positions of SEQ ID NO: 1 and wherein the variant has DNase activity.

In one aspect the invention relates to a DNase variant comprising the substitutions S39P+S59I wherein the positions correspond to the positions of SEQ ID NO: 1 and wherein the variant has DNase activity.

In one aspect the invention relates to a DNase variant comprising the substitutions S39P+S59L wherein the positions correspond to the positions of SEQ ID NO: 1 and wherein the variant has DNase activity.

In one aspect the invention relates to a DNase variant comprising the substitutions S39P+V76L wherein the positions correspond to the positions of SEQ ID NO: 1 and wherein the variant has DNase activity.

In one aspect the invention relates to a DNase variant comprising the substitutions S39P+V76I wherein the positions correspond to the positions of SEQ ID NO: 1 and wherein the variant has DNase activity.

In one aspect the invention relates to a DNase variant comprising the substitutions S39P+Q109R wherein the positions correspond to the positions of SEQ ID NO: 1 and wherein the variant has DNase activity.

In one aspect the invention relates to a DNase variant comprising the substitutions S39P+S116D wherein the positions correspond to the positions of SEQ ID NO: 1 and wherein the variant has DNase activity.

In one aspect the invention relates to a DNase variant comprising the substitutions S39P+S116E wherein the positions correspond to the positions of SEQ ID NO: 1 and wherein the variant has DNase activity.

In one aspect the invention relates to a DNase variant comprising the substitutions S39P+T127V wherein the positions correspond to the positions of SEQ ID NO: 1 and wherein the variant has DNase activity.

In one aspect the invention relates to a DNase variant comprising the substitutions S39P+T127I wherein the positions correspond to the positions of SEQ ID NO: 1 and wherein the variant has DNase activity.

In one aspect the invention relates to a DNase variant comprising the substitutions S39P+T127L wherein the positions correspond to the positions of SEQ ID NO: 1 and wherein the variant has DNase activity.

In one aspect the invention relates to a DNase variant comprising the substitutions S39P+S144P wherein the positions correspond to the positions of SEQ ID NO: 1 and wherein the variant has DNase activity.

In one aspect the invention relates to a DNase variant comprising the substitutions S39P+A147H wherein the positions correspond to the positions of SEQ ID NO: 1 and wherein the variant has DNase activity.

In one aspect the invention relates to a DNase variant comprising the substitutions S39P+S167L wherein the positions correspond to the positions of SEQ ID NO: 1 and wherein the variant has DNase activity.

In one aspect the invention relates to a DNase variant comprising the substitutions S39P+S167I wherein the positions correspond to the positions of SEQ ID NO: 1 and wherein the variant has DNase activity.

In one aspect the invention relates to a DNase variant comprising the substitutions S39P+S167V wherein the positions correspond to the positions of SEQ ID NO: 1 and wherein the variant has DNase activity.

In one aspect the invention relates to a DNase variant comprising the substitutions S39P+G175D wherein the positions correspond to the positions of SEQ ID NO: 1 and wherein the variant has DNase activity.

In one aspect the invention relates to a DNase variant comprising the substitutions S39P+G175E wherein the positions correspond to the positions of SEQ ID NO: 1 and wherein the variant has DNase activity.

In one aspect the invention relates to a DNase variant comprising the substitutions S42G+S57W wherein the positions correspond to the positions of SEQ ID NO: 1 and wherein the variant has DNase activity.

In one aspect the invention relates to a DNase variant comprising the substitutions S42G+S57Y wherein the positions correspond to the positions of SEQ ID NO: 1 and wherein the variant has DNase activity.

In one aspect the invention relates to a DNase variant comprising the substitutions S42G+S57F wherein the positions correspond to the positions of SEQ ID NO: 1 and wherein the variant has DNase activity.

In one aspect the invention relates to a DNase variant comprising the substitutions S42G+S59V wherein the positions correspond to the positions of SEQ ID NO: 1 and wherein the variant has DNase activity.

In one aspect the invention relates to a DNase variant comprising the substitutions S42G+S59I wherein the positions correspond to the positions of SEQ ID NO: 1 and wherein the variant has DNase activity.

In one aspect the invention relates to a DNase variant comprising the substitutions S42G+S59L wherein the positions correspond to the positions of SEQ ID NO: 1 and wherein the variant has DNase activity.

In one aspect the invention relates to a DNase variant comprising the substitutions S42G+V76L wherein the positions correspond to the positions of SEQ ID NO: 1 and wherein the variant has DNase activity.

In one aspect the invention relates to a DNase variant comprising the substitutions S42G+V76I wherein the positions correspond to the positions of SEQ ID NO: 1 and wherein the variant has DNase activity.

In one aspect the invention relates to a DNase variant comprising the substitutions S42G+Q109R wherein the positions correspond to the positions of SEQ ID NO: 1 and wherein the variant has DNase activity.

In one aspect the invention relates to a DNase variant comprising the substitutions S42G+S116D wherein the positions correspond to the positions of SEQ ID NO: 1 and wherein the variant has DNase activity.

In one aspect the invention relates to a DNase variant comprising the substitutions S42G+S116E wherein the positions correspond to the positions of SEQ ID NO: 1 and wherein the variant has DNase activity.

In one aspect the invention relates to a DNase variant comprising the substitutions S42G+T127V wherein the positions correspond to the positions of SEQ ID NO: 1 and wherein the variant has DNase activity.

In one aspect the invention relates to a DNase variant comprising the substitutions S42G+T127I wherein the positions correspond to the positions of SEQ ID NO: 1 and wherein the variant has DNase activity.

In one aspect the invention relates to a DNase variant comprising the substitutions S42G+T127L wherein the positions correspond to the positions of SEQ ID NO: 1 and wherein the variant has DNase activity.

In one aspect the invention relates to a DNase variant comprising the substitutions S42G+S144P wherein the positions correspond to the positions of SEQ ID NO: 1 and wherein the variant has DNase activity.

In one aspect the invention relates to a DNase variant comprising the substitutions S42G+A147H wherein the positions correspond to the positions of SEQ ID NO: 1 and wherein the variant has DNase activity.

In one aspect the invention relates to a DNase variant comprising the substitutions S42G+S167L wherein the positions correspond to the positions of SEQ ID NO: 1 and wherein the variant has DNase activity.

In one aspect the invention relates to a DNase variant comprising the substitutions S42G+S167I wherein the positions correspond to the positions of SEQ ID NO: 1 and wherein the variant has DNase activity.

In one aspect the invention relates to a DNase variant comprising the substitutions S42G+S167V wherein the positions correspond to the positions of SEQ ID NO: 1 and wherein the variant has DNase activity.

In one aspect the invention relates to a DNase variant comprising the substitutions S42G+G175D wherein the positions correspond to the positions of SEQ ID NO: 1 and wherein the variant has DNase activity.

In one aspect the invention relates to a DNase variant comprising the substitutions S42G+G175E wherein the positions correspond to the positions of SEQ ID NO: 1 and wherein the variant has DNase activity.

In one aspect the invention relates to a DNase variant comprising the substitutions S42A+S57W wherein the positions correspond to the positions of SEQ ID NO: 1 and wherein the variant has DNase activity.

In one aspect the invention relates to a DNase variant comprising the substitutions S42A+S57Y wherein the positions correspond to the positions of SEQ ID NO: 1 and wherein the variant has DNase activity.

In one aspect the invention relates to a DNase variant comprising the substitutions S42A+S57F wherein the positions correspond to the positions of SEQ ID NO: 1 and wherein the variant has DNase activity.

In one aspect the invention relates to a DNase variant comprising the substitutions S42A+S59V wherein the positions correspond to the positions of SEQ ID NO: 1 and wherein the variant has DNase activity.

In one aspect the invention relates to a DNase variant comprising the substitutions S42A+S59I wherein the positions correspond to the positions of SEQ ID NO: 1 and wherein the variant has DNase activity.

In one aspect the invention relates to a DNase variant comprising the substitutions S42A+S59L wherein the positions correspond to the positions of SEQ ID NO: 1 and wherein the variant has DNase activity.

In one aspect the invention relates to a DNase variant comprising the substitutions S42A+V76L wherein the positions correspond to the positions of SEQ ID NO: 1 and wherein the variant has DNase activity.

In one aspect the invention relates to a DNase variant comprising the substitutions S42A+V76I wherein the positions correspond to the positions of SEQ ID NO: 1 and wherein the variant has DNase activity.

In one aspect the invention relates to a DNase variant comprising the substitutions S42A+Q109R wherein the positions correspond to the positions of SEQ ID NO: 1 and wherein the variant has DNase activity.

In one aspect the invention relates to a DNase variant comprising the substitutions S42A+S116D wherein the positions correspond to the positions of SEQ ID NO: 1 and wherein the variant has DNase activity.

In one aspect the invention relates to a DNase variant comprising the substitutions S42A+S116E wherein the positions correspond to the positions of SEQ ID NO: 1 and wherein the variant has DNase activity.

In one aspect the invention relates to a DNase variant comprising the substitutions S42A+T127V wherein the positions correspond to the positions of SEQ ID NO: 1 and wherein the variant has DNase activity.

In one aspect the invention relates to a DNase variant comprising the substitutions S42A+T127I wherein the positions correspond to the positions of SEQ ID NO: 1 and wherein the variant has DNase activity.

In one aspect the invention relates to a DNase variant comprising the substitutions S42A+T127L wherein the positions correspond to the positions of SEQ ID NO: 1 and wherein the variant has DNase activity.

In one aspect the invention relates to a DNase variant comprising the substitutions S42A+S144P wherein the positions correspond to the positions of SEQ ID NO: 1 and wherein the variant has DNase activity.

In one aspect the invention relates to a DNase variant comprising the substitutions S42A+A147H wherein the positions correspond to the positions of SEQ ID NO: 1 and wherein the variant has DNase activity.

In one aspect the invention relates to a DNase variant comprising the substitutions S42A+S167L wherein the positions correspond to the positions of SEQ ID NO: 1 and wherein the variant has DNase activity.

In one aspect the invention relates to a DNase variant comprising the substitutions S42A+S167I wherein the positions correspond to the positions of SEQ ID NO: 1 and wherein the variant has DNase activity.

In one aspect the invention relates to a DNase variant comprising the substitutions S42A+S167V wherein the positions correspond to the positions of SEQ ID NO: 1 and wherein the variant has DNase activity.

In one aspect the invention relates to a DNase variant comprising the substitutions S42A+G175D wherein the positions correspond to the positions of SEQ ID NO: 1 and wherein the variant has DNase activity.

In one aspect the invention relates to a DNase variant comprising the substitutions S42A+G175E wherein the positions correspond to the positions of SEQ ID NO: 1 and wherein the variant has DNase activity.

In one aspect the invention relates to a DNase variant comprising the substitutions S42T+S57W wherein the positions correspond to the positions of SEQ ID NO: 1 and wherein the variant has DNase activity.

In one aspect the invention relates to a DNase variant comprising the substitutions S42T+S57Y wherein the positions correspond to the positions of SEQ ID NO: 1 and wherein the variant has DNase activity.

In one aspect the invention relates to a DNase variant comprising the substitutions S42T+S57F wherein the positions correspond to the positions of SEQ ID NO: 1 and wherein the variant has DNase activity.

In one aspect the invention relates to a DNase variant comprising the substitutions S42T+S59V wherein the positions correspond to the positions of SEQ ID NO: 1 and wherein the variant has DNase activity.

In one aspect the invention relates to a DNase variant comprising the substitutions S42T+S59I wherein the positions correspond to the positions of SEQ ID NO: 1 and wherein the variant has DNase activity.

In one aspect the invention relates to a DNase variant comprising the substitutions S42T+S59L wherein the positions correspond to the positions of SEQ ID NO: 1 and wherein the variant has DNase activity.

In one aspect the invention relates to a DNase variant comprising the substitutions S42T+V76L wherein the positions correspond to the positions of SEQ ID NO: 1 and wherein the variant has DNase activity.

In one aspect the invention relates to a DNase variant comprising the substitutions S42T+V76I wherein the positions correspond to the positions of SEQ ID NO: 1 and wherein the variant has DNase activity.

In one aspect the invention relates to a DNase variant comprising the substitutions S42T+Q109R wherein the positions correspond to the positions of SEQ ID NO: 1 and wherein the variant has DNase activity.

In one aspect the invention relates to a DNase variant comprising the substitutions S42T+S116D wherein the positions correspond to the positions of SEQ ID NO: 1 and wherein the variant has DNase activity.

In one aspect the invention relates to a DNase variant comprising the substitutions S42T+S116E wherein the positions correspond to the positions of SEQ ID NO: 1 and wherein the variant has DNase activity.

In one aspect the invention relates to a DNase variant comprising the substitutions S42T+T127V wherein the positions correspond to the positions of SEQ ID NO: 1 and wherein the variant has DNase activity.

In one aspect the invention relates to a DNase variant comprising the substitutions S42T+T1271 wherein the positions correspond to the positions of SEQ ID NO: 1 and wherein the variant has DNase activity.

In one aspect the invention relates to a DNase variant comprising the substitutions S42T+T127L wherein the positions correspond to the positions of SEQ ID NO: 1 and wherein the variant has DNase activity.

In one aspect the invention relates to a DNase variant comprising the substitutions S42T+S144P wherein the positions correspond to the positions of SEQ ID NO: 1 and wherein the variant has DNase activity.

In one aspect the invention relates to a DNase variant comprising the substitutions S42T+A147H wherein the positions correspond to the positions of SEQ ID NO: 1 and wherein the variant has DNase activity.

In one aspect the invention relates to a DNase variant comprising the substitutions S42T+S167L wherein the positions correspond to the positions of SEQ ID NO: 1 and wherein the variant has DNase activity.

In one aspect the invention relates to a DNase variant comprising the substitutions S42T+S167I wherein the positions correspond to the positions of SEQ ID NO: 1 and wherein the variant has DNase activity.

In one aspect the invention relates to a DNase variant comprising the substitutions S42T+S167V wherein the positions correspond to the positions of SEQ ID NO: 1 and wherein the variant has DNase activity.

In one aspect the invention relates to a DNase variant comprising the substitutions S42T+G175D wherein the positions correspond to the positions of SEQ ID NO: 1 and wherein the variant has DNase activity.

In one aspect the invention relates to a DNase variant comprising the substitutions S42T+G175E wherein the positions correspond to the positions of SEQ ID NO: 1 and wherein the variant has DNase activity.

In one aspect the invention relates to a DNase variant comprising the substitutions S57W+S59V wherein the positions correspond to the positions of SEQ ID NO: 1 and wherein the variant has DNase activity.

In one aspect the invention relates to a DNase variant comprising the substitutions S57W+S59I wherein the positions correspond to the positions of SEQ ID NO: 1 and wherein the variant has DNase activity.

In one aspect the invention relates to a DNase variant comprising the substitutions S57W+S59L wherein the positions correspond to the positions of SEQ ID NO: 1 and wherein the variant has DNase activity.

In one aspect the invention relates to a DNase variant comprising the substitutions S57W+V76L wherein the positions correspond to the positions of SEQ ID NO: 1 and wherein the variant has DNase activity.

In one aspect the invention relates to a DNase variant comprising the substitutions S57W+V76I wherein the positions correspond to the positions of SEQ ID NO: 1 and wherein the variant has DNase activity.

In one aspect the invention relates to a DNase variant comprising the substitutions S57W+Q109R wherein the positions correspond to the positions of SEQ ID NO: 1 and wherein the variant has DNase activity.

In one aspect the invention relates to a DNase variant comprising the substitutions S57W+S116D wherein the positions correspond to the positions of SEQ ID NO: 1 and wherein the variant has DNase activity.

In one aspect the invention relates to a DNase variant comprising the substitutions S57W+S116E wherein the positions correspond to the positions of SEQ ID NO: 1 and wherein the variant has DNase activity.

In one aspect the invention relates to a DNase variant comprising the substitutions S57W+T127V wherein the positions correspond to the positions of SEQ ID NO: 1 and wherein the variant has DNase activity.

In one aspect the invention relates to a DNase variant comprising the substitutions S57W+T127I wherein the positions correspond to the positions of SEQ ID NO: 1 and wherein the variant has DNase activity.

In one aspect the invention relates to a DNase variant comprising the substitutions S57W+T127L wherein the positions correspond to the positions of SEQ ID NO: 1 and wherein the variant has DNase activity.

In one aspect the invention relates to a DNase variant comprising the substitutions S57W+S144P wherein the positions correspond to the positions of SEQ ID NO: 1 and wherein the variant has DNase activity.

In one aspect the invention relates to a DNase variant comprising the substitutions S57W+A147H wherein the positions correspond to the positions of SEQ ID NO: 1 and wherein the variant has DNase activity.

In one aspect the invention relates to a DNase variant comprising the substitutions S57W+S167L wherein the positions correspond to the positions of SEQ ID NO: 1 and wherein the variant has DNase activity.

In one aspect the invention relates to a DNase variant comprising the substitutions S57W+S167I wherein the positions correspond to the positions of SEQ ID NO: 1 and wherein the variant has DNase activity.

In one aspect the invention relates to a DNase variant comprising the substitutions S57W+S167V wherein the positions correspond to the positions of SEQ ID NO: 1 and wherein the variant has DNase activity.

In one aspect the invention relates to a DNase variant comprising the substitutions S57W+G175D wherein the positions correspond to the positions of SEQ ID NO: 1 and wherein the variant has DNase activity.

In one aspect the invention relates to a DNase variant comprising the substitutions S57W+G175E wherein the positions correspond to the positions of SEQ ID NO: 1 and wherein the variant has DNase activity.

In one aspect the invention relates to a DNase variant comprising the substitutions S57Y+S59V wherein the positions correspond to the positions of SEQ ID NO: 1 and wherein the variant has DNase activity.

In one aspect the invention relates to a DNase variant comprising the substitutions S57Y+S59I wherein the positions correspond to the positions of SEQ ID NO: 1 and wherein the variant has DNase activity.

In one aspect the invention relates to a DNase variant comprising the substitutions S57Y+S59L wherein the positions correspond to the positions of SEQ ID NO: 1 and wherein the variant has DNase activity.

In one aspect the invention relates to a DNase variant comprising the substitutions S57Y+V76L wherein the positions correspond to the positions of SEQ ID NO: 1 and wherein the variant has DNase activity.

In one aspect the invention relates to a DNase variant comprising the substitutions S57Y+V76I wherein the positions correspond to the positions of SEQ ID NO: 1 and wherein the variant has DNase activity.

In one aspect the invention relates to a DNase variant comprising the substitutions S57Y+Q109R wherein the positions correspond to the positions of SEQ ID NO: 1 and wherein the variant has DNase activity.

In one aspect the invention relates to a DNase variant comprising the substitutions S57Y+S116D wherein the positions correspond to the positions of SEQ ID NO: 1 and wherein the variant has DNase activity.

In one aspect the invention relates to a DNase variant comprising the substitutions S57Y+S116E wherein the positions correspond to the positions of SEQ ID NO: 1 and wherein the variant has DNase activity.

In one aspect the invention relates to a DNase variant comprising the substitutions S57Y+T127V wherein the positions correspond to the positions of SEQ ID NO: 1 and wherein the variant has DNase activity.

In one aspect the invention relates to a DNase variant comprising the substitutions S57Y+T127I wherein the positions correspond to the positions of SEQ ID NO: 1 and wherein the variant has DNase activity.

In one aspect the invention relates to a DNase variant comprising the substitutions S57Y+T127L wherein the positions correspond to the positions of SEQ ID NO: 1 and wherein the variant has DNase activity.

In one aspect the invention relates to a DNase variant comprising the substitutions S57Y+S144P wherein the positions correspond to the positions of SEQ ID NO: 1 and wherein the variant has DNase activity.

In one aspect the invention relates to a DNase variant comprising the substitutions S57Y+A147H wherein the positions correspond to the positions of SEQ ID NO: 1 and wherein the variant has DNase activity.

In one aspect the invention relates to a DNase variant comprising the substitutions S57Y+S167L wherein the positions correspond to the positions of SEQ ID NO: 1 and wherein the variant has DNase activity.

In one aspect the invention relates to a DNase variant comprising the substitutions S57Y+S167I wherein the positions correspond to the positions of SEQ ID NO: 1 and wherein the variant has DNase activity.

In one aspect the invention relates to a DNase variant comprising the substitutions S57Y+S167V wherein the positions correspond to the positions of SEQ ID NO: 1 and wherein the variant has DNase activity.

In one aspect the invention relates to a DNase variant comprising the substitutions S57Y+G175D wherein the positions correspond to the positions of SEQ ID NO: 1 and wherein the variant has DNase activity.

In one aspect the invention relates to a DNase variant comprising the substitutions S57Y+G175E wherein the positions correspond to the positions of SEQ ID NO: 1 and wherein the variant has DNase activity.

In one aspect the invention relates to a DNase variant comprising the substitutions S57F+S59V wherein the positions correspond to the positions of SEQ ID NO: 1 and wherein the variant has DNase activity.

In one aspect the invention relates to a DNase variant comprising the substitutions S57F+S59I wherein the positions correspond to the positions of SEQ ID NO: 1 and wherein the variant has DNase activity.

In one aspect the invention relates to a DNase variant comprising the substitutions S57F+S59L wherein the positions correspond to the positions of SEQ ID NO: 1 and wherein the variant has DNase activity.

In one aspect the invention relates to a DNase variant comprising the substitutions S57F+V76L wherein the positions correspond to the positions of SEQ ID NO: 1 and wherein the variant has DNase activity.

In one aspect the invention relates to a DNase variant comprising the substitutions S57F+V76I wherein the positions correspond to the positions of SEQ ID NO: 1 and wherein the variant has DNase activity.

In one aspect the invention relates to a DNase variant comprising the substitutions S57F+Q109R wherein the positions correspond to the positions of SEQ ID NO: 1 and wherein the variant has DNase activity.

In one aspect the invention relates to a DNase variant comprising the substitutions S57F+Q109R wherein the positions correspond to the positions of SEQ ID NO: 1 and wherein the variant has DNase activity.

In one aspect the invention relates to a DNase variant comprising the substitutions S57F+S116D wherein the positions correspond to the positions of SEQ ID NO: 1 and wherein the variant has DNase activity.

In one aspect the invention relates to a DNase variant comprising the substitutions S57F+S116E wherein the positions correspond to the positions of SEQ ID NO: 1 and wherein the variant has DNase activity.

In one aspect the invention relates to a DNase variant comprising the substitutions S57F+T127V wherein the positions correspond to the positions of SEQ ID NO: 1 and wherein the variant has DNase activity.

In one aspect the invention relates to a DNase variant comprising the substitutions S57F+T1271 wherein the positions correspond to the positions of SEQ ID NO: 1 and wherein the variant has DNase activity.

In one aspect the invention relates to a DNase variant comprising the substitutions S57F+T127L wherein the positions correspond to the positions of SEQ ID NO: 1 and wherein the variant has DNase activity.

In one aspect the invention relates to a DNase variant comprising the substitutions S57F+S144P wherein the positions correspond to the positions of SEQ ID NO: 1 and wherein the variant has DNase activity.

In one aspect the invention relates to a DNase variant comprising the substitutions S57F+A147H wherein the positions correspond to the positions of SEQ ID NO: 1 and wherein the variant has DNase activity.

In one aspect the invention relates to a DNase variant comprising the substitutions S57F+S167L wherein the positions correspond to the positions of SEQ ID NO: 1 and wherein the variant has DNase activity.

In one aspect the invention relates to a DNase variant comprising the substitutions S57F+S167I wherein the positions correspond to the positions of SEQ ID NO: 1 and wherein the variant has DNase activity.

In one aspect the invention relates to a DNase variant comprising the substitutions S57F+S167V wherein the positions correspond to the positions of SEQ ID NO: 1 and wherein the variant has DNase activity.

In one aspect the invention relates to a DNase variant comprising the substitutions S57F+G175D wherein the positions correspond to the positions of SEQ ID NO: 1 and wherein the variant has DNase activity.

In one aspect the invention relates to a DNase variant comprising the substitutions S57F+G175E wherein the positions correspond to the positions of SEQ ID NO: 1 and wherein the variant has DNase activity.

In one aspect the invention relates to a DNase variant comprising the substitutions S59V+V76L wherein the positions correspond to the positions of SEQ ID NO: 1 and wherein the variant has DNase activity.

In one aspect the invention relates to a DNase variant comprising the substitutions S59V+V76I wherein the positions correspond to the positions of SEQ ID NO: 1 and wherein the variant has DNase activity.

In one aspect the invention relates to a DNase variant comprising the substitutions S59V+Q109R wherein the positions correspond to the positions of SEQ ID NO: 1 and wherein the variant has DNase activity.

In one aspect the invention relates to a DNase variant comprising the substitutions S59V+S116D wherein the positions correspond to the positions of SEQ ID NO: 1 and wherein the variant has DNase activity.

In one aspect the invention relates to a DNase variant comprising the substitutions S59V+S116E wherein the positions correspond to the positions of SEQ ID NO: 1 and wherein the variant has DNase activity.

In one aspect the invention relates to a DNase variant comprising the substitutions S59V+T127V wherein the positions correspond to the positions of SEQ ID NO: 1 and wherein the variant has DNase activity.

In one aspect the invention relates to a DNase variant comprising the substitutions S59V+T127I wherein the positions correspond to the positions of SEQ ID NO: 1 and wherein the variant has DNase activity.

In one aspect the invention relates to a DNase variant comprising the substitutions S59V+T127L wherein the positions correspond to the positions of SEQ ID NO: 1 and wherein the variant has DNase activity.

In one aspect the invention relates to a DNase variant comprising the substitutions S59V+S144P wherein the positions correspond to the positions of SEQ ID NO: 1 and wherein the variant has DNase activity.

In one aspect the invention relates to a DNase variant comprising the substitutions S59V+A147H wherein the positions correspond to the positions of SEQ ID NO: 1 and wherein the variant has DNase activity.

In one aspect the invention relates to a DNase variant comprising the substitutions S59V+S167L wherein the positions correspond to the positions of SEQ ID NO: 1 and wherein the variant has DNase activity.

In one aspect the invention relates to a DNase variant comprising the substitutions S59V+S167I wherein the positions correspond to the positions of SEQ ID NO: 1 and wherein the variant has DNase activity.

In one aspect the invention relates to a DNase variant comprising the substitutions S59V+S167V wherein the positions correspond to the positions of SEQ ID NO: 1 and wherein the variant has DNase activity.

In one aspect the invention relates to a DNase variant comprising the substitutions S59V+G175D wherein the positions correspond to the positions of SEQ ID NO: 1 and wherein the variant has DNase activity.

In one aspect the invention relates to a DNase variant comprising the substitutions S59V+G175E wherein the positions correspond to the positions of SEQ ID NO: 1 and wherein the variant has DNase activity.

In one aspect the invention relates to a DNase variant comprising the substitutions S59I+V76L wherein the positions correspond to the positions of SEQ ID NO: 1 and wherein the variant has DNase activity.

In one aspect the invention relates to a DNase variant comprising the substitutions S59I+V761 wherein the positions correspond to the positions of SEQ ID NO: 1 and wherein the variant has DNase activity.

In one aspect the invention relates to a DNase variant comprising the substitutions S59I+Q109R wherein the positions correspond to the positions of SEQ ID NO: 1 and wherein the variant has DNase activity.

In one aspect the invention relates to a DNase variant comprising the substitutions S59I+S116D wherein the positions correspond to the positions of SEQ ID NO: 1 and wherein the variant has DNase activity.

In one aspect the invention relates to a DNase variant comprising the substitutions S59I+S116E wherein the positions correspond to the positions of SEQ ID NO: 1 and wherein the variant has DNase activity.

In one aspect the invention relates to a DNase variant comprising the substitutions S59I+T127V wherein the positions correspond to the positions of SEQ ID NO: 1 and wherein the variant has DNase activity.

In one aspect the invention relates to a DNase variant comprising the substitutions S59I+T127I wherein the positions correspond to the positions of SEQ ID NO: 1 and wherein the variant has DNase activity.

In one aspect the invention relates to a DNase variant comprising the substitutions S59I+T127L wherein the positions correspond to the positions of SEQ ID NO: 1 and wherein the variant has DNase activity.

In one aspect the invention relates to a DNase variant comprising the substitutions S59I+S144P wherein the positions correspond to the positions of SEQ ID NO: 1 and wherein the variant has DNase activity.

In one aspect the invention relates to a DNase variant comprising the substitutions S59I+A147H wherein the positions correspond to the positions of SEQ ID NO: 1 and wherein the variant has DNase activity.

In one aspect the invention relates to a DNase variant comprising the substitutions S59I+S167L wherein the positions correspond to the positions of SEQ ID NO: 1 and wherein the variant has DNase activity.

In one aspect the invention relates to a DNase variant comprising the substitutions S59I+S167I wherein the positions correspond to the positions of SEQ ID NO: 1 and wherein the variant has DNase activity.

In one aspect the invention relates to a DNase variant comprising the substitutions S59I+S167V wherein the positions correspond to the positions of SEQ ID NO: 1 and wherein the variant has DNase activity.

In one aspect the invention relates to a DNase variant comprising the substitutions S59I+G175D wherein the positions correspond to the positions of SEQ ID NO: 1 and wherein the variant has DNase activity.

In one aspect the invention relates to a DNase variant comprising the substitutions S59I+G175E wherein the positions correspond to the positions of SEQ ID NO: 1 and wherein the variant has DNase activity.

In one aspect the invention relates to a DNase variant comprising the substitutions S59L+V76L wherein the positions correspond to the positions of SEQ ID NO: 1 and wherein the variant has DNase activity.

In one aspect the invention relates to a DNase variant comprising the substitutions S59L+V76I wherein the positions correspond to the positions of SEQ ID NO: 1 and wherein the variant has DNase activity.

In one aspect the invention relates to a DNase variant comprising the substitutions S59L+Q109R wherein the positions correspond to the positions of SEQ ID NO: 1 and wherein the variant has DNase activity.

In one aspect the invention relates to a DNase variant comprising the substitutions S59L+S116D wherein the positions correspond to the positions of SEQ ID NO: 1 and wherein the variant has DNase activity.

In one aspect the invention relates to a DNase variant comprising the substitutions S59L+S116E wherein the positions correspond to the positions of SEQ ID NO: 1 and wherein the variant has DNase activity.

In one aspect the invention relates to a DNase variant comprising the substitutions S59L+T127V wherein the positions correspond to the positions of SEQ ID NO: 1 and wherein the variant has DNase activity.

In one aspect the invention relates to a DNase variant comprising the substitutions S59L+T127I wherein the positions correspond to the positions of SEQ ID NO: 1 and wherein the variant has DNase activity.

In one aspect the invention relates to a DNase variant comprising the substitutions S59L+T127L wherein the positions correspond to the positions of SEQ ID NO: 1 and wherein the variant has DNase activity.

In one aspect the invention relates to a DNase variant comprising the substitutions S59L+S144P wherein the positions correspond to the positions of SEQ ID NO: 1 and wherein the variant has DNase activity.

In one aspect the invention relates to a DNase variant comprising the substitutions S59L+A147H wherein the positions correspond to the positions of SEQ ID NO: 1 and wherein the variant has DNase activity.

In one aspect the invention relates to a DNase variant comprising the substitutions S59L+S167L wherein the positions correspond to the positions of SEQ ID NO: 1 and wherein the variant has DNase activity.

In one aspect the invention relates to a DNase variant comprising the substitutions S59L+S167I wherein the positions correspond to the positions of SEQ ID NO: 1 and wherein the variant has DNase activity.

In one aspect the invention relates to a DNase variant comprising the substitutions S59L+S167V wherein the positions correspond to the positions of SEQ ID NO: 1 and wherein the variant has DNase activity.

In one aspect the invention relates to a DNase variant comprising the substitutions S59L+G175D wherein the positions correspond to the positions of SEQ ID NO: 1 and wherein the variant has DNase activity.

In one aspect the invention relates to a DNase variant comprising the substitutions S59L+G175E wherein the positions correspond to the positions of SEQ ID NO: 1 and wherein the variant has DNase activity.

In one aspect the invention relates to a DNase variant comprising the substitutions V76L+Q109R wherein the positions correspond to the positions of SEQ ID NO: 1 and wherein the variant has DNase activity.

In one aspect the invention relates to a DNase variant comprising the substitutions V76L+S116D wherein the positions correspond to the positions of SEQ ID NO: 1 and wherein the variant has DNase activity.

In one aspect the invention relates to a DNase variant comprising the substitutions V76L+S116E wherein the positions correspond to the positions of SEQ ID NO: 1 and wherein the variant has DNase activity.

In one aspect the invention relates to a DNase variant comprising the substitutions V76L+T127V wherein the positions correspond to the positions of SEQ ID NO: 1 and wherein the variant has DNase activity.

In one aspect the invention relates to a DNase variant comprising the substitutions V76L+T127I wherein the positions correspond to the positions of SEQ ID NO: 1 and wherein the variant has DNase activity.

In one aspect the invention relates to a DNase variant comprising the substitutions V76L+T127L wherein the positions correspond to the positions of SEQ ID NO: 1 and wherein the variant has DNase activity.

In one aspect the invention relates to a DNase variant comprising the substitutions V76L+S144P wherein the positions correspond to the positions of SEQ ID NO: 1 and wherein the variant has DNase activity.

In one aspect the invention relates to a DNase variant comprising the substitutions V76L+A147H wherein the positions correspond to the positions of SEQ ID NO: 1 and wherein the variant has DNase activity.

In one aspect the invention relates to a DNase variant comprising the substitutions V76L+S167L wherein the positions correspond to the positions of SEQ ID NO: 1 and wherein the variant has DNase activity.

In one aspect the invention relates to a DNase variant comprising the substitutions V76L+S167I wherein the positions correspond to the positions of SEQ ID NO: 1 and wherein the variant has DNase activity.

In one aspect the invention relates to a DNase variant comprising the substitutions V76L+S167V wherein the positions correspond to the positions of SEQ ID NO: 1 and wherein the variant has DNase activity.

In one aspect the invention relates to a DNase variant comprising the substitutions V76L+G175D wherein the positions correspond to the positions of SEQ ID NO: 1 and wherein the variant has DNase activity.

In one aspect the invention relates to a DNase variant comprising the substitutions V76L+G175E wherein the positions correspond to the positions of SEQ ID NO: 1 and wherein the variant has DNase activity.

In one aspect the invention relates to a DNase variant comprising the substitutions V76I+Q109R wherein the positions correspond to the positions of SEQ ID NO: 1 and wherein the variant has DNase activity.

In one aspect the invention relates to a DNase variant comprising the substitutions V76I+S116D wherein the positions correspond to the positions of SEQ ID NO: 1 and wherein the variant has DNase activity.

In one aspect the invention relates to a DNase variant comprising the substitutions V76I+S116E wherein the positions correspond to the positions of SEQ ID NO: 1 and wherein the variant has DNase activity.

In one aspect the invention relates to a DNase variant comprising the substitutions V76I+T127V wherein the positions correspond to the positions of SEQ ID NO: 1 and wherein the variant has DNase activity.

In one aspect the invention relates to a DNase variant comprising the substitutions V76I+T1271 wherein the positions correspond to the positions of SEQ ID NO: 1 and wherein the variant has DNase activity.

In one aspect the invention relates to a DNase variant comprising the substitutions V76I+T127L wherein the positions correspond to the positions of SEQ ID NO: 1 and wherein the variant has DNase activity.

In one aspect the invention relates to a DNase variant comprising the substitutions V76I+S144P wherein the positions correspond to the positions of SEQ ID NO: 1 and wherein the variant has DNase activity.

In one aspect the invention relates to a DNase variant comprising the substitutions V76I+A147H wherein the positions correspond to the positions of SEQ ID NO: 1 and wherein the variant has DNase activity.

In one aspect the invention relates to a DNase variant comprising the substitutions V76I+S167L wherein the positions correspond to the positions of SEQ ID NO: 1 and wherein the variant has DNase activity.

In one aspect the invention relates to a DNase variant comprising the substitutions V76I+S1671 wherein the positions correspond to the positions of SEQ ID NO: 1 and wherein the variant has DNase activity.

In one aspect the invention relates to a DNase variant comprising the substitutions V76I+S167V wherein the positions correspond to the positions of SEQ ID NO: 1 and wherein the variant has DNase activity.

In one aspect the invention relates to a DNase variant comprising the substitutions V76I+G175D wherein the positions correspond to the positions of SEQ ID NO: 1 and wherein the variant has DNase activity.

In one aspect the invention relates to a DNase variant comprising the substitutions V76I+G175E wherein the positions correspond to the positions of SEQ ID NO: 1 and wherein the variant has DNase activity.

In one aspect the invention relates to a DNase variant comprising the substitutions Q109R+S116D wherein the positions correspond to the positions of SEQ ID NO: 1 and wherein the variant has DNase activity.

In one aspect the invention relates to a DNase variant comprising the substitutions Q109R+S116E wherein the positions correspond to the positions of SEQ ID NO: 1 and wherein the variant has DNase activity.

In one aspect the invention relates to a DNase variant comprising the substitutions Q109R+T127V wherein the positions correspond to the positions of SEQ ID NO: 1 and wherein the variant has DNase activity.

In one aspect the invention relates to a DNase variant comprising the substitutions Q109R+T1271 wherein the positions correspond to the positions of SEQ ID NO: 1 and wherein the variant has DNase activity.

In one aspect the invention relates to a DNase variant comprising the substitutions Q109R+T127L wherein the positions correspond to the positions of SEQ ID NO: 1 and wherein the variant has DNase activity.

In one aspect the invention relates to a DNase variant comprising the substitutions Q109R+S144P wherein the positions correspond to the positions of SEQ ID NO: 1 and wherein the variant has DNase activity.

In one aspect the invention relates to a DNase variant comprising the substitutions Q109R+A147H wherein the positions correspond to the positions of SEQ ID NO: 1 and wherein the variant has DNase activity.

In one aspect the invention relates to a DNase variant comprising the substitutions Q109R+S167L wherein the positions correspond to the positions of SEQ ID NO: 1 and wherein the variant has DNase activity.

In one aspect the invention relates to a DNase variant comprising the substitutions Q109R+S1671 wherein the positions correspond to the positions of SEQ ID NO: 1 and wherein the variant has DNase activity.

In one aspect the invention relates to a DNase variant comprising the substitutions Q109R+S167V wherein the positions correspond to the positions of SEQ ID NO: 1 and wherein the variant has DNase activity.

In one aspect the invention relates to a DNase variant comprising the substitutions Q109R+G175D wherein the positions correspond to the positions of SEQ ID NO: 1 and wherein the variant has DNase activity.

In one aspect the invention relates to a DNase variant comprising the substitutions Q109R+G175E wherein the positions correspond to the positions of SEQ ID NO: 1 and wherein the variant has DNase activity.

In one aspect the invention relates to a DNase variant comprising the substitutions S116D+T127V wherein the positions correspond to the positions of SEQ ID NO: 1 and wherein the variant has DNase activity.

In one aspect the invention relates to a DNase variant comprising the substitutions S116D+T127I wherein the positions correspond to the positions of SEQ ID NO: 1 and wherein the variant has DNase activity.

In one aspect the invention relates to a DNase variant comprising the substitutions S116D+T127L wherein the positions correspond to the positions of SEQ ID NO: 1 and wherein the variant has DNase activity.

In one aspect the invention relates to a DNase variant comprising the substitutions S116D+S144P wherein the positions correspond to the positions of SEQ ID NO: 1 and wherein the variant has DNase activity.

In one aspect the invention relates to a DNase variant comprising the substitutions S116D+A147H wherein the positions correspond to the positions of SEQ ID NO: 1 and wherein the variant has DNase activity.

In one aspect the invention relates to a DNase variant comprising the substitutions S116D+S167L wherein the positions correspond to the positions of SEQ ID NO: 1 and wherein the variant has DNase activity.

In one aspect the invention relates to a DNase variant comprising the substitutions S116D+S167I wherein the positions correspond to the positions of SEQ ID NO: 1 and wherein the variant has DNase activity.

In one aspect the invention relates to a DNase variant comprising the substitutions S116D+S167V wherein the positions correspond to the positions of SEQ ID NO: 1 and wherein the variant has DNase activity.

In one aspect the invention relates to a DNase variant comprising the substitutions S116D+G175D wherein the positions correspond to the positions of SEQ ID NO: 1 and wherein the variant has DNase activity.

In one aspect the invention relates to a DNase variant comprising the substitutions S116D+G175E wherein the positions correspond to the positions of SEQ ID NO: 1 and wherein the variant has DNase activity.

In one aspect the invention relates to a DNase variant comprising the substitutions S116E+T127V wherein the positions correspond to the positions of SEQ ID NO: 1 and wherein the variant has DNase activity.

In one aspect the invention relates to a DNase variant comprising the substitutions S116E+T127I wherein the positions correspond to the positions of SEQ ID NO: 1 and wherein the variant has DNase activity.

In one aspect the invention relates to a DNase variant comprising the substitutions S116E+T127L wherein the positions correspond to the positions of SEQ ID NO: 1 and wherein the variant has DNase activity.

In one aspect the invention relates to a DNase variant comprising the substitutions S116E+S144P wherein the positions correspond to the positions of SEQ ID NO: 1 and wherein the variant has DNase activity.

In one aspect the invention relates to a DNase variant comprising the substitutions S116E+A147H wherein the positions correspond to the positions of SEQ ID NO: 1 and wherein the variant has DNase activity.

In one aspect the invention relates to a DNase variant comprising the substitutions S116E+S167L wherein the positions correspond to the positions of SEQ ID NO: 1 and wherein the variant has DNase activity.

In one aspect the invention relates to a DNase variant comprising the substitutions S116E+S167I wherein the positions correspond to the positions of SEQ ID NO: 1 and wherein the variant has DNase activity.

In one aspect the invention relates to a DNase variant comprising the substitutions S116E+S167V wherein the positions correspond to the positions of SEQ ID NO: 1 and wherein the variant has DNase activity.

In one aspect the invention relates to a DNase variant comprising the substitutions S116E+G175D wherein the positions correspond to the positions of SEQ ID NO: 1 and wherein the variant has DNase activity.

In one aspect the invention relates to a DNase variant comprising the substitutions S116E+G175E wherein the positions correspond to the positions of SEQ ID NO: 1 and wherein the variant has DNase activity.

In one aspect the invention relates to a DNase variant comprising the substitutions T127V+S144P wherein the positions correspond to the positions of SEQ ID NO: 1 and wherein the variant has DNase activity.

In one aspect the invention relates to a DNase variant comprising the substitutions T127V+A147H wherein the positions correspond to the positions of SEQ ID NO: 1 and wherein the variant has DNase activity.

In one aspect the invention relates to a DNase variant comprising the substitutions T127V+S167L wherein the positions correspond to the positions of SEQ ID NO: 1 and wherein the variant has DNase activity.

In one aspect the invention relates to a DNase variant comprising the substitutions T127V+S167I wherein the positions correspond to the positions of SEQ ID NO: 1 and wherein the variant has DNase activity.

In one aspect the invention relates to a DNase variant comprising the substitutions T127V+S167V wherein the positions correspond to the positions of SEQ ID NO: 1 and wherein the variant has DNase activity.

In one aspect the invention relates to a DNase variant comprising the substitutions T127V+G175D wherein the positions correspond to the positions of SEQ ID NO: 1 and wherein the variant has DNase activity.

In one aspect the invention relates to a DNase variant comprising the substitutions T127V+G175E wherein the positions correspond to the positions of SEQ ID NO: 1 and wherein the variant has DNase activity.

In one aspect the invention relates to a DNase variant comprising the substitutions T127I+S144P wherein the positions correspond to the positions of SEQ ID NO: 1 and wherein the variant has DNase activity.

In one aspect the invention relates to a DNase variant comprising the substitutions T127I+A147H wherein the positions correspond to the positions of SEQ ID NO: 1 and wherein the variant has DNase activity.

In one aspect the invention relates to a DNase variant comprising the substitutions T127I+S167L wherein the positions correspond to the positions of SEQ ID NO: 1 and wherein the variant has DNase activity.

In one aspect the invention relates to a DNase variant comprising the substitutions T127I+S1671 wherein the positions correspond to the positions of SEQ ID NO: 1 and wherein the variant has DNase activity.

In one aspect the invention relates to a DNase variant comprising the substitutions T127I+S167V wherein the positions correspond to the positions of SEQ ID NO: 1 and wherein the variant has DNase activity.

In one aspect the invention relates to a DNase variant comprising the substitutions T127I+G175D wherein the positions correspond to the positions of SEQ ID NO: 1 and wherein the variant has DNase activity.

In one aspect the invention relates to a DNase variant comprising the substitutions T127I+G175E wherein the positions correspond to the positions of SEQ ID NO: 1 and wherein the variant has DNase activity.

In one aspect the invention relates to a DNase variant comprising the substitutions T127L+S144P wherein the positions correspond to the positions of SEQ ID NO: 1 and wherein the variant has DNase activity.

In one aspect the invention relates to a DNase variant comprising the substitutions T127L+A147H wherein the positions correspond to the positions of SEQ ID NO: 1 and wherein the variant has DNase activity.

In one aspect the invention relates to a DNase variant comprising the substitutions T127L+S167L wherein the positions correspond to the positions of SEQ ID NO: 1 and wherein the variant has DNase activity.

In one aspect the invention relates to a DNase variant comprising the substitutions T127L+S167I wherein the positions correspond to the positions of SEQ ID NO: 1 and wherein the variant has DNase activity.

In one aspect the invention relates to a DNase variant comprising the substitutions T127L+S167V wherein the positions correspond to the positions of SEQ ID NO: 1 and wherein the variant has DNase activity.

In one aspect the invention relates to a DNase variant comprising the substitutions T127L+G175D wherein the positions correspond to the positions of SEQ ID NO: 1 and wherein the variant has DNase activity.

In one aspect the invention relates to a DNase variant comprising the substitutions T127L+G175E wherein the positions correspond to the positions of SEQ ID NO: 1 and wherein the variant has DNase activity.

In one aspect the invention relates to a DNase variant comprising the substitutions S144P+A147H wherein the positions correspond to the positions of SEQ ID NO: 1 and wherein the variant has DNase activity.

In one aspect the invention relates to a DNase variant comprising the substitutions S144P+S167L wherein the positions correspond to the positions of SEQ ID NO: 1 and wherein the variant has DNase activity.

In one aspect the invention relates to a DNase variant comprising the substitutions S144P+S167I wherein the positions correspond to the positions of SEQ ID NO: 1 and wherein the variant has DNase activity.

In one aspect the invention relates to a DNase variant comprising the substitutions S144P+S167V wherein the positions correspond to the positions of SEQ ID NO: 1 and wherein the variant has DNase activity.

In one aspect the invention relates to a DNase variant comprising the substitutions S144P+G175D wherein the positions correspond to the positions of SEQ ID NO: 1 and wherein the variant has DNase activity.

In one aspect the invention relates to a DNase variant comprising the substitutions S144P+G175E wherein the positions correspond to the positions of SEQ ID NO: 1 and wherein the variant has DNase activity.

In one aspect the invention relates to a DNase variant comprising the substitutions A147H+S167L wherein the positions correspond to the positions of SEQ ID NO: 1 and wherein the variant has DNase activity.

In one aspect the invention relates to a DNase variant comprising the substitutions A147H+S167I wherein the positions correspond to the positions of SEQ ID NO: 1 and wherein the variant has DNase activity.

In one aspect the invention relates to a DNase variant comprising the substitutions A147H+S167V wherein the positions correspond to the positions of SEQ ID NO: 1 and wherein the variant has DNase activity.

In one aspect the invention relates to a DNase variant comprising the substitutions A147H+G175D wherein the positions correspond to the positions of SEQ ID NO: 1 and wherein the variant has DNase activity.

In one aspect the invention relates to a DNase variant comprising the substitutions A147H+G175E wherein the positions correspond to the positions of SEQ ID NO: 1 and wherein the variant has DNase activity.

In one aspect the invention relates to a DNase variant comprising the substitutions S167L+G175D wherein the positions correspond to the positions of SEQ ID NO: 1 and wherein the variant has DNase activity.

In one aspect the invention relates to a DNase variant comprising the substitutions S167L+G175E wherein the positions correspond to the positions of SEQ ID NO: 1 and wherein the variant has DNase activity.

In one aspect the invention relates to a DNase variant comprising the substitutions S167I+G175D wherein the positions correspond to the positions of SEQ ID NO: 1 and wherein the variant has DNase activity.

In one aspect the invention relates to a DNase variant comprising the substitutions S167I+G175E wherein the positions correspond to the positions of SEQ ID NO: 1 and wherein the variant has DNase activity.

In one aspect the invention relates to a DNase variant comprising the substitutions S167V+G175D wherein the positions correspond to the positions of SEQ ID NO: 1 and wherein the variant has DNase activity.

In one aspect the invention relates to a DNase variant comprising the substitutions S167V+G175E wherein the positions correspond to the positions of SEQ ID NO: 1 and wherein the variant has DNase activity.

In some preferred respects the DNase variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence of the mature parent DNase.

In some preferred respects the DNase variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1.

In some aspects, the improved property is increased stability e.g. improved detergent stability, improved in-wash stability and improved thermostability. Some aspects of the invention relate to DNase variants having an improvement factor above 1 when the DNase variants are tested for a property of interest in a relevant assay, wherein the property of the reference DNase is given a value of 1. In some aspects, the property is stability, such as storage stability. Some aspects of the invention relate to DNase variants having an improvement factor above 1 when the DNase variants are tested for a property of interest in the assay described in Example 2, 3, 4, 5 or 6, wherein the property of the reference DNase is given a value of 1. In some aspects, the property is stability, such as storage stability.

In some aspects, the improved property is increased stability e.g. improved detergent stability, improved in-wash stability and improved thermostability. Some aspects of the invention relate to DNase variants having an improvement factor above 1 when the DNase variants are tested for a property of interest in a relevant assay, wherein the property of the reference DNase is given a value of 1. In some aspects, the property is stability, such as storage stability.

In some aspects, the improved property is improved detergent stability.

In some aspects, the improved property is improved protease stability.

In some aspects, the improved property is improved stability in the presence of sulfite.

A variant according to the invention is improved under the measured conditions when the residual activity ratio, defined as $$\text{Residual Activity Ratio } (RAR) = \frac{RA_{variant}}{RA_{reference}}$$

is above 1 compared to the reference DNase, as shown in Examples 3, 4 and 5. In some aspects, the variant is improved compared to the reference DNase in at least one of the assays A, B or C, where Assay A measure improved protease stability, Assay B measure improved stability in the presence of sulfite and Assay C measure improved detergent stability, as shown in Examples 3, 4 and 5. In some aspects, the variant is improved compared to the reference DNase in at least two of the assays A, B or C, where Assay A measure improved protease stability (example 4), Assay B measure improved stability in the presence of sulfite (example 5) and Assay C (example 3) measure improved detergent stability, as shown in Examples 3, 4 and 5. In some aspects, the variant is improved compared to the reference DNase in all the assays A, B or C, where Assay A measure improved protease stability, Assay B measure improved stability in the presence of sulfite and Assay C measure improved detergent stability, as shown in Examples 3, 4 and 5.

In some aspects, the variants according to the invention have improved stability relative to a reference DNase measured as an residual activity ratio (RAR) that is greater than 1.0.

The Residual Activity Ratio (RAR) for the DNase variants of the invention may be calculated as $RA_{variant}/RA_{reference}$. Improved variants were identified as variants having residual activity ratio (RAR) larger than 1.0 compared to the reference DNase, as shown in Example 3, 4 and 5.

In some aspects, the variants according to the invention have improved stability relative to a reference DNase measured as an Half-life Improvement Factor (HIF) that is greater than 1.0.

The Half-life Improvement Factor (HIF) for the DNase variants of the invention may be calculated as $T_{1/2variant}/T_{1/2reference}$. Improved variants were identified as variants having a Half-life Improvement Factor HIF larger than 1.0 compared to the reference DNase, as shown in Example 2 or 6. Productive combinations of mutations according to the invention are those which result in an improvement factor e.g. HIF or RAR above 1, or said in another way where the combination of mutations result in a variant which have at least one improved property compared to the starting molecule i.e. the precursor, reference parent polypeptide etc. In a particular preferred aspect, the combination of mutations according to the invention results in DNase variants having improved stability where HIF>1.0. In some aspects, the variants according to the invention have a Half-life Improvement Factor (HIF) which is at least 1.1; 1.2; 1.3; 1.4; 1.5; 1.6; 1.7; 1.8; 1.9; 2.0; 2.1; 2.2; 2.3; 2.4; 2.5; 2.6; 2.7, 2.8; 2.9; 3.0, 3.1; 3.2; 3.3; 3.4; 3.5, 3.6, 3.7, 3.8, 3.9; 4.0, 4.1; 4.2; 4.3; 4.4; 4.5, 4.6, 4.7, 4.8, 4.9, 5.0, 5.1; 5.2; 5.3; 5.4; 5.5, 5.6, 5.7, 5.8, 5.9; 3.0, 6.1; 6.2; 6.3; 6.4; 6.5, 6.6, 6.7, 6.8, 6.9; 7.0, 7.1; 7.2; 7.3; 7.4; 7.5, 7.6, 7.7, 7.8, 7.9; 8.0, 8.1; 8.2; 8.3; 8.4; 8.5, 8.6, 8.7, 8.8, 8.9; 9.0, 9.1; 9.2; 9.3; 9.4; 9.5, 9.6, 9.7, 9.8, 9.9; 10.0, 10.1; 10.2; 10.3; 10.4; 10.5, 10.6, 10.7, 10.8, 10.9; 12, 15, 16, 20, 25 or 30 compared to e reference DNase e.g. SEQ ID NO: 1 or SEQ ID NO: 28.

In a particular preferred aspect, the combination of mutations according to the invention results in DNase variants having improved stability, where RAR>1.0. In some aspects, the variants according to the invention have a Residual Activity Ratio (RAR) which is at least 1.1; 1.2; 1.3; 1.4; 1.5; 1.6; 1.7; 1.8; 1.9; 2.0; 2.1; 2.2; 2.3; 2.4; 2.5; 2.6; 2.7, 2.8; 2.9; 3.0, 3.1; 3.2; 3.3; 3.4; 3.5, 3.6, 3.7, 3.8, 3.9; 4.0, 4.1; 4.2; 4.3; 4.4; 4.5, 4.6, 4.7, 4.8, 4.9, 5.0, 5.1; 5.2; 5.3; 5.4; 5.5, 5.6, 5.7, 5.8, 5.9; 3.0, 6.1; 6.2; 6.3; 6.4; 6.5, 6.6, 6.7, 6.8, 6.9; 7.0, 7.1; 7.2; 7.3; 7.4; 7.5, 7.6, 7.7, 7.8, 7.9; 8.0, 8.1; 8.2; 8.3; 8.4; 8.5, 8.6, 8.7, 8.8, 8.9; 9.0, 9.1; 9.2; 9.3; 9.4; 9.5, 9.6, 9.7, 9.8, 9.9; 10.0, 10.1; 10.2; 10.3; 10.4; 10.5, 10.6, 10.7, 10.8, 10.9; 12, 15, 16, 20, 25 or 30 compared to a reference DNase e.g. SEQ ID NO: 1 or SEQ ID NO: 28.

One preferred embodiment relates to a DNase variant having improved stability, wherein HIF>1.0, compared to SEQ ID NO: 1 or compared to SEQ ID NO: 28. One preferred embodiment relates to a DNase variant having improved stability, wherein the Half-life Improvement Factor is at least 1.5, compared to SEQ ID NO: 1 or compared to SEQ ID NO: 28, when measured as described in Example 2 or 6.

One preferred embodiment relates to a DNase variant having improved stability, wherein RAR>1.0, compared to SEQ ID NO: 1 or compared to SEQ ID NO: 28. One preferred embodiment relates to a DNase variant having improved stability, wherein the residual activity ratio (RAR) is at least 1.5, compared to SEQ ID NO: 1 or compared to SEQ ID NO: 28, when measured as described in Example 3, 4, 5 or 7.

One preferred embodiment relates to a DNase variant having improved stability, wherein HIF>1.0 compared to SEQ ID NO: 1 or compared to SEQ ID NO: 28. One preferred embodiment relates to a DNase variant having improved stability, wherein the Half-life Improvement Factor (HIF) is at least 1.2 e.g. 1.5, compared to SEQ ID NO: 1 or compared to SEQ ID NO: 28, wherein HIF is calculated as $T_{1/2DNasevariant}/T_{1/2reference}$ and the half-life ($T_{1/2}$ minutes) for the DNase variants and the DNase reference (e.g. SEQ ID NO: 1 or SEQ ID NO: 28) is calculated as: 20 minutes× LN(0.5)/LN(RA) and the residual activity (RA) for each DNase variant and the reference DNase (e.g. SEQ ID NO: 1 or SEQ ID NO: 28) is calculated as: slope (stress sample, 48.5° C. for 20 min)/slope(unstressed sample, 21° C. for 20 min).

One preferred embodiment relates to a DNase variant having improved stability, wherein residual activity ratio (RAR)>1.0 compared to SEQ ID NO: 1 or compared to SEQ ID NO: 28. One preferred embodiment relates to a DNase variant having improved stability, wherein the residual activity ratio (RAR) is at least 1.2 e.g. 1.5, compared to SEQ ID NO: 1 or compared to SEQ ID NO: 28, wherein RAR is calculated as, $$\text{Residual Activity Ratio } (RAR) = \frac{RA_{variant}}{RA_{reference}}$$

as described in Assay A, in the Example section.

One preferred aspect of the invention relates to a DNase variant, which compared to a DNase with SEQ ID NO: 1, comprises two or more substitutions selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein the positions correspond to the positions of SEQ ID NO: 1 (numbering according to SEQ ID NO: 1), wherein the variant has a sequence identity to the polypeptide shown in SEQ ID NO: 1 or the polypeptide show in SEQ ID NO: 28 of at least 90%, wherein the variant has DNase activity and wherein the DNase variant has improved stability, measured as having an improvement factor e.g. RAR or HIF>1.0, compared to the DNase having the polypeptide sequence shown in SEQ ID NO: 1 or shown in SEQ ID NO: 28.

In some preferred aspects, a DNase variant of the invention comprise an alteration at two or more positions selected from the group consisting of 1, 13, 22, 25, 27, 39, 42, 57, 59, 76, 109, 116, 127, 144, 147, 167 and 175, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1) and wherein the variant has at least on improved property compared to the parent DNase e.g. a DNase comprising the polypeptide having the amino acid sequence shown in SEQ ID NO: 1, preferably the improved property is improved stability, wherein stability is tested as described in example 1.

In some preferred aspects, a DNase variant of the invention comprises two or more substitutions (compared to SEQ ID NO: 1), wherein the substitutions are selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1) and wherein the variant has at least on improved property compared to the parent DNase e.g. a DNase comprising the polypeptide having the amino acid sequence shown in SEQ ID NO: 1, preferably the improved property is, improved stability, wherein stability is tested as described in Example 2 to Example 6.

In some preferred aspects, a DNase variant of the invention comprise one or more substitution set(s) (compared to SEQ ID NO: 1) selected from the group consisting of: T1I+S13Y, T1I+T22P, T1I+S25P, T1I+S27L, T1I+S39P, T1I+S42G, T1I+S42A, T1I+S42T, T1I+S57W, T1I+S57Y, T1I+S57F, T1I+S59V, T1I+S59I, T1I+S59L, T1I+V76L, T1I+V76I, T1I+Q109R, T1I+S116D, T1I+S116E, T1I+T127V, T1I+T127I, T1I+T127L, T1I+S144P, T1I+A147H, T1I+S167L, T1I+S167I, T1I+S167V, T1I+G175D, T1I+G175E, T1L+S13Y, T1L+T22P, T1L+S25P, T1L+S27L, T1L+S39P, T1L+S42G, T1L+S42A, T1L+S42T, T1L+S57W, T1L+S57Y, T1L+S57F, T1L+S59V, T1L+S59I, T1L+S59L, T1L+V76L, T1L+V76I, T1L+Q109R, T1L+S116D, T1L+S116E, T1L+T127V, T1L+T127I, T1L+T127L, T1L+S144P, T1L+A147H, T1L+S167L, T1L+S167I, T1L+S167V, T1L+G175D, T1L+G175E, T1V+S13Y, T1V+T22P, T1V+S25P, T1V+S27L, T1V+S39P, T1V+S42G, T1V+S42A, T1V+S42T, T1V+S57W, T1V+S57Y, T1V+S57F, T1V+S59V, T1V+S59I, T1V+S59L, T1V+V76L, T1V+V76I, T1V+Q109R, T1V+S116D, T1V+S116E, T1V+T127V, T1V+T127I, T1V+T127L, T1V+S144P, T1V+A147H, T1V+S167L, T1V+S167I, T1V+S167V, T1V+G175D, T1V+G175E, S13Y+T22P, S13Y+S25P, S13Y+S27L, S13Y+S39P, S13Y+S42G, S13Y+S42A, S13Y+S42T, S13Y+S57W, S13Y+S57Y, S13Y+S57F, S13Y+S59V, S13Y+S59I, S13Y+S59L, S13Y+V76L, S13Y+V76I, S13Y+Q109R, S13Y+S116D, S13Y+S116E, S13Y+T127V, S13Y+T127I, S13Y+T127L, S13Y+S144P, S13Y+A147H, S13Y+S167L, S13Y+S167I, S13Y+S167V, S13Y+G175D, S13Y+G175E, T22P+S25P, T22P+S27L, T22P+S39P, T22P+S42G, T22P+S42A, T22P+S42T, T22P+S57W, T22P+S57Y, T22P+S57F, T22P+S59V, T22P+S59I, T22P+S59L, T22P+V76L, T22P+V76I, T22P+Q109R, T22P+S116D, T22P+S116E, T22P+T127V, T22P+T127I, T22P+T127L, T22P+S144P, T22P+A147H, T22P+S167L, T22P+S167I, T22P+S167V, T22P+G175D, T22P+G175E, S25P+S27L, S25P+S39P, S25P+S42G, S25P+S42A, S25P+S42T, S25P+S57W, S25P+S57Y, S25P+S57F, S25P+S59V, S25P+S59I, S25P+S59L, S25P+V76L, S25P+V76I, S25P+Q109R, S25P+S116D, S25P+S116E, S25P+T127V, S25P+T127I, S25P+T127L, S25P+S144P, S25P+A147H, S25P+S167L, S25P+S167I, S25P+S167V, S25P+G175D, S25P+G175E, S27L+S39P, S27L+S42G, S27L+S42A, S27L+S42T, S27L+S57W, S27L+S57Y, S27L+S57F, S27L+S59V, S27L+S59I, S27L+S59L, S27L+V76L, S27L+V76I, S27L+Q109R, S27L+S116D, S27L+S116E, S27L+T127V, S27L+T127I, S27L+T127L, S27L+S144P, S27L+A147H, S27L+S167L, S27L+S167I, S27L+S167V, S27L+G175D, S27L+G175E, S39P+S42G, S39P+S42A, S39P+S42T, S39P+S57W, S39P+S57Y, S39P+S57F, S39P+S59V, S39P+S59I, S39P+S59L, S39P+V76L, S39P+V76I, S39P+Q109R, S39P+S116D, S39P+S116E, S39P+T127V, S39P+T127I, S39P+T127L, S39P+S144P, S39P+A147H, S39P+S167L, S39P+S167I, S39P+S167V, S39P+G175D, S39P+G175E, S42G+S57W, S42G+S57Y, S42G+S57F, S42G+S59V, S42G+S59I, S42G+S59L, S42G+V76L, S42G+V76I, S42G+Q109R, S42G+S116D, S42G+S116E, S42G+T127V, S42G+T127I, S42G+T127L, S42G+S144P, S42G+A147H, S42G+S167L, S42G+S167I, S42G+S167V, S42G+G175D, S42G+G175E, S42A+S57W, S42A+S57Y, S42A+S57F, S42A+S59V, S42A+S59I, S42A+S59L, S42A+V76L, S42A+V76I, S42A+Q109R, S42A+S116D, S42A+S116E, S42A+T127V, S42A+T127I, S42A+T127L, S42A+S144P, S42A+A147H, S42A+S167L, S42A+S167I, S42A+S167V, S42A+G175D, S42A+G175E, S42T+S57W, S42T+S57Y, S42T+S57F, S42T+S59V, S42T+S59I, S42T+S59L, S42T+V76L, S42T+V76I, S42T+Q109R, S42T+S116D, S42T+S116E, S42T+T127V, S42T+T127I, S42T+T127L, S42T+S144P, S42T+A147H, S42T+S167L, S42T+S167I, S42T+S167V, S42T+G175D, S42T+G175E, S57W+S59V, S57W+S59I, S57W+S59L, S57W+V76L, S57W+V76I, S57W+Q109R, S57W+S116D, S57W+S116E, S57W+T127V, S57W+T127I, S57W+T127L, S57W+S144P, S57W+A147H, S57W+S167L, S57W+S167I, S57W+S167V, S57W+G175D, S57W+G175E, S57Y+S59V, S57Y+S59I, S57Y+S59L, S57Y+V76L, S57Y+V76I, S57Y+Q109R, S57Y+S116D, S57Y+S116E, S57Y+T127V, S57Y+T127I, S57Y+T127L, S57Y+S144P, S57Y+A147H, S57Y+S167L, S57Y+S167I, S57Y+S167V, S57Y+G175D, S57Y+G175E, S57F+S59V, S57F+S59I, S57F+S59L, S57F+V76L, S57F+V76I, S57F+Q109R, S57F+S116D, S57F+S116E, S57F+T127V, S57F+T127I, S57F+T127L, S57F+S144P, S57F+A147H, S57F+S167L, S57F+S167I, S57F+S167V, S57F+G175D, S57F+G175E, S59V+V76L, S59V+V76I, S59V+Q109R, S59V+S116D, S59V+S116E, S59V+T127V, S59V+T127I, S59V+T127L, S59V+S144P, S59V+A147H, S59V+S167L, S59V+S167I, S59V+S167V, S59V+G175D, S59V+G175E, S59I+V76L, S59I+V76I, S59I+Q109R, S59I+S116D, S59I+S116E, S59I+T127V, S59I+T127I, S59I+T127L, S59I+S144P, S59I+A147H, S59I+S167L, S59I+S167I, S59I+S167V, S59I+G175D, S59I+G175E, S59L+V76L, S59L+V76I, S59L+Q109R, S59L+S116D, S59L+S116E, S59L+T127V, S59L+T127I, S59L+T127L, S59L+S144P, S59L+A147H, S59L+S167L, S59L+S167I, S59L+S167V, S59L+G175D, S59L+G175E, V76L+Q109R, V76L+S116D, V76L+S116E, V76L+T127V, V76L+T127I, V76L+T127L, V76L+S144P, V76L+A147H, V76L+S167L, V76L+S167I, V76L+S167V, V76L+G175D, V76L+G175E, V76I+Q109R, V76I+S116D, V76I+S116E, V76I+T127V, V76I+T127I, V76I+T127L, V76I+S144P, V76I+A147H, V76I+S167L, V76I+S167I, V76I+S167V, V76I+G175D, V76I+G175E, Q109R+S116D, Q109R+S116E, Q109R+T127V, Q109R+T127I, Q109R+T127L, Q109R+S144P, Q109R+A147H, Q109R+S167L, Q109R+S167I, Q109R+S167V, Q109R+G175D, Q109R+G175E, S116D+T127V, S116D+T127I, S116D+T127L, S116D+S144P, S116D+A147H, S116D+S167L, S116D+S167I, S116D+S167V, S116D+G175D, S116D+G175E, S116E+T127V, S116E+T127I, S116E+T127L, S116E+S144P, S116E+A147H, S116E+S167L, S116E+S167I, S116E+S167V, S116E+G175D, S116E+G175E, T127V+S144P, T127V+A147H, T127V+S167L, T127V+S167I, T127V+S167V, T127V+G175D, T127V+G175E, T127I+S144P, T127I+A147H, T127I+S167L, T127I+S167I, T127I+S167V, T127I+G175D, T127I+G175E, T127L+S144P, T127L+A147H, T127L+S167L, T127L+S167I, T127L+S167V, T127L+G175D, T127L+G175E, S144P+A147H, S144P+S167L, S144P+S167I, S144P+S167V, S144P+G175D, S144P+G175E, A147H+S167L, A147H+S167I, A147H+S167V, A147H+G175D, A147H+G175E, S167L+G175D, S167L+G175E, S167I+G175D, S167I+G175E, S167V+G175D and S167V+G175E, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1) and wherein the variant has at least on improved property compared to the parent DNase e.g. a DNase comprising the polypeptide having the amino acid sequence shown in SEQ ID NO: 1, preferably the improved property is, improved stability, wherein stability is tested as described in example 2 to 6.

In some aspects, the DNase variant of the invention has an improved stability, measured as Half-life Improvement Factor, HIF, compared to the parent or compared to the DNase having the polypeptide shown in SEQ ID NO: 1, compared to a DNase having the polypeptide sequence shown in SEQ ID NO: 28 or compared to a DNase having the identical amino acid sequence of the DNase variant but not having the alterations at two or more of the specified positions.

In some aspects, the DNase variant of the invention has an improved stability, measured as residual activity ratio, RAR, compared to the parent or compared to the DNase having the polypeptide shown in SEQ ID NO: 1, compared to a DNase having the polypeptide sequence shown in SEQ ID NO: 28 or compared to a DNase having the identical amino acid sequence of the DNase variant but not having the alterations at two or more of the specified positions.

In some preferred aspects, a DNase variant of the invention comprise an alteration at two or more positions selected from the group consisting of 1, 13, 22, 25, 27, 39, 42, 57, 59, 76, 109, 116, 127, 144, 147, 167 and 175, wherein each position corresponds to the position of the polypeptide of SEQ ID NO: 1, wherein each alteration provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred aspects, a DNase variant of the invention comprises two or more substitutions (compared to SEQ ID NO: 1), wherein the substitutions are selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred aspects, a DNase variant of the invention comprises two or more substitutions (compared to SEQ ID NO: 1), wherein the substitutions are selected from the group consisting of: T1I, T1V, S13Y, T22P, S25P, S27L, S39P, S42G, S42A, S42T, S57W, S57F, S59V, S59I, S59L, V76L, Q109R, S116D, S116E, T127V, T127I, T127L, S144P, A147H, S167L, S167I, S167V, G175D and G175E, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred aspects, a DNase variant of the invention comprises two or more substitutions (compared to SEQ ID NO: 1), wherein the substitutions are selected from the group consisting of: T1I, T1V, S13Y, T22P, S25P, S27L, S39P, S42G, S42A, S42T, S57W, S57F, S59V, S59I, S59L, V76L, Q109R, S116D, S116E, T127V, T127I, T127L, S144P, S167L, S167I, S167V, G175D and G175E, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred aspects, a DNase variant of the invention comprise one or more substitution set (compared to SEQ ID NO: 1) selected from the group consisting of: T1I+S13Y, T1I+T22P, T1I+S25P, T1I+S27L, T1I+S39P, T1I+S42G, T1I+S42A, T1I+S42T, T1I+S57W, T1I+S57Y, T1I+S57F, T1I+S59V, T1I+S59I, T1I+S59L, T1I+V76L, T1I+V76I, T1I+Q109R, T1I+S116D, T1I+S116E, T1I+T127V, T1I+T127I, T1I+T127L, T1I+S144P, T1I+A147H, T1I+S167L, T1I+S167I, T1I+S167V, T1I+G175D, T1I+G175E, T1L+S13Y, T1L+T22P, T1L+S25P, T1L+S27L, T1L+S39P, T1L+S42G, T1L+S42A, T1L+S42T, T1L+S57W, T1L+S57Y, T1L+S57F, T1L+S59V, T1L+S59I, T1L+S59L, T1L+V76L, T1L+V76I, T1L+Q109R, T1L+S116D, T1L+S116E, T1L+T127V, T1L+T127I, T1L+T127L, T1L+S144P, T1L+A147H, T1L+S167L, T1L+S167I, T1L+S167V, T1L+G175D, T1L+G175E, T1V+S13Y, T1V+T22P, T1V+S25P, T1V+S27L, T1V+S39P, T1V+S42G, T1V+S42A, T1V+S42T, T1V+S57W, T1V+S57Y, T1V+S57F, T1V+S59V, T1V+S59I, T1V+S59L, T1V+V76L, T1V+V76I, T1V+Q109R, T1V+S116D, T1V+S116E, T1V+T127V, T1V+T127I, T1V+T127L, T1V+S144P, T1V+A147H, T1V+S167L, T1V+S167I, T1V+S167V, T1V+G175D, T1V+G175E, S13Y+T22P, S13Y+S25P, S13Y+S27L, S13Y+S39P, S13Y+S42G, S13Y+S42A, S13Y+S42T, S13Y+S57W, S13Y+S57Y, S13Y+S57F, S13Y+S59V, S13Y+S59I, S13Y+S59L, S13Y+V76L, S13Y+V76I, S13Y+Q109R, S13Y+S116D, S13Y+S116E, S13Y+T127V, S13Y+T127I, S13Y+T127L, S13Y+S144P, S13Y+A147H, S13Y+S167L, S13Y+S167I, S13Y+S167V, S13Y+G175D, S13Y+G175E, T22P+S25P, T22P+S27L, T22P+S39P, T22P+S42G, T22P+S42A, T22P+S42T, T22P+S57W, T22P+S57Y, T22P+S57F, T22P+S59V, T22P+S59I, T22P+S59L, T22P+V76L, T22P+V76I, T22P+Q109R, T22P+S116D, T22P+S116E, T22P+T127V, T22P+T127I, T22P+T127L, T22P+S144P, T22P+A147H, T22P+S167L, T22P+S167I, T22P+S167V, T22P+G175D, T22P+G175E, S25P+S27L, S25P+S39P, S25P+S42G, S25P+S42A, S25P+S42T, S25P+S57W, S25P+S57Y, S25P+S57F, S25P+S59V, S25P+S59I, S25P+S59L, S25P+V76L, S25P+V76I, S25P+Q109R, S25P+S116D, S25P+S116E, S25P+T127V, S25P+T127I, S25P+T127L, S25P+S144P, S25P+A147H, S25P+S167L, S25P+S167I, S25P+S167V, S25P+G175D, S25P+G175E, S27L+S39P, S27L+S42G, S27L+S42A, S27L+S42T, S27L+S57W, S27L+S57Y, S27L+S57F, S27L+S59V, S27L+S59I, S27L+S59L, S27L+V76L, S27L+V76I, S27L+Q109R, S27L+S116D, S27L+S116E, S27L+T127V, S27L+T127I, S27L+T127L, S27L+S144P, S27L+A147H, S27L+S167L, S27L+S167I, S27L+S167V, S27L+G175D, S27L+G175E, S39P+S42G, S39P+S42A, S39P+S42T, S39P+S57W, S39P+S57Y, S39P+S57F, S39P+S59V, S39P+S59I, S39P+S59L, S39P+V76L, S39P+V76I, S39P+Q109R, S39P+S116D, S39P+S116E, S39P+T127V, S39P+T127I, S39P+T127L, S39P+S144P, S39P+A147H, S39P+S167L, S39P+S167I, S39P+S167V, S39P+G175D, S39P+G175E, S42G+S57W, S42G+S57Y, S42G+S57F, S42G+S59V, S42G+S59I, S42G+S59L, S42G+V76L, S42G+V76I, S42G+Q109R, S42G+S116D, S42G+S116E, S42G+T127V, S42G+T127I, S42G+T127L, S42G+S144P, S42G+A147H, S42G+S167L, S42G+S167I, S42G+S167V, S42G+G175D, S42G+G175E, S42A+S57W, S42A+S57Y, S42A+S57F, S42A+S59V, S42A+S59I, S42A+S59L, S42A+V76L, S42A+V76I, S42A+Q109R, S42A+S116D, S42A+S116E, S42A+T127V, S42A+T127I, S42A+T127L, S42A+S144P, S42A+A147H, S42A+S167L, S42A+S167I, S42A+S167V, S42A+G175D, S42A+G175E, S42T+S57W, S42T+S57Y, S42T+S57F, S42T+S59V, S42T+S59I, S42T+S59L, S42T+V76L, S42T+V76I, S42T+Q109R, S42T+S116D, S42T+S116E, S42T+T127V, S42T+T127I, S42T+T127L, S42T+S144P, S42T+A147H, S42T+S167L, S42T+S167I, S42T+S167V, S42T+G175D, S42T+G175E, S57W+S59V, S57W+S59I, S57W+S59L, S57W+V76L, S57W+V76I, S57W+Q109R, S57W+S116D, S57W+S116E, S57W+T127V, S57W+T127I, S57W+T127L, S57W+S144P, S57W+A147H, S57W+S167L, S57W+S167I, S57W+S167V, S57W+G175D, S57W+G175E, S57Y+S59V, S57Y+S59I, S57Y+S59L, S57Y+V76L, S57Y+V76I, S57Y+Q109R, S57Y+S116D, S57Y+S116E, S57Y+T127V, S57Y+T127I, S57Y+T127L, S57Y+S144P, S57Y+A147H, S57Y+S167L, S57Y+S167I, S57Y+S167V, S57Y+G175D, S57Y+G175E, S57F+S59V, S57F+S59I, S57F+S59L, S57F+V76L, S57F+V76I, S57F+Q109R, S57F+S116D, S57F+S116E, S57F+T127V, S57F+T127I, S57F+T127L, S57F+S144P, S57F+A147H, S57F+S167L, S57F+S167I, S57F+S167V, S57F+G175D, S57F+G175E, S59V+V76L, S59V+V76I, S59V+Q109R, S59V+S116D, S59V+S116E, S59V+T127V, S59V+T127I, S59V+T127L, S59V+S144P, S59V+A147H, S59V+S167L, S59V+S167I, S59V+S167V, S59V+G175D, S59V+G175E, S59I+V76L, S59I+V76I, S59I+Q109R, S59I+S116D, S59I+S116E, S59I+T127V, S59I+T127I, S59I+T127L, S59I+S144P, S59I+A147H, S59I+S167L, S59I+S167I, S59I+S167V, S59I+G175D, S59I+G175E, S59L+V76L, S59L+V76I, S59L+Q109R, S59L+S116D, S59L+S116E, S59L+T127V, S59L+T127I, S59L+T127L, S59L+S144P, S59L+A147H, S59L+S167L, S59L+S167I, S59L+S167V, S59L+G175D, S59L+G175E, V76L+Q109R, V76L+S116D, V76L+S116E, V76L+T127V, V76L+T127I, V76L+T127L, V76L+S144P, V76L+A147H, V76L+S167L, V76L+S167I, V76L+S167V, V76L+G175D, V76L+G175E, V76I+Q109R, V76I+S116D, V76I+S116E, V76I+T127V, V76I+T127I, V76I+T127L, V76I+S144P, V76I+A147H, V76I+S167L, V76I+S167I, V76I+S167V, V76I+G175D, V76I+G175E, Q109R+S116D, Q109R+S116E, Q109R+T127V, Q109R+T127I, Q109R+T127L, Q109R+S144P, Q109R+A147H, Q109R+S167L, Q109R+S167I, Q109R+S167V, Q109R+G175D, Q109R+G175E, S116D+T127V, S116D+T127I, S116D+T127L, S116D+S144P, S116D+A147H, S116D+S167L, S116D+S167I, S116D+S167V, S116D+G175D, S116D+G175E, S116E+T127V, S116E+T127I, S116E+T127L, S116E+S144P, S116E+A147H, S116E+S167L, S116E+S167I, S116E+S167V, S116E+G175D, S116E+G175E, T127V+S144P, T127V+A147H, T127V+S167L, T127V+S167I, T127V+S167V, T127V+G175D, T127V+G175E, T127I+S144P, T127I+A147H, T127I+S167L, T127I+S167I, T127I+S167V, T127I+G175D, T127I+G175E, T127L+S144P, T127L+A147H, T127L+S167L, T127L+S167I, T127L+S167V, T127L+G175D, T127L+G175E, S144P+A147H, S144P+S167L, S144P+S167I, S144P+S167V, S144P+G175D, S144P+G175E, A147H+S167L, A147H+S167I, A147H+S167V, A147H+G175D, A147H+G175E, S167L+G175D, S167L+G175E, S167I+G175D, S167I+G175E, S167V+G175D and S167V+G175E, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred embodiment of the invention the DNase variant of the invention comprises one or more of the following substitutions sets: T1I+T22P, T1I+S39P, T1I+S42G, T1I+S57W, T1I+S59V, T1I+V76L, T1I+S116D, T1I+T127V, T1I+S167L, T1I+G175D, T22P+S42G, T22P+V76L, T22P+S116D, T22P+T127V, T22P+A147H, T22P+G175D, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+S144P, S39P+A147H, S39P+S167L, S42G+S57W, S42G+S59V, S42G+V76L, S42G+S116D, S42G+T127V, S42G+S144P, S42G+A147H, S42G+S167L, S42G+G175D, S57W+S59V, S57W+S116D, S57W+T127V, S57W+A147H, S59V+V76L, S59V+S116D, S59V+A147H, S59V+S167L, S59V+G175D, V76L+S116D, V76L+T127V, V76L+S144P, V76L+A147H, V76L+S167L, V76L+G175D, S116D+T127V, S116D+S144P, S116D+A147H, S116D+S167L, S116D+G175D, T127V+S144P, T127V+A147H, T127V+S167L, T127V+G175D, S144P+A147H, S144P+S167L or S167L+G175D.

In some preferred embodiment of the invention the DNase variant of the invention comprises one or more of the following substitutions sets: T1I+T22P, T1I+S39P, T1I+S42G, T1I+S57W, T1I+S59V, T1I+V76L, T1I+S116D, T1I+T127V, T1I+S167L, T1I+G175D, T22P+S42G, T22P+V76L, T22P+S116D, T22P+T127V, T22P+A147H, T22P+G175D, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+S144P, S39P+A147H, S39P+S167L, S42G+S57W, S42G+S59V, S42G+V76L, S42G+S116D, S42G+T127V, S42G+S144P, S42G+S167L, S42G+G175D, S57W+S59V, S57W+S116D, S57W+T127V, S57W+A147H, S59V+V76L, S59V+S116D, S59V+A147H, S59V+S167L, S59V+G175D, V76L+S116D, V76L+T127V, V76L+S144P, V76L+A147H, V76L+S167L, V76L+G175D, S116D+T127V, S116D+S144P, S116D+A147H, S116D+S167L, S116D+G175D, T127V+S144P, T127V+A147H, T127V+S167L, T127V+G175D, S144P+A147H, S144P+S167L or S167L+G175D.

In some preferred aspects, a DNase variant of the invention comprise one or more substitution set (compared to SEQ ID NO: 1) selected from the group consisting of: T1I+T22P, T1I+S39P, T1I+S42G, T1I+S57W, T1I+S59V, T1I+V76L, T1I+S116D, T1I+T127V, T1I+S167L, T1I+G175D, T22P+S42G, T22P+V76L, T22P+S116D, T22P+T127V, T22P+A147H, T22P+G175D, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+S144P, S39P+A147H, S39P+S167L, S42G+S57W, S42G+S59V, S42G+V76L, S42G+S116D, S42G+T127V, S42G+S144P, S42G+A147H, S42G+S167L, S42G+G175D, S57W+S59V, S57W+S116D, S57W+T127V, S57W+A147H, S59V+V76L, S59V+S116D, S59V+A147H, S59V+S167L, S59V+G175D, V76L+S116D, V76L+T127V, V76L+S144P, V76L+A147H, V76L+S167L, V76L+G175D, S116D+T127V, S116D+S144P, S116D+A147H, S116D+S167L, S116D+G175D, T127V+S144P, T127V+A147H, T127V+S167L, T127V+G175D, S144P+A147H, S144P+S167L and S167L+G175D, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the DNase variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred aspects, a DNase variant of the invention comprise one or more substitution set (compared to SEQ ID NO: 1) selected from the group consisting of: T1I+T22P, T1I+S39P, T1I+S42G, T1I+S57W, T1I+S59V, T1I+V76L, T1I+S116D, T1I+T127V, T1I+S167L, T1I+G175D, T22P+S42G, T22P+V76L, T22P+S116D, T22P+T127V, T22P+A147H, T22P+G175D, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+S144P, S39P+A147H, S39P+S167L, S42G+S57W, S42G+S59V, S42G+V76L, S42G+S116D, S42G+T127V, S42G+S144P, S42G+S167L, S42G+G175D, S57W+S59V, S57W+S116D, S57W+T127V, S57W+A147H, S59V+V76L, S59V+S116D, S59V+A147H, S59V+S167L, S59V+G175D, V76L+S116D, V76L+T127V, V76L+S144P, V76L+A147H, V76L+S167L, V76L+G175D, S116D+T127V, S116D+S144P, S116D+A147H, S116D+S167L, S116D+G175D, T127V+S144P, T127V+A147H, T127V+S167L, T127V+G175D, S144P+A147H, S144P+S167L and S167L+G175D, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the DNase variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In one preferred embodiment the combination of mutations comprises a synergistic effect i.e. the Half-life Improvement Factor (HIF) of the combination of e.g. two mutations is larger than the sum of the Half-life Improvement Factor (HIF) for each mutation individually.

In some preferred embodiment of the invention the DNase variant of the invention comprises one or more of the following substitutions sets: T1I+S39P, T1I+S42G, T22P+S116D, T22P+T127V, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+A147H, S39P+S167L, S42G+S57W, S42G+S59V, S42G+V76L, S42G+S116D, S42G+T127V, S42G+S144P, S42G+A147H, S42G+S167L, S42G+G175D, S57W+S59V, S57W+S116D, S57W+T127V, S59V+V76L, S59V+S116D, S59V+A147H, V76L+S116D, V76L+T127V, S116D+S144P, S116D+A147H, S116D+S167L, T127V+S144P, T127V+A147H, T127V+S167L, T127V+G175D or S144P+A147H.

In some preferred embodiment of the invention the DNase variant of the invention comprises one or more of the following substitutions sets: T1I+S39P, T1I+S42G, T22P+S116D, T22P+T127V, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+A147H, S39P+S167L, S42G+S57W, S42G+S59V, S42G+V76L, S42G+S116D, S42G+T127V, S42G+S144P, S42G+S167L, S42G+G175D, S57W+S59V, S57W+S116D, S57W+T127V, S59V+V76L, S59V+S116D, S59V+A147H, V76L+S116D, V76L+T127V, S116D+S144P, S116D+A147H, S116D+S167L, T127V+S144P, T127V+A147H, T127V+S167L, T127V+G175D or S144P+A147H.

In some preferred aspects, a DNase variant of the invention comprise one or more substitution set (compared to SEQ ID NO: 1) selected from the group consisting of: T1I+S39P, T1I+S42G, T22P+S116D, T22P+T127V, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+A147H, S39P+S167L, S42G+S57W, S42G+S59V, S42G+V76L, S42G+S116D, S42G+T127V, S42G+S144P, S42G+A147H, S42G+S167L, S42G+G175D, S57W+S59V, S57W+S116D, S57W+T127V, S59V+V76L, S59V+S116D, S59V+A147H, V76L+S116D, V76L+T127V, S116D+S144P, S116D+A147H, S116D+S167L, T127V+S144P, T127V+A147H, T127V+S167L, T127V+G175D and S144P+A147H, wherein each substitution provides a DNase variant having an increase in stability measured as Half-Life Improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred aspects, a DNase variant of the invention comprise one or more substitution set (compared to SEQ ID NO: 1) selected from the group consisting of: T1I+S39P, T1I+S42G, T22P+S116D, T22P+T127V, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+A147H, S39P+S167L, S42G+S57W, S42G+S59V, S42G+V76L, S42G+S116D, S42G+T127V, S42G+S144P, S42G+S167L, S42G+G175D, S57W+S59V, S57W+S116D, S57W+T127V, S59V+V76L, S59V+S116D, S59V+A147H, V76L+S116D, V76L+T127V, S116D+S144P, S116D+A147H, S116D+S167L, T127V+S144P, T127V+A147H, T127V+S167L, T127V+G175D and S144P+A147H, wherein each substitution provides a DNase variant having an increase in stability measured as Half-Life Improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

The variants of the invention preferably comprise the conservative motifs [D/M/L][S/T]GYSR[D/N] (SEQ ID NO: 25) or ASXNRSKG (SEQ ID NO: 26), which are shared among DNases of the GYS-clade as described below. The ASXNRSKG motif correspond to pos 125 to 133 of SEQ ID NO: 1 and the [D/M/L][S/T]GYSR[D/N] motif correspond to positions 26 to 32 of SEQ ID NO: 1. As explained in "Definitions" a Glade comprises a group of polypeptides clustered together based on homologous features traced to a common ancestor. Polypeptides forming a group e.g. a Glade as shown in a phylogenetic tree often share common properties and are more closely related than other polypeptides not in the Glade.

Thus, one preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise an alteration at two or more positions selected from the list consisting of positions: 1, 13, 22, 25, 27, 39, 42, 57, 59, 76, 109, 116, 127, 144, 147, 167 and 175, wherein each position corresponds to the position of the polypeptide of SEQ ID NO: 1, wherein each alteration provides a DNase variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1).

One preferred aspect of the invention relates to a variant of a DNase parent, wherein the variant comprises two or more substitutions (compared to SEQ ID NO: 1), wherein the substitutions are selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein each substitution provides a DNase variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1).

One preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise one or more substitution set(s) (compared to SEQ ID NO: 1) selected from the group consisting of: T1I+S13Y, T1I+T22P, T1I+S25P, T1I+S27L, T1I+S39P, T1I+S42G, T1I+S42A, T1I+S42T, T1I+S57W, T1I+S57Y, T1I+S57F, T1I+S59V, T1I+S59I, T1I+S59L, T1I+V76L, T1I+V76I, T1I+Q109R, T1I+S116D, T1I+S116E, T1I+T127V, T1I+T127I, T1I+T127L, T1I+S144P, T1I+A147H, T1I+S167L, T1I+S167I, T1I+S167V, T1I+G175D, T1I+G175E, T1L+S13Y, T1L+T22P, T1L+S25P, T1L+S27L, T1L+S39P, T1L+S42G, T1L+S42A, T1L+S42T, T1L+S57W, T1L+S57Y, T1L+S57F, T1L+S59V, T1L+S59I, T1L+S59L, T1L+V76L, T1L+V76I, T1L+Q109R, T1L+S116D, T1L+S116E, T1L+T127V, T1L+T127I, T1L+T127L, T1L+S144P, T1L+A147H, T1L+S167L, T1L+S167I, T1L+S167V, T1L+G175D, T1L+G175E, T1V+S13Y, T1V+T22P, T1V+S25P, T1V+S27L, T1V+S39P, T1V+S42G, T1V+S42A, T1V+S42T, T1V+S57W, T1V+S57Y, T1V+S57F, T1V+S59V, T1V+S59I, T1V+S59L, T1V+V76L, T1V+V76I, T1V+Q109R, T1V+S116D, T1V+S116E, T1V+T127V, T1V+T127I, T1V+T127L, T1V+S144P, T1V+A147H, T1V+S167L, T1V+S167I, T1V+S167V, T1V+G175D, T1V+G175E, S13Y+T22P, S13Y+S25P, S13Y+S27L, S13Y+S39P, S13Y+S42G, S13Y+S42A, S13Y+S42T, S13Y+S57W, S13Y+S57Y, S13Y+S57F, S13Y+S59V, S13Y+S59I, S13Y+S59L, S13Y+V76L, S13Y+V76I, S13Y+Q109R, S13Y+S116D, S13Y+S116E, S13Y+T127V, S13Y+T127I, S13Y+T127L, S13Y+S144P, S13Y+A147H, S13Y+S167L, S13Y+S167I, S13Y+S167V, S13Y+G175D, S13Y+G175E, T22P+S25P, T22P+S27L, T22P+S39P, T22P+S42G, T22P+S42A, T22P+S42T, T22P+S57W, T22P+S57Y, T22P+S57F, T22P+S59V, T22P+S59I, T22P+S59L, T22P+V76L, T22P+V76I, T22P+Q109R, T22P+S116D, T22P+S116E, T22P+T127V, T22P+T127I, T22P+T127L, T22P+S144P, T22P+A147H, T22P+S167L, T22P+S167I, T22P+S167V, T22P+G175D, T22P+G175E, S25P+S27L, S25P+S39P, S25P+S42G, S25P+S42A, S25P+S42T, S25P+S57W, S25P+S57Y, S25P+S57F, S25P+S59V, S25P+S59I, S25P+S59L, S25P+V76L, S25P+V76I, S25P+Q109R, S25P+S116D, S25P+S116E, S25P+T127V, S25P+T127I, S25P+T127L, S25P+S144P, S25P+A147H, S25P+S167L, S25P+S167I, S25P+S167V, S25P+G175D, S25P+G175E, S27L+S39P, S27L+S42G, S27L+S42A, S27L+S42T, S27L+S57W, S27L+S57Y, S27L+S57F, S27L+S59V, S27L+S59I, S27L+S59L, S27L+V76L, S27L+V76I, S27L+Q109R, S27L+S116D, S27L+S116E, S27L+T127V, S27L+T127I, S27L+T127L, S27L+S144P, S27L+A147H, S27L+S167L, S27L+S167I, S27L+S167V, S27L+G175D, S27L+G175E, S39P+S42G, S39P+S42A, S39P+S42T, S39P+S57W, S39P+S57Y, S39P+S57F, S39P+S59V, S39P+S59I, S39P+S59L, S39P+V76L, S39P+V76I, S39P+Q109R, S39P+S116D, S39P+S116E, S39P+T127V, S39P+T127I, S39P+T127L, S39P+S144P, S39P+A147H, S39P+S167L, S39P+S167I, S39P+S167V, S39P+G175D, S39P+G175E, S42G+S57W, S42G+S57Y, S42G+S57F, S42G+S59V, S42G+S59I, S42G+S59L, S42G+V76L, S42G+V76I, S42G+Q109R, S42G+S116D, S42G+S116E, S42G+T127V, S42G+T127I, S42G+T127L, S42G+S144P, S42G+A147H, S42G+S167L, S42G+S167I, S42G+S167V, S42G+G175D, S42G+G175E, S42A+S57W, S42A+S57Y, S42A+S57F, S42A+S59V, S42A+S59I, S42A+S59L, S42A+V76L, S42A+V76I, S42A+Q109R, S42A+S116D, S42A+S116E, S42A+T127V, S42A+T127I, S42A+T127L, S42A+S144P, S42A+A147H, S42A+S167L, S42A+S167I, S42A+S167V, S42A+G175D, S42A+G175E, S42T+S57W, S42T+S57Y, S42T+S57F, S42T+S59V, S42T+S59I, S42T+S59L, S42T+V76L, S42T+V76I, S42T+Q109R, S42T+S116D, S42T+S116E, S42T+T127V, S42T+T127I, S42T+T127L, S42T+S144P, S42T+A147H, S42T+S167L, S42T+S167I, S42T+S167V, S42T+G175D, S42T+G175E, S57W+S59V, S57W+S59I, S57W+S59L, S57W+V76L, S57W+V76I, S57W+Q109R, S57W+S116D, S57W+S116E, S57W+T127V, S57W+T127I, S57W+T127L, S57W+S144P, S57W+A147H, S57W+S167L, S57W+S167I, S57W+S167V, S57W+G175D, S57W+G175E, S57Y+S59V, S57Y+S59I, S57Y+S59L, S57Y+V76L, S57Y+V76I, S57Y+Q109R, S57Y+S116D, S57Y+S116E, S57Y+T127V, S57Y+T127I, S57Y+T127L, S57Y+S144P, S57Y+A147H, S57Y+S167L, S57Y+S167I, S57Y+S167V, S57Y+G175D, S57Y+G175E, S57F+S59V, S57F+S59I, S57F+S59L, S57F+V76L, S57F+V76I, S57F+Q109R, S57F+S116D, S57F+S116E, S57F+T127V, S57F+T127I, S57F+T127L, S57F+S144P, S57F+A147H, S57F+S167L, S57F+S167I, S57F+S167V, S57F+G175D, S57F+G175E, S59V+V76L, S59V+V76I, S59V+Q109R, S59V+S116D, S59V+S116E, S59V+T127V, S59V+T127I, S59V+T127L, S59V+S144P, S59V+A147H, S59V+S167L, S59V+S167I, S59V+S167V, S59V+G175D, S59V+G175E, S59I+V76L, S59I+V76I, S59I+Q109R, S59I+S116D, S59I+S116E, S59I+T127V, S59I+T127I, S59I+T127L, S59I+S144P, S59I+A147H, S59I+S167L, S59I+S167I, S59I+S167V, S59I+G175D, S59I+G175E, S59L+V76L, S59L+V76I, S59L+Q109R, S59L+S116D, S59L+S116E, S59L+T127V, S59L+T127I, S59L+T127L, S59L+S144P, S59L+A147H, S59L+S167L, S59L+S167I, S59L+S167V, S59L+G175D, S59L+G175E, V76L+Q109R, V76L+S116D, V76L+S116E, V76L+T127V, V76L+T127I, V76L+T127L, V76L+S144P, V76L+A147H, V76L+S167L, V76L+S167I, V76L+S167V, V76L+G175D, V76L+G175E, V76I+Q109R, V76I+S116D, V76I+S116E, V76I+T127V, V76I+T127I, V76I+T127L, V76I+S144P, V76I+A147H, V76I+S167L, V76I+S167I, V76I+S167V, V76I+G175D, V76I+G175E, Q109R+S116D, Q109R+S116E, Q109R+T127V, Q109R+T127I, Q109R+T127L, Q109R+S144P, Q109R+A147H, Q109R+S167L, Q109R+S167I, Q109R+S167V, Q109R+G175D, Q109R+G175E, S116D+T127V, S116D+T127I, S116D+T127L, S116D+S144P, S116D+A147H, S116D+S167L, S116D+S167I, S116D+S167V, S116D+G175D, S116D+G175E, S116E+T127V, S116E+T127I, S116E+T127L, S116E+S144P, S116E+A147H, S116E+S167L, S116E+S167I, S116E+S167V, S116E+G175D, S116E+G175E, T127V+S144P, T127V+A147H, T127V+S167L, T127V+S167I, T127V+S167V, T127V+G175D, T127V+G175E, T127I+S144P, T127I+A147H, T127I+S167L, T127I+S167I, T127I+S167V, T127I+G175D, T127I+G175E, T127L+S144P, T127L+A147H, T127L+S167L, T127L+S167I, T127L+S167V, T127L+G175D, T127L+G175E, S144P+A147H, S144P+S167L, S144P+S167I, S144P+S167V, S144P+G175D, S144P+G175E, A147H+S167L, A147H+S167I, A147H+S167V, A147H+G175D, A147H+G175E, S167L+G175D, S167L+G175E, S167I+G175D, S167I+G175E, S167V+G175D and S167V+G175E, wherein each substitution provides a DNase variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1).

One preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise an alteration at two or more positions selected from the list consisting of 1, 13, 22, 25, 27, 39, 42, 57, 59, 76, 109, 116, 127, 144, 147, 167 and 175, wherein each position corresponds to the position of the polypeptide of SEQ ID NO: 1, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1.

One preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise comprises two or more of the substitutions selected from the group consisting of: T1V, S13Y, S27L, S39P, S42A, S42T, S57W, S57F, S59V, S59I, S59L, S116E, T127I, T127L, S144P, S167L, S167I, S167V, G175D and G175E, wherein the positions correspond to the positions of SEQ ID NO: 1 (numbering according to SEQ ID NO: 1), wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1.

One preferred aspect of the invention relates to a variant of a DNase parent, wherein the variant comprises two or more substitutions (compared to SEQ ID NO: 1), wherein the substitutions is/are selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

One preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise one or more substitution set (compared to SEQ ID NO: 1) selected from the group consisting of: T1I+S13Y, T1I+T22P, T1I+S25P, T1I+S27L, T1I+S39P, T1I+S42G, T1I+S42A, T1I+S42T, T1I+S57W, T1I+S57Y, T1I+S57F, T1I+S59V, T1I+S59I, T1I+S59L, T1I+V76L, T1I+V76I, T1I+Q109R, T1I+S116D, T1I+S116E, T1I+T127V, T1I+T127I, T1I+T127L, T1I+S144P, T1I+A147H, T1I+S167L, T1I+S167I, T1I+S167V, T1I+G175D, T1I+G175E, T1L+S13Y, T1L+T22P, T1L+S25P, T1L+S27L, T1L+S39P, T1L+S42G, T1L+S42A, T1L+S42T, T1L+S57W, T1L+S57Y, T1L+S57F, T1L+S59V, T1L+S59I, T1L+S59L, T1L+V76L, T1L+V76I, T1L+Q109R, T1L+S116D, T1L+S116E, T1L+T127V, T1L+T127I, T1L+T127L, T1L+S144P, T1L+A147H, T1L+S167L, T1L+S167I, T1L+S167V, T1L+G175D, T1L+G175E, T1V+S13Y, T1V+T22P, T1V+S25P, T1V+S27L, T1V+S39P, T1V+S42G, T1V+S42A, T1V+S42T, T1V+S57W, T1V+S57Y, T1V+S57F, T1V+S59V, T1V+S59I, T1V+S59L, T1V+V76L, T1V+V76I, T1V+Q109R, T1V+S116D, T1V+S116E, T1V+T127V, T1V+T127I, T1V+T127L, T1V+S144P, T1V+A147H, T1V+S167L, T1V+S167I, T1V+S167V, T1V+G175D, T1V+G175E, S13Y+T22P, S13Y+S25P, S13Y+S27L, S13Y+S39P, S13Y+S42G, S13Y+S42A, S13Y+S42T, S13Y+S57W, S13Y+S57Y, S13Y+S57F, S13Y+S59V, S13Y+S59I, S13Y+S59L, S13Y+V76L, S13Y+V76I, S13Y+Q109R, S13Y+S116D, S13Y+S116E, S13Y+T127V, S13Y+T127I, S13Y+T127L, S13Y+S144P, S13Y+A147H, S13Y+S167L, S13Y+S167I, S13Y+S167V, S13Y+G175D, S13Y+G175E, T22P+S25P, T22P+S27L, T22P+S39P, T22P+S42G, T22P+S42A, T22P+S42T, T22P+S57W, T22P+S57Y, T22P+S57F, T22P+S59V, T22P+S59I, T22P+S59L, T22P+V76L, T22P+V76I, T22P+Q109R, T22P+S116D, T22P+S116E, T22P+T127V, T22P+T127I, T22P+T127L, T22P+S144P, T22P+A147H, T22P+S167L, T22P+S167I, T22P+S167V, T22P+G175D, T22P+G175E, S25P+S27L, S25P+S39P, S25P+S42G, S25P+S42A, S25P+S42T, S25P+S57W, S25P+S57Y, S25P+S57F, S25P+S59V, S25P+S59I, S25P+S59L, S25P+V76L, S25P+V76I, S25P+Q109R, S25P+S116D, S25P+S116E, S25P+T127V, S25P+T127I, S25P+T127L, S25P+S144P, S25P+A147H, S25P+S167L, S25P+S167I, S25P+S167V, S25P+G175D, S25P+G175E, S27L+S39P, S27L+S42G, S27L+S42A, S27L+S42T, S27L+S57W, S27L+S57Y, S27L+S57F, S27L+S59V, S27L+S59I, S27L+S59L, S27L+V76L, S27L+V76I, S27L+Q109R, S27L+S116D, S27L+S116E, S27L+T127V, S27L+T127I, S27L+T127L, S27L+S144P, S27L+A147H, S27L+S167L, S27L+S167I, S27L+S167V, S27L+G175D, S27L+G175E, S39P+S42G, S39P+S42A, S39P+S42T, S39P+S57W, S39P+S57Y, S39P+S57F, S39P+S59V, S39P+S59I, S39P+S59L, S39P+V76L, S39P+V76I, S39P+Q109R, S39P+S116D, S39P+S116E, S39P+T127V, S39P+T127I, S39P+T127L, S39P+S144P, S39P+A147H, S39P+S167L, S39P+S167I, S39P+S167V, S39P+G175D, S39P+G175E, S42G+S57W, S42G+S57Y, S42G+S57F, S42G+S59V, S42G+S59I, S42G+S59L, S42G+V76L, S42G+V76I, S42G+Q109R, S42G+S116D, S42G+S116E, S42G+T127V, S42G+T127I, S42G+T127L, S42G+S144P, S42G+A147H, S42G+S167L, S42G+S167I, S42G+S167V, S42G+G175D, S42G+G175E, S42A+S57W, S42A+S57Y, S42A+S57F, S42A+S59V, S42A+S59I, S42A+S59L, S42A+V76L, S42A+V76I, S42A+Q109R, S42A+S116D, S42A+S116E, S42A+T127V, S42A+T127I, S42A+T127L, S42A+S144P, S42A+A147H, S42A+S167L, S42A+S167I, S42A+S167V, S42A+G175D, S42A+G175E, S42T+S57W, S42T+S57Y, S42T+S57F, S42T+S59V, S42T+S59I, S42T+S59L, S42T+V76L, S42T+V76I, S42T+Q109R, S42T+S116D, S42T+S116E, S42T+T127V, S42T+T127I, S42T+T127L, S42T+S144P, S42T+A147H, S42T+S167L, S42T+S167I, S42T+S167V, S42T+G175D, S42T+G175E, S57W+S59V, S57W+S59I, S57W+S59L, S57W+V76L, S57W+V76I, S57W+Q109R, S57W+S116D, S57W+S116E, S57W+T127V, S57W+T127I, S57W+T127L, S57W+S144P, S57W+A147H, S57W+S167L, S57W+S167I, S57W+S167V, S57W+G175D, S57W+G175E, S57Y+S59V, S57Y+S59I, S57Y+S59L, S57Y+V76L, S57Y+V76I, S57Y+Q109R, S57Y+S116D, S57Y+S116E, S57Y+T127V, S57Y+T127I, S57Y+T127L, S57Y+S144P, S57Y+A147H, S57Y+S167L, S57Y+S167I, S57Y+S167V, S57Y+G175D, S57Y+G175E, S57F+S59V, S57F+S59I, S57F+S59L, S57F+V76L, S57F+V76I, S57F+Q109R, S57F+S116D, S57F+S116E, S57F+T127V, S57F+T127I, S57F+T127L, S57F+S144P, S57F+A147H, S57F+S167L, S57F+S167I, S57F+S167V, S57F+G175D, S57F+G175E, S59V+V76L, S59V+V76I, S59V+Q109R, S59V+S116D, S59V+S116E, S59V+T127V, S59V+T127I, S59V+T127L, S59V+S144P, S59V+A147H, S59V+S167L, S59V+S167I, S59V+S167V, S59V+G175D, S59V+G175E, S59I+V76L, S59I+V76I, S59I+Q109R, S59I+S116D, S59I+S116E, S59I+T127V, S59I+T127I, S59I+T127L, S59I+S144P, S59I+A147H, S59I+S167L, S59I+S167I, S59I+S167V, S59I+G175D, S59I+G175E, S59L+V76L, S59L+V76I, S59L+Q109R, S59L+S116D, S59L+S116E, S59L+T127V, S59L+T127I, S59L+T127L, S59L+S144P, S59L+A147H, S59L+S167L, S59L+S167I, S59L+S167V, S59L+G175D, S59L+G175E, V76L+Q109R, V76L+S116D, V76L+S116E, V76L+T127V, V76L+T127I, V76L+T127L, V76L+S144P, V76L+A147H, V76L+S167L, V76L+S167I, V76L+S167V, V76L+G175D, V76L+G175E, V76I+Q109R, V76I+S116D, V76I+S116E, V76I+T127V, V76I+T127I, V76I+T127L, V76I+S144P, V76I+A147H, V76I+S167L, V76I+S167I, V76I+S167V, V76I+G175D, V76I+G175E, Q109R+S116D, Q109R+S116E, Q109R+T127V, Q109R+T127I, Q109R+T127L, Q109R+S144P, Q109R+A147H, Q109R+S167L, Q109R+S167I, Q109R+S167V, Q109R+G175D, Q109R+G175E, S116D+T127V, S116D+T127I, S116D+T127L, S116D+S144P, S116D+A147H, S116D+S167L, S116D+S167I, S116D+S167V, S116D+G175D, S116D+G175E, S116E+T127V, S116E+T127I, S116E+T127L, S116E+S144P, S116E+A147H, S116E+S167L, S116E+S167I, S116E+S167V, S116E+G175D, S116E+G175E, T127V+S144P, T127V+A147H, T127V+S167L, T127V+S167I, T127V+S167V, T127V+G175D, T127V+G175E, T127I+S144P, T127I+A147H, T127I+S167L, T127I+S167I, T127I+S167V, T127I+G175D, T127I+G175E, T127L+S144P, T127L+A147H, T127L+S167L, T127L+S167I, T127L+S167V, T127L+G175D, T127L+G175E, S144P+A147H, S144P+S167L, S144P+S167I, S144P+S167V, S144P+G175D, S144P+G175E, A147H+S167L, A147H+S167I, A147H+S167V, A147H+G175D, A147H+G175E, S167L+G175D, S167L+G175E, S167I+G175D, S167I+G175E, S167V+G175D and S167V+G175E, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

Preferably a DNase variant of the invention comprises one or more of the following substitution sets: T1I+T22P, T1I+S39P, T1I+S42G, T1I+S57W, T1I+S59V, T1I+V76L, T1I+S116D, T1I+T127V, T1I+S167L, T1I+G175D, T22P+S42G, T22P+V76L, T22P+S116D, T22P+T127V, T22P+A147H, T22P+G175D, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+S144P, S39P+A147H, S39P+S167L, S42G+S57W, S42G+S59V, S42G+V76L, S42G+S116D, S42G+T127V, S42G+S144P, S42G+A147H, S42G+S167L, S42G+G175D, S57W+S59V, S57W+S116D, S57W+T127V, S57W+A147H, S59V+V76L, S59V+S116D, S59V+A147H, S59V+S167L, S59V+G175D, V76L+S116D, V76L+T127V, V76L+S144P, V76L+A147H, V76L+S167L, V76L+G175D, S116D+T127V, S116D+S144P, S116D+A147H, S116D+S167L, S116D+G175D, T127V+S144P, T127V+A147H, T127V+S167L, T127V+G175D, S144P+A147H, S144P+S167L or S167L+G175D.

Preferably a DNase variant of the invention comprises one or more of the following substitution sets: T1I+T22P, T1I+S39P, T1I+S42G, T1I+S57W, T1I+S59V, T1I+V76L, T1I+S116D, T1I+T127V, T1I+S167L, T1I+G175D, T22P+S42G, T22P+V76L, T22P+S116D, T22P+T127V, T22P+A147H, T22P+G175D, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+S144P, S39P+A147H, S39P+S167L, S42G+S57W, S42G+S59V, S42G+V76L, S42G+S116D, S42G+T127V, S42G+S144P, S42G+S167L, S42G+G175D, S57W+S59V, S57W+S116D, S57W+T127V, S57W+A147H, S59V+V76L, S59V+S116D, S59V+A147H, S59V+S167L, S59V+G175D, V76L+S116D, V76L+T127V, V76L+S144P, V76L+A147H, V76L+S167L, V76L+G175D, S116D+T127V, S116D+S144P, S116D+A147H, S116D+S167L, S116D+G175D, T127V+S144P, T127V+A147H, T127V+S167L, T127V+G175D, S144P+A147H, S144P+S167L or S167L+G175D.

One preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise one or more substitution set (compared to SEQ ID NO: 1) selected from the group consisting of: T1I+T22P, T1I+S39P, T1I+S42G, T1I+S57W, T1I+S59V, T1I+V76L, T1I+S116D, T1I+T127V, T1I+S167L, T1I+G175D, T22P+S42G, T22P+V76L, T22P+S116D, T22P+T127V, T22P+A147H, T22P+G175D, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+S144P, S39P+A147H, S39P+S167L, S42G+S57W, S42G+S59V, S42G+V76L, S42G+S116D, S42G+T127V, S42G+S144P, S42G+A147H, S42G+S167L, S42G+G175D, S57W+S59V, S57W+S116D, S57W+T127V, S57W+A147H, S59V+V76L, S59V+S116D, S59V+A147H, S59V+S167L, S59V+G175D, V76L+S116D, V76L+T127V, V76L+S144P, V76L+A147H, V76L+S167L, V76L+G175D, S116D+T127V, S116D+S144P, S116D+A147H, S116D+S167L, S116D+G175D, T127V+S144P, T127V+A147H, T127V+S167L, T127V+G175D, S144P+A147H, S144P+S167L and S167L+G175D, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

One preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise one or more substitution set (compared to SEQ ID NO: 1) selected from the group consisting of: T1I+T22P, T1I+S39P, T1I+S42G, T1I+S57W, T1I+S59V, T1I+V76L, T1I+S116D, T1I+T127V, T1I+S167L, T1I+G175D, T22P+S42G, T22P+V76L, T22P+S116D, T22P+T127V, T22P+A147H, T22P+G175D, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+S144P, S39P+A147H, S39P+S167L, S42G+S57W, S42G+S59V, S42G+V76L, S42G+S116D, S42G+T127V, S42G+S144P, S42G+S167L, S42G+G175D, S57W+S59V, S57W+S116D, S57W+T127V, S57W+A147H, S59V+V76L, S59V+S116D, S59V+A147H, S59V+S167L, S59V+G175D, V76L+S116D, V76L+T127V, V76L+S144P, V76L+A147H, V76L+S167L, V76L+G175D, S116D+T127V, S116D+S144P, S116D+A147H, S116D+S167L, S116D+G175D, T127V+S144P, T127V+A147H, T127V+S167L, T127V+G175D, S144P+A147H, S144P+S167L and S167L+G175D, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

Preferably a DNase variant of the invention comprises one or more of the following substitution sets: T1I+S39P, T1I+S42G, T22P+S116D, T22P+T127V, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+A147H, S39P+S167L, S42G+S57W, S42G+S59V, S42G+V76L, S42G+S116D, S42G+T127V, S42G+S144P, S42G+A147H, S42G+S167L, S42G+G175D, S57W+S59V, S57W+S116D, S57W+T127V, S59V+V76L, S59V+S116D, S59V+A147H, V76L+S116D, V76L+T127V, S116D+S144P, S116D+A147H, S116D+S167L, T127V+S144P, T127V+A147H, T127V+S167L, T127V+G175D or S144P+A147H.

Preferably a DNase variant of the invention comprises one or more of the following substitution sets: T1I+S39P, T1I+S42G, T22P+S116D, T22P+T127V, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+A147H, S39P+S167L, S42G+S57W, S42G+S59V, S42G+V76L, S42G+S116D, S42G+T127V, S42G+S144P, S42G+S167L, S42G+G175D, S57W+S59V, S57W+S116D, S57W+T127V, S59V+V76L, S59V+S116D, S59V+A147H, V76L+S116D, V76L+T127V, S116D+S144P, S116D+A147H, S116D+S167L, T127V+S144P, T127V+A147H, T127V+S167L, T127V+G175D or S144P+A147H.

One preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise one or more substitution set (compared to SEQ ID NO: 1) selected from the group consisting of: T1I+S39P, T1I+S42G, T22P+S116D, T22P+T127V, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+A147H, S39P+S167L, S42G+S57W, S42G+S59V, S42G+V76L, S42G+S116D, S42G+T127V, S42G+S144P, S42G+A147H, S42G+S167L, S42G+G175D, S57W+S59V, S57W+S116D, S57W+T127V, S59V+V76L, S59V+S116D, S59V+A147H, V76L+S116D, V76L+T127V, S116D+S144P, S116D+A147H, S116D+S167L, T127V+S144P, T127V+A147H, T127V+S167L, T127V+G175D and S144P+A147H, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

One preferred aspect of the invention relates to a variant of a DNase parent, wherein the variant comprises one or both motifs [D/M/L][S/T]GYSR[D/N] (SEQ ID NO: 25) or ASXNRSKG (SEQ ID NO: 26), and wherein the variant comprise one or more substitution set (compared to SEQ ID NO: 1) selected from the group consisting of: T1I+S39P, T1I+S42G, T22P+S116D, T22P+T127V, S25P+S39P, S25P+S42G, S25P+S59V, S25P+V76L, S25P+S116D, S25P+T127V, S25P+S167L, S39P+S42G, S39P+S57W, S39P+S59V, S39P+V76L, S39P+S116D, S39P+T127V, S39P+A147H, S39P+S167L, S42G+S57W, S42G+S59V, S42G+V76L, S42G+S116D, S42G+T127V, S42G+S144P, S42G+S167L, S42G+G175D, S57W+S59V, S57W+S116D, S57W+T127V, S59V+V76L, S59V+S116D, S59V+A147H, V76L+S116D, V76L+T127V, S116D+S144P, S116D+A147H, S116D+S167L, T127V+S144P, T127V+A147H, T127V+S167L, T127V+G175D and S144P+A147H, wherein each substitution provides a DNase variant having an increase in stability measured as half-life improvement factor, HIF, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent DNase e.g. a DNase comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

The variants according to the invention may comprise additional mutations to the ones listed above. These additional modifications should preferably not significantly change the improved properties of the variant DNase.

Addition of any one of the mutations T1 I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D or G175E, have shown to improve stability. What have also been shown is adding more than one provides increased and even synergistic additional stability to the parent molecule or starting molecule e.g. such as SEQ ID NO: 1 or polypeptides having at least 80% sequence identity hereto, se e.g. examples 2 to 6. In one preferred embodiment the variant of the invention comprises at least three substitutions wherein the substitutions are selected from the group consisting of: T1I, S13Y, T22P, S25P, S27L, S39P, S42G, S57W, S59V, V76L, Q109R, S116D, T127V, S144P, A147H, S167L and G175D. In one embodiment the DNase variant is selected from the group consisting of:

T1I+S13Y+T22P, T1I+S13Y+S25P, T1I+S13Y+S27L, T1I+S13Y+S39P, T1I+S13Y+S42G, T1I+S13Y+S57W, T1I+S13Y+S59V, T1I+S13Y+V76L, T1I+S13Y+Q109R, T1I+S13Y+S116D, T1I+S13Y+T127V, T1I+S13Y+S144P, T1I+S13Y+A147H, T1I+S13Y+S167L, T1I+S13Y+G175D, T1I+T22P+S25P, T1I+T22P+S27L, T1I+T22P+S39P, T1I+T22P+S42G, T1I+T22P+S57W, T1I+T22P+S59V, T1I+T22P+V76L, T1I+T22P+Q109R, T1I+T22P+S116D, T1I+T22P+T127V, T1I+T22P+S144P, T1I+T22P+A147H, T1I+T22P+S167L, T1I+T22P+G175D, T1I+S25P+S27L, T1I+S25P+S39P, T1I+S25P+S42G, T1I+S25P+S57W, T1I+S25P+S59V, T1I+S25P+V76L, T1I+S25P+Q109R, T1I+S25P+S116D, T1I+S25P+T127V, T1I+S25P+S144P, T1I+S25P+A147H, T1I+S25P+S167L, T1I+S25P+G175D, T1I+S27L+S39P, T1I+S27L+S42G, T1I+S27L+S57W, T1I+S27L+S59V, T1I+S27L+V76L, T1I+S27L+Q109R, T1I+S27L+S116D, T1I+S27L+T127V, T1I+S27L+S144P, T1I+S27L+A147H, T1I+S27L+S167L, T1I+S27L+G175D, T1I+S39P+S42G, T1I+S39P+S57W, T1I+S39P+S59V, T1I+S39P+V76L, T1I+S39P+Q109R, T1I+S39P+S116D, T1I+S39P+T127V, T1I+S39P+S144P, T1I+S39P+A147H, T1I+S39P+S167L, T1I+S39P+G175D, T1I+S42G+S57W, T1I+S42G+S59V, T1I+S42G+V76L, T1I+S42G+Q109R, T1I+S42G+S116D, T1I+S42G+T127V, T1I+S42G+S144P, T1I+S42G+A147H, T1I+S42G+S167L, T1I+S42G+G175D, T1I+S57W+S59V, T1I+S57W+V76L, T1I+S57W+Q109R, T1I+S57W+S116D, T1I+S57W+T127V, T1I+S57W+S144P, T1I+S57W+A147H, T1I+S57W+S167L, T1I+S57W+G175D, T1I+S59V+V76L, T1I+S59V+Q109R, T1I+S59V+S116D, T1I+S59V+T127V, T1I+S59V+S144P, T1I+S59V+A147H, T1I+S59V+S167L, T1I+S59V+G175D, T1I+V76L+Q109R, T1I+V76L+S116D, T1I+V76L+T127V, T1I+V76L+S144P, T1I+V76L+A147H, T1I+V76L+S167L, T1I+V76L+G175D, T1I+Q109R+S116D, T1I+Q109R+T127V, T1I+Q109R+S144P, T1I+Q109R+A147H, T1I+Q109R+S167L, T1I+Q109R+G175D, T1I+S116D+T127V, T1I+S116D+S144P, T1I+S116D+A147H, T1I+S116D+S167L, T1I+S116D+G175D, T1I+T127V+S144P, T1I+T127V+A147H, T1I+T127V+S167L, T1I+T127V+G175D, T1I+S144P+A147H, T1I+S144P+S167L, T1I+S144P+G175D, T1I+A147H+S167L, T1I+A147H+G175D, T1I+S167L+G175D, S13Y+T22P+S25P, S13Y+T22P+S27L, S13Y+T22P+S39P, S13Y+T22P+S42G, S13Y+T22P+S57W, S13Y+T22P+S59V, S13Y+T22P+V76L, S13Y+T22P+Q109R, S13Y+T22P+S116D, S13Y+T22P+T127V, S13Y+T22P+S144P, S13Y+T22P+A147H, S13Y+T22P+S167L, S13Y+T22P+G175D, S13Y+S25P+S27L, S13Y+S25P+S39P, S13Y+S25P+S42G, S13Y+S25P+S57W, S13Y+S25P+S59V, S13Y+S25P+V76L, S13Y+S25P+Q109R, S13Y+S25P+S116D, S13Y+S25P+T127V, S13Y+S25P+S144P, S13Y+S25P+A147H, S13Y+S25P+S167L, S13Y+S25P+G175D, S13Y+S27L+S39P, S13Y+S27L+S42G, S13Y+S27L+S57W, S13Y+S27L+S59V, S13Y+S27L+V76L, S13Y+S27L+Q109R, S13Y+S27L+S116D, S13Y+S27L+T127V, S13Y+S27L+S144P, S13Y+S27L+A147H, S13Y+S27L+S167L, S13Y+S27L+G175D, S13Y+S39P+S42G, S13Y+S39P+S57W, S13Y+S39P+S59V, S13Y+S39P+V76L, S13Y+S39P+Q109R, S13Y+S39P+S116D, S13Y+S39P+T127V, S13Y+S39P+S144P, S13Y+S39P+A147H, S13Y+S39P+S167L, S13Y+S39P+G175D, S13Y+S42G+S57W, S13Y+S42G+S59V, S13Y+S42G+V76L, S13Y+S42G+Q109R, S13Y+S42G+S116D, S13Y+S42G+T127V, S13Y+S42G+S144P, S13Y+S42G+A147H, S13Y+S42G+S167L, S13Y+S42G+G175D, S13Y+S57W+S59V, S13Y+S57W+V76L, S13Y+S57W+Q109R, S13Y+S57W+S116D, S13Y+S57W+T127V, S13Y+S57W+S144P, S13Y+S57W+A147H, S13Y+S57W+S167L, S13Y+S57W+G175D, S13Y+S59V+V76L, S13Y+S59V+Q109R, S13Y+S59V+S116D, S13Y+S59V+T127V, S13Y+S59V+S144P, S13Y+S59V+A147H, S13Y+S59V+S167L, S13Y+S59V+G175D, S13Y+V76L+Q109R, S13Y+V76L+S116D, S13Y+V76L+T127V, S13Y+V76L+S144P, S13Y+V76L+A147H, S13Y+V76L+S167L, S13Y+V76L+G175D, S13Y+Q109R+S116D, S13Y+Q109R+T127V, S13Y+Q109R+S144P, S13Y+Q109R+A147H, S13Y+Q109R+S167L, S13Y+Q109R+G175D, S13Y+S116D+T127V, S13Y+S116D+S144P, S13Y+S116D+A147H, S13Y+S116D+S167L, S13Y+S116D+G175D, S13Y+T127V+S144P, S13Y+T127V+A147H, S13Y+T127V+S167L, S13Y+T127V+G175D, S13Y+S144P+A147H, S13Y+S144P+S167L, S13Y+S144P+G175D, S13Y+A147H+S167L, S13Y+A147H+G175D, S13Y+S167L+G175D, T22P+S25P+S27L, T22P+S25P+S39P, T22P+S25P+S42G, T22P+S25P+S57W, T22P+S25P+S59V, T22P+S25P+V76L, T22P+S25P+Q109R, T22P+S25P+S116D, T22P+S25P+T127V, T22P+S25P+S144P, T22P+S25P+A147H, T22P+S25P+S167L, T22P+S25P+G175D, T22P+S27L+S39P, T22P+S27L+S42G, T22P+S27L+S57W, T22P+S27L+S59V, T22P+S27L+V76L, T22P+S27L+Q109R, T22P+S27L+S116D, T22P+S27L+T127V, T22P+S27L+S144P, T22P+S27L+A147H, T22P+S27L+S167L, T22P+S27L+G175D, T22P+S39P+

S42G, T22P+S39P+S57W, T22P+S39P+S59V, T22P+S39P+V76L, T22P+S39P+Q109R, T22P+S39P+S116D, T22P+S39P+T127V, T22P+S39P+S144P, T22P+S39P+A147H, T22P+S39P+S167L, T22P+S39P+G175D, T22P+S42G+S57W, T22P+S42G+S59V, T22P+S42G+V76L, T22P+S42G+Q109R, T22P+S42G+S116D, T22P+S42G+T127V, T22P+S42G+S144P, T22P+S42G+A147H, T22P+S42G+S167L, T22P+S42G+G175D, T22P+S57W+S59V, T22P+S57W+V76L, T22P+S57W+Q109R, T22P+S57W+S116D, T22P+S57W+T127V, T22P+S57W+S144P, T22P+S57W+A147H, T22P+S57W+S167L, T22P+S57W+G175D, T22P+S59V+V76L, T22P+S59V+Q109R, T22P+S59V+S116D, T22P+S59V+T127V, T22P+S59V+S144P, T22P+S59V+A147H, T22P+S59V+S167L, T22P+S59V+G175D, T22P+V76L+Q109R, T22P+V76L+S116D, T22P+V76L+T127V, T22P+V76L+S144P, T22P+V76L+A147H, T22P+V76L+S167L, T22P+V76L+G175D, T22P+Q109R+S116D, T22P+Q109R+T127V, T22P+Q109R+S144P, T22P+Q109R+A147H, T22P+Q109R+S167L, T22P+Q109R+G175D, T22P+S116D+T127V, T22P+S116D+S144P, T22P+S116D+A147H, T22P+S116D+S167L, T22P+S116D+G175D, T22P+T127V+S144P, T22P+T127V+A147H, T22P+T127V+S167L, T22P+T127V+G175D, T22P+S144P+A147H, T22P+S144P+S167L, T22P+S144P+G175D, T22P+A147H+S167L, T22P+A147H+G175D, T22P+S167L+G175D, S25P+S27L+S39P, S25P+S27L+S42G, S25P+S27L+S57W, S25P+S27L+S59V, S25P+S27L+V76L, S25P+S27L+Q109R, S25P+S27L+S116D, S25P+S27L+T127V, S25P+S27L+S144P, S25P+S27L+A147H, S25P+S27L+S167L, S25P+S27L+G175D, S25P+S39P+S42G, S25P+S39P+S57W, S25P+S39P+S59V, S25P+S39P+V76L, S25P+S39P+Q109R, S25P+S39P+S116D, S25P+S39P+T127V, S25P+S39P+S144P, S25P+S39P+A147H, S25P+S39P+S167L, S25P+S39P+G175D, S25P+S42G+S57W, S25P+S42G+S59V, S25P+S42G+V76L, S25P+S42G+Q109R, S25P+S42G+S116D, S25P+S42G+T127V, S25P+S42G+S144P, S25P+S42G+A147H, S25P+S42G+S167L, S25P+S42G+G175D, S25P+S57W+S59V, S25P+S57W+V76L, S25P+S57W+Q109R, S25P+S57W+S116D, S25P+S57W+T127V, S25P+S57W+S144P, S25P+S57W+A147H, S25P+S57W+S167L, S25P+S57W+G175D, S25P+S59V+V76L, S25P+S59V+Q109R, S25P+S59V+S116D, S25P+S59V+T127V, S25P+S59V+S144P, S25P+S59V+A147H, S25P+S59V+S167L, S25P+S59V+G175D, S25P+V76L+Q109R, S25P+V76L+S116D, S25P+V76L+T127V, S25P+V76L+S144P, S25P+V76L+A147H, S25P+V76L+S167L, S25P+V76L+G175D, S25P+Q109R+S116D, S25P+Q109R+T127V, S25P+Q109R+S144P, S25P+Q109R+A147H, S25P+Q109R+S167L, S25P+Q109R+G175D, S25P+S116D+T127V, S25P+S116D+S144P, S25P+S116D+A147H, S25P+S116D+S167L, S25P+S116D+G175D, S25P+T127V+S144P, S25P+T127V+A147H, S25P+T127V+S167L, S25P+T127V+G175D, S25P+S144P+A147H, S25P+S144P+S167L, S25P+S144P+G175D, S25P+A147H+S167L, S25P+A147H+G175D, S25P+S167L+G175D, S27L+S39P+S42G, S27L+S39P+S57W, S27L+S39P+S59V, S27L+S39P+V76L, S27L+S39P+Q109R, S27L+S39P+S116D, S27L+S39P+T127V, S27L+S39P+S144P, S27L+S39P+A147H, S27L+S39P+S167L, S27L+S39P+G175D, S27L+S42G+S57W, S27L+S42G+S59V, S27L+S42G+V76L, S27L+S42G+Q109R, S27L+S42G+S116D, S27L+S42G+T127V, S27L+S42G+S144P, S27L+S42G+A147H, S27L+S42G+S167L, S27L+S42G+G175D, S27L+S57W+S59V, S27L+S57W+V76L, S27L+S57W+Q109R, S27L+S57W+S116D, S27L+S57W+T127V, S27L+S57W+S144P, S27L+S57W+A147H, S27L+S57W+S167L, S27L+S57W+G175D, S27L+S59V+V76L, S27L+S59V+Q109R, S27L+S59V+S116D, S27L+S59V+T127V, S27L+S59V+S144P, S27L+S59V+A147H, S27L+S59V+S167L, S27L+S59V+G175D, S27L+V76L+Q109R, S27L+V76L+S116D, S27L+V76L+T127V, S27L+V76L+S144P, S27L+V76L+A147H, S27L+V76L+S167L, S27L+V76L+G175D, S27L+Q109R+S116D, S27L+Q109R+T127V, S27L+Q109R+S144P, S27L+Q109R+A147H, S27L+Q109R+S167L, S27L+Q109R+G175D, S27L+S116D+T127V, S27L+S116D+S144P, S27L+S116D+A147H, S27L+S116D+S167L, S27L+S116D+G175D, S27L+T127V+S144P, S27L+T127V+A147H, S27L+T127V+S167L, S27L+T127V+G175D, S27L+S144P+A147H, S27L+S144P+S167L, S27L+S144P+G175D, S27L+A147H+S167L, S27L+A147H+G175D, S27L+S167L+G175D, S39P+S42G+S57W, S39P+S42G+S59V, S39P+S42G+V76L, S39P+S42G+Q109R, S39P+S42G+S116D, S39P+S42G+T127V, S39P+S42G+S144P, S39P+S42G+A147H, S39P+S42G+S167L, S39P+S42G+G175D, S39P+S57W+S59V, S39P+S57W+V76L, S39P+S57W+Q109R, S39P+S57W+S116D, S39P+S57W+T127V, S39P+S57W+S144P, S39P+S57W+A147H, S39P+S57W+S167L, S39P+S57W+G175D, S39P+S59V+V76L, S39P+S59V+Q109R, S39P+S59V+S116D, S39P+S59V+T127V, S39P+S59V+S144P, S39P+S59V+A147H, S39P+S59V+S167L, S39P+S59V+G175D, S39P+V76L+Q109R, S39P+V76L+S116D, S39P+V76L+T127V, S39P+V76L+S144P, S39P+V76L+A147H, S39P+V76L+S167L, S39P+V76L+G175D, S39P+Q109R+S116D, S39P+Q109R+T127V, S39P+Q109R+S144P, S39P+Q109R+A147H, S39P+Q109R+S167L, S39P+Q109R+G175D, S39P+S116D+T127V, S39P+S116D+S144P, S39P+S116D+A147H, S39P+S116D+S167L, S39P+S116D+G175D, S39P+T127V+S144P, S39P+T127V+A147H, S39P+T127V+S167L, S39P+T127V+G175D, S39P+S144P+A147H, S39P+S144P+S167L, S39P+S144P+G175D, S39P+A147H+S167L, S39P+A147H+G175D, S39P+S167L+G175D, S42G+S57W+S59V, S42G+S57W+V76L, S42G+S57W+Q109R, S42G+S57W+S116D, S42G+S57W+T127V, S42G+S57W+S144P, S42G+S57W+A147H, S42G+S57W+S167L, S42G+S57W+G175D, S42G+S59V+V76L, S42G+S59V+Q109R, S42G+S59V+S116D, S42G+S59V+T127V, S42G+S59V+S144P, S42G+S59V+A147H, S42G+S59V+S167L, S42G+S59V+G175D, S42G+V76L+Q109R, S42G+V76L+S116D, S42G+V76L+T127V, S42G+V76L+S144P, S42G+V76L+A147H, S42G+V76L+S167L, S42G+V76L+G175D, S42G+Q109R+S116D, S42G+Q109R+T127V, S42G+Q109R+S144P, S42G+Q109R+A147H, S42G+Q109R+S167L, S42G+Q109R+G175D, S42G+S116D+T127V, S42G+S116D+S144P, S42G+S116D+A147H, S42G+S116D+S167L, S42G+S116D+G175D, S42G+T127V+S144P, S42G+T127V+A147H, S42G+T127V+S167L, S42G+T127V+G175D, S42G+S144P+A147H, S42G+S144P+S167L, S42G+S144P+G175D, S42G+A147H+S167L, S42G+A147H+G175D, S42G+S167L+G175D, S57W+S59V+V76L, S57W+S59V+Q109R, S57W+S59V+S116D, S57W+S59V+T127V, S57W+S59V+S144P, S57W+S59V+A147H, S57W+S59V+S167L, S57W+S59V+G175D, S57W+V76L+Q109R, S57W+V76L+S116D, S57W+V76L+T127V, S57W+V76L+S144P, S57W+V76L+A147H, S57W+V76L+S167L, S57W+V76L+G175D, S57W+Q109R+S116D, S57W+Q109R+T127V, S57W+Q109R+S144P, S57W+Q109R+A147H, S57W+Q109R+S167L, S57W+Q109R+G175D, S57W+S116D+T127V, S57W+S116D+S144P, S57W+S116D+A147H, S57W+S116D+S167L, S57W+S116D+G175D, S57W+T127V+S144P, S57W+T127V+A147H, S57W+

T127V+S167L, S57W+T127V+G175D, S57W+S144P+A147H, S57W+S144P+S167L, S57W+S144P+G175D, S57W+A147H+S167L, S57W+A147H+G175D, S57W+S167L+G175D, S59V+V76L+Q109R, S59V+V76L+S116D, S59V+V76L+T127V, S59V+V76L+S144P, S59V+V76L+A147H, S59V+V76L+S167L, S59V+V76L+G175D, S59V+Q109R+S116D, S59V+Q109R+T127V, S59V+Q109R+S144P, S59V+Q109R+A147H, S59V+Q109R+S167L, S59V+Q109R+G175D, S59V+S116D+T127V, S59V+S116D+S144P, S59V+S116D+A147H, S59V+S116D+S167L, S59V+S116D+G175D, S59V+T127V+S144P, S59V+T127V+A147H, S59V+T127V+S167L, S59V+T127V+G175D, S59V+S144P+A147H, S59V+S144P+S167L, S59V+S144P+G175D, S59V+A147H+S167L, S59V+A147H+G175D, S59V+S167L+G175D, V76L+Q109R+S116D, V76L+Q109R+T127V, V76L+Q109R+S144P, V76L+Q109R+A147H, V76L+Q109R+S167L, V76L+Q109R+G175D, V76L+S116D+T127V, V76L+S116D+S144P, V76L+S116D+A147H, V76L+S116D+S167L, V76L+S116D+G175D, V76L+T127V+S144P, V76L+T127V+A147H, V76L+T127V+S167L, V76L+T127V+G175D, V76L+S144P+A147H, V76L+S144P+S167L, V76L+S144P+G175D, V76L+A147H+S167L, V76L+A147H+G175D, V76L+S167L+G175D, Q109R+S116D+T127V, Q109R+S116D+S144P, Q109R+S116D+A147H, Q109R+S116D+S167L, Q109R+S116D+G175D, Q109R+T127V+S144P, Q109R+T127V+A147H, Q109R+T127V+S167L, Q109R+T127V+G175D, Q109R+S144P+A147H, Q109R+S144P+S167L, Q109R+S144P+G175D, Q109R+A147H+S167L, Q109R+A147H+G175D, Q109R+S167L+G175D, S116D+T127V+S144P, S116D+T127V+A147H, S116D+T127V+S167L, S116D+T127V+G175D, S116D+S144P+A147H, S116D+S144P+S167L, S116D+S144P+G175D, S116D+A147H+S167L, S116D+A147H+G175D, S116D+S167L+G175D, T127V+S144P+A147H, T127V+S144P+S167L, T127V+S144P+G175D, T127V+A147H+S167L, T127V+A147H+G175D, T127V+S167L+G175D, S144P+A147H+S167L, S144P+A147H+G175D, S144P+S167L+G175D and A147H+S167L+G175D.

In one embodiment the two or more mutations are selected from any of the following T1I, S13Y, T22P, S25P, S27L, S39P, S42G, S57W, S59V, V76L, Q109R, S116, T127V, S144P, A147H, S167L or G175D. In one embodiment the two or more mutations are selected from any of the following T1I, S13Y, T22P, S25P, S27L, S39P, S42G, S57W, S59V, V76L, Q109R, S116D, T127V, S144P, A147H, S167L or G175D, preferably wherein the variant comprises more than 10 mutations, preferably 11, 12, 13, 14, 15, 16 or all of the mutations: T1I, S13Y, T22P, S25P, S27L, S39P, S42G, S57W, S59V, V76L, Q109R, S116D, T127V, S144P, A147H, S167L or G175D.

In one particular preferred embodiment the DNase variant is selected from any of the following: T1I+S13Y+T22P+S25P+S27L+S39P+S42G+S57W+S59V+V76L+Q109R+S116D+T127V+S144P; T1I+S13Y+T22P+S25P+S27L+S39P+S42G+S57W+S59V+V76L+Q109R+S116D+T127V+A147H; T1I+S13Y+T22P+S25P+S27L+S39P+S42G+S57W+S59V+V76L+Q109R+S116D+T127V+S167L; T1I+S13Y+T22P+S25P+S27L+S39P+S42G+S57W+S59V+V76L+Q109R+S116D+T127V+G175D; T1I+S13Y+T22P+S25P+S27L+S39P+S42G+S57W+S59V+V76L+Q109R+S116D+S144P+A147H; T1I+S13Y+T22P+S25P+S27L+S39P+S42G+S57W+S59V+V76L+Q109R+S116D+S144P+S167L; T1I+S13Y+T22P+S25P+S27L+S39P+S42G+S57W+S59V+V76L+Q109R+S116D+S144P+G175D T1I+S13Y+T22P+S25P+S27L+S39P+S42G+S57W+S59V+V76L+Q109R+S116D+A147H+S167L; T1I+S13Y+T22P+S25P+S27L+S39P+S42G+S57W+S59V+V76L+Q109R+S116D+A147H+G175D T1I+S13Y+T22P+S25P+S27L+S39P+S42G+S57W+S59V+V76L+Q109R+S116D+S167L+G175D; T1I+S13Y+T22P+S25P+S27L+S39P+S42G+S57W+S59V+V76L+Q109R+T127V+S144P+A147H; T1I+S13Y+T22P+S25P+S27L+S39P+S42G+S57W+S59V+V76L+Q109R+T127V+S144P+S167L; T1I+S13Y+T22P+S25P+S27L+S39P+S42G+S57W+S59V+V76L+Q109R+T127V+S144P+G175D; T1I+S13Y+T22P+S25P+S27L+S39P+S42G+S57W+S59V+V76L+Q109R+T127V+A147H+S167L; T1I+S13Y+T22P+S25P+S27L+S39P+S42G+S57W+S59V+V76L+Q109R+T127V+A147H+G175D; T1I+S13Y+T22P+S25P+S27L+S39P+S42G+S57W+S59V+V76L+Q109R+T127V+S167L+G175D; T1I+S13Y+T22P+S25P+S27L+S39P+S42G+S57W+S59V+V76L+Q109R+S144P+A147H+S167L; T1I+S13Y+T22P+S25P+S27L+S39P+S42G+S57W+S59V+V76L+Q109R+S144P+A147H+G175D T1I+S13Y+T22P+S25P+S27L+S39P+S42G+S57W+S59V+V76L+Q109R+S144P+S167L+G175D; T1I+S13Y+T22P+S25P+S27L+S39P+S42G+S57W+S59V+V76L+Q109R+A147H+S167L+G175D; T1I+S13Y+T22P+S25P+S27L+S39P+S42G+S57W+S59V+V76L+S116D+T127V+S144P+A147H; T1I+S13Y+T22P+S25P+S27L+S39P+S42G+S57W+S59V+V76L+S116D+T127V+S144P+S167L; T1I+S13Y+T22P+S25P+S27L+S39P+S42G+S57W+S59V+V76L+S116D+T127V+S144P+G175D; T1I+S13Y+T22P+S25P+S27L+S39P+S42G+S57W+S59V+V76L+S116D+T127V+A147H+S167L; T1I+S13Y+T22P+S25P+S27L+S39P+S42G+S57W+S59V+V76L+S116D+T127V+A147H+G175D; T1I+S13Y+T22P+S25P+S27L+S39P+S42G+S57W+S59V+V76L+S116D+T127V+S167L+G175D; T1I+S13Y+T22P+S25P+S27L+S39P+S42G+S57W+S59V+V76L+S116D+S144P+A147H+S167L; T1I+S13Y+T22P+S25P+S27L+S39P+S42G+S57W+S59V+V76L+S116D+S144P+A147H+G175D; T1I+S13Y+T22P+S25P+S27L+S39P+S42G+S57W+S59V+V76L+S116D+S144P+S167L+G175D; T1I+S13Y+T22P+S25P+S27L+S39P+S42G+S57W+S59V+V76L+S116D+A147H+S167L+G175D; T1I+S13Y+T22P+S25P+S27L+S39P+S42G+S57W+S59V+V76L+T127V+S144P+A147H+S167L; T1I+S13Y+T22P+S25P+S27L+S39P+S42G+S57W+S59V+V76L+T127V+S144P+A147H+G175D; T1I+S13Y+T22P+S25P+S27L+S39P+S42G+S57W+S59V+V76L+T127V+S144P+S167L+G175D; T1I+S13Y+T22P+S25P+S27L+S39P+S42G+S57W+S59V+V76L+T127V+A147H+S167L+G175D; T1I+S13Y+T22P+S25P+S27L+S39P+S42G+S57W+S59V+V76L+S144P+A147H+S167L+G175D; T1I+S13Y+T22P+S25P+S27L+S39P+S42G+S57W+S59V+Q109R+S116D+T127V+S144P+A147H T1I+S13Y+T22P+S25P+S27L+S39P+S42G+S57W+S59V+Q109R+S116D+T127V+S144P+S167 L T1I+S13Y+T22P+S25P+S27L+S39P+S42G+S57W+S59V+Q109R+S116D+T127V+S144P+G175D; T1I+S13Y+T22P+S25P+S27L+S39P+S42G+S57W+S59V+Q109R+S116D+T127V+A147H+S167 L T1I+S13Y+T22P+S25P+S27L+S39P+S42G+S57W+S59V+Q109R+S116D+T127V+A147H+G175D; T1I+S13Y+T22P+S25P+S27L+S39P+S42G+S57W+S59V+Q109R+S116D+T127V+S167L+G175D; T1I+S13Y+T22P+S25P+S27L+S39P+S42G+S57W+S59V+Q109R+S116D+S144P+A147H+S167; T1I+S13Y+T22P+S25P+S27L+S39P+S42G+S57W+S59V+Q109R+S116D+S144P+A147H+G175D; T1I+S13Y+T22P+S25P+S27L+S39P+S42G+S57W+S59V+Q109R+S116D+S144P+S167L+G175D; T1I+S13Y+T22P+S25P+S27L+S39P+

S42G+S57W+S59V+Q109R+S116D+A147H+S167L+G175D; T1I+S13Y+T22P+S25P+S27L+S39P+S42G+S57W+S59V+Q109R+T127V+S144P+A147H+S167; T1I+S13Y+T22P+S25P+S27L+S39P+S42G+S57W+S59V+Q109R+T127V+S144P+A147H+G175D; T1I+S13Y+T22P+S25P+S27L+S39P+S42G+S57W+S59V+Q109R+T127V+S144P+S167L+G175; T1I+S13Y+T22P+S25P+S27L+S39P+S42G+S57W+S59V+Q109R+T127V+A147H+S167L+G175D; T1I+S13Y+T22P+S25P+S27L+S39P+S42G+S57W+S59V+Q109R+S144P+A147H+S167L+G175D; T1I+S13Y+T22P+S25P+S27L+S39P+S42G+S57W+S59V+S116D+T127V+S144P+A147H+S167 L T1I+S13Y+T22P+S25P+S27L+S39P+S42G+S57W+S59V+S116D+T127V+S144P+A147H+G175D; T1I+S13Y+T22P+S25P+S27L+S39P+S42G+S57W+S59V+S116D+T127V+S144P+S167L+G175D; T1I+S13Y+T22P+S25P+S27L+S39P+S42G+S57W+S59V+S116D+T127V+A147H+S167L+G175D; T1I+S13Y+T22P+S25P+S27L+S39P+S42G+S57W+S59V+S116D+S144P+A147H+S167L+G175D; T1I+S13Y+T22P+S25P+S27L+S39P+S42G+S57W+S59V+T127V+S144P+A147H+S167L+G175D; T1I+S13Y+T22P+S25P+S27L+S39P+S42G+S57W+V76L+Q109R+S116D+T127V+S144P+A147H T1I+S13Y+T22P+S25P+S27L+S39P+S42G+S57W+V76L+Q109R+S116D+T127V+S144P+S167L; T1I+S13Y+T22P+S25P+S27L+S39P+S42G+S57W+V76L+Q109R+S116D+T127V+S144P+G175D; T1I+S13Y+T22P+S25P+S27L+S39P+S42G+S57W+V76L+Q109R+S116D+T127V+A147H+S167 L T1I+S13Y+T22P+S25P+S27L+S39P+S42G+S57W+V76L+Q109R+S116D+T127V+A147H+T1I+S13Y+T22P+S25P+S27L+S39P+S42G+S57W+V76L+Q109R+S116D+T127V+S167L+G175D; T1I+S13Y+T22P+S25P+S27L+S39P+S42G+S57W+V76L+Q109R+S116D+S144P+A147H+S167 L T1I+S13Y+T22P+S25P+S27L+S39P+S42G+S57W+V76L+Q109R+S116D+S144P+A147H+G175D; T1I+S13Y+T22P+S25P+S27L+S39P+S42G+S57W+V76L+Q109R+S116D+S144P+S167L+G175D; T1I+S13Y+T22P+S25P+S27L+S39P+S42G+S57W+V76L+Q109R+S116D+A147H+S167L+G175D; T1I+S13Y+T22P+S25P+S27L+S39P+S42G+S57W+V76L+Q109R+T127V+S144P+A147H+S167 L T1I+S13Y+T22P+S25P+S27L+S39P+S42G+S57W+V76L+Q109R+T127V+S144P+A147H+G175D; T1I+S13Y+T22P+S25P+S27L+S39P+S42G+S57W+V76L+Q109R+T127V+S144P+S167L+G175D; T1I+S13Y+T22P+S25P+S27L+S39P+S42G+S57W+V76L+Q109R+T127V+A147H+S167L+G175D; T1I+S13Y+T22P+S25P+S27L+S39P+S42G+S57W+V76L+Q109R+S144P+A147H+S167L+G175D; T1I+S13Y+T22P+S25P+S27L+S39P+S42G+S57W+V76L+S116D+T127V+S144P+A147H+S167L T1I+S13Y+T22P+S25P+S27L+S39P+S42G+S57W+V76L+S116D+T127V+S144P+A147H+G175D; T1I+S13Y+T22P+S25P+S27L+S39P+S42G+S57W+V76L+S116D+T127V+S144P+S167L+G175D; T1I+S13Y+T22P+S25P+S27L+S39P+S42G+S57W+V76L+S116D+T127V+A147H+S167L+G175D; T1I+S13Y+T22P+S25P+S27L+S39P+S42G+S57W+V76L+S116D+S144P+A147H+S167L+G175D; T1I+S13Y+T22P+S25P+S27L+S39P+S42G+S57W+V76L+T127V+S144P+A147H+S167L+G175D; T1I+S13Y+T22P+S25P+S27L+S39P+S42G+S57W+Q109R+S116D+T127V+S144P+A147H+S167L; T1I+S13Y+T22P+S25P+S27L+S39P+S42G+S57W+Q109R+S116D+T127V+S144P+A147H+G175D; T1I+S13Y+T22P+S25P+S27L+S39P+S42G+S57W+Q109R+S116D+T127V+S144P+S167L+G175D; T1I+S13Y+T22P+S25P+S27L+S39P+S42G+S57W+Q109R+S116D+T127V+A147H+

S167L+G175D; T1I+S13Y+T22P+S25P+S27L+S39P+S42G+S57W+Q109R+S116D+S144P+A147H+S167L+G175D; T1I+S13Y+T22P+S25P+S27L+S39P+S42G+S57W+Q109R+T127V+S144P+A147H+S167L+G175D; T1I+S13Y+T22P+S25P+S27L+S39P+S42G+S57W+S116D+T127V+S144P+A147H+S167L+G175D; T1I+S13Y+T22P+S25P+S27L+S39P+S42G+S59V+V76L+Q109R+S116D+T127V+S144P+A147H T1I+S13Y+T22P+S25P+S27L+S39P+S42G+S59V+V76L+Q109R+S116D+T127V+S144P+S167L T1I+S13Y+T22P+S25P+S27L+S39P+S42G+S59V+V76L+Q109R+S116D+T127V+S144P+G175D; T1I+S13Y+T22P+S25P+S27L+S39P+S42G+S59V+V76L+Q109R+S116D+T127V+A147H+S167L T1I+S13Y+T22P+S25P+S27L+S39P+S42G+S59V+V76L+Q109R+S116D+T127V+A147H+G175D; T1I+S13Y+T22P+S25P+S27L+S39P+S42G+S59V+V76L+Q109R+S116D+T127V+S167L+G175D T1I+S13Y+T22P+S25P+S27L+S39P+S42G+S59V+V76L+Q109R+S116D+S144P+A147H+S167L T1I+S13Y+T22P+S25P+S27L+S39P+S42G+S59V+V76L+Q109R+S116D+S144P+A147H+G175D; T1I+S13Y+T22P+S25P+S27L+S39P+S42G+S59V+V76L+Q109R+S116D+S144P+S167L+G175D T1I+S13Y+T22P+S25P+S27L+S39P+S42G+S59V+V76L+Q109R+S116D+A147H+S167L+G175 D T1I+S13Y+T22P+S25P+S27L+S39P+S42G+S59V+V76L+Q109R+T127V+S144P+A147H+S167L T1I+S13Y+T22P+S25P+S27L+S39P+S42G+S59V+V76L+Q109R+T127V+S144P+A147H+T1I+S13Y+T22P+S25P+S27L+S39P+S42G+S59V+V76L+Q109R+T127V+S144P+S167L+G175D T1I+S13Y+T22P+S25P+S27L+S39P+S42G+S59V+V76L+Q109R+T127V+A147H+S167L+G175D T1I+S13Y+T22P+S25P+S27L+S39P+S42G+S59V+V76L+Q109R+S144P+A147H+S167L+G175D T1I+S13Y+T22P+S25P+S27L+S39P+S42G+S59V+V76L+S116D+T127V+S144P+A147H+S167L; T1I+S13Y+T22P+S25P+S27L+S39P+S42G+S59V+V76L+S116D+T127V+S144P+A147H+G175D T1I+S13Y+T22P+S25P+S27L+S39P+S42G+S59V+V76L+S116D+T127V+S144P+S167L+G175D T1I+S13Y+T22P+S25P+S27L+S39P+S42G+S59V+V76L+S116D+T127V+A147H+S167L+G175D T1I+S13Y+T22P+S25P+S27L+S39P+S42G+S59V+V76L+S116D+S144P+A147H+S167L+G175D T1I+S13Y+T22P+S25P+S27L+S39P+S42G+S59V+V76L+T127V+S144P+A147H+S167L+G175D T1I+S13Y+T22P+S25P+S27L+S39P+S42G+S59V+Q109R+S116D+T127V+S144P+A147H+S167L; T1I+S13Y+T22P+S25P+S27L+S39P+S42G+S59V+Q109R+S116D+T127V+S144P+A147H+G175D; T1I+S13Y+T22P+S25P+S27L+S39P+S42G+S59V+Q109R+S116D+T127V+S144P+S167L+G175D; T1I+S13Y+T22P+S25P+S27L+S39P+S42G+S59V+Q109R+S116D+T127V+A147H+S167L+G175D; T1I+S13Y+T22P+S25P+S27L+S39P+S42G+S59V+Q109R+S116D+S144P+A147H+S167L+G175D; T1I+S13Y+T22P+S25P+S27L+S39P+S42G+S59V+Q109R+T127V+S144P+A147H+S167L+G175D; T1I+S13Y+T22P+S25P+S27L+S39P+S42G+S59V+S116D+T127V+S144P+A147H+S167L+G175D; T1I+S13Y+T22P+S25P+S27L+S39P+S42G+V76L+Q109R+S116D+T127V+S144P+A147H+S167L; T1I+S13Y+T22P+S25P+S27L+S39P+S42G+V76L+Q109R+S116D+T127V+S144P+A147H+T1I+S13Y+T22P+S25P+S27L+S39P+S42G+V76L+Q109R+S116D+T127V+S144P+S167L+G175D; T1I+S13Y+T22P+S25P+S27L+S39P+S42G+V76L+Q109R+S116D+T127V+A147H+S167L+G175D; T1I+S13Y+T22P+S25P+S27L+S39P+S42G+V76L+Q109R+S116D+S144P+A147H+S167L+G175D; T1I+S13Y+T22P+S25P+S27L+S39P+S42G+

V76L+Q109R+T127V+S144P+A147H+S167L+G175D; T1I+S13Y+T22P+S25P+S27L+S39P+S42G+V76L+S116D+T127V+S144P+A147H+S167L+G175D; T1I+S13Y+T22P+S25P+S27L+S39P+S42G+Q109R+S116D+T127V+S144P+A147H+S167L+G175D; T1I+S13Y+T22P+S25P+S27L+S39P+S57W+S59V+V76L+Q109R+S116D+T127V+S144P+A147H; T1I+S13Y+T22P+S25P+S27L+S39P+S57W+S59V+V76L+Q109R+S116D+T127V+S144P+S167L T1I+S13Y+T22P+S25P+S27L+S39P+S57W+S59V+V76L+Q109R+S116D+T127V+S144P+G175D; T1I+S13Y+T22P+S25P+S27L+S39P+S57W+S59V+V76L+Q109R+S116D+T127V+A147H+S167L T1I+S13Y+T22P+S25P+S27L+S39P+S57W+S59V+V76L+Q109R+S116D+T127V+A147H+G175D; T1I+S13Y+T22P+S25P+S27L+S39P+S57W+S59V+V76L+Q109R+S116D+T127V+S167L+G175D; T1I+S13Y+T22P+S25P+S27L+S39P+S57W+S59V+V76L+Q109R+S116D+S144P+A147H+S167L; T1I+S13Y+T22P+S25P+S27L+S39P+S57W+S59V+V76L+Q109R+S116D+S144P+A147H+G175D; T1I+S13Y+T22P+S25P+S27L+S39P+S57W+S59V+V76L+Q109R+S116D+S144P+S167L+G175D; T1I+S13Y+T22P+S25P+S27L+S39P+S57W+S59V+V76L+Q109R+S116D+A147H+S167L+G175D; T1I+S13Y+T22P+S25P+S27L+S39P+S57W+S59V+V76L+Q109R+T127V+S144P+A147H+S167L T1I+S13Y+T22P+S25P+S27L+S39P+S57W+S59V+V76L+Q109R+T127V+S144P+A147H+G175D; T1I+S13Y+T22P+S25P+S27L+S39P+S57W+S59V+V76L+Q109R+T127V+S144P+S167L+G175D; T1I+S13Y+T22P+S25P+S27L+S39P+S57W+S59V+V76L+Q109R+T127V+A147H+S167L+G175D; T1I+S13Y+T22P+S25P+S27L+S39P+S57W+S59V+V76L+Q109R+S144P+A147H+S167L+G175D; T1I+S13Y+T22P+S25P+S27L+S39P+S57W+S59V+V76L+S116D+T127V+S144P+A147H+S167L T1I+S13Y+T22P+S25P+S27L+S39P+S57W+S59V+V76L+S116D+T127V+S144P+A147H+G175D; T1I+S13Y+T22P+S25P+S27L+S39P+S57W+S59V+V76L+S116D+T127V+S144P+S167L+G175D T1I+S13Y+T22P+S25P+S27L+S39P+S57W+S59V+V76L+S116D+T127V+A147H+S167L+G175D T1I+S13Y+T22P+S25P+S27L+S39P+S57W+S59V+V76L+S116D+S144P+A147H+S167L+G175D; T1I+S13Y+T22P+S25P+S27L+S39P+S57W+S59V+V76L+T127V+S144P+A147H+S167L+G175D T1I+S13Y+T22P+S25P+S27L+S39P+S57W+S59V+Q109R+S116D+T127V+S144P+A147H+S167L; T1I+S13Y+T22P+S25P+S27L+S39P+S57W+S59V+Q109R+S116D+T127V+S144P+A147H+G175D; T1I+S13Y+T22P+S25P+S27L+S39P+S57W+S59V+Q109R+S116D+T127V+S144P+S167L+G175D; T1I+S13Y+T22P+S25P+S27L+S39P+S57W+S59V+Q109R+S116D+T127V+A147H+S167L+G175D; T1I+S13Y+T22P+S25P+S27L+S39P+S57W+S59V+Q109R+S116D+S144P+A147H+S167L+G175D; T1I+S13Y+T22P+S25P+S27L+S39P+S57W+S59V+Q109R+T127V+S144P+A147H+S167L+G175D; T1I+S13Y+T22P+S25P+S27L+S39P+S57W+S59V+S116D+T127V+S144P+A147H+S167L+G175D; T1I+S13Y+T22P+S25P+S27L+S39P+S57W+V76L+Q109R+S116D+T127V+S144P+A147H+S167L; T1I+S13Y+T22P+S25P+S27L+S39P+S57W+V76L+Q109R+S116D+T127V+S144P+A147H+G175D; T1I+S13Y+T22P+S25P+S27L+S39P+S57W+V76L+Q109R+S116D+T127V+S144P+S167L+G175D; T1I+S13Y+T22P+S25P+S27L+S39P+S57W+V76L+Q109R+S116D+T127V+A147H+S167L+G175D; T1I+S13Y+T22P+S25P+S27L+S39P+S57W+V76L+Q109R+S116D+S144P+A147H+S167L+G175D; T1I+S13Y+T22P+S25P+S27L+S39P+S57W+V76L+Q109R+T127V+S144P+A147H+S167L+G175D; T1I+S13Y+T22P+S25P+S27L+S39P+S57W+V76L+S116D+T127V+S144P+A147H+S167L+G175D; T1I+S13Y+T22P+S25P+S27L+S39P+S57W+Q109R+S116D+T127V+S144P+A147H+S167L+G175D; T1I+S13Y+T22P+S25P+S27L+S39P+S59V+V76L+Q109R+S116D+T127V+S144P+A147H+S167L; T1I+S13Y+T22P+S25P+S27L+S39P+S59V+V76L+Q109R+S116D+T127V+S144P+A147H+G175D; T1I+S13Y+T22P+S25P+S27L+S39P+S59V+V76L+Q109R+S116D+T127V+S144P+S167L+G175D; T1I+S13Y+T22P+S25P+S27L+S39P+S59V+V76L+Q109R+S116D+T127V+A147H+S167L+G175D; T1I+S13Y+T22P+S25P+S27L+S39P+S59V+V76L+Q109R+S116D+S144P+A147H+S167L+G175D; T1I+S13Y+T22P+S25P+S27L+S39P+S59V+V76L+Q109R+T127V+S144P+A147H+S167L+G175D; T1I+S13Y+T22P+S25P+S27L+S39P+S59V+V76L+S116D+T127V+S144P+A147H+S167L+G175D; T1I+S13Y+T22P+S25P+S27L+S39P+S59V+Q109R+S116D+T127V+S144P+A147H+S167L+G175D; T1I+S13Y+T22P+S25P+S27L+S39P+V76L+Q109R+S116D+T127V+S144P+A147H+S167L+G175D; T1I+S13Y+T22P+S25P+S27L+S42G+S57W+S59V+V76L+Q109R+S116D+T127V+S144P+A147; T1I+S13Y+T22P+S25P+S27L+S42G+S57W+S59V+V76L+Q109R+S116D+T127V+S144P+S167; T1I+S13Y+T22P+S25P+S27L+S42G+S57W+S59V+V76L+Q109R+S116D+T127V+S144P+G175D; T1I+S13Y+T22P+S25P+S27L+S42G+S57W+S59V+V76L+Q109R+S116D+T127V+A147H+S167; T1I+S13Y+T22P+S25P+S27L+S42G+S57W+S59V+V76L+Q109R+S116D+T127V+A147H+G175D; T1I+S13Y+T22P+S25P+S27L+S42G+S57W+S59V+V76L+Q109R+S116D+T127V+S167L+G175; T1I+S13Y+T22P+S25P+S27L+S42G+S57W+S59V+V76L+Q109R+S116D+S144P+A147H+S167; T1I+S13Y+T22P+S25P+S27L+S42G+S57W+S59V+V76L+Q109R+S116D+S144P+A147H+G175D; T1I+S13Y+T22P+S25P+S27L+S42G+S57W+S59V+V76L+Q109R+S116D+S144P+S167L+G175; T1I+S13Y+T22P+S25P+S27L+S42G+S57W+S59V+V76L+Q109R+S116D+A147H+S167L+G175D; T1I+S13Y+T22P+S25P+S27L+S42G+S57W+S59V+V76L+Q109R+T127V+S144P+A147H+S167; T1I+S13Y+T22P+S25P+S27L+S42G+S57W+S59V+V76L+Q109R+T127V+S144P+A147H+G175D; T1I+S13Y+T22P+S25P+S27L+S42G+S57W+S59V+V76L+Q109R+T127V+S144P+S167L+G175D; T1I+S13Y+T22P+S25P+S27L+S42G+S57W+S59V+V76L+Q109R+T127V+A147H+S167L+G175D; T1I+S13Y+T22P+S25P+S27L+S42G+S57W+S59V+V76L+Q109R+S144P+A147H+S167L+G175D; T1I+S13Y+T22P+S25P+S27L+S42G+S57W+S59V+V76L+S116D+T127V+S144P+A147H+S167L T1I+S13Y+T22P+S25P+S27L+S42G+S57W+S59V+V76L+S116D+T127V+S144P+A147H+G175D; T1I+S13Y+T22P+S25P+S27L+S42G+S57W+S59V+V76L+S116D+T127V+S144P+S167L+G175D; T1I+S13Y+T22P+S25P+S27L+S42G+S57W+S59V+V76L+S116D+T127V+A147H+S167L+G175D; T1I+S13Y+T22P+S25P+S27L+S42G+S57W+S59V+V76L+S116D+S144P+A147H+S167L+G175D; T1I+S13Y+T22P+S25P+S27L+S42G+S57W+S59V+V76L+T127V+S144P+A147H+S167L+G175D; T1I+S13Y+T22P+S25P+S27L+S42G+S57W+S59V+Q109R+S116D+T127V+S144P+A147H+S167L; T1I+S13Y+T22P+S25P+S27L+S42G+S57W+S59V+Q109R+S116D+T127V+S144P+A147H+G175D; T1I+S13Y+T22P+S25P+S27L+S42G+S57W+S59V+Q109R+S116D+T127V+S144P+S167L+G175D; T1I+S13Y+T22P+S25P+S27L+S42G+S57W+S59V+Q109R+S116D+T127V+A147H+S167L+G175D; T1I+

S13Y+T22P+S25P+S27L+S42G+S57W+S59V+Q109R+S116D+S144P+A147H+S167L+G175D; T1I+S13Y+T22P+S25P+S27L+S42G+S57W+S59V+Q109R+T127V+S144P+A147H+S167L+G175D; T1I+S13Y+T22P+S25P+S27L+S42G+S57W+S59V+S116D+T127V+S144P+A147H+S167L+G175D; T1I+S13Y+T22P+S25P+S27L+S42G+S57W+V76L+Q109R+S116D+T127V+S144P+A147H+S167L; T1I+S13Y+T22P+S25P+S27L+S42G+S57W+V76L+Q109R+S116D+T127V+S144P+A147H+G175D; T1I+S13Y+T22P+S25P+S27L+S42G+S57W+V76L+Q109R+S116D+T127V+S144P+S167L+G175D; T1I+S13Y+T22P+S25P+S27L+S42G+S57W+V76L+Q109R+S116D+T127V+A147H+S167L+G175D; T1I+S13Y+T22P+S25P+S27L+S42G+S57W+V76L+Q109R+S116D+S144P+A147H+S167L+G175D; T1I+S13Y+T22P+S25P+S27L+S42G+S57W+V76L+Q109R+T127V+S144P+A147H+S167L+G175D; T1I+S13Y+T22P+S25P+S27L+S42G+S57W+V76L+S116D+T127V+S144P+A147H+S167L+G175D; T1I+S13Y+T22P+S25P+S27L+S42G+S57W+Q109R+S116D+T127V+S144P+A147H+S167L+G175D; T1I+S13Y+T22P+S25P+S27L+S42G+S59V+V76L+Q109R+S116D+T127V+S144P+A147H+S167L; T1I+S13Y+T22P+S25P+S27L+S42G+S59V+V76L+Q109R+S116D+T127V+S144P+A147H+G175D; T1I+S13Y+T22P+S25P+S27L+S42G+S59V+V76L+Q109R+S116D+T127V+S144P+S167L+G175D; T1I+S13Y+T22P+S25P+S27L+S42G+S59V+V76L+Q109R+S116D+T127V+A147H+S167L+T1I+S13Y+T22P+S25P+S27L+S42G+S59V+V76L+Q109R+S116D+S144P+A147H+S167L+G175D; T1I+S13Y+T22P+S25P+S27L+S42G+S59V+V76L+Q109R+T127V+S144P+A147H+S167L+G175D; T1I+S13Y+T22P+S25P+S27L+S42G+S59V+V76L+S116D+T127V+S144P+A147H+S167L+G175D; T1I+S13Y+T22P+S25P+S27L+S42G+S59V+Q109R+S116D+T127V+S144P+A147H+S167L+G175D; T1I+S13Y+T22P+S25P+S27L+S42G+V76L+Q109R+S116D+T127V+S144P+A147H+S167L+G175D; T1I+S13Y+T22P+S25P+S27L+S57W+S59V+V76L+Q109R+S116D+T127V+S144P+A147H+S167L; T1I+S13Y+T22P+S25P+S27L+S57W+S59V+V76L+Q109R+S116D+T127V+S144P+A147H+G175D; T1I+S13Y+T22P+S25P+S27L+S57W+S59V+V76L+Q109R+S116D+T127V+S144P+S167L+G175D; T1I+S13Y+T22P+S25P+S27L+S57W+S59V+V76L+Q109R+S116D+T127V+A147H+S167L+G175D; T1I+S13Y+T22P+S25P+S27L+S57W+S59V+V76L+Q109R+S116D+S144P+A147H+S167L+G175D; T1I+S13Y+T22P+S25P+S27L+S57W+S59V+V76L+Q109R+T127V+S144P+A147H+S167L+G175D; T1I+S13Y+T22P+S25P+S27L+S57W+S59V+V76L+S116D+T127V+S144P+A147H+S167L+G175D; T1I+S13Y+T22P+S25P+S27L+S57W+S59V+Q109R+S116D+T127V+S144P+A147H+S167L+G175D; T1I+S13Y+T22P+S25P+S27L+S57W+V76L+Q109R+S116D+T127V+S144P+A147H+S167L+G175D; T1I+S13Y+T22P+S25P+S27L+S59V+V76L+Q109R+S116D+T127V+S144P+A147H+S167L+G175D; T1I+S13Y+T22P+S25P+S39P+S42G+S57W+S59V+V76L+Q109R+S116D+T127V+S144P+A147H; T1I+S13Y+T22P+S25P+S39P+S42G+S57W+S59V+V76L+Q109R+S116D+T127V+S144P+S167L; T1I+S13Y+T22P+S25P+S39P+S42G+S57W+S59V+V76L+Q109R+S116D+T127V+S144P+G175D; T1I+S13Y+T22P+S25P+S39P+S42G+S57W+S59V+V76L+Q109R+S116D+T127V+A147H+S167L; T1I+S13Y+T22P+S25P+S39P+S42G+S57W+S59V+V76L+Q109R+S116D+T127V+A147H+G175D; T1I+S13Y+T22P+S25P+S39P+S42G+S57W+S59V+V76L+Q109R+S116D+T127V+S167L+G175D; T1I+S13Y+T22P+S25P+S39P+S42G+S57W+S59V+V76L+Q109R+S116D+S144P+A147H+S167; T1I+S13Y+T22P+S25P+S39P+S42G+S57W+S59V+V76L+Q109R+S116D+S144P+A147H+G175D; T1I+S13Y+T22P+S25P+S39P+S42G+S57W+S59V+V76L+Q109R+S116D+S144P+S167L+G175D; T1I+S13Y+T22P+S25P+S39P+S42G+S57W+S59V+V76L+Q109R+S116D+A147H+S167L+G175D; T1I+S13Y+T22P+S25P+S39P+S42G+S57W+S59V+V76L+Q109R+T127V+S144P+A147H+S167; T1I+S13Y+T22P+S25P+S39P+S42G+S57W+S59V+V76L+Q109R+T127V+S144P+A147H+G175D; T1I+S13Y+T22P+S25P+S39P+S42G+S57W+S59V+V76L+Q109R+T127V+S144P+S167L+G175; T1I+S13Y+T22P+S25P+S39P+S42G+S57W+S59V+V76L+Q109R+T127V+A147H+S167L+G175D; T1I+S13Y+T22P+S25P+S39P+S42G+S57W+S59V+V76L+Q109R+S144P+A147H+S167L+G175D; T1I+S13Y+T22P+S25P+S39P+S42G+S57W+S59V+V76L+S116D+T127V+S144P+A147H+S167; T1I+S13Y+T22P+S25P+S39P+S42G+S57W+S59V+V76L+S116D+T127V+S144P+A147H+G175D; T1I+S13Y+T22P+S25P+S39P+S42G+S57W+S59V+V76L+S116D+T127V+S144P+S167L+G175 D; T1I+S13Y+T22P+S25P+S39P+S42G+S57W+S59V+V76L+S116D+T127V+A147H+S167L+G175 D; T1I+S13Y+T22P+S25P+S39P+S42G+S57W+S59V+V76L+S116D+S144P+A147H+S167L+G175 D; T1I+S13Y+T22P+S25P+S39P+S42G+S57W+S59V+V76L+T127V+S144P+A147H+S167L+G175 D; T1I+S13Y+T22P+S25P+S39P+S42G+S57W+S59V+Q109R+S116D+T127V+S144P+A147H+S167L; T1I+S13Y+T22P+S25P+S39P+S42G+S57W+S59V+Q109R+S116D+T127V+S144P+A147H+G175D; T1I+S13Y+T22P+S25P+S39P+S42G+S57W+S59V+Q109R+S116D+T127V+S144P+S167L+G17 5D; T1I+S13Y+T22P+S25P+S39P+S42G+S57W+S59V+Q109R+S116D+T127V+A147H+S167L+G175D; T1I+S13Y+T22P+S25P+S39P+S42G+S57W+S59V+Q109R+S116D+S144P+A147H+S167L+G175D; T1I+S13Y+T22P+S25P+S39P+S42G+S57W+S59V+Q109R+T127V+S144P+A147H+S167L+G175D; T1I+S13Y+T22P+S25P+S39P+S42G+S57W+S59V+S116D+T127V+S144P+A147H+S167L+G175D; T1I+S13Y+T22P+S25P+S39P+S42G+S57W+V76L+Q109R+S116D+T127V+S144P+A147H+S167L; T1I+S13Y+T22P+S25P+S39P+S42G+S57W+V76L+Q109R+S116D+T127V+S144P+A147H+G175D; T1I+S13Y+T22P+S25P+S39P+S42G+S57W+V76L+Q109R+S116D+T127V+S144P+S167L+G175D; T1I+S13Y+T22P+S25P+S39P+S42G+S57W+V76L+Q109R+S116D+T127V+A147H+S167L+G175D; T1I+S13Y+T22P+S25P+S39P+S42G+S57W+V76L+Q109R+S116D+S144P+A147H+S167L+G175D; T1I+S13Y+T22P+S25P+S39P+S42G+S57W+V76L+Q109R+T127V+S144P+A147H+S167L+G175D; T1I+S13Y+T22P+S25P+S39P+S42G+S57W+V76L+S116D+T127V+S144P+A147H+S167L+G175D; T1I+S13Y+T22P+S25P+S39P+S42G+S57W+Q109R+S116D+T127V+S144P+A147H+S167L+G175D; T1I+S13Y+T22P+S25P+S39P+S42G+S59V+V76L+Q109R+S116D+T127V+S144P+A147H+S167L; T1I+S13Y+T22P+S25P+S39P+S42G+S59V+V76L+Q109R+S116D+T127V+S144P+A147H+G175D; T1I+S13Y+T22P+S25P+S39P+S42G+S59V+V76L+Q109R+S116D+T127V+S144P+S167L+G175D; T1I+S13Y+T22P+S25P+S39P+S42G+S59V+V76L+Q109R+S116D+T127V+A147H+S167L+G175D; T1I+S13Y+T22P+S25P+S39P+S42G+S59V+V76L+Q109R+S116D+S144P+A147H+S167L+G175D; T1I+S13Y+T22P+S25P+S39P+S42G+S59V+V76L+Q109R+T127V+S144P+A147H+S167L+G175D; T1I+S13Y+T22P+S25P+S39P+

S42G+S59V+V76L+S116D+T127V+S144P+A147H+S167L+G175D; T1I+S13Y+T22P+S25P+S39P+S42G+S59V+Q109R+S116D+T127V+S144P+A147H+S167L+G175D; T1I+S13Y+T22P+S25P+S39P+S42G+V76L+Q109R+S116D+T127V+S144P+A147H+S167L+G175D; T1I+S13Y+T22P+S25P+S39P+S57W+S59V+V76L+Q109R+S116D+T127V+S144P+A147H+S167L; T1I+S13Y+T22P+S25P+S39P+S57W+S59V+V76L+Q109R+S116D+T127V+S144P+A147H+G175D; T1I+S13Y+T22P+S25P+S39P+S57W+S59V+V76L+Q109R+S116D+T127V+S144P+S167L+G175D; T1I+S13Y+T22P+S25P+S39P+S57W+S59V+V76L+Q109R+S116D+T127V+A147H+S167L+G175D; T1I+S13Y+T22P+S25P+S39P+S57W+S59V+V76L+Q109R+S116D+S144P+A147H+S167L+G175D; T1I+S13Y+T22P+S25P+S39P+S57W+S59V+V76L+Q109R+T127V+S144P+A147H+S167L+G175D; T1I+S13Y+T22P+S25P+S39P+S57W+S59V+V76L+S116D+T127V+S144P+A147H+S167L+G175D; T1I+S13Y+T22P+S25P+S39P+S57W+S59V+Q109R+S116D+T127V+S144P+A147H+S167L+G175D; T1I+S13Y+T22P+S25P+S39P+S57W+V76L+Q109R+S116D+T127V+S144P+A147H+S167L+G175D; T1I+S13Y+T22P+S25P+S39P+S59V+V76L+Q109R+S116D+T127V+S144P+A147H+S167L+G175D; T1I+S13Y+T22P+S25P+S42G+S57W+S59V+V76L+Q109R+S116D+T127V+S144P+A147H+S167L; T1I+S13Y+T22P+S25P+S42G+S57W+S59V+V76L+Q109R+S116D+T127V+S144P+A147H+T1I+S13Y+T22P+S25P+S42G+S57W+S59V+V76L+Q109R+S116D+T127V+S144P+S167L+G175D; T1I+S13Y+T22P+S25P+S42G+S57W+S59V+V76L+Q109R+S116D+T127V+A147H+S167L+G175D; T1I+S13Y+T22P+S25P+S42G+S57W+S59V+V76L+Q109R+S116D+S144P+A147H+S167L+G175D; T1I+S13Y+T22P+S25P+S42G+S57W+S59V+V76L+Q109R+T127V+S144P+A147H+S167L+G175D; T1I+S13Y+T22P+S25P+S42G+S57W+S59V+V76L+S116D+T127V+S144P+A147H+S167L+G175D; T1I+S13Y+T22P+S25P+S42G+S57W+S59V+Q109R+S116D+T127V+S144P+A147H+S167L+G175D; T1I+S13Y+T22P+S25P+S42G+S57W+V76L+Q109R+S116D+T127V+S144P+A147H+S167L+G175D; T1I+S13Y+T22P+S25P+S42G+S59V+V76L+Q109R+S116D+T127V+S144P+A147H+S167L+G175D; T1I+S13Y+T22P+S25P+S57W+S59V+V76L+Q109R+S116D+T127V+S144P+A147H+S167L+G175D; T1I+S13Y+T22P+S27L+S39P+S42G+S57W+S59V+V76L+Q109R+S116D+T127V+S144P+A147H; T1I+S13Y+T22P+S27L+S39P+S42G+S57W+S59V+V76L+Q109R+S116D+T127V+S144P+S167L; T1I+S13Y+T22P+S27L+S39P+S42G+S57W+S59V+V76L+Q109R+S116D+T127V+S144P+G175D; T1I+S13Y+T22P+S27L+S39P+S42G+S57W+S59V+V76L+Q109R+S116D+T127V+A147H+S167L; T1I+S13Y+T22P+S27L+S39P+S42G+S57W+S59V+V76L+Q109R+S116D+T127V+A147H+G175D; T1I+S13Y+T22P+S27L+S39P+S42G+S57W+S59V+V76L+Q109R+S116D+T127V+S167L+G175D; T1I+S13Y+T22P+S27L+S39P+S42G+S57W+S59V+V76L+Q109R+S116D+S144P+A147H+S167L; T1I+S13Y+T22P+S27L+S39P+S42G+S57W+S59V+V76L+Q109R+S116D+S144P+A147H+G175D; T1I+S13Y+T22P+S27L+S39P+S42G+S57W+S59V+V76L+Q109R+S116D+S144P+S167L+G175D; T1I+S13Y+T22P+S27L+S39P+S42G+S57W+S59V+V76L+Q109R+S116D+A147H+S167L+G175D; T1I+S13Y+T22P+S27L+S39P+S42G+S57W+S59V+V76L+Q109R+T127V+S144P+A147H+S167L; T1I+S13Y+T22P+S27L+S39P+S42G+S57W+S59V+V76L+Q109R+T127V+S144P+A147H+G175D; T1I+S13Y+T22P+S27L+S39P+S42G+S57W+

S59V+V76L+Q109R+T127V+S144P+S167L+G175D; T1I+S13Y+T22P+S27L+S39P+S42G+S57W+S59V+V76L+Q109R+T127V+A147H+S167L+G175D; T1I+S13Y+T22P+S27L+S39P+S42G+S57W+S59V+V76L+Q109R+S144P+A147H+S167L+G175D; T1I+S13Y+T22P+S27L+S39P+S42G+S57W+S59V+V76L+S116D+T127V+S144P+A147H+S167L T1I+S13Y+T22P+S27L+S39P+S42G+S57W+S59V+V76L+S116D+T127V+S144P+A147H+G175D; T1I+S13Y+T22P+S27L+S39P+S42G+S57W+S59V+V76L+S116D+T127V+S144P+S167L+G175D; T1I+S13Y+T22P+S27L+S39P+S42G+S57W+S59V+V76L+S116D+T127V+A147H+S167L+G175D; T1I+S13Y+T22P+S27L+S39P+S42G+S57W+S59V+V76L+S116D+S144P+A147H+S167L+G175D; T1I+S13Y+T22P+S27L+S39P+S42G+S57W+S59V+V76L+T127V+S144P+A147H+S167L+G175D; T1I+S13Y+T22P+S27L+S39P+S42G+S57W+S59V+Q109R+S116D+T127V+S144P+A147H+S167L; T1I+S13Y+T22P+S27L+S39P+S42G+S57W+S59V+Q109R+S116D+T127V+S144P+A147H+G175D; T1I+S13Y+T22P+S27L+S39P+S42G+S57W+S59V+Q109R+S116D+T127V+S144P+S167L+G175D; T1I+S13Y+T22P+S27L+S39P+S42G+S57W+S59V+Q109R+S116D+T127V+A147H+S167L+G175D; T1I+S13Y+T22P+S27L+S39P+S42G+S57W+S59V+Q109R+S116D+S144P+A147H+S167L+ T1I+S13Y+T22P+S27L+S39P+S42G+S57W+S59V+Q109R+T127V+S144P+A147H+S167L+G175D; T1I+S13Y+T22P+S27L+S39P+S42G+S57W+S59V+S116D+T127V+S144P+A147H+S167L+G175D; T1I+S13Y+T22P+S27L+S39P+S42G+S57W+V76L+Q109R+S116D+T127V+S144P+A147H+S167L; T1I+S13Y+T22P+S27L+S39P+S42G+S57W+V76L+Q109R+S116D+T127V+S144P+A147H+G175D; T1I+S13Y+T22P+S27L+S39P+S42G+S57W+V76L+Q109R+S116D+T127V+S144P+S167L+G175D; T1I+S13Y+T22P+S27L+S39P+S42G+S57W+V76L+Q109R+S116D+T127V+A147H+S167L+G175D; T1I+S13Y+T22P+S27L+S39P+S42G+S57W+V76L+Q109R+S116D+S144P+A147H+S167L+G175D; T1I+S13Y+T22P+S27L+S39P+S42G+S57W+V76L+Q109R+T127V+S144P+A147H+S167L+G175D; T1I+S13Y+T22P+S27L+S39P+S42G+S57W+V76L+S116D+T127V+S144P+A147H+S167L+G175D; T1I+S13Y+T22P+S27L+S39P+S42G+S57W+Q109R+S116D+T127V+S144P+A147H+S167L+G175D; T1I+S13Y+T22P+S27L+S39P+S42G+S59V+V76L+Q109R+S116D+T127V+S144P+A147H+S167L; T1I+S13Y+T22P+S27L+S39P+S42G+S59V+V76L+Q109R+S116D+T127V+S144P+A147H+G175D; T1I+S13Y+T22P+S27L+S39P+S42G+S59V+V76L+Q109R+S116D+T127V+S144P+S167L+G175D; T1I+S13Y+T22P+S27L+S39P+S42G+S59V+V76L+Q109R+S116D+T127V+A147H+S167L+G175D; T1I+S13Y+T22P+S27L+S39P+S42G+S59V+V76L+Q109R+S116D+S144P+A147H+S167L+G175D; T1I+S13Y+T22P+S27L+S39P+S42G+S59V+V76L+Q109R+T127V+S144P+A147H+S167L+G175D; T1I+S13Y+T22P+S27L+S39P+S42G+S59V+V76L+S116D+T127V+S144P+A147H+S167L+G175D; T1I+S13Y+T22P+S27L+S39P+S42G+S59V+Q109R+S116D+T127V+S144P+A147H+S167L+G175D; T1I+S13Y+T22P+S27L+S39P+S42G+V76L+Q109R+S116D+T127V+S144P+A147H+S167L+G175D; T1I+S13Y+T22P+S27L+S39P+S57W+S59V+V76L+Q109R+S116D+T127V+S144P+A147H+S167L; T1I+S13Y+T22P+S27L+S39P+S57W+S59V+V76L+Q109R+S116D+T127V+S144P+A147H+G175D; T1I+S13Y+T22P+S27L+S39P+S57W+S59V+V76L+Q109R+S116D+T127V+S144P+S167L+G175D; T1I+S13Y+T22P+S27L+S39P+S57W+S59V+V76L+

Q109R+S116D+T127V+A147H+S167L+G175D; T1I+S13Y+T22P+S27L+S39P+S57W+S59V+V76L+Q109R+S116D+S144P+A147H+S167L+G175D; T1I+S13Y+T22P+S27L+S39P+S57W+S59V+V76L+Q109R+T127V+S144P+A147H+S167L+G175D; T1I+S13Y+T22P+S27L+S39P+S57W+S59V+V76L+S116D+T127V+S144P+A147H+S167L+G175D; T1I+S13Y+T22P+S27L+S39P+S57W+S59V+Q109R+S116D+T127V+S144P+A147H+S167L+G175D; T1I+S13Y+T22P+S27L+S39P+S57W+V76L+Q109R+S116D+T127V+S144P+A147H+S167L+G175D; T1I+S13Y+T22P+S27L+S39P+S59V+V76L+Q109R+S116D+T127V+S144P+A147H+S167L+G175D; T1I+S13Y+T22P+S27L+S42G+S57W+S59V+V76L+Q109R+S116D+T127V+S144P+A147H+S167L; T1I+S13Y+T22P+S27L+S42G+S57W+S59V+V76L+Q109R+S116D+T127V+S144P+A147H+G175D; T1I+S13Y+T22P+S27L+S42G+S57W+S59V+V76L+Q109R+S116D+T127V+S144P+S167L+G175D; T1I+S13Y+T22P+S27L+S42G+S57W+S59V+V76L+Q109R+S116D+T127V+A147H+S167L+G175D; T1I+S13Y+T22P+S27L+S42G+S57W+S59V+V76L+Q109R+S116D+S144P+A147H+S167L+G175D; T1I+S13Y+T22P+S27L+S42G+S57W+S59V+V76L+Q109R+T127V+S144P+A147H+S167L+T1I+S13Y+T22P+S27L+S42G+S57W+S59V+V76L+S116D+T127V+S144P+A147H+S167L+G175D; T1I+S13Y+T22P+S27L+S42G+S57W+S59V+Q109R+S116D+T127V+S144P+A147H+S167L+G175D; T1I+S13Y+T22P+S27L+S42G+S57W+V76L+Q109R+S116D+T127V+S144P+A147H+S167L+G175D; T1I+S13Y+T22P+S27L+S42G+S59V+V76L+Q109R+S116D+T127V+S144P+A147H+S167L+G175D; T1I+S13Y+T22P+S27L+S57W+S59V+V76L+Q109R+S116D+T127V+S144P+A147H+S167L+G175D; T1I+S13Y+T22P+S39P+S42G+S57W+S59V+V76L+Q109R+S116D+T127V+S144P+A147H+S167L; T1I+S13Y+T22P+S39P+S42G+S57W+S59V+V76L+Q109R+S116D+T127V+S144P+A147H+G175D; T1I+S13Y+T22P+S39P+S42G+S57W+S59V+V76L+Q109R+S116D+T127V+S144P+S167L+G175D; T1I+S13Y+T22P+S39P+S42G+S57W+S59V+V76L+Q109R+S116D+T127V+A147H+S167L+G175D; T1I+S13Y+T22P+S39P+S42G+S57W+S59V+V76L+Q109R+S116D+S144P+A147H+S167L+G175D; T1I+S13Y+T22P+S39P+S42G+S57W+S59V+V76L+Q109R+T127V+S144P+A147H+S167L+G175D; T1I+S13Y+T22P+S39P+S42G+S57W+S59V+V76L+S116D+T127V+S144P+A147H+S167L+G175D; T1I+S13Y+T22P+S39P+S42G+S57W+S59V+Q109R+S116D+T127V+S144P+A147H+S167L+G175D; T1I+S13Y+T22P+S39P+S42G+S57W+V76L+Q109R+S116D+T127V+S144P+A147H+S167L+G175D; T1I+S13Y+T22P+S39P+S42G+S59V+V76L+Q109R+S116D+T127V+S144P+A147H+S167L+G175D; T1I+S13Y+T22P+S39P+S57W+S59V+V76L+Q109R+S116D+T127V+S144P+A147H+S167L+G175D; T1I+S13Y+T22P+S42G+S57W+S59V+V76L+Q109R+S116D+T127V+S144P+A147H+S167L+G175D; T1I+S13Y+S25P+S27L+S39P+S42G+S57W+S59V+V76L+Q109R+S116D+T127V+S144P+A147H, T1I+S13Y+S25P+S27L+S39P+S42G+S57W+S59V+V76L+Q109R+S116D+T127V+S144P+S167L; T1I+S13Y+S25P+S27L+S39P+S42G+S57W+S59V+V76L+Q109R+S116D+T127V+S144P+G175D; T1I+S13Y+S25P+S27L+S39P+S42G+S57W+S59V+V76L+Q109R+S116D+T127V+A147H+S167 L T1I+S13Y+S25P+S27L+S39P+S42G+S57W+S59V+V76L+Q109R+S116D+T127V+A147H+G175D; T1I+S13Y+S25P+S27L+S39P+S42G+S57W+S59V+V76L+Q109R+S116D+T127V+S167L+G175D; T1I+S13Y+S25P+S27L+S39P+S42G+S57W+S59V+V76L+Q109R+S116D+S144P+A147H+S167L; T1I+S13Y+S25P+S27L+S39P+S42G+S57W+S59V+V76L+Q109R+S116D+S144P+A147H+G175D; T1I+S13Y+S25P+S27L+S39P+S42G+S57W+S59V+V76L+Q109R+S116D+S144P+S167L+G175D; T1I+S13Y+S25P+S27L+S39P+S42G+S57W+S59V+V76L+Q109R+S116D+A147H+S167L+G175D; T1I+S13Y+S25P+S27L+S39P+S42G+S57W+S59V+V76L+Q109R+T127V+S144P+A147H+S167 L T1I+S13Y+S25P+S27L+S39P+S42G+S57W+S59V+V76L+Q109R+T127V+S144P+A147H+G175D; T1I+S13Y+S25P+S27L+S39P+S42G+S57W+S59V+V76L+Q109R+T127V+S144P+S167L+G175D; T1I+S13Y+S25P+S27L+S39P+S42G+S57W+S59V+V76L+Q109R+T127V+A147H+S167L+G175D; T1I+S13Y+S25P+S27L+S39P+S42G+S57W+S59V+V76L+Q109R+S144P+A147H+S167L+G175D; T1I+S13Y+S25P+S27L+S39P+S42G+S57W+S59V+V76L+S116D+T127V+S144P+A147H+S167L T1I+S13Y+S25P+S27L+S39P+S42G+S57W+S59V+V76L+S116D+T127V+S144P+A147H+G175D; T1I+S13Y+S25P+S27L+S39P+S42G+S57W+S59V+V76L+S116D+T127V+S144P+S167L+T1I+S13Y+S25P+S27L+S39P+S42G+S57W+S59V+V76L+S116D+T127V+A147H+S167L+G175D; T1I+S13Y+S25P+S27L+S39P+S42G+S57W+S59V+V76L+S116D+S144P+A147H+S167L+G175D; T1I+S13Y+S25P+S27L+S39P+S42G+S57W+S59V+V76L+T127V+S144P+A147H+S167L+G175D; T1I+S13Y+S25P+S27L+S39P+S42G+S57W+S59V+Q109R+S116D+T127V+S144P+A147H+S167L; T1I+S13Y+S25P+S27L+S39P+S42G+S57W+S59V+Q109R+S116D+T127V+S144P+A147H+G175D; T1I+S13Y+S25P+S27L+S39P+S42G+S57W+S59V+Q109R+S116D+T127V+S144P+S167L+G175D; T1I+S13Y+S25P+S27L+S39P+S42G+S57W+S59V+Q109R+S116D+T127V+A147H+S167L+G175D; T1I+S13Y+S25P+S27L+S39P+S42G+S57W+S59V+Q109R+S116D+S144P+A147H+S167L+G175D; T1I+S13Y+S25P+S27L+S39P+S42G+S57W+S59V+Q109R+T127V+S144P+A147H+S167L+G175D; T1I+S13Y+S25P+S27L+S39P+S42G+S57W+S59V+S116D+T127V+S144P+A147H+S167L+G175D; T1I+S13Y+S25P+S27L+S39P+S42G+S57W+V76L+Q109R+S116D+T127V+S144P+A147H+S167L; T1I+S13Y+S25P+S27L+S39P+S42G+S57W+V76L+Q109R+S116D+T127V+S144P+A147H+G175D; T1I+S13Y+S25P+S27L+S39P+S42G+S57W+V76L+Q109R+S116D+T127V+S144P+S167L+G175D; T1I+S13Y+S25P+S27L+S39P+S42G+S57W+V76L+Q109R+S116D+T127V+A147H+S167L+G175D; T1I+S13Y+S25P+S27L+S39P+S42G+S57W+V76L+Q109R+S116D+S144P+A147H+S167L+G175D; T1I+S13Y+S25P+S27L+S39P+S42G+S57W+V76L+Q109R+T127V+S144P+A147H+S167L+G175D; T1I+S13Y+S25P+S27L+S39P+S42G+S57W+V76L+S116D+T127V+S144P+A147H+S167L+G175D; T1I+S13Y+S25P+S27L+S39P+S42G+S57W+Q109R+S116D+T127V+S144P+A147H+S167L+G175D; T1I+S13Y+S25P+S27L+S39P+S42G+S59V+V76L+Q109R+S116D+T127V+S144P+A147H+S167L; T1I+S13Y+S25P+S27L+S39P+S42G+S59V+V76L+Q109R+S116D+T127V+S144P+A147H+G175D; T1I+S13Y+S25P+S27L+S39P+S42G+S59V+V76L+Q109R+S116D+T127V+S144P+S167L+G175D; T1I+S13Y+S25P+S27L+S39P+S42G+S59V+V76L+Q109R+S116D+T127V+A147H+S167L+G175D; T1I+S13Y+S25P+S27L+S39P+S42G+S59V+V76L+Q109R+S116D+S144P+A147H+S167L+G175D; T1I+S13Y+S25P+S27L+S39P+S42G+S59V+V76L+Q109R+T127V+S144P+A147H+S167L+G175D; T1I+S13Y+S25P+S27L+S39P+S42G+

S59V+V76L+S116D+T127V+S144P+A147H+S167L+G175D; T1I+S13Y+S25P+S27L+S39P+S42G+S59V+Q109R+S116D+T127V+S144P+A147H+S167L+G175D; T1I+S13Y+S25P+S27L+S39P+S42G+V76L+Q109R+S116D+T127V+S144P+A147H+S167L+G175D; T1I+S13Y+S25P+S27L+S39P+S57W+S59V+V76L+Q109R+S116D+T127V+S144P+A147H+S167L; T1I+S13Y+S25P+S27L+S39P+S57W+S59V+V76L+Q109R+S116D+T127V+S144P+A147H+G175D; T1I+S13Y+S25P+S27L+S39P+S57W+S59V+V76L+Q109R+S116D+T127V+S144P+S167L+G175 D; T1I+S13Y+S25P+S27L+S39P+S57W+S59V+V76L+Q109R+S116D+T127V+A147H+S167L+G175D; T1I+S13Y+S25P+S27L+S39P+S57W+S59V+V76L+Q109R+S116D+S144P+A147H+S167L+G175D; T1I+S13Y+S25P+S27L+S39P+S57W+S59V+V76L+Q109R+T127V+S144P+A147H+S167L+G175D; T1I+S13Y+S25P+S27L+S39P+S57W+S59V+V76L+S116D+T127V+S144P+A147H+S167L+G175D; T1I+S13Y+S25P+S27L+S39P+S57W+S59V+Q109R+S116D+T127V+S144P+A147H+S167L+T1I+S13Y+S25P+S27L+S39P+S57W+V76L+Q109R+S116D+T127V+S144P+A147H+S167L+G175D; T1I+S13Y+S25P+S27L+S39P+S59V+V76L+Q109R+S116D+T127V+S144P+A147H+S167L+G175D; T1I+S13Y+S25P+S27L+S42G+S57W+S59V+V76L+Q109R+S116D+T127V+S144P+A147H+S167L; T1I+S13Y+S25P+S27L+S42G+S57W+S59V+V76L+Q109R+S116D+T127V+S144P+A147H+G175D; T1I+S13Y+S25P+S27L+S42G+S57W+S59V+V76L+Q109R+S116D+T127V+S144P+S167L+G175D; T1I+S13Y+S25P+S27L+S42G+S57W+S59V+V76L+Q109R+S116D+T127V+A147H+S167L+G175D; T1I+S13Y+S25P+S27L+S42G+S57W+S59V+V76L+Q109R+S116D+S144P+A147H+S167L+G175D; T1I+S13Y+S25P+S27L+S42G+S57W+S59V+V76L+Q109R+T127V+S144P+A147H+S167L+G175D; T1I+S13Y+S25P+S27L+S42G+S57W+S59V+V76L+S116D+T127V+S144P+A147H+S167L+G175D; T1I+S13Y+S25P+S27L+S42G+S57W+S59V+Q109R+S116D+T127V+S144P+A147H+S167L+G175D; T1I+S13Y+S25P+S27L+S42G+S57W+V76L+Q109R+S116D+T127V+S144P+A147H+S167L+G175D; T1I+S13Y+S25P+S27L+S42G+S59V+V76L+Q109R+S116D+T127V+S144P+A147H+S167L+G175D; T1I+S13Y+S25P+S27L+S57W+S59V+V76L+Q109R+S116D+T127V+S144P+A147H+S167L+G175D; T1I+S13Y+S25P+S39P+S42G+S57W+S59V+V76L+Q109R+S116D+T127V+S144P+A147H+S167L; T1I+S13Y+S25P+S39P+S42G+S57W+S59V+V76L+Q109R+S116D+T127V+S144P+A147H+G175D; T1I+S13Y+S25P+S39P+S42G+S57W+S59V+V76L+Q109R+S116D+T127V+S144P+S167L+G175D; T1I+S13Y+S25P+S39P+S42G+S57W+S59V+V76L+Q109R+S116D+T127V+A147H+S167L+G175D; T1I+S13Y+S25P+S39P+S42G+S57W+S59V+V76L+Q109R+S116D+S144P+A147H+S167L+G175D; T1I+S13Y+S25P+S39P+S42G+S57W+S59V+V76L+Q109R+T127V+S144P+A147H+S167L+G175D; T1I+S13Y+S25P+S39P+S42G+S57W+S59V+V76L+S116D+T127V+S144P+A147H+S167L+G175D; T1I+S13Y+S25P+S39P+S42G+S57W+S59V+Q109R+S116D+T127V+S144P+A147H+S167L+G175D; T1I+S13Y+S25P+S39P+S42G+S57W+V76L+Q109R+S116D+T127V+S144P+A147H+S167L+G175D; T1I+S13Y+S25P+S39P+S42G+S59V+V76L+Q109R+S116D+T127V+S144P+A147H+S167L+G175D; T1I+S13Y+S25P+S39P+S57W+S59V+V76L+Q109R+S116D+T127V+S144P+A147H+S167L+G175D; T1I+S13Y+S25P+S42G+S57W+S59V+V76L+Q109R+S116D+T127V+S144P+A147H+S167L+G175D; T1I+S13Y+S27L+S39P+S42G+S57W+S59V+V76L+Q109R+S116D+T127V+S144P+A147H+S167L; T1I+S13Y+S27L+S39P+S42G+S57W+S59V+V76L+Q109R+S116D+T127V+S144P+A147H+G175D; T1I+S13Y+S27L+S39P+S42G+S57W+S59V+V76L+Q109R+S116D+T127V+S144P+S167L+G175D; T1I+S13Y+S27L+S39P+S42G+S57W+S59V+V76L+Q109R+S116D+T127V+A147H+S167L+G175D; T1I+S13Y+S27L+S39P+S42G+S57W+S59V+V76L+Q109R+S116D+S144P+A147H+S167L+G175D; T1I+S13Y+S27L+S39P+S42G+S57W+S59V+V76L+Q109R+T127V+S144P+A147H+S167L+G175D; T1I+S13Y+S27L+S39P+S42G+S57W+S59V+V76L+S116D+T127V+S144P+A147H+S167L+G175D; T1I+S13Y+S27L+S39P+S42G+S57W+S59V+Q109R+S116D+T127V+S144P+A147H+S167L+G175D; T1I+S13Y+S27L+S39P+S42G+S57W+V76L+Q109R+S116D+T127V+S144P+A147H+S167L+G175D; T1I+S13Y+S27L+S39P+S42G+S59V+V76L+Q109R+S116D+T127V+S144P+A147H+S167L+T1I+S13Y+S27L+S39P+S57W+S59V+V76L+Q109R+S116D+T127V+S144P+A147H+S167L+G175D; T1I+S13Y+S27L+S42G+S57W+S59V+V76L+Q109R+S116D+T127V+S144P+A147H+S167L+G175D; T1I+S13Y+S39P+S42G+S57W+S59V+V76L+Q109R+S116D+T127V+S144P+A147H+S167L+G175D; T1I+T22P+S25P+S27L+S39P+S42G+S57W+S59V+V76L+Q109R+S116D+T127V+S144P+A147H; T1I+T22P+S25P+S27L+S39P+S42G+S57W+S59V+V76L+Q109R+S116D+T127V+S144P+S167L; T1I+T22P+S25P+S27L+S39P+S42G+S57W+S59V+V76L+Q109R+S116D+T127V+S144P+G175D; T1I+T22P+S25P+S27L+S39P+S42G+S57W+S59V+V76L+Q109R+S116D+T127V+A147H+S167L; T1I+T22P+S25P+S27L+S39P+S42G+S57W+S59V+V76L+Q109R+S116D+T127V+A147H+G175D; T1I+T22P+S25P+S27L+S39P+S42G+S57W+S59V+V76L+Q109R+S116D+T127V+S167L+G175D; T1I+T22P+S25P+S27L+S39P+S42G+S57W+S59V+V76L+Q109R+S116D+S144P+A147H+S167L; T1I+T22P+S25P+S27L+S39P+S42G+S57W+S59V+V76L+Q109R+S116D+S144P+A147H+G175D; T1I+T22P+S25P+S27L+S39P+S42G+S57W+S59V+V76L+Q109R+S116D+S144P+S167L+G175D; T1I+T22P+S25P+S27L+S39P+S42G+S57W+S59V+V76L+Q109R+S116D+A147H+S167L+G175D; T1I+T22P+S25P+S27L+S39P+S42G+S57W+S59V+V76L+Q109R+T127V+S144P+A147H+S167L; T1I+T22P+S25P+S27L+S39P+S42G+S57W+S59V+V76L+Q109R+T127V+S144P+A147H+G175D; T1I+T22P+S25P+S27L+S39P+S42G+S57W+S59V+V76L+Q109R+T127V+S144P+S167L+G175D; T1I+T22P+S25P+S27L+S39P+S42G+S57W+S59V+V76L+Q109R+T127V+A147H+S167L+G175D; T1I+T22P+S25P+S27L+S39P+S42G+S57W+S59V+V76L+Q109R+S144P+A147H+S167L+G175D; T1I+T22P+S25P+S27L+S39P+S42G+S57W+S59V+V76L+S116D+T127V+S144P+A147H+S167L T1I+T22P+S25P+S27L+S39P+S42G+S57W+S59V+V76L+S116D+T127V+S144P+A147H+G175D; T1I+T22P+S25P+S27L+S39P+S42G+S57W+S59V+V76L+S116D+T127V+S144P+S167L+G175D; T1I+T22P+S25P+S27L+S39P+S42G+S57W+S59V+V76L+S116D+T127V+A147H+S167L+G175D; T1I+T22P+S25P+S27L+S39P+S42G+S57W+S59V+V76L+S116D+S144P+A147H+S167L+G175D; T1I+T22P+S25P+S27L+S39P+S42G+S57W+S59V+V76L+T127V+S144P+A147H+S167L+G175D; T1I+T22P+S25P+S27L+S39P+S42G+S57W+S59V+Q109R+S116D+T127V+S144P+A147H+S167L; T1I+T22P+S25P+S27L+S39P+S42G+S57W+S59V+Q109R+S116D+T127V+S144P+A147H+G175D; T1I+T22P+S25P+S27L+S39P+S42G+S57W+

S59V+Q109R+S116D+T127V+S144P+S167L+G175D; T1I+T22P+S25P+S27L+S39P+S42G+S57W+S59V+Q109R+S116D+T127V+A147H+S167L+G175D; T1I+T22P+S25P+S27L+S39P+S42G+S57W+S59V+Q109R+S116D+S144P+A147H+S167L+G175D; T1I+T22P+S25P+S27L+S39P+S42G+S57W+S59V+Q109R+T127V+S144P+A147H+S167L+G175D; T1I+T22P+S25P+S27L+S39P+S42G+S57W+S59V+S116D+T127V+S144P+A147H+S167L+G175D; T1I+T22P+S25P+S27L+S39P+S42G+S57W+V76L+Q109R+S116D+T127V+S144P+A147H+S167L; T1I+T22P+S25P+S27L+S39P+S42G+S57W+V76L+Q109R+S116D+T127V+S144P+A147H+G175D; T1I+T22P+S25P+S27L+S39P+S42G+S57W+V76L+Q109R+S116D+T127V+S144P+S167L+G175D; T1I+T22P+S25P+S27L+S39P+S42G+S57W+V76L+Q109R+S116D+T127V+A147H+S167L+T1I+T22P+S25P+S27L+S39P+S42G+S57W+V76L+Q109R+S116D+S144P+A147H+S167L+G175D; T1I+T22P+S25P+S27L+S39P+S42G+S57W+V76L+Q109R+T127V+S144P+A147H+S167L+G175D; T1I+T22P+S25P+S27L+S39P+S42G+S57W+V76L+S116D+T127V+S144P+A147H+S167L+G175D; T1I+T22P+S25P+S27L+S39P+S42G+S57W+Q109R+S116D+T127V+S144P+A147H+S167L+G175D; T1I+T22P+S25P+S27L+S39P+S42G+S59V+V76L+Q109R+S116D+T127V+S144P+A147H+S167L; T1I+T22P+S25P+S27L+S39P+S42G+S59V+V76L+Q109R+S116D+T127V+S144P+A147H+G175D; T1I+T22P+S25P+S27L+S39P+S42G+S59V+V76L+Q109R+S116D+T127V+S144P+S167L+G175D; T1I+T22P+S25P+S27L+S39P+S42G+S59V+V76L+Q109R+S116D+T127V+A147H+S167L+G175D; T1I+T22P+S25P+S27L+S39P+S42G+S59V+V76L+Q109R+S116D+S144P+A147H+S167L+G175D; T1I+T22P+S25P+S27L+S39P+S42G+S59V+V76L+Q109R+T127V+S144P+A147H+S167L+G175D; T1I+T22P+S25P+S27L+S39P+S42G+S59V+V76L+S116D+T127V+S144P+A147H+S167L+G175D; T1I+T22P+S25P+S27L+S39P+S42G+S59V+Q109R+S116D+T127V+S144P+A147H+S167L+G175D; T1I+T22P+S25P+S27L+S39P+S42G+V76L+Q109R+S116D+T127V+S144P+A147H+S167L+G175D; T1I+T22P+S25P+S27L+S39P+S57W+S59V+V76L+Q109R+S116D+T127V+S144P+A147H+S167L; T1I+T22P+S25P+S27L+S39P+S57W+S59V+V76L+Q109R+S116D+T127V+S144P+A147H+G175D; T1I+T22P+S25P+S27L+S39P+S57W+S59V+V76L+Q109R+S116D+T127V+S144P+S167L+G175D; T1I+T22P+S25P+S27L+S39P+S57W+S59V+V76L+Q109R+S116D+T127V+A147H+S167L+G175D; T1I+T22P+S25P+S27L+S39P+S57W+S59V+V76L+Q109R+S116D+S144P+A147H+S167L+G175D; T1I+T22P+S25P+S27L+S39P+S57W+S59V+V76L+Q109R+T127V+S144P+A147H+S167L+G175D; T1I+T22P+S25P+S27L+S39P+S57W+S59V+V76L+S116D+T127V+S144P+A147H+S167L+G175D; T1I+T22P+S25P+S27L+S39P+S57W+S59V+Q109R+S116D+T127V+S144P+A147H+S167L+G175D; T1I+T22P+S25P+S27L+S39P+S57W+V76L+Q109R+S116D+T127V+S144P+A147H+S167L+G175D; T1I+T22P+S25P+S27L+S39P+S59V+V76L+Q109R+S116D+T127V+S144P+A147H+S167L+G175D; T1I+T22P+S25P+S27L+S42G+S57W+S59V+V76L+Q109R+S116D+T127V+S144P+A147H+S167L; T1I+T22P+S25P+S27L+S42G+S57W+S59V+V76L+Q109R+S116D+T127V+S144P+A147H+G175D; T1I+T22P+S25P+S27L+S42G+S57W+S59V+V76L+Q109R+S116D+T127V+S144P+S167L+G175D; T1I+T22P+S25P+S27L+S42G+S57W+S59V+V76L+Q109R+S116D+T127V+A147H+S167L+G175D; T1I+T22P+S25P+S27L+S42G+S57W+S59V+V76L+Q109R+S116D+S144P+A147H+S167L+G175D; T1I+T22P+S25P+S27L+S42G+S57W+S59V+V76L+Q109R+T127V+S144P+A147H+S167L+G175D; T1I+T22P+S25P+S27L+S42G+S57W+S59V+V76L+S116D+T127V+S144P+A147H+S167L+G175D; T1I+T22P+S25P+S27L+S42G+S57W+S59V+Q109R+S116D+T127V+S144P+A147H+S167L+G175D; T1I+T22P+S25P+S27L+S42G+S57W+V76L+Q109R+S116D+T127V+S144P+A147H+S167L+G175D; T1I+T22P+S25P+S27L+S42G+S59V+V76L+Q109R+S116D+T127V+S144P+A147H+S167L+G175D; T1I+T22P+S25P+S27L+S57W+S59V+V76L+Q109R+S116D+T127V+S144P+A147H+S167L+G175D; T1I+T22P+S25P+S39P+S42G+S57W+S59V+V76L+Q109R+S116D+T127V+S144P+A147H+S167L; T1I+T22P+S25P+S39P+S42G+S57W+S59V+V76L+Q109R+S116D+T127V+S144P+A147H+G175D; T1I+T22P+S25P+S39P+S42G+S57W+S59V+V76L+Q109R+S116D+T127V+S144P+S167L+G175D; T1I+T22P+S25P+S39P+S42G+S57W+S59V+V76L+Q109R+S116D+T127V+A147H+S167L+G175D; T1I+T22P+S25P+S39P+S42G+S57W+S59V+V76L+Q109R+S116D+S144P+A147H+S167L+G175D; T1I+T22P+S25P+S39P+S42G+S57W+S59V+V76L+Q109R+T127V+S144P+A147H+S167L+G175D; T1I+T22P+S25P+S39P+S42G+S57W+S59V+V76L+S116D+T127V+S144P+A147H+S167L+G175D; T1I+T22P+S25P+S39P+S42G+S57W+S59V+Q109R+S116D+T127V+S144P+A147H+S167L+G175D; T1I+T22P+S25P+S39P+S42G+S57W+V76L+Q109R+S116D+T127V+S144P+A147H+S167L+G175D; T1I+T22P+S25P+S39P+S42G+S59V+V76L+Q109R+S116D+T127V+S144P+A147H+S167L+G175D; T1I+T22P+S25P+S39P+S57W+S59V+V76L+Q109R+S116D+T127V+S144P+A147H+S167L+G175D; T1I+T22P+S25P+S42G+S57W+S59V+V76L+Q109R+S116D+T127V+S144P+A147H+S167L+G175D; T1I+T22P+S27L+S39P+S42G+S57W+S59V+V76L+Q109R+S116D+T127V+S144P+A147H+S167L; T1I+T22P+S27L+S39P+S42G+S57W+S59V+V76L+Q109R+S116D+T127V+S144P+A147H+G175D; T1I+T22P+S27L+S39P+S42G+S57W+S59V+V76L+Q109R+S116D+T127V+S144P+S167L+G175D; T1I+T22P+S27L+S39P+S42G+S57W+S59V+V76L+Q109R+S116D+T127V+A147H+S167L+G175D; T1I+T22P+S27L+S39P+S42G+S57W+S59V+V76L+Q109R+S116D+S144P+A147H+S167L+G175D; T1I+T22P+S27L+S39P+S42G+S57W+S59V+V76L+Q109R+T127V+S144P+A147H+S167L+G175D; T1I+T22P+S27L+S39P+S42G+S57W+S59V+V76L+S116D+T127V+S144P+A147H+S167L+G175D; T1I+T22P+S27L+S39P+S42G+S57W+S59V+Q109R+S116D+T127V+S144P+A147H+S167L+G175D; T1I+T22P+S27L+S39P+S42G+S57W+V76L+Q109R+S116D+T127V+S144P+A147H+S167L+G175D; T1I+T22P+S27L+S39P+S42G+S59V+V76L+Q109R+S116D+T127V+S144P+A147H+S167L+G175D; T1I+T22P+S27L+S39P+S57W+S59V+V76L+Q109R+S116D+T127V+S144P+A147H+S167L+G175D; T1I+T22P+S27L+S42G+S57W+S59V+V76L+Q109R+S116D+T127V+S144P+A147H+S167L+G175D; T1I+T22P+S39P+S42G+S57W+S59V+V76L+Q109R+S116D+T127V+S144P+A147H+S167L+G175D; T1I+S25P+S27L+S39P+S42G+S57W+S59V+V76L+Q109R+S116D+T127V+S144P+A147H+S167L; T1I+S25P+S27L+S39P+S42G+S57W+S59V+V76L+Q109R+S116D+T127V+S144P+A147H+G175D; T1I+S25P+S27L+S39P+S42G+S57W+S59V+V76L+Q109R+S116D+T127V+S144P+S167L+G175D; T1I+S25P+S27L+S39P+S42G+S57W+S59V+V76L+Q109R+S116D+T127V+A147H+S167L+G175D; T1I+S25P+S27L+S39P+S42G+S57W+S59V+

V76L+Q109R+S116D+S144P+A147H+S167L+G175D; T1I+S25P+S27L+S39P+S42G+S57W+S59V+V76L+Q109R+T127V+S144P+A147H+S167L+G175D; T1I+S25P+S27L+S39P+S42G+S57W+S59V+V76L+S116D+T127V+S144P+A147H+S167L+G175D; T1I+S25P+S27L+S39P+S42G+S57W+S59V+Q109R+S116D+T127V+S144P+A147H+S167L+G175D; T1I+S25P+S27L+S39P+S42G+S57W+V76L+Q109R+S116D+T127V+S144P+A147H+S167L+G175D; T1I+S25P+S27L+S39P+S42G+S59V+V76L+Q109R+S116D+T127V+S144P+A147H+S167L+G175D; T1I+S25P+S27L+S39P+S57W+S59V+V76L+Q109R+S116D+T127V+S144P+A147H+S167L+T1I+S25P+S27L+S42G+S57W+S59V+V76L+Q109R+S116D+T127V+S144P+A147H+S167L+G175D; T1I+S25P+S39P+S42G+S57W+S59V+V76L+Q109R+S116D+T127V+S144P+A147H+S167L+G175D; or T1I+S27L+S39P+S42G+S57W+S59V+V76L+Q109R+S116D+T127V+S144P+A147H+S167L+G175D.

In a preferred embodiment the DNase variant is selected from any of the following: T1I+S13Y+T22P+S25P+S27L+S39P+S42G+S57W+S59V+V76L+Q109R+S116D+T127V+S144P+A147H; T1I+S13Y+T22P+S25P+S27L+S39P+S42G+S57W+S59V+V76L+Q109R+S116D+T127V+S144P+S167L; T1I+S13Y+T22P+S25P+S27L+S39P+S42G+S57W+S59V+V76L+Q109R+S116D+T127V+S144P+G175D; T1I+S13Y+T22P+S25P+S27L+S39P+S42G+S57W+S59V+V76L+Q109R+S116D+T127V+A147H+S167L; T1I+S13Y+T22P+S25P+S27L+S39P+S42G+S57W+S59V+V76L+Q109R+S116D+T127V+A147H+G175D; T1I+S13Y+T22P+S25P+S27L+S39P+S42G+S57W+S59V+V76L+Q109R+S116D+T127V+S167L+G175D; T1I+S13Y+T22P+S25P+S27L+S39P+S42G+S57W+S59V+V76L+Q109R+S116D+S144P+A147H+S167L; T1I+S13Y+T22P+S25P+S27L+S39P+S42G+S57W+S59V+V76L+Q109R+S116D+S144P+A147H+G175D; T1I+S13Y+T22P+S25P+S27L+S39P+S42G+S57W+S59V+V76L+Q109R+S116D+S144P+S167L+G175D; T1I+S13Y+T22P+S25P+S27L+S39P+S42G+S57W+S59V+V76L+Q109R+S116D+A147H+S167L+G175D; T1I+S13Y+T22P+S25P+S27L+S39P+S42G+S57W+S59V+V76L+Q109R+T127V+S144P+A147H+S167L; T1I+S13Y+T22P+S25P+S27L+S39P+S42G+S57W+S59V+V76L+Q109R+T127V+S144P+A147H+G175D; T1I+S13Y+T22P+S25P+S27L+S39P+S42G+S57W+S59V+V76L+Q109R+T127V+S144P+S167L+G175D; T1I+S13Y+T22P+S25P+S27L+S39P+S42G+S57W+S59V+V76L+Q109R+T127V+A147H+S167L+G175D; T1I+S13Y+T22P+S25P+S27L+S39P+S42G+S57W+S59V+V76L+Q109R+S144P+A147H+S167L+G175D; T1I+S13Y+T22P+S25P+S27L+S39P+S42G+S57W+S59V+V76L+S116D+T127V+S144P+A147H+S167L T1I+S13Y+T22P+S25P+S27L+S39P+S42G+S57W+S59V+V76L+S116D+T127V+S144P+A147H+G175D; T1I+S13Y+T22P+S25P+S27L+S39P+S42G+S57W+S59V+V76L+S116D+T127V+S144P+S167L+G175D; T1I+S13Y+T22P+S25P+S27L+S39P+S42G+S57W+S59V+V76L+S116D+T127V+A147H+S167L+G175D; T1I+S13Y+T22P+S25P+S27L+S39P+S42G+S57W+S59V+V76L+S116D+S144P+A147H+S167L+G175D; T1I+S13Y+T22P+S25P+S27L+S39P+S42G+S57W+S59V+V76L+T127V+S144P+A147H+S167L+G175D; T1I+S13Y+T22P+S25P+S27L+S39P+S42G+S57W+S59V+Q109R+S116D+T127V+S144P+A147 H+S167L T1I+S13Y+T22P+S25P+S27L+S39P+S42G+S57W+S59V+Q109R+S116D+T127V+S144P+A147 H+G175D; T1I+S13Y+T22P+S25P+S27L+S39P+S42G+S57W+S59V+Q109R+S116D+T127V+S144P+S167 L+G175D; T1I+S13Y+T22P+S25P+S27L+S39P+S42G+S57W+S59V+Q109R+S116D+T127V+A147H+S167 L+G175D; T1I+S13Y+T22P+S25P+S27L+S39P+S42G+S57W+S59V+Q109R+S116D+S144P+A147H+S167 L+G175D; T1I+S13Y+T22P+S25P+S27L+S39P+S42G+S57W+S59V+Q109R+T127V+S144P+A147H+S167 L+G175D; T1I+S13Y+T22P+S25P+S27L+S39P+S42G+S57W+S59V+S116D+T127V+S144P+A147H+S167 L+G175D; T1I+S13Y+T22P+S25P+S27L+S39P+S42G+S57W+V76L+Q109R+S116D+T127V+S144P+A147 H+S167L; T1I+S13Y+T22P+S25P+S27L+S39P+S42G+S57W+V76L+Q109R+S116D+T127V+S144P+A147 H+G175D; T1I+S13Y+T22P+S25P+S27L+S39P+S42G+S57W+V76L+Q109R+S116D+T127V+S144P+S167 L+G175D; T1I+S13Y+T22P+S25P+S27L+S39P+S42G+S57W+V76L+Q109R+S116D+T127V+A147H+S167 L+G175D; T1I+S13Y+T22P+S25P+S27L+S39P+S42G+S57W+V76L+Q109R+S116D+S144P+A147H+S167 L+G175D; T1I+S13Y+T22P+S25P+S27L+S39P+S42G+S57W+V76L+Q109R+T127V+S144P+A147H+S167 L+G175D; T1I+S13Y+T22P+S25P+S27L+S39P+S42G+S57W+V76L+S116D+T127V+S144P+A147H+S167L+G175D; T1I+S13Y+T22P+S25P+S27L+S39P+S42G+S57W+Q109R+S116D+T127V+S144P+A147H+S16 7L+G175D; T1I+S13Y+T22P+S25P+S27L+S39P+S42G+S59V+V76L+Q109R+S116D+T127V+S144P+A147H+S167L; T1I+S13Y+T22P+S25P+S27L+S39P+S42G+S59V+V76L+Q109R+S116D+T127V+S144P+A147H+G175D; T1I+S13Y+T22P+S25P+S27L+S39P+S42G+S59V+V76L+Q109R+S116D+T127V+S144P+S167L+G175D; T1I+S13Y+T22P+S25P+S27L+S39P+S42G+S59V+V76L+Q109R+S116D+T127V+A147H+S167L+G175D; T1I+S13Y+T22P+S25P+S27L+S39P+S42G+S59V+V76L+Q109R+S116D+S144P+A147H+S167L+G175D; T1I+S13Y+T22P+S25P+S27L+S39P+S42G+S59V+V76L+Q109R+T127V+S144P+A147H+S167L+G175D; T1I+S13Y+T22P+S25P+S27L+S39P+S42G+S59V+V76L+S116D+T127V+S144P+A147H+S167L+G175D; T1I+S13Y+T22P+S25P+S27L+S39P+S42G+S59V+Q109R+S116D+T127V+S144P+A147H+S167 L+G175D; T1I+S13Y+T22P+S25P+S27L+S39P+S42G+V76L+Q109R+S116D+T127V+S144P+A147H+S167 L+G175D; T1I+S13Y+T22P+S25P+S27L+S39P+S57W+S59V+V76L+Q109R+S116D+T127V+S144P+A147 H+S167L; T1I+S13Y+T22P+S25P+S27L+S39P+S57W+S59V+V76L+Q109R+S116D+T127V+S144P+A147 H+G175D; T1I+S13Y+T22P+S25P+S27L+S39P+S57W+S59V+V76L+Q109R+S116D+T127V+S144P+S167L+G175D; T1I+S13Y+T22P+S25P+S27L+S39P+S57W+S59V+V76L+Q109R+S116D+T127V+A147H+S167L+G175D; T1I+S13Y+T22P+S25P+S27L+S39P+S57W+S59V+V76L+Q109R+S116D+S144P+A147H+S167 L+G175D; T1I+S13Y+T22P+S25P+S27L+S39P+S57W+S59V+V76L+Q109R+T127V+S144P+A147H+S167L+G175D; T1I+S13Y+T22P+S25P+S27L+S39P+S57W+S59V+V76L+S116D+T127V+S144P+A147H+S167L+G175D; T1I+S13Y+T22P+S25P+S27L+S39P+S57W+S59V+Q109R+S116D+T127V+S144P+A147H+S16 7L+G175D; T1I+S13Y+T22P+S25P+S27L+S39P+S57W+V76L+Q109R+S116D+T127V+S144P+A147H+S167 L+G175D; T1I+S13Y+T22P+S25P+S27L+S39P+S59V+V76L+Q109R+S116D+T127V+S144P+A147H+S167 L+G175D; T1I+S13Y+T22P+S25P+S27L+S42G+S57W+S59V+V76L+Q109R+S116D+T127V+S144P+A147 H+S167L; T1I+S13Y+T22P+S25P+S27L+S42G+S57W+S59V+V76L+Q109R+S116D+T127V+

S144P+A147 H+G175D; T1I+S13Y+T22P+S25P+S27L+S42G+S57W+S59V+V76L+Q109R+S116D+T127V+S144P+S167 L+G175D; T1I+S13Y+T22P+S25P+S27L+S42G+S57W+S59V+V76L+Q109R+S116D+T127V+A147H+S167 L+G175D; T1I+S13Y+T22P+S25P+S27L+S42G+S57W+S59V+V76L+Q109R+S116D+S144P+A147H+S167 L+G175D; T1I+S13Y+T22P+S25P+S27L+S42G+S57W+S59V+V76L+Q109R+T127V+S144P+A147H+S167 L+G175D; T1I+S13Y+T22P+S25P+S27L+S42G+S57W+S59V+V76L+S116D+T127V+S144P+A147H+S167L+G175D; T1I+S13Y+T22P+S25P+S27L+S42G+S57W+S59V+Q109R+S116D+T127V+S144P+A147H+S16 7L+G175D; T1I+S13Y+T22P+S25P+S27L+S42G+S57W+V76L+Q109R+S116D+T127V+S144P+A147H+S16 7L+G175D; T1I+S13Y+T22P+S25P+S27L+S42G+S59V+V76L+Q109R+S116D+T127V+S144P+A147H+S167 L+G175D; T1I+S13Y+T22P+S25P+S27L+S57W+S59V+V76L+Q109R+S116D+T127V+S144P+A147H+S167 L+G175D; T1I+S13Y+T22P+S25P+S39P+S42G+S57W+S59V+V76L+Q109R+S116D+T127V+S144P+A147 H+S167L; T1I+S13Y+T22P+S25P+S39P+S42G+S57W+S59V+V76L+Q109R+S116D+T127V+S144P+A147 H+G175D; T1I+S13Y+T22P+S25P+S39P+S42G+S57W+S59V+V76L+Q109R+S116D+T127V+S144P+S167 L+G175D; T1I+S13Y+T22P+S25P+S39P+S42G+S57W+S59V+V76L+Q109R+S116D+T127V+A147H+S167 L+G175D; T1I+S13Y+T22P+S25P+S39P+S42G+S57W+S59V+V76L+Q109R+S116D+S144P+A147H+S167 L+G175D; T1I+S13Y+T22P+S25P+S39P+S42G+S57W+S59V+V76L+Q109R+T127V+S144P+A147H+S167 L+G175D; T1I+S13Y+T22P+S25P+S39P+S42G+S57W+S59V+V76L+S116D+T127V+S144P+A147H+S167 L+G175D; T1I+S13Y+T22P+S25P+S39P+S42G+S57W+S59V+Q109R+S116D+T127V+S144P+A147H+S16 7L+G175D; T1I+S13Y+T22P+S25P+S39P+S42G+S57W+V76L+Q109R+S116D+T127V+S144P+A147H+S16 7L+G175D; T1I+S13Y+T22P+S25P+S39P+S42G+S59V+V76L+Q109R+S116D+T127V+S144P+A147H+S167 L+G175D; T1I+S13Y+T22P+S25P+S39P+S57W+S59V+V76L+Q109R+S116D+T127V+S144P+A147H+S16 7L+G175D; T1I+S13Y+T22P+S25P+S42G+S57W+S59V+V76L+Q109R+S116D+T127V+S144P+A147H+S16 7L+G175D; T1I+S13Y+T22P+S27L+S39P+S42G+S57W+S59V+V76L+Q109R+S116D+T127V+S144P+A147 H+S167L; T1I+S13Y+T22P+S27L+S39P+S42G+S57W+S59V+V76L+Q109R+S116D+T127V+S144P+A147 H+G175D; T1I+S13Y+T22P+S27L+S39P+S42G+S57W+S59V+V76L+Q109R+S116D+T127V+S144P+S167 L+G175D; T1I+S13Y+T22P+S27L+S39P+S42G+S57W+S59V+V76L+Q109R+S116D+T127V+A147H+S167 L+G175D; T1I+S13Y+T22P+S27L+S39P+S42G+S57W+S59V+V76L+Q109R+S116D+S144P+A147H+S167 L+G175D; T1I+S13Y+T22P+S27L+S39P+S42G+S57W+S59V+V76L+Q109R+T127V+S144P+A147H+S167 L+G175D; T1I+S13Y+T22P+S27L+S39P+S42G+S57W+S59V+V76L+S116D+T127V+S144P+A147H+S167L+G175D; T1I+S13Y+T22P+S27L+S39P+S42G+S57W+S59V+Q109R+S116D+T127V+S144P+A147H+S16 7L+G175D; T1I+S13Y+T22P+S27L+S39P+S42G+S57W+V76L+Q109R+S116D+T127V+S144P+A147H+S16 7L+G175D; T1I+S13Y+T22P+S27L+S39P+S42G+S59V+V76L+Q109R+S116D+T127V+S144P+A147H+S167 L+G175D; T1I+S13Y+T22P+S27L+S39P+S57W+S59V+V76L+Q109R+S116D+T127V+S144P+A147H+S167 L+G175D; T1I+S13Y+T22P+S27L+S42G+S57W+S59V+V76L+Q109R+S116D+T127V+S144P+A147H+S16 7L+G175D; T1I+S13Y+T22P+S39P+S42G+S57W+S59V+V76L+Q109R+S116D+T127V+S144P+A147H+S16 7L+G175D; T1I+S13Y+S25P+S27L+S39P+S42G+S57W+S59V+V76L+Q109R+S116D+T127V+S144P+A147 H+S167L; T1I+S13Y+S25P+S27L+S39P+S42G+S57W+S59V+V76L+Q109R+S116D+T127V+S144P+A147 H+G175D; T1I+S13Y+S25P+S27L+S39P+S42G+S57W+S59V+V76L+Q109R+S116D+T127V+S144P+S167 L+G175D; T1I+S13Y+S25P+S27L+S39P+S42G+S57W+S59V+V76L+Q109R+S116D+T127V+A147H+S167 L+G175D; T1I+S13Y+S25P+S27L+S39P+S42G+S57W+S59V+V76L+Q109R+S116D+S144P+A147H+S167 L+G175D; T1I+S13Y+S25P+S27L+S39P+S42G+S57W+S59V+V76L+Q109R+T127V+S144P+A147H+S167 L+G175D; T1I+S13Y+S25P+S27L+S39P+S42G+S57W+S59V+V76L+S116D+T127V+S144P+A147H+S167L+G175D; T1I+S13Y+S25P+S27L+S39P+S42G+S57W+S59V+Q109R+S116D+T127V+S144P+A147H+S16 7L+G175D; T1I+S13Y+S25P+S27L+S39P+S42G+S57W+V76L+Q109R+S116D+T127V+S144P+A147H+S16 7L+G175D; T1I+S13Y+S25P+S27L+S39P+S42G+S59V+V76L+Q109R+S116D+T127V+S144P+A147H+S167 L+G175D; T1I+S13Y+S25P+S27L+S39P+S57W+S59V+V76L+Q109R+S116D+T127V+S144P+A147H+S16 7L+G175D; T1I+S13Y+S25P+S27L+S42G+S57W+S59V+V76L+Q109R+S116D+T127V+S144P+A147H+S16 7L+G175D; T1I+S13Y+S25P+S39P+S42G+S57W+S59V+V76L+Q109R+S116D+T127V+S144P+A147H+S16 7L+G175D; T1I+S13Y+S27L+S39P+S42G+S57W+S59V+V76L+Q109R+S116D+T127V+S144P+A147H+S16 7L+G175D; T1I+T22P+S25P+S27L+S39P+S42G+S57W+S59V+V76L+Q109R+S116D+T127V+S144P+A147 H+S167L; T1I+T22P+S25P+S27L+S39P+S42G+S57W+S59V+V76L+Q109R+S116D+T127V+S144P+A147 H+G175D; T1I+T22P+S25P+S27L+S39P+S42G+S57W+S59V+V76L+Q109R+S116D+T127V+S144P+S167 L+G175D; T1I+T22P+S25P+S27L+S39P+S42G+S57W+S59V+V76L+Q109R+S116D+T127V+A147H+S167 L+G175D; T1I+T22P+S25P+S27L+S39P+S42G+S57W+S59V+V76L+Q109R+S116D+S144P+A147H+S167 L+G175D; T1I+T22P+S25P+S27L+S39P+S42G+S57W+S59V+V76L+Q109R+T127V+S144P+A147H+S167 L+G175D; T1I+T22P+S25P+S27L+S39P+S42G+S57W+S59V+V76L+S116D+T127V+S144P+A147H+S167L+G175D; T1I+T22P+S25P+S27L+S39P+S42G+S57W+S59V+Q109R+S116D+T127V+S144P+A147H+S16 7L+G175D; T1I+T22P+S25P+S27L+S39P+S42G+S57W+V76L+Q109R+S116D+T127V+S144P+A147H+S16 7L+G175D; T1I+T22P+S25P+S27L+S39P+S42G+S59V+V76L+Q109R+S116D+T127V+S144P+A147H+S167 L+G175D; T1I+T22P+S25P+S27L+S39P+S57W+S59V+V76L+Q109R+S116D+T127V+S144P+A147H+S167 L+G175D; T1I+T22P+S25P+S27L+S42G+S57W+S59V+V76L+Q109R+S116D+T127V+S144P+A147H+S16 7L+G175D; T1I+T22P+S25P+S39P+S42G+S57W+S59V+V76L+Q109R+S116D+T127V+S144P+A147H+S16 7L+G175D; T1I+T22P+S27L+S39P+S42G+S57W+S59V+V76L+Q109R+S116D+T127V+S144P+A147H+S16 7L+G175D; T1I+S25P+S27L+S39P+S42G+S57W+S59V+V76L+Q109R+S116D+T127V+S144P+A147H+S16 7L+G175D; S13Y+T22P+S25P+S27L+S39P+S42G+S57W+S59V+V76L+Q109R+S116D+T127V+S144P+A14 7H+S167L; S13Y+T22P+S25P+S27L+S39P+S42G+S57W+S59V+V76L+Q109R+S116D+T127V+S144P+A14 7H+G175D; S13Y+T22P+S25P+S27L+S39P+S42G+S57W+S59V+V76L+Q109R+S116D+T127V+S144P+S167L+G175D; S13Y+T22P+S25P+S27L+S39P+S42G+S57W+S59V+V76L+Q109R+S116D+T127V+

A147H+S167L+G175D; S13Y+T22P+S25P+S27L+S39P+S42G+S57W+S59V+V76L+Q109R+S116D+S144P+A147H+S167L+G175D; S13Y+T22P+S25P+S27L+S39P+S42G+S57W+S59V+V76L+Q109R+T127V+S144P+A147H+S16 7L+G175D; S13Y+T22P+S25P+S27L+S39P+S42G+S57W+S59V+V76L+S116D+T127V+S144P+A147H+S16 7L+G175D; S13Y+T22P+S25P+S27L+S39P+S42G+S57W+S59V+Q109R+S116D+T127V+S144P+A147H+S 167L+G175D; S13Y+T22P+S25P+S27L+S39P+S42G+S57W+V76L+Q109R+S116D+T127V+S144P+A147H+S1 67L+G175D; S13Y+T22P+S25P+S27L+S39P+S42G+S59V+V76L+Q109R+S116D+T127V+S144P+A147H+S1 67L+G175D; S13Y+T22P+S25P+S27L+S39P+S57W+S59V+V76L+Q109R+S116D+T127V+S144P+A147H+S1 67L+G175D; S13Y+T22P+S25P+S27L+S42G+S57W+S59V+V76L+Q109R+S116D+T127V+S144P+A147H+S1 67L+G175D; S13Y+T22P+S25P+S39P+S42G+S57W+S59V+V76L+Q109R+S116D+T127V+S144P+A147H+S 167L+G175D; S13Y+T22P+S27L+S39P+S42G+S57W+S59V+V76L+Q109R+S116D+T127V+S144P+A147H+S1 67L+G175D; S13Y+S25P+S27L+S39P+S42G+S57W+S59V+V76L+Q109R+S116D+T127V+S144P+A147H+S 167L+G175D; or T22P+S25P+S27L+S39P+S42G+S57W+S59V+V76L+Q109R+S116D+T127V+S144P+A147H+S1 67L+G175D.

In one embodiment the DNase variant is selected from any of the following variants: T1I+S13Y+T22P+S25P+S27L+S39P+S42G+S57W+S59V+V76L+Q109R+S116D+T127V+S144P+A147H+S167L; T1I+S13Y+T22P+S25P+S27L+S39P+S42G+S57W+S59V+V76L+Q109R+S116D+T127V+S144P+A147H+G175D; T1I+S13Y+T22P+S25P+S27L+S39P+S42G+S57W+S59V+V76L+Q109R+S116D+T127V+S144P+S167L+G175D; T1I+S13Y+T22P+S25P+S27L+S39P+S42G+S57W+S59V+V76L+Q109R+S116D+T127V+A147H+S167L+G175D; T1I+S13Y+T22P+S25P+S27L+S39P+S42G+S57W+S59V+V76L+Q109R+S116D+S144P+A147H+S167L+G175D; T1I+S13Y+T22P+S25P+S27L+S39P+S42G+S57W+S59V+V76L+Q109R+T127V+S144P+A147H+S167L+G175D; T1I+S13Y+T22P+S25P+S27L+S39P+S42G+S57W+S59V+V76L+S116D+T127V+S144P+A147H+S167L+G175D; T1I+S13Y+T22P+S25P+S27L+S39P+S42G+S57W+S59V+Q109R+S116D+T127V+S144P+A147 H+S167L+G175D; T1I+S13Y+T22P+S25P+S27L+S39P+S42G+S57W+V76L+Q109R+S116D+T127V+S144P+A147 H+S167L+G175D; T1I+S13Y+T22P+S25P+S27L+S39P+S42G+S59V+V76L+Q109R+S116D+T127V+S144P+A147H+S167L+G175D; T1I+S13Y+T22P+S25P+S27L+S39P+S57W+S59V+V76L+Q109R+S116D+T127V+S144P+A147 H+S167L+G175D; T1I+S13Y+T22P+S25P+S27L+S42G+S57W+S59V+V76L+Q109R+S116D+T127V+S144P+A147 H+S167L+G175D; T1I+S13Y+T22P+S25P+S39P+S42G+S57W+S59V+V76L+Q109R+S116D+T127V+S144P+A147 H+S167L+G175D; T1I+S13Y+T22P+S27L+S39P+S42G+S57W+S59V+V76L+Q109R+S116D+T127V+S144P+A147 H+S167L+G175D; T1I+S13Y+S25P+S27L+S39P+S42G+S57W+S59V+V76L+Q109R+S116D+T127V+S144P+A147 H+S167L+G175D; T1I+T22P+S25P+S27L+S39P+S42G+S57W+S59V+V76L+Q109R+S116D+T127V+S144P+A147 H+S167L+G175D; or S13Y+T22P+S25P+S27L+S39P+S42G+S57W+S59V+V76L+Q109R+S116D+T127V+S144P+A14 7H+S167L+G175D.

In one preferred embodiment the DNase variant of the invention comprises at least four substitutions wherein the substitutions are selected from the group consisting of: T1I, T22P, S57W, V76L, A147H, S167L and G175D. In one embodiment the DNase variant is selected from the group consisting of: T1I+T22P+S57W+V76L, T1I+T22P+S57W+A147H, T1I+T22P+S57W+S167L, T1I+T22P+S57W+G175D, T1I+T22P+V76L+A147H, T1I+T22P+V76L+S167L, T1I+T22P+V76L+G175D, T1I+T22P+A147H+S167L, T1I+T22P+A147H+G175D, T1I+T22P+S167L+G175D, T1I+S57W+V76L+A147H, T1I+S57W+V76L+S167L, T1I+S57W+V76L+G175D, T1I+S57W+A147H+S167L, T1I+S57W+A147H+G175D, T1I+S57W+S167L+G175D, T1I+V76L+A147H+S167L, T1I+V76L+A147H+G175D, T1I+V76L+S167L+G175D, T1I+A147H+S167L+G175D, T22P+S57W+V76L+A147H, T22P+S57W+V76L+S167L, T22P+S57W+V76L+G175D, T22P+S57W+A147H+S167L, T22P+S57W+A147H+G175D, T22P+S57W+S167L+G175D, T22P+V76L+A147H+S167L, T22P+V76L+A147H+G175D, T22P+V76L+S167L+G175D, T22P+A147H+S167L+G175D, S57W+V76L+A147H+S167L, S57W+V76L+A147H+G175D, S57W+V76L+S167L+G175D, S57W+A147H+S167L+G175D, and V76L+A147H+S167L+G175D.

In one preferred embodiment the DNase variant of the invention comprises at least five substitutions wherein the substitutions are selected from the group consisting of: T1I, T22P, S57W, V76L, A147H, S167L and G175D. In one embodiment the DNase variant is selected from the group consisting of: T1 I+T22P+S57W+V76L+A147H, T1I+T22P+S57W+V76L+S167L, T1I+T22P+S57W+V76L+G175D, T1I+T22P+S57W+A147H+S167L, T1I+T22P+S57W+A147H+G175D, T1I+T22P+S57W+S167L+G175D, T1I+T22P+V76L+A147H+S167L, T1I+T22P+V76L+A147H+G175D, T1I+T22P+V76L+S167L+G175D, T1I+T22P+A147H+S167L+G175D, T1I+S57W+V76L+A147H+S167L, T1I+S57W+V76L+A147H+G175D, T1I+S57W+V76L+S167L+G175D, T1I+S57W+A147H+S167L+G175D, T1I+V76L+A147H+S167L+G175D, T22P+S57W+V76L+A147H+S167L, T22P+S57W+V76L+A147H+G175D, T22P+S57W+V76L+S167L+G175D, T22P+S57W+A147H+S167L+G175D, T22P+V76L+A147H+S167L+G175D, and S57W+V76L+A147H+S167L+G175D.

In one preferred embodiment the DNase variant of the invention comprises at least five substitutions wherein the substitutions are selected from the group consisting of: T1I, T22P, S57W, V76L, A147H, S167L and G175D. In one embodiment the DNase variant is selected from the group consisting of:

T1I+T22P+S57W+V76L+A147H+S167L,
T1I+T22P+S57W+V76L+A147H+G175D,
T1I+T22P+S57W+V76L+S167L+G175D,
T1I+T22P+S57W+A147H+S167L+G175D,
T1I+T22P+V76L+A147H+S167L+G175D,
T1I+S57W+V76L+A147H+S167L+G175D,
T22P+S57W+V76L+A147H+S167L+G175D, and
T1I+T22P+S57W+V76L+A147H+S167L+G175D In one embodiment the DNase variant of the invention comprises two or more of the substitutions selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein the DNase variant further comprises at least one additional mutation selected from the group consisting of: G4N, T5F, T5C, P6V, P6G, S7D, S7T, K8V, S9K, S9Q, S9V, S9L, S9F, S9P, S9R, A10D, A10M, A10I, A10Q, A10V, A10L, A10K, Q12S, Q12V, Q12E, S13D, S13Q, S13F, S13R, S13V, S13N, S13H, S13M, S13W, S13K, S13L, S13E, Q14M, Q14R, N16S, A17C, A17V, A17E, A17T, T19K, T19L, T19S, T19I, T19V, K21E, K21M, G24Y, S27N, S271, S27M, S27D, S27V, S27F, S27A, S27C, S27E, G28L, Y29W, S30K, S30D, S30H, S30T, D32Q, 138V, 138M, S39A, Q40V, V49R, L51I, K52I, K52H, A55S, D56I, D56L, D56T, Y58A, Y58T, N61D, P63A, T65L, T65I, T65V, T65R, T65K, S68V, S68I, S68W, S68Y, S68H, S68C, S68T, S68L, T77N, T77Y, T77W, T77R, F78I, F78H, F78Y, F78C, T79G, T79R, N80K, S82L, S82E, S82K, S82R, S82H, D83C, D83F, D83L, L92T, A93G, E94N, G99S, S101D, S101A, S102M, S102L, S102V, S102A, S102K, S102T, S102R, T104P, T104A, T105V, T105I, K107L, K107C, K107R, K107H, K107S, K107M, K107E, K107A, K107D, Q109S, A112S, A125K, S1261, S126E, S126A, S126C, S130E, G132R, D135R, T138Q, W139R, R143E, R143K, G145V, G145E, G145D, G145A, G149S, K152H, K152R, S156C, S156G, S156K, S156R, S156T, S156A, T157S, Y159F, K160V, W161L, W161Y, G162Q, G162D, G162M, G162R, G162A, G162S, G162E, G162L, G162K, G162V, G162H, S164R, S164T, Q166D, S168V, S168E, S168D, S168L, K170S, K170L, K170F, K170R, T171D, T171E, T171A, T171C, A172G, A172S, L173T, L173A, L173V, Q174L, M176H, L177I, N178D, N178E, N178T, N178S, N178A, S179E, S181R, S181E, S181D, S181F, S181H, S181W, S181L, S181M, S181Y, S181Q, S181G, S181A, Y182M, Y182C, Y182K, Y182G, Y182A, Y182S, Y182V, Y182D, Y182Q, Y182F, Y182L, Y182N, Y1821, Y182E, Y182T and Y182W, wherein the positions correspond to the positions of SEQ ID NO: 1 and wherein the DNase variant has at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1.

In one embodiment the DNase variant of the invention comprises two or more of the substitutions selected from the group consisting of: T1I, T1V, S13Y, T22P, S25P, S27L, S39P, S42G, S42A, S42T, S57W, S57F, S59V, S59I, S59L, V76L, Q109R, S116D, S116E, T127V, T127I, T127L, S144P, S167L, S167I, S167V, G175D and G175E, wherein the DNase variant further comprises at least one additional mutation selected from the group consisting of: G4N, T5F, T5C, P6V, P6G, S7D, S7T, K8V, S9K, S9Q, S9V, S9L, S9F, S9P, S9R, A10D, A10M, A10I, A10Q, A10V, A10L, A10K, Q12S, Q12V, Q12E, S13D, S13Q, S13F, S13R, S13V, S13N, S13H, S13M, S13W, S13K, S13L, S13E, Q14M, Q14R, N16S, A17C, A17V, A17E, A17T, T19K, T19L, T19S, T19I, T19V, K21E, K21M, G24Y, S27N, S271, S27M, S27D, S27V, S27F, S27A, S27C, S27E, G28L, Y29W, S30K, S30D, S30H, S30T, D32Q, 138V, 138M, S39A, Q40V, V49R, L51I, K52I, K52H, A55S, D56I, D56L, D56T, Y58A, Y58T, N61D, P63A, T65L, T65I, T65V, T65R, T65K, S68V, S68I, S68W, S68Y, S68H, S68C, S68T, S68L, T77N, T77Y, T77W, T77R, F78I, F78H, F78Y, F78C, T79G, T79R, N80K, S82L, S82E, S82K, S82R, S82H, D83C, D83F, D83L, L92T, A93G, E94N, G99S, S101D, S101A, S102M, S102L, S102V, S102A, S102K, S102T, S102R, T104P, T104A, T105V, T105I, K107L, K107C, K107R, K107H, K107S, K107M, K107E, K107A, K107D, Q109S, A112S, A125K, S1261, S126E, S126A, S126C, S130E, G132R, D135R, T138Q, W139R, R143E, R143K, G145V, G145E, G145D, G145A, G149S, K152H, K152R, S156C, S156G, S156K, S156R, S156T, S156A, T157S, Y159F, K160V, W161L, W161Y, G162Q, G162D, G162M, G162R, G162A, G162S, G162E, G162L, G162K, G162V, G162H, S164R, S164T, Q166D, S168V, S168E, S168D, S168L, K170S, K170L, K170F, K170R, T171D, T171E, T171A, T171C, A172G, A172S, L173T, L173A, L173V, Q174L, M176H, L177I, N178D, N178E, N178T, N178S, N178A, S179E, S181R, S181E, S181D, S181F, S181H, S181W, S181L, S181M, S181Y, S181Q, S181G, S181A, Y182M, Y182C, Y182K, Y182G, Y182A, Y182S, Y182V, Y182D, Y182Q, Y182F, Y182L, Y182N, Y1821, Y182E, Y182T and Y182W, wherein the positions correspond to the positions of SEQ ID NO: 1 and wherein the DNase variant has at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1.

It will be clear the person skilled in the art that when the additional substitution is at position, which is selected in the first group of two substitutions e.g. S27L, then this DNase will not comprise the additional mutation S27F, i.e. the substitution S to L at position 27 is not further substituted from L to F i.e. to another amino acid. Thus, the DNase variants having additional mutations have at least three mutations compared to the parent e.g. compared to SEQ ID NO: 1 and at least two mutations selected from the group consisting of T1I, T1V, S13Y, T22P, S25P, S27L, S39P, S42G, S42A, S42T, S57W, S57F, S59V, S59I, S59L, V76L, Q109R, S116D, S116E, T127V, T127I, T127L, S144P, S167L, S167I, S167V, G175D and G175E.

In one embodiment the DNase variant of the invention comprises two or more of the substitutions selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein the DNase variant further comprises an additional mutation selected from the group consisting of: G4N, T5F, T5C, P6V, P6G, S7D, S7T, K8V, S9K, S9Q, S9V, S9L, S9F, S9P, S9R, A10D, A10M, A10I, A10Q, A10V, A10L, A10K, Q12S, Q12V, Q12E, S13D, S13Q, S13F, S13R, S13V, S13N, S13H, S13M, S13W, S13K, S13L, S13E, Q14M, Q14R, N16S, A17C, A17V, A17E, A17T, T19K, T19L, T19S, T19I, T19V, K21E, K21M, G24Y, S27N, S271, S27M, S27D, S27V, S27F, S27A, S27C, S27E, G28L, Y29W, S30K, S30D, S30H, S30T, D32Q, 138V, 138M, S39A, Q40V, V49R, L51I, K52I, K52H, A55S, D56I, D56L, D56T, Y58A, Y58T, N61D, P63A, T65L, T65I, T65V, T65R, T65K, S68V, S68I, S68W, S68Y, S68H, S68C, S68T, S68L, T77N, T77Y, T77W, T77R, F78I, F78H, F78Y, F78C, T79G, T79R, N80K, S82L, S82E, S82K, S82R, S82H, D83C, D83F, D83L, L92T, A93G, E94N, G99S, S101D, S101A, S102M, S102L, S102V, S102A, S102K, S102T, S102R, T104P, T104A, T105V, T105I, K107L, K107C, K107R, K107H, K107S, K107M, K107E, K107A, K107D, Q109S, A112S, A125K, S1261, S126E, S126A, S126C, S130E, G132R, D135R, T138Q, W139R, R143E, R143K, G145V, G145E, G145D, G145A, G149S, K152H, K152R, S156C, S156G, S156K, S156R, S156T, S156A, T157S, Y159F, K160V, W161L, W161Y, G162Q, G162D, G162M, G162R, G162A, G162S, G162E, G162L, G162K, G162V, G162H, S164R, S164T, Q166D, S168V, S168E, S168D, S168L, K170S, K170L, K170F, K170R, T171D, T171E, T171A, T171C, A172G, A172S, L173T, L173A, L173V, Q174L, M176H, L177I, N178D, N178E, N178T, N178S, N178A, S179E, S181R, S181E, S181D, S181F, S181H, S181W, S181L, S181M, S181Y, S181Q, S181G, S181A, Y182M, Y182C, Y182K, Y182G, Y182A, Y182S, Y182V, Y182D, Y182Q, Y182F, Y182L, Y182N, Y1821, Y182E, Y182T and Y182W, wherein the positions correspond to the positions of SEQ ID NO: 1, wherein the DNase variant has at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1 and wherein the DNase variant comprises at least three substitutions compared to SEQ ID NO: 1.

In one embodiment the DNase variant of the invention comprises two or more of the substitutions selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein the DNase variant further comprises an additional mutation selected from the group consisting of: G4N, T5F, T5C, P6V, P6G, S7D, S7T, K8V, S9K, S9Q, S9V, S9L, S9F, S9P, S9R, A10D, A10M, A10I, A10Q, A10V, A10L, A10K, Q12S, Q12V, Q12E, S13D, Q14M, Q14R, N16S, A17C, A17V, A17E, A17T, T19K, T19L, T19S, T19I, T19V, K21E, K21M, G24Y, G28L, Y29W, S30K, S30D, S30H, S30T, D32Q, 138V, 138M, S39A, Q40V, V49R, L51I, K52I, K52H, A55S, D56I, D56L, D56T, Y58A, Y58T, N61D, P63A, T65L, T65I, T65V, T65R, T65K, S68V, S68I, S68W, S68Y, S68H, S68C, S68T, S68L, T77N, T77Y, T77W, T77R, F78I, F78H, F78Y, F78C, T79G, T79R, N80K, S82L, S82E, S82K, S82R, S82H, D83C, D83F, D83L, L92T, A93G, E94N, G99S, S101D, S101A, S102M, S102L, S102V, S102A, S102K, S102T, S102R, T104P, T104A, T105V, T105I, K107L, K107C, K107R, K107H, K107S, K107M, K107E, K107A, K107D A112S, A125K, S1261, S126E, S126A, S126C, S130E, G132R, D135R, T138Q, W139R, R143E, R143K, G145V, G145E, G145D, G145A, G149S, K152H, K152R, S156C, S156G, S156K, S156R, S156T, S156A, T157S, Y159F, K160V, W161L, W161Y, G162Q, G162D, G162M, G162R, G162A, G162S, G162E, G162L, G162K, G162V, G162H, S164R, S164T, Q166D, S168V, S168E, S168D, S168L, K170S, K170L, K170F, K170R, T171D, T171E, T171A, T171C, A172G, A172S, L173T, L173A, L173V, Q174L, M176H, L177I, N178D, N178E, N178T, N178S, N178A, S179E, S181R, S181E, S181D, S181F, S181H, S181W, S181L, S181M, S181Y, S181Q, S181G, S181A, Y182M, Y182C, Y182K, Y182G, Y182A, Y182S, Y182V, Y182D, Y182Q, Y182F, Y182L, Y182N, Y1821, Y182E, Y182T and Y182W, wherein the positions correspond to the positions of SEQ ID NO: 1 and wherein the DNase variant has at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1.

In one embodiment the DNase variant of the invention comprises two or more of the substitutions selected from the group consisting of: T1I, T1V, S13Y, T22P, S25P, S27L, S39P, S42G, S42A, S42T, S57W, S57F, S59V, S59I, S59L, V76L, Q109R, S116D, S116E, T127V, T127I, T127L, S144P, A147H, S167L, S167I, S167V, G175D and G175E, wherein the DNase variant further comprises an additional mutation selected from the group consisting of S27K, S27R, L33R, L33V, L33Y, S39C, S39P, D56I, D56L, S57Y, T65L, T65V, T65R, S66W, T77Y, A147H, G162S, G162D, Q166D, G175N, N178D and S181L, wherein the positions correspond to the positions of SEQ ID NO: 1 and wherein the DNase variant has at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1 or SEQ ID NO: 28.

In one embodiment the DNase variant of the invention comprises two or more of the substitutions selected from the group consisting of: T1I, T1V, S13Y, T22P, S25P, S27L, S39P, S42G, S42A, S42T, S57W, S57F, S59V, S59I, S59L, V76L, Q109R, S116D, S116E, T127V, T127I, T127L, S144P, A147H, S167L, S167I, S167V, G175D and G175E, wherein the DNase variant further comprises an additional mutation selected from the group consisting of G4K, S7G, K8R, S91, N16G, S27K, S27R, D32F, D321, D32L, D32R, D32V, L33H, L33R, L33K, L33V, L33Y, S39C, G41P, S42H, D45E, Q48D, S57Y, N61E, T65M, T65W, S66R, S66M, S66W, S66Y, S66V, P91L, F78L, S101N, S106L, S106R, S106H, Q109E, A112E, T127P, S130A, S130Y, T138D, Q140V, Q140G, A147P, C148A, W154Y, T157V, Y159A, Y159R, G162C, Q174N, L177Y, S179L and C180A, wherein the positions correspond to the positions of SEQ ID NO: 1 and wherein the DNase variant has at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1 or SEQ ID NO: 28.

In one embodiment the DNase variant is selected from the group consisting of DNase variants comprising the mutations: T1I+K21E+T22P+S25P+S39P+S57W+V76L+T127V+A147H+S167L+G175D, T1I+K21E+T22P+S57W+V76L+K107E+T127V+A147H+S167L+G175D, T1I+K21E+T22P+S57W+V76L+S116D+T127V+A147H+S167L+G175D, T1I+S57W+A147Q, T1I+T22P+D45E+D56I+S57W+V76L+A112E+S116D+T127V+A147H+S167L+G175D, T1I+T22P+D56I+S57W+N61E+V76L+A93G+A147H+S167L+G175D, T1I+T22P+D56I+S57W+S68V+V76L+A147H+S167L+G175N+N178D, T1I+T22P+D56I+S57W+S68V+V76L+A147H+S167L+T171D+G175D, T1I+T22P+D56I+S57W+S68V+V76L+K107E+Q109R+A147H+S167L+G175D, T1I+T22P+D56I+S57W+S68V+V76L+Q109R+A147H+S167L+G175D, T1I+T22P+D56I+S57W+V76L+A93G+A147H+S167L+G175D, T1I+T22P+D56I+S57W+V76L+K107E+S116D+A147H+S167L+G175D, T1I+T22P+D56I+S57W+V76L+K107E+T127V+A147H+S167L+G175D, T1I+T22P+D56I+S57W+V76L+Q109K+S116D+T127V+A147H+S167L+G175D, T1I+T22P+D56I+S57W+V76L+Q109R+S116D+A147H+G162S+S167L+G175D, T1I+T22P+D56I+S57W+V76L+Q109R+S116D+A147H+S167L+G175D, T1I+T22P+D56I+S57W+V76L+S116D+A147H+Q166D+S167L+G175D, T1I+T22P+D56I+S57W+V76L+T127V+A147H+G162S+S167L+G175D, T1I+T22P+D56I+S57Y+S68V+V76L+A147H+S167L+G175D, T1I+T22P+S25P+D56I+S57W+V76L+T127V+A147H+S167L+G175D, T1I+T22P+S25P+S57W+V76L+S116D+T127V+A147H+S167L+G175D, T1I+T22P+S39A+S57W+N61E+V76L+A147H+S167L+T171D+G175D, T1I+T22P+S39A+S57W+N61E+V76L+Q109R+A147H+S167L+G175D, T1I+T22P+S39A+S57W+V76L+A147H+Q166D+S167L+G175D, T1I+T22P+S39A+S57W+V76L+A147H+S167L+T171D+G175D, T1I+T22P+S39A+S57W+V76L+Q109R+A147H+Q166D+S167L+G175D, T1I+T22P+S39P+D56I+S57W+V76L+A147H+G162S+S167L+G175D, T1I+T22P+S39P+D56I+S57W+V76L+K107E+A147H+S167L+G175D, T1I+T22P+S39P+D56I+S57W+V76L+T127V+A147H+S167L+G175D, T1I+T22P+S39P+S57W+V76L+S116D+A147H+G162S+S167L+G175D, T1I+T22P+S39P+S57W+V76L+S116D+A147H+Q166D+S167L+

G175D, T1I+T22P+S39P+S57W+V76L+T127V+A147H+Q166D+S167L+G175D, T1I+T22P+S39P+S57W+V76L+T127V+A147H+S167L+G175D, T1I+T22P+S57W+A147H+S167L+G175D, T1I+T22P+S57W+N61E+S68V+V76L+A147H+G162Q+S167L+G175D, T1I+T22P+S57W+N61E+V76L+Q109R+A147H+Q166D+S167L+G175D, T1I+T22P+S57W+N61E+V76L+Q109R+A147H+S167L+T171D+G175D, T1I+T22P+S57W+V76K+T104A+T127P+A147H+G162Q+S167L+G175D, T1I+T22P+S57W+V76L+A147H+S167F+G175D, T1I+T22P+S57W+V76L+A147H+S167L, T1I+T22P+S57W+V76L+A147H+S167L+G175D, T1I+T22P+S57W+V76L+A147H+S167L+G175E, T1I+T22P+S57W+V76L+A147H+S167L+T171D+G175D, T1I+T22P+S57W+V76L+A93G+A147H+G162Q+S167L+G175D, T1I+T22P+S57W+V76L+A93G+A147H+Q166D+S167L+G175D, T1I+T22P+S57W+V76L+A93G+A147H+S167L+G175D, T1I+T22P+S57W+V76L+K107E+S116D+T127V+A147H+S167L+G175D, T1I+T22P+S57W+V76L+Q109R+A147H+Q166D+S167L+T171D+G175D, T1I+T22P+S57W+V76L+Q109R+A147H+S167L+T171D+G175D, T1L+N16G+T22P+D56I+S57Y+S68V+V76L+A147R, T1L+N16G+T22P+S57Y+S68V+V76L+A93G+A147R+S167M, T1L+T22P+D56I+S57Y+A147R+S167M, T1L+T22P+D56I+S57Y+N61E+S68V+V76L+A147R, T1L+T22P+D56I+S57Y+N61E+S68V+V76L+A147R+G175E, T1L+T22P+D56I+S57Y+N61E+S68V+V76L+A147R+S167M, T1L+T22P+D56I+S57Y+S68V+V76L+A147R, T1L+T22P+D56I+S57Y+S68V+V76L+A147R+G162Q, T1L+T22P+D56I+S57Y+S68V+V76L+A147R+G162Q+G175D, T1L+T22P+D56I+S57Y+S68V+V76L+A147R+G162Q+G175E, T1L+T22P+D56I+S57Y+S68V+V76L+A147R+G162Q+S167M, T1L+T22P+D56I+S57Y+S68V+V76L+A147R+G175D, T1L+T22P+D56I+S57Y+S68V+V76L+A147R+S167M+G175E, T1L+T22P+D56I+S57Y+S68V+V76L+A147R+T171D, T1L+T22P+D56I+S57Y+S68V+V76L+A93G+A147R, T1L+T22P+D56I+S57Y+S68V+V76L+A93G+A147R+S167M, T1L+T22P+D56I+S57Y+S68V+V76L+F78L+A147R, T1L+T22P+D56I+S57Y+S68V+V76L+P91L+Q109R+A147R+G175E, T1L+T22P+D56I+S57Y+S68V+V76L+Q109R+A147R, T1L+T22P+D56I+S57Y+S68V+V76L+Q109R+A147R+G175D, T1L+T22P+S39A+D56I+S57Y+S68V+V76L+A147R, T1L+T22P+S39A+D56I+S57Y+S68V+V76L+A147R+G175E, T1L+T22P+S57W+S68V+V76K+A147R, T1L+T22P+S57Y+S68V+V76L+A147R+G162Q+S167M+G175D, T1L+T22P+S57Y+S68V+V76L+A93G+A147R+S167M, T1L+T22P+S57Y+S68V+V76L+A93G+A147R+S167M+G175E, and T1L+T22P+S57Y+S68V+V76L+Q109R+A147R+S167T.

In one embodiment the DNase variant is selected from the group consisting of DNase variants comprising the mutations: T1I+G4K+S13Y+T22P+S27L+S39P+S42G+D56I+S57W+S59V+V76L+Q109R+S116D+T127V+S 144P+A147H+S167L+G175D; T1I+K8R+S13Y+T22P+S27L+S39P+S42G+D56I+S57W+S59V+V76L+Q109R+S116D+T127V+S1 44P+A147H+S167L+G175D; T1I+S13Y+S27L+S39P+S42G+D56I+S57W+S59V+V76L+Q109R+S116D+T127V+S144P+A147H+S167L+G175D; T1I+S13Y+T22P+E23G+S27L+S42G+S57W+S59V+V76L+Q109R+S116D+T127V+D133N+S144 P+A147H+S167L+G175D; T1I+S13Y+T22P+S25P+S27L+L33K+S39P+S42G+D56I+S57W+S59V+S66Y+V76L+Q109R+S11 6D+T127V+S144P+A147H+S167L+G175D; T1I+S13Y+T22P+S25P+S27L+L33K+S39P+S42G+D56L+S57W+S59V+T65V+S66Y+V76L+T77Y+Q109R+S116D+T127V+S144P+A147H+G162E+S167L+G175D; T1I+S13Y+T22P+S25P+S27L+L33K+S39P+S42G+D56L+S57W+S59V+T65V+S66Y+V76L+T77Y+Q109R+S116D+T127V+S144P+A147H+S167L+G175D; T1I+S13Y+T22P+S25P+S27L+L33K+S39P+S42G+S57W+S59V+S66W+V76L+T77Y+Q109R+S1 16D+T127V+S144P+A147H+S167L+G175D; T1I+S13Y+T22P+S25P+S27L+L33K+S39P+S42G+S57W+S59V+S66Y+V76L+T77Y+Q109R+S1 16D+T127V+S144P+A147H+S167L+G175D; T1I+S13Y+T22P+S25P+S27L+L33K+S39P+S42G+S57W+S59V+T65L+V76L+T77Y+Q109R+S11 6D+T127V+S144P+A147H+S167L+G175D; T1I+S13Y+T22P+S25P+S27L+L33K+S39P+S42G+S57W+S59V+T65V+S66Y+V76L+T77Y+Q109R+S116D+T127V+S144P+A147H+G162D+S167L+G175D; T1I+S13Y+T22P+S25P+S27L+L33K+S39P+S42G+S57W+S59V+T65V+S66Y+V76L+T77Y+Q109R+S116D+T127V+S144P+A147H+S167L+G175D+S181E; T1I+S13Y+T22P+S25P+S27L+L33K+S39P+S42G+S57W+S59V+T65V+V76L+T77Y+Q109R+S1 16D+T127V+S144P+A147H+S167L+G175D; T1I+S13Y+T22P+S25P+S27L+S30P+S39P+S42G+S57W+S59V+S68V+V76L+T77Y+Q109R+T1 27V+S144P+A147H+S167L+G175D; T1I+S13Y+T22P+S25P+S27L+S39P+D56I+S57W+S59V+V76L+Q109R+S116D+T127V+S144P+A147H+S167L+G175D; T1I+S13Y+T22P+S25P+S27L+S39P+S42C+S57W+S59V+S68V+V76L+T77Y+Q109R+S116D+T 127V+S144P+A147H+S167L+G175D; T1I+S13Y+T22P+S25P+S27L+S39P+S42G+D56I+S57W+S59V+S68V+V76L+Q109R+S116D+T1 27V+S144P+A147H+S167L+G175D; T1I+S13Y+T22P+S25P+S27L+S39P+S42G+D56I+S57W+S59V+T65L+V76L+Q109R+S116D+T1 27V+S144P+A147H+S167L+G175D; T1I+S13Y+T22P+S25P+S27L+S39P+S42G+D56I+S57W+S59V+T65V+V76L+Q109R+S116D+T1 27V+S144P+A147H+S167L+G175D; T1I+S13Y+T22P+S25P+S27L+S39P+S42G+D56I+S57W+S59V+V76L+Q109R+S116D+T127V+S 144P+A147H+Q166D+S167L+G175D; T1I+S13Y+T22P+S25P+S27L+S39P+S42G+D56I+S57W+S59V+V76L+Q109R+S116D+T127V+S 144P+A147H+S167L+G175D; T1I+S13Y+T22P+S25P+S27L+S39P+S42G+D56I+S57W+S59V+V76L+Q109R+T127V+S144P+A 147H+S167L+G175D; T1I+S13Y+T22P+S25P+S27L+S39P+S42G+D56I+S57W+S59V+V76L+T77Y+Q109R+S116D+T1 27V+S144P+A147H+S167L+G175D; T1I+S13Y+T22P+S25P+S27L+S39P+S42G+D56L+S57W+S59V+T65V+S66Y+V76L+T77Y+Q10 9R+S116D+T127V+S144P+A147H+G162D+S167L+G175D; T1I+S13Y+T22P+S25P+S27L+S39P+S42G+D56L+S57W+S59V+T65V+S66Y+V76L+T77Y+Q10 9R+S116D+T127V+S144P+A147H+S167L+G175D+S181E; T1I+S13Y+T22P+S25P+S27L+S39P+S42G+D56L+S57W+S59V+T65V+S66Y+V76L+T77Y+S106 L+Q109R+S116D+T127V+S144P+A147H+S167L+G175D; T1I+S13Y+T22P+S25P+S27L+S39P+S42G+S57W+S59V+S68V+V76L+Q109R+S116D+T127V+S144P+A147H+S167L; T1I+S13Y+T22P+S25P+S27L+S39P+S42G+S57W+S59V+S68V+V76L+Q109R+S116D+T127V+S144P+A147H+S167L+G175D; T1I+S13Y+T22P+S25P+S27L+S39P+S42G+S57W+S59V+S68V+V76L+Q109R+S116D+T127V+S144P+A147H+S167L+G175D+N178D; T1I+S13Y+T22P+S25P+S27L+S39P+S42G+S57W+S59V+S68V+V76L+Q109R+S116D+T127V+S144P+A147H+S167L+G175D+N178E; T1I+S13Y+T22P+S25P+S27L+S39P+S42G+S57W+S59V+S68V+V76L+Q109R+S116D+T127V+S144P+A147H+S167L+N178D; T1I+S13Y+T22P+S25P+S27L+S39P+S42G+S57W+S59V+S68V+V76L+Q109R+T127V+S144P+A147H+S167L+G175D;

T1I+S13Y+T22P+S25P+S27L+S39P+S42G+S57W+S59V+S68V+V76L+T77Y+Q109R+S116D+T127V+S144P+A147H+Q166D+S167L+G175D; T1I+S13Y+T22P+S25P+S27L+S39P+S42G+S57W+S59V+S68V+V76L+T77Y+Q109R+S116D+T127V+S144P+A147H+S167L; T1I+S13Y+T22P+S25P+S27L+S39P+S42G+S57W+S59V+S68V+V76L+T77Y+Q109R+S116D+T127V+S144P+A147H+S167L+G175D+N178E; T1I+S13Y+T22P+S25P+S27L+S39P+S42G+S57W+S59V+S68V+V76L+T77Y+Q109R+S116D+T127V+S144P+A147H+S167L+N178D; T1I+S13Y+T22P+S25P+S27L+S39P+S42G+S57W+S59V+T65L+S66W+V76L+T77Y+Q109R+S116D+T127V+S144P+A147H+S167L+G175D; T1I+S13Y+T22P+S25P+S27L+S39P+S42G+S57W+S59V+T65L+S66Y+V76L+T77Y+Q109R+S116D+T127V+S144P+A147H+S167L+G175D; T1I+S13Y+T22P+S25P+S27L+S39P+S42G+S57W+S59V+T65V+S66W+V76L+T77Y+Q109R+S116D+T127V+S144P+A147H+S167L+G175D; T1I+S13Y+T22P+S25P+S27L+S39P+S42G+S57W+S59V+T65V+S66Y+V76L+T77Y+Q109R+S116D+T127V+S144P+A147H+G162D+S167L+G175D; T1I+S13Y+T22P+S25P+S27L+S39P+S42G+S57W+S59V+S66Y+V76L+T77Y+Q109R+S116D+T127V+S144P+A147H+G162D+S167L+G175D+S181E; T1I+S13Y+T22P+S25P+S27L+S39P+S42G+S57W+S59V+T65V+S66Y+V76L+T77Y+Q109R+S116D+T127V+S144P+A147H+S167L+G175D; T1I+S13Y+T22P+S25P+S27L+S39P+S42G+S57W+S59V+T65V+S66Y+V76L+T77Y+Q109R+S116D+T127V+S144P+A147H+S167L+G175D+S181E; T1I+S13Y+T22P+S25P+S27L+S39P+S42G+S57W+S59V+T65V+S66Y+V76L+T77Y+S106L+Q109R+S116D+T127V+S144P+A147H+G162D+S167L+G175D; T1I+S13Y+T22P+S25P+S27L+S39P+S42G+S57W+S59V+T65V+S66Y+V76L+T77Y+S106L+Q109R+S116D+T127V+S144P+A147H+S167L+G175D; T1I+S13Y+T22P+S25P+S27L+S39P+S42G+S57W+S59V+T65V+S66Y+V76L+T77Y+S106L+Q109R+S116D+T127V+S144P+A147H+S167L+G175D+S181E; T1I+S13Y+T22P+S25P+S27L+S39P+S42G+S57W+S59V+V76L+Q109R+S116D+T127V+S144P+A147H+S167L+G175D; T1I+S13Y+T22P+S25P+S27L+S39P+S42G+S57W+S59V+V76L+T77Y+Q109R+S116D+T127V+S144P+A147H+S167L+G175D; T1I+S13Y+T22P+S25P+S27L+S39P+S57W+S59V+S68V+V76L+Q109R+S116D+T127V+S144P+A147H+S167L+G175D; T1I+S13Y+T22P+S25P+S27R+L33R+S39P+S42G+S57W+S59V+S66Y+V76L+T77Y+Q109R+S116D+T127V+S144P+A147H+S167L+G175D; T1I+S13Y+T22P+S25P+S27R+S39P+S42G+D56I+S57W+S59V+V76L+Q109R+S116D+T127V+S144P+A147H+S167L+G175D; T1I+S13Y+T22P+S25P+S27R+S39P+S42G+S57W+S59V+S66W+V76L+T77Y+Q109R+S116D+T127V+S144P+A147H+S167L+G175D; T1I+S13Y+T22P+S27K+L33K+S39P+S42G+D56I+S57W+S59V+T65V+S66Y+V76L+Q109R+S116D+T127V+S144P+A147H+G162D+S167L+G175D; T1I+S13Y+T22P+S27K+L33K+S39P+S42G+D56L+S57W+S59V+T65L+S66Y+V76L+Q109R+S116D+T127V+S144P+A147H+G162D+S167L+G175D; T1I+S13Y+T22P+S27K+L33K+S39P+S42G+D56L+S57W+S59V+T65V+S66Y+V76L+Q109R+S116D+T127V+S144P+A147H+G162D+S167L+G175D; T1I+S13Y+T22P+S27K+L33K+S39P+S42G+S57W+S59V+T65V+S66Y+V76L+T77Y+Q109R+S116D+T127V+S144P+A147H+G162D+S167L+G175D+S181E; T1I+S13Y+T22P+S27K+L33K+S39P+S42G+S57W+S59V+T65V+S66Y+V76L+T77Y+Q109R+S116D+T127V+S144P+A147H+S167L+G175D; T1I+S13Y+T22P+S27K+S39P+S42G+D56I+S57W+S59V+T65L+V76L+Q109R+S116D+T127V+S130A+S144P+A147H+S167L+G175D; T1I+S13Y+T22P+S27K+S39P+S42G+D56I+S57W+S59V+T65V+V76L+Q109R+S116D+T127V+S130A+S144P+A147H+S167L+G175D; T1I+S13Y+T22P+S27K+S39P+S42G+D56I+S57W+S59V+T65V+V76L+S106L+Q109R+S116D+T127V+S144P+A147H+S167L+G175D; T1I+S13Y+T22P+S27K+S39P+S42G+D56I+S57W+S59V+V76L+Q109R+S116D+T127V+S130A+S144P+A147H+G162D+S167L+G175D; T1I+S13Y+T22P+S27K+S39P+S42G+D56I+S57W+S59V+V76L+Q109R+S116D+T127V+S144P+A147H+G162D+S167L+G175D; T1I+S13Y+T22P+S27K+S39P+S42G+D56I+S57W+S59V+V76L+S106L+Q109R+S116D+T127V+S130A+S144P+A147H+S167L+G175D; T1I+S13Y+T22P+S27K+S39P+S42G+D56I+S57W+S59V+V76L+S106L+Q109R+S116D+T127V+S144P+A147H+G162D+S167L+G175D; T1I+S13Y+T22P+S27K+S39P+S42G+D56I+S57W+S59V+V76L+S106L+Q109R+S116D+T127V+S144P+A147H+S167L+G175D; T1I+S13Y+T22P+S27K+S39P+S42G+D56L+S57W+S59V+T65L+V76L+Q109R+S116D+T127V+S144P+A147H+S167L+G175D; T1I+S13Y+T22P+S27K+S39P+S42G+D56L+S57W+S59V+T65V+V76L+Q109R+S116D+T127V+S144P+A147H+S167L+G175D; T1I+S13Y+T22P+S27K+S39P+S42G+D56L+S57W+S59V+V76L+Q109R+S116D+T127V+S130A+S144P+A147H+S167L+G175D; T1I+S13Y+T22P+S27K+S39P+S42G+D56L+S57W+S59V+V76L+Q109R+S116D+T127V+S144P+A147H+S167L+G175D; T1I+S13Y+T22P+S27K+S39P+S42G+S57W+S59V+T65V+S66Y+V76L+T77Y+Q109R+S116D+T127V+S144P+A147H+G162D+S167L+G175D; T1I+S13Y+T22P+S27K+S39P+S42G+S57W+S59V+T65V+S66Y+V76L+T77Y+Q109R+S116D+T127V+S144P+A147H+S167L+G175D+S181E; T1I+S13Y+T22P+S27K+S42G+S57W+S59V+V76L+Q109R+S116D+T127V+S144P+A147H+S167L+G175D; T1I+S13Y+T22P+S27L+D32L+S42G+S57W+S59V+V76L+Q109R+S116D+T127V+S144P+A147H+S167L+G175D; T1I+S13Y+T22P+S27L+D32R+S42G+S57W+S59V+V76L+Q109R+S116D+T127V+S144P+A147H+S167L+G175D; T1I+S13Y+T22P+S27L+D32V+S42G+S57W+S59V+V76L+Q109R+S116D+T127V+S144P+A147H+S167L+G175D; T1I+S13Y+T22P+S27L+L33H+S42G+S57W+S59V+V76L+Q109R+S116D+T127V+S144P+A147H+S167L+G175D; T1I+S13Y+T22P+S27L+L33K+S39P+S42G+D56I+S57W+S59V+S66W+V76L+Q109R+S116D+T127V+S144P+A147H+S167L+G175D; T1I+S13Y+T22P+S27L+L33K+S39P+S42G+D56I+S57W+S59V+S66Y+V76L+Q109R+S116D+T127V+S144P+A147H+S167L+G175D; T1I+S13Y+T22P+S27L+L33K+S39P+S42G+D56I+S57W+S59V+T65L+S66Y+V76L+Q109R+S116D+T127V+S144P+A147H+G162D+S167L+G175D; T1I+S13Y+T22P+S27L+L33K+S39P+S42G+D56I+S57W+S59V+T65L+V76L+Q109R+S116D+T127V+S144P+A147H+S167L+G175D; T1I+S13Y+T22P+S27L+L33K+S39P+S42G+D56I+S57W+S59V+T65V+S66Y+V76L+Q109R+S116D+T127V+S144P+A147H+G162D+S167L+G175D; T1I+S13Y+T22P+S27L+L33K+S39P+S42G+D56I+S57W+S59V+T65V+V76L+Q109R+S116D+T127V+S144P+A147H+S167L+G175D; T1I+S13Y+T22P+S27L+L33K+S39P+S42G+D56I+S57W+S59V+V76L+Q109R+S116D+T127V+S144P+A147H+S167L+G175D; T1I+S13Y+T22P+S27L+L33K+S39P+S42G+D56L+S57W+S59V+T65L+S66Y+V76L+Q109R+S116D+T127V+S144P+A147H+G162D+S167L+G175D; T1I+S13Y+T22P+S27L+L33K+S39P+S42G+D56L+

S57W+S59V+T65V+S66Y+V76L+Q109R+S116D+T127V+S144P+A147H+G162D+S167L+G175D; T1I+S13Y+T22P+S27L+L33R+S42G+S57W+S59V+V76L+Q109R+S116D+T127V+S144P+A147H+S167L+G175D; T1I+S13Y+T22P+S27L+L33V+S42G+S57W+S59V+V76L+Q109R+S116D+T127V+S144P+A147H+S167L+G175D; T1I+S13Y+T22P+S27L+L33Y+S42G+S57W+S59V+V76L+Q109R+S116D+T127V+S144P+A147H+S167L+G175D; T1I+S13Y+T22P+S27L+S39C+S42G+S57W+S59V+V76L+Q109R+S116D+T127V+S144P+A147H+S167L+G175D; T1I+S13Y+T22P+S27L+S39P+D56I+S57W+S59V+V76L+Q109R+S116D+T127V+S144P+A147H+S167L+G175D; T1I+S13Y+T22P+S27L+S39P+S42G+D56I+S57W+S59D+V76L+Q109R+S116D+T127V+S144P+A147H+S167L+G175D; T1I+S13Y+T22P+S27L+S39P+S42G+D56I+S57W+S59E+V76L+Q109R+S116D+T127V+S144P+A147H+S167L+G175D; T1I+S13Y+T22P+S27L+S39P+S42G+D56I+S57W+S59G+V76L+Q109R+S116D+T127V+S144P+A147H+S167L+G175D; T1I+S13Y+T22P+S27L+S39P+S42G+D56I+S57W+S59V+Q109R+S116D+T127V+S144P+A147H+S167L+G175D; T1I+S13Y+T22P+S27L+S39P+S42G+D56I+S57W+S59V+S66Y+V76L+Q109R+S116D+T127V+S144P+A147H+S167L+G175D; T1I+S13Y+T22P+S27L+S39P+S42G+D56I+S57W+S59V+S68V+V76L+Q109R+S116D+T127V+S144P+A147H+S167L+G175D; T1I+S13Y+T22P+S27L+S39P+S42G+D56I+S57W+S59V+T65L+S66W+V76L+Q109R+S116D+T127V+S144P+A147H+S167L+G175D; T1I+S13Y+T22P+S27L+S39P+S42G+D56I+S57W+S59V+T65L+V76L+Q109R+S116D+T127V+S130A+S144P+A147H+G162D+S167L+G175D; T1I+S13Y+T22P+S27L+S39P+S42G+D56I+S57W+S59V+T65L+V76L+Q109R+S116D+T127V+S144P+A147H+G162D+S167L+G175D; T1I+S13Y+T22P+S27L+S39P+S42G+D56I+S57W+S59V+T65L+V76L+Q109R+S116D+T127V+S144P+A147H+S167L+G175D; T1I+S13Y+T22P+S27L+S39P+S42G+D56I+S57W+S59V+T65L+V76L+S106L+Q109R+S116D+T127V+S130A+S144P+A147H+S167L+G175D; T1I+S13Y+T22P+S27L+S39P+S42G+D56I+S57W+S59V+T65L+V76L+S106L+Q109R+S116D+T127V+S144P+A147H+G162D+S167L+G175D; T1I+S13Y+T22P+S27L+S39P+S42G+D56I+S57W+S59V+T65L+V76L+S106L+Q109R+S116D+T127V+S144P+A147H+S167L+G175D; T1I+S13Y+T22P+S27L+S39P+S42G+D56I+S57W+S59V+T65V+V76L+Q109R+S116D+T127V+S130A+S144P+A147H+G162D+S167L+G175D; T1I+S13Y+T22P+S27L+S39P+S42G+D56I+S57W+S59V+T65V+V76L+Q109R+S116D+T127V+S130A+S144P+A147H+S167L+G175D; T1I+S13Y+T22P+S27L+S39P+S42G+D56I+S57W+S59V+T65V+V76L+Q109R+S116D+T127V+S144P+A147H+G162D+S167L+G175D; T1I+S13Y+T22P+S27L+S39P+S42G+D56I+S57W+S59V+T65V+V76L+Q109R+S116D+T127V+S144P+A147H+S167L+G175D; T1I+S13Y+T22P+S27L+S39P+S42G+D56I+S57W+S59V+T65V+V76L+S106L+Q109R+S116D+T127V+S144P+A147H+G162D+S167L+G175D; T1I+S13Y+T22P+S27L+S39P+S42G+D56I+S57W+S59V+V76L+Q109R+S116D+S144P+A147H+S167L+G175D; T1I+S13Y+T22P+S27L+S39P+S42G+D56I+S57W+S59V+V76L+Q109R+S116D+T127V+A147H+S167L+G175D; T1I+S13Y+T22P+S27L+S39P+S42G+D56I+S57W+S59V+V76L+Q109R+S116D+T127V+S144P+A147H+G162D+S167L+G175D; T1I+S13Y+T22P+S27L+S39P+S42G+D56I+S57W+S59V+V76L+Q109R+S116D+T127V+S144P+A147H+G162E+S167L+G175D; T1I+S13Y+T22P+S27L+S39P+S42G+D56I+S57W+S59V+V76L+Q109R+S116D+T127V+S144P+A147H+G175D; T1I+S13Y+T22P+S27L+S39P+S42G+D56I+S57W+S59V+V76L+Q109R+S116D+T127V+S144P+A147H+S167L; T1I+S13Y+T22P+S27L+S39P+S42G+D56I+S57W+S59V+V76L+Q109R+S116D+T127V+S144P+A147H+S167L+G175D; T1I+S13Y+T22P+S27L+S39P+S42G+D56I+S57W+S59V+V76L+Q109R+S116D+T127V+S144P+A147K+S167L+G175D; T1I+S13Y+T22P+S27L+S39P+S42G+D56I+S57W+S59V+V76L+Q109R+S116D+T127V+S144P+A147R+S167L+G175D; T1I+S13Y+T22P+S27L+S39P+S42G+D56I+S57W+S59V+V76L+Q109R+S116D+T127V+S144P+S167L+G175D; T1I+S13Y+T22P+S27L+S39P+S42G+D56I+S57W+S59V+V76L+Q109R+S116D+T127V+T138D+S144P+A147H+S167L+G175D; T1I+S13Y+T22P+S27L+S39P+S42G+D56I+S57W+S59V+V76L+Q109R+T127V+S144P+A147H+S167L+G175D; T1I+S13Y+T22P+S27L+S39P+S42G+D56I+S57W+S59V+V76L+S106L+Q109R+S116D+T127V+S130A+S144P+A147H+G162D+S167L+G175D; T1I+S13Y+T22P+S27L+S39P+S42G+D56I+S57W+S59V+V76L+S106L+Q109R+S116D+T127V+S144P+A147H+G162D+S167L+G175D; T1I+S13Y+T22P+S27L+S39P+S42G+D56I+S57W+S59V+V76L+S106L+Q109R+S116D+T127V+S144P+A147H+S167L+G175D; T1I+S13Y+T22P+S27L+S39P+S42G+D56I+S57W+S59V+V76L+S106R+Q109R+S116D+T127V+S144P+A147H+S167L+G175D; T1I+S13Y+T22P+S27L+S39P+S42G+D56I+S57W+S59V+V76L+T77Y+Q109R+S116D+T127V+S144P+A147H+Q166D+S167L+G175D; T1I+S13Y+T22P+S27L+S39P+S42G+D56I+S57W+S59V+V76L+T77Y+Q109R+S116D+T127V+S144P+A147H+S167L+G175D; T1I+S13Y+T22P+S27L+S39P+S42G+D56I+S57W+V76L+Q109R+S116D+T127V+S144P+A147H+S167L+G175D; T1I+S13Y+T22P+S27L+S39P+S42G+D56I+S57Y+S59V+V76L+Q109R+S116D+T127V+S144P+A147H+S167L+G175D; T1I+S13Y+T22P+S27L+S39P+S42G+D56I+S59V+V76L+Q109R+S116D+T127V+S144P+A147H+S167L+G175D; T1I+S13Y+T22P+S27L+S39P+S42G+D56L+S57W+S59V+T65L+V76L+Q109R+S116D+T127V+S130A+S144P+A147H+S167L+G175D; T1I+S13Y+T22P+S27L+S39P+S42G+D56L+S57W+S59V+T65L+V76L+Q109R+S116D+T127V+S144P+A147H+G162D+S167L+G175D; T1I+S13Y+T22P+S27L+S39P+S42G+D56L+S57W+S59V+T65L+V76L+S106L+Q109R+S116D+T127V+S144P+A147H+S167L+G175D; T1I+S13Y+T22P+S27L+S39P+S42G+D56L+S57W+S59V+T65V+V76L+Q109R+S116D+T127V+S130A+S144P+A147H+S167L+G175D; T1I+S13Y+T22P+S27L+S39P+S42G+D56L+S57W+S59V+T65V+V76L+Q109R+S116D+T127V+S144P+A147H+G162D+S167L+G175D; T1I+S13Y+T22P+S27L+S39P+S42G+D56L+S57W+S59V+T65V+V76L+S106L+Q109R+S116D+T127V+S144P+A147H+S167L+G175D; T1I+S13Y+T22P+S27L+S39P+S42G+D56L+S57W+S59V+V76L+Q109R+S116D+T127V+S130A+S144P+A147H+G162D+S167L+G175D; T1I+S13Y+T22P+S27L+S39P+S42G+D56L+S57W+S59V+V76L+Q109R+S116D+T127V+S144P+A147H+G162D+S167L+G175D; T1I+S13Y+T22P+S27L+S39P+S42G+D56L+S57W+S59V+V76L+Q109R+S116D+T127V+S144P+A147H+S167L+G175D; T1I+S13Y+T22P+S27L+S39P+S42G+D56L+S57W+S59V+V76L+S106L+Q109R+S116D+T127V+S130A+S144P+A147H+G162D+S167L+G175D; T1I+S13Y+T22P+S27L+S39P+S42G+D56L+S57W+S59V+V76L+S106L+Q109R+S116D+T127V+S130A+S144P+A147H+S167L+G175D; T1I+S13Y+T22P+S27L+S39P+S42G+D56L+S57W+

S59V+V76L+S106L+Q109R+S116D+T127V+S144P+A147H+G162D+S167L+G175D; T1I+S13Y+T22P+S27L+S39P+S42H+D56I+S57W+S59V+V76L+Q109R+S116D+T127V+S144P+A147H+S167L+G175D; T1I+S13Y+T22P+S27L+S42G+D56L+S57W+S59V+V76L+Q109R+S116D+T127V+S144P+A147 H+S167L+G175D; T1I+S13Y+T22P+S27L+S42G+S57W+S59V+S66R+V76L+Q109R+S116D+T127V+S144P+A147 H+S167L+G175D; T1I+S13Y+T22P+S27L+S42G+S57W+S59V+S66W+V76L+Q109R+S116D+T127V+S144P+A147 H+S167L+G175D; T1I+S13Y+T22P+S27L+S42G+S57W+S59V+S66Y+V76L+Q109R+S116D+T127V+S144P+A147 H+S167L+G175D; T1I+S13Y+T22P+S27L+S42G+S57W+S59V+T65L+V76L+Q109R+S116D+T127V+S144P+A147 H+S167L+G175D; T1I+S13Y+T22P+S27L+S42G+S57W+S59V+T65M+V76L+Q109R+S116D+T127V+S144P+A147 H+S167L+G175D; T1I+S13Y+T22P+S27L+S42G+S57W+S59V+T65R+V76L+Q109R+S116D+T127V+S144P+A147 H+S167L+G175D; T1I+S13Y+T22P+S27L+S42G+S57W+S59V+V76L+Q109R+S116D+T127V+Q140G+S144P+A14 7H+S167L+G175D; T1I+S13Y+T22P+S27L+S42G+S57W+S59V+V76L+Q109R+S116D+T127V+Q140V+S144P+A14 7H+S167L+G175D; T1I+S13Y+T22P+S27L+S42G+S57W+S59V+V76L+Q109R+S116D+T127V+S130Y+S144P+A14 7H+S167L+G175D; T1I+S13Y+T22P+S27L+S42G+S57W+S59V+V76L+Q109R+S116D+T127V+S144P+A147H+C14 8A+S167L+G175D+S179L+C180A; T1I+S13Y+T22P+S27L+S42G+S57W+S59V+V76L+Q109R+S116D+T127V+S144P+A147H+G16 2C+S167L+G175D; T1I+S13Y+T22P+S27L+S42G+S57W+S59V+V76L+Q109R+S116D+T127V+S144P+A147H+G16 2D+S167L+G175D; T1I+S13Y+T22P+S27L+S42G+S57W+S59V+V76L+Q109R+S116D+T127V+S144P+A147H+G16 2E+S167L+G175D; T1I+S13Y+T22P+S27L+S42G+S57W+S59V+V76L+Q109R+S116D+T127V+S144P+A147H+K16 0V+S167L+G175D; T1I+S13Y+T22P+S27L+S42G+S57W+S59V+V76L+Q109R+S116D+T127V+S144P+A147H+S16 7L+G175D+S179L; T1I+S13Y+T22P+S27L+S42G+S57W+S59V+V76L+Q109R+S116D+T127V+S144P+A147H+S16 7L+G175D+S181E; T1I+S13Y+T22P+S27L+S42G+S57W+S59V+V76L+Q109R+S116D+T127V+S144P+A147H+W15 4Y+S167L+G175D; T1I+S13Y+T22P+S27L+S42G+S57W+S59V+V76L+S101N+Q109R+S116D+T127V+S144P+A14 7H+S167L+G175D; T1I+S13Y+T22P+S27L+S42G+S57W+S59V+V76L+S106L+Q109R+S116D+T127V+S144P+A147 H+S167L+G175D; T1I+S13Y+T22P+S27R+S39P+S42G+D56I+S57W+S59V+T65V+V76L+Q109R+S116D+T127V+S144P+A147H+S167L+G175D; T1I+S13Y+T22P+S27R+S39P+S42G+D56I+S57W+S59V+V76L+Q109R+S116D+T127V+S130A+S144P+A147H+G162D+S167L+G175D; T1I+S13Y+T22P+S27R+S39P+S42G+D56I+S57W+S59V+V76L+Q109R+S116D+T127V+S144P+A147H+S167L+G175D; T1I+S13Y+T22P+S27R+S39P+S42G+D56I+S57W+S59V+V76L+S106L+Q109R+S116D+T127V+S130A+S144P+A147H+S167L+G175D; T1I+S13Y+T22P+S27R+S39P+S42G+D56I+S57W+S59V+V76L+S106L+Q109R+S116D+T127V+S144P+A147H+G162D+S167L+G175D; T1I+S13Y+T22P+S27R+S39P+S42G+D56L+S57W+S59V+S66Y+V76L+Q109R+S116D+T127V+S144P+A147H+S167L+G175D; T1I+S13Y+T22P+S27R+S39P+S42G+D56L+S57W+S59V+T65L+V76L+Q109R+S116D+T127V+S144P+A147H+S167L+G175D; T1I+S13Y+T22P+S27R+S39P+S42G+D56L+S57W+S59V+T65V+V76L+Q109R+S116D+T127V+S144P+A147H+G162D+S167L+G175D; T1I+S13Y+T22P+S27R+S39P+S42G+D56L+S57W+S59V+T65V+V76L+Q109R+S116D+T127V+S144P+A147H+S167L+G175D; T1I+S13Y+T22P+S27R+S39P+S42G+D56L+S57W+S59V+V76L+S106L+Q109R+S116D+T127V+S130A+S144P+A147H+G162D+S167L+G175D; T1I+S13Y+T22P+S27R+S42G+S57W+S59V+V76L+Q109R+S116D+T127V+S144P+A147H+S16 7L+G175D; T1I+S13Y+T22P+S27V+S39P+S42G+D56I+S57W+S59V+V76L+Q109R+S116D+T127V+S144P+A147H+S167L+G175D; T1I+S13Y+T22P+S39P+S42G+D56I+S57W+S59V+V76L+Q109R+S116D+T127V+S144P+A147H+S167L+G175D; T1I+S7G+S13Y+T22P+S27L+S39P+S42G+D56I+S57W+S59V+V76L+Q109R+S116D+T127V+S 144P+A147H+S167L+G175D; T1I+S9I+S13Y+T22P+S27L+S42G+S57W+S59V+V76L+Q109R+S116D+T127V+S144P+A147H+S167L+G175D; T1I+T22P+S27L+S39P+S42G+D56I+S57W+S59V+V76L+Q109R+S116D+T127V+S144P+A147H+S167L+G175D; and T1V+S13Y+T22P+S27L+S39P+S42G+D56I+S57W+S59V+V76L+Q109R+S116D+T127V+S144P+A147H+S167L+G175D.

Particular preferred DNase variants includes a variant comprising any of the following substations, compared to SEQ ID NO: 1 i.e. numbering compared to SEQ ID NO: 1, wherein the DNase variant is selected from the group consisting of:

i. T1I+S13Y+T22P+S25P+S27L+S39P+S42G+S57W+S59V+V76L+S144P+A147H+S16 7L+G175D;
ii. T1I+S13Y+T22P+S27L+S42G+S57W+S59V+V76L+Q109R+S116D+T127V+S144P+A 147H+S167L+G175D;
iii. T1I+S13Y+T22P+S25P+S27L+S39P+S42G+S57W+S59V+V76L+Q109R+S116D+T12 7V+S144P+A147H+S167L+G175D;
iv. T1I+S13Y+T22P+S25P+S27L+S39P+S42G+S57W+S59V+V76L+T77Y+Q109R+S116 D+T127V+S144P+A147H+S167L+G175D;
v. T1I+T22P+D56I+S57W+V76L+Q109R+S116D+A147H+G162S+S167L+G175N+N178;
vi. T1I+S13Y+T22P+S27L+S39P+S42G+D56I+S57W+S59V+V76L+Q109R+S116D+T127 V+S144P+A147H+S167L+G175D;
vii. T1I+T22P+S25P+S27L+S42G+D56I+S57Y+S59V+V76L+T77Y+Q109R+S116D+T127 V+S144P+A147H+Q166D+S167L+G175D+S181L;
viii. T1I+S13Y+T22P+S25P+S27L+S39P+S42G+D56I+S57W+S59V+V76L+Q109R+S116 D+T127V+S144P+A147H+S167L+G175D;
ix. T1I+S13Y+T22P+S25P+S27L+S39P+S42G+D56I+S57W+S59V+V76L+Q109R+S116 D+T127V+S144P+A147H+Q166D+S167L+G175D;
x. T1I+S13Y+T22P+S27R+S39P+S42G+D56I+S57W+S59V+V76L+Q109R+S116D+T12 7V+S144P+A147H+S167L+G175D;
xi. T1I+S13Y+T22P+S27L+S39P+S42G+D56I+S57W+S59V+T65L+V76L+Q109R+S116D+T127V+S144P+A147H+S167L+G175D;
xii. T1I+S13Y+T22P+S27L+L33K+S39P+S42G+D56I+S57W+S59V+T65V+V76L+Q109R+S116D+T127V+S144P+A147H+S167L+G175D;
xiii. T1I+S13Y+T22P+S25P+S27R+S39P+S42G+S57W+S59V+S66W+V76L+T77Y+Q109R+S116D+T127V+S144P+A147H+S167L+G175D;
xiv. T1I+S13Y+T22P+S25P+S27L+L33K+S39P+S42G+S57W+S59V+T65V+V76L+T77Y+Q109R+S116D+T127V+S144P+A147H+S167L+G175D;

xv. T1I+S13Y+T22P+S25P+S27L+L33K+S39P+S42G+S57W+S59V+S66Y+V76L+T77Y+Q109R+S116D+T127V+S144P+A147H+S167L+G175D;

xvi. T1I+S13Y+T22P+S25P+S27L+S39P+S42G+S57W+S59V+T65V+S66Y+V76L+T77Y+Q109R+S116D+T127V+S144P+A147H+S167L+G175D;

xvii. T1I+S13Y+T22P+S27L+S39P+S42G+D56L+S57W+S59V+T65V+V76L+Q109R+S116 D+T127V+S144P+A147H+G162D+S167L+G175D;

xviii. T1I+S13Y+T22P+S27R+S39P+S42G+D56L+S57W+S59V+T65V+V76L+Q109R+S116 D+T127V+S144P+A147H+S167L+G175D;

xix. T1I+S13Y+T22P+S27R+S39P+S42G+D56L+S57W+S59V+T65V+V76L+Q109R+S116 D+T127V+S144P+A147H+G162D+S167L+G175D;

xx. T1I+S13Y+T22P+S27K+S39P+S42G+D56I+S57W+S59V+T65V+V76L+S106L+Q109R+S116D+T127V+S144P+A147H+S167L+G175D;

xxi. T1I+S13Y+T22P+S27K+S39P+S42G+D56I+S57W+S59V+T65V+V76L+Q109R+S116 D+T127V+S130A+S144P+A147H+S167L+G175D;

xxii. T1I+S13Y+T22P+S27L+S39P+S42G+D56L+S57W+S59V+T65L+V76L+Q109R+S116 D+T127V+S130A+S144P+A147H+S167L+G175D; and xxiii. T1I+S13Y+T22P+S27L+S39P+S42G+D56I+S57W+S59V+T65V+V76L+Q109R+S116D+T127V+S144P+A147H+G162D+S167L+G175.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, *J. Mol. Biol.* 224: 899-904; Wlodaver et al., 1992, *FEBS Lett.* 309: 59-64.

Parent DNase Preferably the parent DNase is selected from any of the enzyme classes E.C. 3.1.11, E.C. 3.1.12, E.C. 3.1.15, E.C. 3.1.16, E.C. 3.1.21, E.C 3.1.22, E.C 3.1.23, E.C 3.1.24 and E.C.3.1.25.

Preferably, the DNase parent is obtained from a microorganism and the DNase is a microbial enzyme. The DNase is preferably of fungal or bacterial origin.

The DNase parent is preferably obtainable from *Bacillus* e.g. *Bacillus*, such as a *Bacillus cibi, Bacillus* sp-62451, *Bacillus horikoshii, Bacillus* sp-16840, *Bacillus* sp-62668, *Bacillus* sp-13395, *Bacillus homeckiae, Bacillus* sp-11238, *Bacillus* idriensis, *Bacillus* sp-62520, *Bacillus algicola, Bacillus vietnamensis, Bacillus hwajinpoensis, Bacillus indicus, Bacillus marisflavi, Bacillus luciferensis, Bacillus* sp. SA2-6.

The DNase parent preferably belongs to the group of DNases comprised in the GYS-clade, which are DNases comprising the conservative motifs [D/M/L][S/T]GYSR[D/N] (SEQ ID NO: 25) or ASXNRSKG (SEQ ID NO: 26) and which share similar structural and functional properties, see e.g alignment in FIG. 1 and generation of phylogenetic trees in example 11 of WO 2017/060475. The DNases of the GYS-clade are preferably obtained from *Bacillus* genus.

One embodiment of the invention relates to a variant of a DNase parent of the GYS-clade having DNase activity, optionally wherein the parent comprises one or both motifs [D/M/L][S/T]GYSR[D/N] (SEQ ID NO: 25), ASXNRSKG (SEQ ID NO: 26) and wherein the polypeptide is selected from the group of polypeptides:

a) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1, b) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 2, c) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 3, d) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 4, e) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 5, f) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 6, g) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 7, h) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 8, i) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 9, j) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 10, k) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 11, l) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 12, m) a polypeptide having at least 60%, at least 70%, at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 13, n) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 14, o) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 15, p) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 16, q) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 17, r) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 18, s) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 19, t) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 20, u) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 21, v) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 22, w) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 23, and x) a polypeptide having at least 60%, at least 70%, at least 80% at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 24.

Polypeptides having DNase activity and which comprise the GYS-clade motifs have shown particularly good deep cleaning properties e.g. the DNases are particularly effective in removing or reducing components of organic matter, such as biofilm components, from an item such as a textile or a hard surface.

In some preferred aspect, the invention relates to a variant of a DNase parent, wherein the DNase parent belongs to the GYS-clade and wherein the parent DNase comprises one or both motifs [D/M/L][S/T]GYSR[D/N] (SEQ ID NO: 25) or ASXNRSKG (SEQ ID NO: 26).

The parent DNases may be (a) a polypeptide having at least 60% sequence identity to the mature polypeptide of SEQ ID NO: 1, (b) a polypeptide encoded by a polynucleotide that hybridizes under high stringency conditions with the mature polypeptide coding sequence or the full-length complement hereof; or (c) a polypeptide encoded by a polynucleotide having at least 60% sequence identity to the mature polypeptide coding sequence.

In some aspects, the parent has a sequence identity to the polypeptide shown in SEQ ID NO: 1 of at least 60%, at least 65%, at least 70%, at least 75%, at least 80%, at least 85%, at least 90%, at least 95%, such as at least 96%, at least 97%, at least 98%, at least 99% or 100% sequence identity to the polypeptide shown in SEQ ID NO: 1, which have DNase activity. In one aspect, the amino acid sequence of the parent differs by up to 10 amino acids, e.g., 2, 3, 4, 5, 6, 7, 8, 9, or 10, from the polypeptide shown in SEQ ID NO: 1.

In some aspects, the parent comprises or consists of the amino acid sequence of SEQ ID NO: 1.

In some aspects, the parent is a *Bacillus* DNase, e.g. a *bacillus* cibi DNase, e.g., the DNase disclosed herein as SEQ ID NO: 1.

Use of DNase Variants

The DNase variants of the invention are suitable for use in cleaning such as laundry. Thus, some aspect of the invention relates a method for laundering an item, wherein the method comprises the steps of:

a. Exposing an item to a wash liquor comprising a DNase variant of the invention;

b. Completing at least one wash cycle; and c. Optionally rinsing the item, wherein the item is a textile or a hard surface.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In some aspects the temperature of the wash liquor is 30° C.

The DNase variants of the invention may be added to a wash liquor.

The concentration of the DNase variant enzyme in the wash liquor is typically in the range of 0.00001-1000 ppm enzyme protein, such as in the range of 0.00004-100 ppm enzyme protein, such as in the range of 0.00008-100 enzyme protein, in the range of 0.0001-100 enzyme protein, in the range of 0.0002-100 enzyme protein, in the range of 0.0004-100 enzyme protein, in the range of 0.0008-100 enzyme protein, in the range of 0.001-100 ppm enzyme protein, in the range of 0.01-100 ppm enzyme protein, in the range of 1-1000 ppm enzyme protein, preferably in the range of 0.05-50 ppm enzyme protein, more preferably in the range of 0.1-50 ppm enzyme protein, more preferably in the range of 0.1-30 ppm enzyme protein, more preferably in the range of 0.5-20 ppm enzyme protein, and most preferably in the range of 0.5-10 ppm enzyme protein.

In some aspects the DNase variants of the present invention are effective in preventing and/or reducing the malodor. The presence of biofilm, body soil e.g. cell debris, sebum or EPS implies that the laundry items become sticky and therefore soil adheres to the sticky areas. This soil sticked to the laundry has shown difficult to reduce by commercially available detergent compositions. Further, when dirty laundry items are washed together with less dirty laundry items the dirt present in the wash liquor tend to adhere to the laundry (e.g. by re-deposition) in particular if the laundry is sticky as described above. As a result, hereof, the laundry item is more "soiled" after wash than before wash. In some aspects, the DNase variants of the invention have improved deep cleaning properties compared to the parent DNase and in some aspects, the DNase variants of the invention reduce stickiness and/or re-deposition.

In some aspects, the invention relates to the use of a DNase variant according to the invention for deep cleaning of an item, wherein the item is a fabric or a hard surface.

Further, the invention relates to the use of a DNase variant according to the invention for preventing and/or reducing the adherence of soil to an item. In some aspect, the item is textile. When the soil does not adhere to the item, the item appears cleaner. Thus, the invention further relates to the use of a DNase variant according to the invention for maintaining or improving the whiteness of the item.

The present invention further relates to detergent compositions comprising a DNase variant according to the invention preferably with a detergent adjunct ingredient. The detergent composition comprising a DNase variant according to the invention may be used for deep cleaning of an item, for preventing and/or reducing the stickiness of an item, for pretreating stains on the item, for preventing and/or reducing redeposition of soil during a wash cycle, for preventing and/or reducing adherence of soil to an item, for maintaining or improving the whiteness of an item and/or for preventing and/or reducing malodor from an item.

Preparation of Variants

The present invention also relates to a method for obtaining a DNase variant having at least one improved property compared to the parent DNase e.g. compared to the polypeptide shown in SEQ ID NO: 1.

One aspect of the invention relates to method for obtaining a DNase variant, comprising;

a) introducing into a parent DNase two or more substitutions selected from: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E; and b) recovering the variant, wherein the variant has DNase activity.

The method preferably comprises introduction of 2-20, e.g. 2-10 and 2-5, such as 2, 3, 4, 5, 6, 7, 8, 9, 10, 11, 12, 13, 14, 15, 16, 17, 18, 19 or 20 alterations compared to the polypeptide shown in SEQ ID NO: 1.

Some aspects of the invention relate to a method for obtaining a DNase variant, comprising introducing into a parent DNase an alteration at one or more positions, wherein the DNase parent belong to the GYS-clade and wherein the parent DNase comprises one or both motifs [D/M/L][S/T]GYSR[D/N] (SEQ ID NO: 25) or ASXNRSKG (SEQ ID NO: 26).

Some aspects of the invention relate to a method for obtaining a DNase variant, comprising introducing into a parent DNase an alteration at one or more positions, wherein the parent DNase is selected from the group of polypeptides:

a) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1, b) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 2, c) a polypeptide having at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 3, d) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 4, e) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 5, f) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 6, g) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 7, h) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 8, i) a polypeptide having at least 80%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 9, j) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 10, k) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 11, l) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 12, m) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 13, n) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 14, o) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 15, p) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 16, q) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 17, r) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 18, s) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 19, t) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 20, u) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 21, v) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 22, w) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 23, and x) a polypeptide having at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 24.

Some aspect relates to a method of obtaining a DNase variant wherein the parent DNase is obtained from *bacillus* genus.

Some aspect relates to a method of obtaining a DNase variant wherein the DNase parent has at least 60%, at least 70%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1.

The variants of the invention may be prepared by procedures such as those mentioned below.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Nucleic Acid Constructs

The present invention also relates to nucleic acid constructs comprising a polynucleotide encoding the DNase variants of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, Gene 69: 301-315), *Streptomyces coelicolor agarase* gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Bacillus nidulans* acetamidase, *Bacillus niger* neutral alpha-amylase, *Bacillus niger* acid stable alpha-amylase, *Bacillus niger* or *Bacillus awamori* glucoamylase (glaA), *Bacillus cibi* TAKA amylase, *Bacillus cibi* alkaline protease, *Bacillus cibi* triose phosphate isomerase, *Fusarium oxysporum* trypsin-like protease (WO 96/00787), *Fusarium venenatum* amyloglucosidase (WO 00/56900), *Fusarium venenatum* Dada (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2 tpi promoter (a modified promoter from an *Bacillus* neutral alpha-amylase gene in which the untranslated leader has been replaced by an untranslated leader from an *Bacillus* triose phosphate isomerase gene; non-limiting examples include modified promoters from an *Bacillus niger* neutral alpha-amylase gene in which the untranslated leader has been replaced by an untranslated leader from an *Bacillus nidulans* or *Bacillus cibi* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO 1), *Saccharomyces cerevisiae* galactokinase (GAL1), *Saccharomyces cerevisiae* alcohol dehydrogenase/glyceraldehyde-3 phosphate dehydrogenase (ADH1, ADH2/GAP), *Saccharomyces cerevisiae* triose phosphate isomerase (TPI), *Saccharomyces cerevisiae* metallothionein (CUP1), and *Saccharo-*

*myces cerevisiae* 3 phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3' terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Bacillus nidulans* acetamidase, *Bacillus nidulans* anthranilate synthase, *Bacillus niger* glucoamylase, *Bacillus niger* alpha-glucosidase, *Bacillus cibi* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3 phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene. Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5' terminus of the polynucleotide encoding the polypeptide. Any leader that is functional in the host cell may be used.

Preferred leaders for filamentous fungal host cells are obtained from the genes for *Bacillus cibi* TAKA amylase and *Bacillus nidulans* triose phosphate isomerase.

Suitable leaders for yeast host cells are obtained from the genes for *Saccharomyces cerevisiae* enolase (ENO 1), *Saccharomyces cerevisiae* 3 phosphoglycerate kinase, *Saccharomyces cerevisiae* alpha-factor, and *Saccharomyces cerevisiae* alcohol dehydrogenase/glyceraldehyde-3 phosphate dehydrogenase (ADH2/GAP).

The control sequence may also be a polyadenylation sequence, a sequence operably linked to the 3' terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Bacillus nidulans* anthranilate synthase, *Bacillus niger* glucoamylase, *Bacillus niger* alpha-glucosidase *Bacillus cibi* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N terminus of a polypeptide and directs the polypeptide into the cell's secretory pathway. The 5' end of the coding sequence of the polynucleotide may inherently contain a signal peptide coding sequence naturally linked in translation reading frame with the segment of the coding sequence that encodes the polypeptide. Alternatively, the 5' end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews S7: 109-137.

Effective signal peptide coding sequences for filamentous fungal host cells are the signal peptide coding sequences obtained from the genes for *Bacillus niger* neutral amylase, *Bacillus niger* glucoamylase, *Bacillus cibi* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N terminus of a polypeptide and the signal peptide sequence is positioned next to the N terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Bacillus niger* glucoamylase promoter, *Bacillus cibi* TAKA alpha-amylase promoter, and *Bacillus cibi* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide encoding the DNase variants of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. In a further aspect, polynucleotide sequence codons have been modified by nucleotide substitutions to correspond to the codon usage of the host organism intended for production of the polypeptide of the present invention. The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5' phosphate decarboxylase), sC (sulfate adenyltransferase), and trpC (anthranilate synthase), as well as equivalents thereof. Preferred for use in a *Bacillus* cell are *Bacillus nidulans* or *Bacillus cibi* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In some aspects, the dual selectable marker is an hph-tk dual selectable marker system.

The vector preferably contains an element(s) that permits integration of the vector into the host cell's genome or autonomous replication of the vector in the cell independent of the genome. For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a Streptomyces cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a Streptococcus cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Bacillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Bacillus awamori, Bacillus foetidus, Bacillus fumigatus, Bacillus japonicus, Bacillus nidulans, Bacillus niger, Bacillus cibi, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerea-*

*lis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Bacillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a DNase variant of the present invention, comprising (a) cultivating a cell, under conditions conducive for production of the DNase variants; and optionally, (b) recovering the DNase variant. In some aspects, the cell is an *Bacillus* cell. In another aspect, the cell is an *Bacillus cibi* cell.

The present invention also relates to methods of producing a DNase variant of the present invention, comprising (a) cultivating a recombinant host cell of the present invention under conditions conducive for production of the DNase variant; and optionally, (b) recovering the DNase variant.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The DNase variant may be detected using methods known in the art that are specific for the DNase variant polypeptide. These detection methods include, but are not limited to, use of specific antibodies, formation of an enzyme product, or disappearance of an enzyme substrate. For example, an enzyme assay may be used to determine the activity of the polypeptide.

The DNase variant polypeptide may be recovered using methods known in the art. For example, the DNase variant polypeptide may be recovered from the nutrient medium by conventional procedures including, but not limited to, collection, centrifugation, filtration, extraction, spray-drying, evaporation, or precipitation. In some aspects, a fermentation broth comprising the DNase variant is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the variant.

Compositions

The present invention further relates to a detergent composition comprising at least one DNase variant according to the invention and preferably a detergent adjunct ingredient. The detergent composition may be used for improving deep-cleaning effect, including but not limited to deep cleaning of an item, for preventing and/or reducing the stickiness of an item, for pretreating stains on the item, for preventing and/or reducing redeposition of soil during a wash cycle, for preventing and/or reducing adherence of soil to an item, for maintaining or improving the whiteness of an item and for preventing and/or reducing malodor from an item. The DNase variants of the invention are useful in powder and liquid detergent.

In some aspects of the invention, the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

The detergent adjunct ingredient may be a surfactant. One advantage of including a surfactant in a detergent composition comprising a DNase variant is that the wash performance is improved. In some aspects, the detergent adjunct ingredient is a builder or a clay soil removal/anti-redeposition agent.

In some aspects, detergent adjunct ingredient is an enzyme. The detergent composition may comprise one or more enzymes, as specified below. The one or more enzymes may be selected from the group consisting of proteases, amylases, lipases, cutinases, cellulases, endoglucanases, xyloglucanases, pectinases, pectin lyases, xanthanases, peroxidaes, haloperoxygenases, catalases and mannanases. Specific enzymes suitable for the detergent compositions of the invention are described below.

The detergent composition may be formulated as a bar, a homogenous tablet, and a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

Some aspects of the present invention relate to laundry or cleaning compositions comprising a DNase, preferably at a level of from about 0.000001 wt % to about 1 wt %, from about 0.0001 wt % to about 1 wt %, from about 0.0002 wt % to about 1 wt %, from about 0.0005 wt % to about 1 wt %, from about 0.001 wt % to about 1 wt %, from about 0.002 wt % to about 1 wt %, from about 0.005 wt % to about 1 wt %, preferably from about 0.01 wt % to about 0.5 wt %, preferably from 0.0002 wt % to about 1 wt % by weight (wt %) of the composition. The amounts are wt % per unit active enzyme e.g. from about 0.00001 wt % to about 1 wt % of DNase by weight of the composition.

The concentration of the active enzyme having DNase activity is preferably at least 0.00001%, preferably at least 0.00002%, preferably at least 0.0001 wt %, preferably at least 0.0002 wt %, preferably at least 0.001 wt %, preferably at least 0.002 wt %, preferably at least 0.005 wt %, preferably at least 0.01 wt ')/0, preferably at least 0.02 wt')/0, preferably at least 0.05 wt % preferably at least 0.1 wt % of the total detergent concentration.

The amount enzyme may also be in ppm (mg/L) active enzyme protein. Thus, in one aspect 30 the amount of DNase in the composition is at least 0.00001 ppm, 0.00002 ppm, 0.00005 ppm, 0.0001 ppm, 0.0002 ppm, 0.0005 ppm, 0.001 ppm, 0.002 ppm, 0.005 ppm, 0.01 ppm, 0.02 ppm, 0.05 ppm, 0.1 ppm, 0.2 ppm, 0.5 ppm, 1 ppm, 2 ppm, 2 ppm, 10 ppm or at least 20 ppm DNase enzymes. In one aspect, the amount of DNase in the composition is in the range from about 0.00001 ppm to about 10 ppm, or in the range from about 0.0001 ppm to about 2 ppm or in the range from about 0.001 ppm to 35 about 2 ppm DNase enzymes.

In some aspects, the detergent composition is a liquid or powder laundry detergent, suitable for e.g. washing at high temperature and/or pH, such as at or above 40° C. and/or at or above pH 8. In some aspects, the detergent composition is a liquid or powder laundry detergent, suitable for e.g. washing at low temperature and/or pH, such as at or below 20° C. and/or pH 6. The detergent may also be formulated as a unit dose detergent and/or compact detergent optionally with minimum or no water. The detergent may also be a dish wash detergent. The laundry and dish wash detergents may be phosphate-free.

Surfactants

A surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl) ammonium, bis(2-hydroxyethyl) ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants includes Plurafac™, Lutensol™ and Pluronic™ from BASF, Dehypon™ series from Cognis and Genapol™ series from Clariant.

Builders

A builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In a laundry detergent, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N"-(2-hydroxyethyl)ethylenediamine-N,N,N'-triacetic acid (HEDTA), diethanolglycine (DEG), and combinations and salts thereof. Phosphonates suitable for use herein include 1-hydroxyethane-1,1-diphosphonic acid (HEDP), ethylenediaminetetrakis (methylenephosphonicacid) (EDTMPA), diethylenetriaminepentakis (methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), hexamethylenediaminetetrakis (methylenephosphonic acid) (HDTMP). The composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly (acrylic acid) (PAA) or copoly (acrylic acid/maleic acid) (PAA/PMA) or polyaspartic acid. Further exemplary builders and/or co-builders are described in, e.g., WO 09/102854, U.S. Pat. No. 5,977,053. In some aspects, the builder is a non-phosphorus based builder such as citric acid and/or methylglycine-N, N-diacetic acid (MGDA) and/or glutamic-N, N-diacetic acid (GLDA) and/or salts thereof. The liquid composition may also be phosphate free in that instance the preferred builders includes citrate and/or methylglycine-N, N-diacetic acid (MGDA) and/or glutamic-N, N-diacetic acid (GLDA) and/or salts thereof.

Bleach Components

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of hydrogen peroxide: Suitable sources of hydrogen peroxide are inorganic persalts, including alkali metal salts such as sodium percarbonate and sodium perborates (usually mono- or tetrahydrate), and hydrogen peroxideurea (1/1).

Sources of peracids: Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-$\alpha$-naphthoic acid, peroxyphthalic acid, peroxylauric acid, peroxystearic acid, ∈-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally ATC is multifunctional, as the citrate released in the perhydrolysis reaction may function as a builder.

Bleach catalysts and boosters: The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (Mn-TACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn (Me3-TACN)](PF6)2, and [2,2',2"-nitrilotris(ethane-1,2-diylazanylylidene-κN-methanylylidene)triphenolato-κ3O] manganese(III). The bleach catalysts may also be other metal compounds, such as iron or cobalt complexes.

In some aspects, where a source of a peracid is included, an organic bleach catalyst or bleach booster may be used having one of the following formulae:

(i)

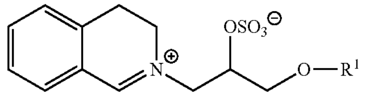

(ii)

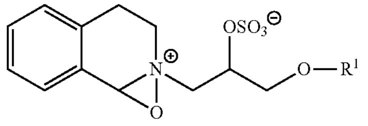

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO 2007/087258, WO 2007/087244, WO 2007/087259, EP 1867708 (Vitamin K) and WO 2007/087242. Suitable photobleaches may for example be sulfonated zinc or aluminium phthalocyanines.

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan, including the exemplary non-limiting components shown in below.

Hydrotropes

The detergent composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fibre protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, polyaspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent composition of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO 2007/087243.

Enzymes

The detergent composition may comprise one or more additional enzymes such as a protease, lipase, cutinase, amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/001544.

Other cellulases are endo-beta-1,4-glucanase enzyme having a sequence of at least 97% identity to the amino acid sequence of position 1 to position 773 of SEQ ID NO: 2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes NS), Cellusoft™ (Novozymes NS), Whitezyme™ (Novozymes NS), Clazinase™, and Puradax HA™ (Genencor International Inc.), and KAC-500(B)™ (Kao Corporation).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a neutral protease such as a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens.*

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus Lentus* protease shown in SEQ ID NO: 1 of WO 2016/001449. More preferred the protease variants may comprise one or more of the following mutations: S3T, V41, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V1021, V102Y, V102N, S104A, G116V, G116R, H118D, H118N, A1205, S126L, P127Q, S128A, S154D, A156E, G157D, G157P, S158E, Y161A, R164S, Q176E, N179E, S182E, Q185N, A188P, G189E, V193M, N198D, V1991, Y203W, S206G, L211Q, L211D, N212D, N2125, M2165, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO: 1 of WO 2016/001449 or the *Bacillus amylolichenifaciens* protease (BPN') shown in SEQ ID NO: 2 of WO2016/001449. The protease variants preferably have at least 80% sequence identity to the polypeptide shown in SEQ ID NO: 1 or SEQ ID NO: 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes NS), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N. V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases which can be used together with the DNases of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 1 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+1201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID NO: 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T16S, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T1311, T1651, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T1311+T1651+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Further suitable amylases are alpha-amylase variants comprising a modification in one or more positions corresponding to positions 1, 54, 56, 72, 109, 113, 116, 134, 140, 159, 167, 169, 172, 173, 174, 181, 182, 183, 184, 189, 194, 195, 206, 255, 260, 262, 265, 284, 289, 304, 305, 347, 391, 395, 439, 469, 444, 473, 476, or 477 of SEQ ID NO: 1, wherein the alpha-amylase variant has a sequence identity of at least 75% but less than 100% to SEQ ID NO: 13 or SEQ ID NO: 14 of WO 2016/180748.

Other examples are amylase variants such as those described in WO 2011/098531, WO 2013/001078 and WO 2013/001087.

Commercially available amylases are Duramyl™, Termamyl™, Fungamyl™, Stainzyme Stainzyme Plus™, Natalase™, Liquozyme X and BAN™ (from Novozymes NS), and Rapidase™, Purastar™/Effectenz™, Powerase and Preferenz S100 (from Genencor International Inc./DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an aspect, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred aspect, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella saline* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Bacillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly (ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent composition may preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino)stilbene-2,2'-disulfonate, 4,4'-bis-(2,4-dianilino-s-triazin-6-ylamino) stilbene-2,2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Tinopal CBS-X is a 4,4'-bis-(sulfostyryl)-biphenyl disodium salt also known as Disodium Distyrylbiphenyl Disulfonate.

Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Other Materials

Any detergent components known in the art for use in the cleaning composition of the invention may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Formulation of Detergent Products

The detergent composition may be in any convenient form, e.g., a bar, a homogenous tablet, a tablet having two or more layers, a regular or compact powder, a granule, a paste, a gel, or a regular, compact or concentrated liquid.

Detergent formulation forms: Layers (same or different phases), Pouches, versus forms for Machine dosing unit.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US 2009/0011970 A1)

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Granular Detergent Formulations

A granular detergent may be formulated as described in WO 09/092699, EP 1705241, EP 1382668, WO 07/001262, U.S. Pat. No. 6,472,364, WO 04/074419 or WO 09/102854. Other useful detergent formulations are described in WO 09/124162, WO 09/124163, WO 09/117340, WO 09/117341, WO 09/117342, WO 09/072069, WO 09/063355, WO 09/132870, WO 09/121757, WO 09/112296, WO 09/112298, WO 09/103822, WO 09/087033, WO 09/050026, WO 09/047125, WO 09/047126, WO 09/047127, WO 09/047128, WO 09/021784, WO 09/010375, WO 09/000605, WO 09/122125, WO 09/095645, WO 09/040544, WO 09/040545, WO 09/024780, WO 09/004295, WO 09/004294, WO 09/121725, WO 09/115391, WO 09/115392, WO 09/074398, WO 09/074403, WO 09/068501, WO 09/065770, WO 09/021813, WO 09/030632, and WO 09/015951.

WO 2011025615, WO 2011016958, WO 2011005803, WO 2011005623, WO 2011005730, WO 2011005844, WO 2011005904, WO 2011005630, WO 2011005830, WO 2011005912, WO 2011005905, WO 2011005910, WO 2011005813, WO 2010135238, WO 2010120863, WO 2010108002, WO 2010111365, WO 2010108000, WO 2010107635, WO 2010090915, WO 2010033976, WO 2010033746, WO 2010033747, WO 2010033897, WO 2010033979, WO 2010030540, WO 2010030541, WO 2010030539, WO 2010024467, WO 2010024469, WO 2010024470, WO 2010025161, WO 2010014395, WO 2010044905,

WO 2010145887, WO 2010142503, WO 2010122051, WO 2010102861, WO 2010099997, WO 2010084039, WO 2010076292, WO 2010069742, WO 2010069718, WO 2010069957, WO 2010057784, WO 2010054986, WO 2010018043, WO 2010003783, WO 2010003792,

WO 2011023716, WO 2010142539, WO 2010118959, WO 2010115813, WO 2010105942, WO 2010105961, WO 2010105962, WO 2010094356, WO 2010084203, WO 2010078979, WO 2010072456, WO 2010069905, WO 2010076165, WO 2010072603, WO 2010066486, WO 2010066631, WO 2010066632, WO 2010063689, WO 2010060821, WO 2010049187, WO 2010031607, WO 2010000636.

Formulation of Enzyme in Co-Granule

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink components and the composition additionally comprises from 20 to 80 wt % detergent moisture sink components. WO 2013/188331 also relates to a method of treating and/or cleaning a surface, preferably a fabric surface comprising the steps of (i) contacting said surface with the detergent composition as claimed and described herein aqueous wash liquor, (ii) rinsing and/or drying the surface.

Assays and Detergent Compositions

Composition of Model Detergent a (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w (weight percent %))

Composition of Model Detergent T (Powder)

Ingredients: 11% LAS, 2% AS/AEOS, 2% soap, 3% AEO, 15.15% sodium carbonate, 3% sodium slilcate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Assay I: Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 μl of enzyme solutions are added and DNase activity is observed as colorless zones around the spotted enzyme solutions.

Assay II: Testing of DNase Activity

DNase activity was determined by using the DNaseAlert™ Kit (11-02-01-04, IDT Intergrated DNA Technologies) according to the supplier's manual. Briefly, 95 μl DNase sample was mixed with 5 μl substrate in a microtiter plate, and fluorescence was immediately measured using a Clariostar microtiter reader from BMG Labtech (536 nm excitation, 556 nm emission).

Assay A-C

Activity of Purified Samples

Before testing the DNase samples for stability in Assay A, B or C they were analyzed for activity according to following procedure. Purified DNase samples were diluted to 7.5 ppm in a 96 well plate using a dilution buffer (50 mM Tris-HCl, pH7+0.1% Triton X-100) on a Hamilton Nimbus 4 channel liquid handler. A standard curve of DNase (e.g. SEQ ID NO: 1 or SEQ ID NO: 28) at 2.5, 5 and 7.5 ppm was prepared accordingly.

12 μl normalized DNase sample is added to 228 μl Model A and the solution is shaken for 90s at 2000 rpm (2 mm orbit). 10 μl of the sample is added to 190 μl DNA substrate (3.3 mg/ml Salmon sperm DNA+50 mM Tris-HCl, pH7+5 mM MgCl2+5 mM $CaCl_2$)) and the 96 well plate containing the samples and DNA substrate are mixed at 1500 rpm for 90 s (Orbit 2 mm). The plate is incubated for 1 h at room temperature and DNase activity measured according to the procedure: The Hamilton STAR measures the viscosity of the samples and thereby the activity of the DNase using ViPr assay technology as described in (WO2011/107472 A1) by aspirating 100 μl of the assay solution with a standard clear CORE 300 μl tip at a speed of 50 μl/s. The solution is dispensed back to the original well at 10 μl/s and the measurement repeated 5 times. The pressure data during the aspiration step from all of the 96 wells are collected and the pressure value at 1000 ms after start of the aspiration is taken for calculation of the DNase activity in Relative units (RU). Relative units are calculated by division of the buffer value (blank; 1000 ms) by the pressure value (1000 ms) of a given sample subtracted by 1. Samples that show activity below 2.5 ppm compared to the standard curve are adjusted to a level at least >10 ppm and below <20 ppm. All samples are transferred in triplicate to a 96 well plate with a 5 ppm DNase (e.g. SEQ ID NO: 1 or SEQ ID NO: 28) sample as reference.

Assay A

The 96 well plate with the normalized DNase samples and a and dilutions of DNase (SEQ ID NO: 28) was loaded on the Hamilton STAR robot equipped with a 96 channel TADM head which allows the simultaneous measuring of pressure in the head space of each single pipette channel. 12 µl normalized DNase sample is added to 228 µl Model A with Protease (136 ppm). The solution is shaken for 90s at 2000 rpm (2 mm orbit) and 80 µl of the solution are added to two PCR plates. Plate A (Stress) is incubated at 40° C. and plate B (Reference) at 4° C. for 24 h. Plate A and B are transferred to room temperature. 190 µl DNA substrate (3.3 mg/ml Salmon sperm DNA+50 mM Tris-HCl, pH7+5 mM MgCl2+5 mM $CaCl_2$)) is added to 2×96 well plates. 10 µl of sample from plate A and plate B respectively are added to corresponding plates containing DNA substrate. The samples and DNA are mixed at 1500 rpm for 90 s (Orbit 2 mm) and incubated for 1h at room temperature. The Hamilton STAR measures the viscosity using ViPr assay technology as described in (WO2011/107472 A1) by aspirating 100 µl with a standard clear CORE 300 µl tip at a speed of 50 µl/s. The solution is dispensed back to the original well at 10 µl/s and the measurement repeated 5 times. The pressure data during the aspiration step from all of the 96 wells are collected and the pressure value at 1000 ms after start of the aspiration is taken for calculation of the DNase activity in Relative units (RU). Relative units are calculated by division of the buffer value (blank; 1000 ms) by the pressure value (1000 ms) of a given sample subtracted by 1. Relative activity (RA) is calculated by $$\text{Residual Activity (\%)} = \frac{RU_{variant}}{RU_{reference}} * 100$$

Assay B

Conditions and activity determination of DNase variants as described in Assay A except that DNase samples were exposed to Model A detergent+0.4% $K_2SO_3$ for 1 hours at 60° C. The detergent solution is prepared by mixing Model A (50 g) with 0.2 g K2503 for 1h under vigorous stirring.

Assay C

Conditions and activity determination of DNase variants as described in Assay A except that DNase samples were exposed to Model A detergent alone for 2 hours at 62°.

Residual Activity Ratio (RAR)

The residual activity ration for each condition was calculated by using a stabilized variant as reference. The variants were tested in 3 conditions described above and the RAR calculated by using the following formula:

$$\text{Residual Activity Ratio}(RAR) = \frac{RA_{variant}}{RA_{reference}}$$

Methods

General methods of PCR, cloning, ligation nucleotides etc. are well-known to a person skilled in the art and may for example be found in "Molecular cloning: A laboratory manual", Sambrook et al. (1989), Cold Spring Harbor lab., Cold Spring Harbor, N.Y.; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

EXAMPLES

Example 1: Construction of Variants by Site-Directed Mutagenesis

Site-directed variants were constructed of the *Bacillus cibi* DNase (SEQ ID NO: 1), comprising specific substitutions according to the invention. The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence.

Mutagenic oligos were designed corresponding to the DNA sequence flanking the desired site(s) of mutation, separated by the DNA base pairs defining the insertions/deletions/substitutions, and purchased from an oligo vendor such as Life Technologies. In order to test the DNase variants of the invention, the mutated DNA comprising a variant of the invention are integrated into a competent *B. subtilis* strain by homologous recombination, fermented using standard protocols (yeast extract based media, 3-4 days, 30° C.), and screened by activity assay.

Expression and Purification

The constructed variants were plated on LB agar supplemented with 6 ug/ml chloramphenicol and grown for 37° C. for one day. After growth, colonies were picked to individual wells of standard 96-well microtiter plates containing 200 ul TBgly broth supplemented with 6 ug/ml chloramphenicol and trace metals (50 mM FeCl3, 20 mM $CaCl_2$), 10 mM MnCl2, 10 mM ZnSO4, 2 mM CuCl2, and 2 mM NiCl2, (F. William Studier, "Protein production by auto-induction in high-density shaking cultures", Protein Expression and Purification, 41 (2005) 207-234).

The wild type *Bacillus cibi* DNase, was also inoculated as reference in four wells on each microtiter plate. The microtiter plates were grown for three days at 30° C. with shaking at 220 rpm. After growth, the supernatants were screened for residual activity after stressing them for 20 minutes at 48.5° C. in the presence of 96% (v/v) Model A.

Example 2: Testing DNase Variants for Stability

Each supernatant sample were split into two identical samples by transferring 10 ul supernatant to two 96-well standard microtiter plates each containing 240 ul Model A. After shaking for five minutes at 7500 rpm in a microtiter plate shaker, one microtiter plate was incubated at room temperature (21° C.=reference condition) for 20 min and the other microtiter plate was incubated in a 96-well PCR block at the stress temperature (48.5° C.=stress condition) also for 20 min. Both sets of samples (the reference condition and the stressed condition) were diluted 100-fold in dilution buffer (50 mM Tris, HCl, pH 7.5) before assaying the activity by usage of the DNAseAlert Substrate™ solution (Integrated DNA Technologies/Belgium, part #11-04-02-04, www.idtdna.com/pages/products/reagents/nuclease-detection-products).

DNase Activity Assay

For the DNase activity measurement, 10 ul 100-fold diluted reference DNase sample and stress DNase sample were transferred to a new 384-well microtiter plate and 40 ul DNAseAlert assay solution was added (50 mM TrisHCl, pH. 7.5, 5 mM MnCl2, 6 nM DNAseAlert Substrate™). The fluorescence (excitation 536 nm and emission 556 nm) was read each 90 seconds for a total of 30 minutes. From the kinetic curves, the slope of the reference sample (activity under reference conditions) and the corresponding stress sample (activity under stress conditions) was determined by linear regression. The residual activity (RA) for each DNase variant and the reference DNase (SEQ ID NO: 1) was calculated as: slope (stress sample)/slope(reference sample).

Half-Life Improvement Factor

The Half-life Improvement Factor ($T_{1/2}$ in minutes) for the DNase variants and the DNase reference (SEQ ID NO: 1) was calculated as: 20 minutes×LN(0.5)/LN(RA). The Half-life Improvement Factor (HIF) for the variants was calculated as $T_{1/2variant}/T_{1/2reference}$. Improved variants were identified as variants having a Half-life Improvement Factor HIF larger than 1.0 (HIF reference (SEQ ID NO: 1)=1.0).

TABLE 1

Half life improvement factor for *Bacillus cibi* (SEQ ID NO: 1) DNase variants

| Mutation A | Mutation B | HIF A + B |
|---|---|---|
| T1I | T22P | 4.21 |
| T1I | S39P | 3.15 |
| T1I | S42G | 3.31 |
| T1I | S57W | 5.34 |
| T1I | S59V | 2.90 |
| T1I | V76L | 4.02 |
| T1I | S116D | 3.04 |
| T1I | T127V | 3.79 |
| T1I | S167L | 2.93 |
| T1I | G175D | 4.66 |
| T22P | S42G | 2.60 |
| T22P | V76L | 3.42 |
| T22P | S116D | 3.18 |
| T22P | T127V | 3.97 |
| T22P | A147H | 4.06 |
| T22P | G175D | 2.74 |
| S25P | S39P | 1.62 |
| S25P | S42G | 1.81 |
| S25P | S59V | 1.62 |
| S25P | V76L | 1.88 |
| S25P | S116D | 1.85 |
| S25P | T127V | 1.91 |

TABLE 1-continued

Half life improvement factor for *Bacillus cibi* (SEQ ID NO: 1) DNase variants

| Mutation A | Mutation B | HIF A + B |
|---|---|---|
| S25P | S167L | 1.78 |
| S39P | S42G | 2.06 |
| S39P | S57W | 4.28 |
| S39P | S59V | 1.55 |
| S39P | V76L | 2.45 |
| S39P | S116D | 1.82 |
| S39P | T127V | 2.23 |
| S39P | S144P | 1.41 |
| S39P | A147H | 5.06 |
| S39P | S167L | 2.18 |
| S42G | S57W | 6.78 |
| S42G | S59V | 1.91 |
| S42G | V76L | 2.57 |
| S42G | S116D | 2.15 |
| S42G | T127V | 2.87 |
| S42G | S144P | 1.65 |
| S42G | A147H | 5.39 |
| S42G | S167L | 2.16 |
| S42G | G175D | 3.24 |
| S57W | S59V | 4.72 |
| S57W | S116D | 5.11 |
| S57W | T127V | 7.51 |
| S57W | A147H | 8.78 |
| S59V | V76L | 2.11 |
| S59V | S116D | 2.08 |
| S59V | A147H | 3.85 |
| S59V | S167L | 1.71 |
| S59V | G175D | 2.05 |
| V76L | S116D | 2.18 |
| V76L | T127V | 3.04 |
| V76L | S144P | 2.08 |
| V76L | A147H | 4.55 |
| V76L | S167L | 2.21 |
| V76L | G175D | 2.98 |
| S116D | T127V | 1.91 |
| S116D | S144P | 2.12 |
| S116D | A147H | 5.17 |
| S116D | S167L | 2.00 |
| S116D | G175D | 2.31 |
| T127V | S144P | 2.44 |
| T127V | A147H | 7.02 |
| T127V | S167L | 2.40 |
| T127V | G175D | 2.87 |
| S144P | A147H | 4.09 |
| S144P | S167L | 1.89 |
| S167L | G175D | 2.38 |

Example 3: Relative Activity Ratio of DNase Variants Relative to Reference Sample in Detergent (Assay C)

Test conditions: DNase variants were stressed for 2 hours at 62° C. in a model detergent and compared to the reference sample (SEQ ID NO: 28)

TABLE 2

| Mutations relative to *B. cibi* (SEQ ID NO: 1) | RAR Detergent (Assay C) |
|---|---|
| DNase variant (SEQ ID NO: 28) | 1.00 |
| T1I S13Y T22P S27K S42G S57W S59V V76L Q109R S116D T127V S144P A147H S167L G175D | 1.15 |
| T1I S13Y T22P S27R S42G S57W S59V V76L Q109R S116D T127V S144P A147H S167L G175D | 1.63 |
| T1I S13Y T22P S27L L33R S42G S57W S59V V76L Q109R S116D T127V S144P A147H S167L G175D | 1.37 |
| T1I S13Y T22P S27L L33V S42G S57W S59V V76L Q109R S116D T127V S144P A147H S167L G175D | 1.47 |

TABLE 2-continued

| Mutations relative to *B. cibi* (SEQ ID NO: 1) | RAR Detergent (Assay C) |
|---|---|
| T1I S13Y T22P S27L L33Y S42G S57W S59V V76L Q109R S116D T127V S144P A147H S167L G175D | 1.58 |
| T1I S13Y T22P S27L S39C S42G S57W S59V V76L Q109R S116D T127V S144P A147H S167L G175D | 1.62 |
| T1I S13Y T22P S27L S39P D56I S57W S59V V76L Q109R S116D T127V S144P A147H S167L G175D | 1.30 |
| T1I S13Y T22P S27L S39P S42G D56I S57W S59V Q109R S116D T127V S144P A147H S167L G175D | 1.48 |
| T1I S13Y T22P S27L S39P S42G D56I S57W S59V V76L Q109R S116D S144P A147H S167L G175D | 1.27 |
| T1I S13Y T22P S27L S39P S42G D56I S57W S59V V76L Q109R S116D T127V A147H S167L G175D | 1.96 |
| T1I S13Y T22P S27L S39P S42G D56I S57W S59V V76L Q109R S116D T127V S144P A147H G175D | 1.35 |
| T1I S13Y T22P S27L S39P S42G D56I S57W S59V V76L Q109R S116D T127V S144P A147H S167L | 2.02 |
| T1I S13Y T22P S27L S39P S42G D56I S57W S59V V76L Q109R S116D T127V S144P S167L G175D | 1.21 |
| T1I S13Y T22P S27L S39P S42G D56I S57W V76L Q109R S116D T127V S144P A147H S167L G175D | 2.07 |
| T1I S13Y T22P S27L S39P S42G D56I S59V V76L Q109R S116D T127V S144P A147H S167L G175D | 1.15 |
| T1I S13Y T22P S27L S42G D56L S57W S59V V76L Q109R S116D T127V S144P A147H S167L G175D | 1.55 |
| T1I S13Y T22P S27L S42G S57W S59V S66W V76L Q109R S116D T127V S144P A147H S167L G175D | 1.14 |
| T1I S13Y T22P S27L S42G S57W S59V T65M V76L Q109R S116D T127V S144P A147H S167L G175D | 1.19 |
| T1I S13Y T22P S27L S42G S57W S59V T65R V76L Q109R S116D T127V S144P A147H S167L G175D | 1.77 |
| T1I S13Y T22P S27L S42G S57W S59V V76L Q109R S116D T127V Q140V S144P A147H S167L G175D | 1.20 |
| T1I S13Y T22P S27L S42G S57W S59V V76L Q109R S116D T127V S144P A147H G162C S167L G175D | 1.10 |
| T1I S13Y T22P S27L S42G S57W S59V V76L Q109R S116D T127V S144P A147H G162D S167L G175D | 1.28 |
| T1I S13Y T22P S27L S42G S57W S59V V76L Q109R S116D T127V S144P A147H G162E S167L G175D | 1.19 |
| T1I S13Y T22P S27L S42G S57W S59V V76L Q109R S116D T127V S144P A147H S167L G175D S181E | 1.78 |
| T1I S13Y T22P S27L S42G S57W S59V V76L S101N Q109R S116D T127V S144P A147H S167L G175D | 1.85 |
| T1I S13Y T22P S39P S42G D56I S57W S59V V76L Q109R S116D T127V S144P A147H S167L G175D | 2.03 |
| T1I S9I S13Y T22P S27L S42G S57W S59V V76L Q109R S116D T127V S144P A147H S167L G175D | 1.18 |
| T1I T22P S27L S39P S42G D56I S57W S59V V76L Q109R S116D T127V S144P A147H S167L G175D | 1.94 |
| T1I S13Y T22P S25P S27L S39P S42G S57W S59V V76L Q109R S116D T127V S144P A147H S167L G175D | 1.34 |
| T1I S13Y T22P S27K S39P S42G D56L S57W S59V V76L Q109R S116D T127V S144P A147H S167L G175D | 3.30 |
| T1I S13Y T22P S27L S39P S42G D56I S57W S59D V76L Q109R S116D T127V S144P A147H S167L G175D | 1.73 |
| T1I S13Y T22P S27L S39P S42G D56I S57W S59E V76L Q109R S116D T127V S144P A147H S167L G175D | 1.98 |
| T1I S13Y T22P S27L S39P S42G D56I S57W S59G V76L Q109R S116D T127V S144P A147H S167L G175D | 1.73 |
| T1I S13Y T22P S27L S39P S42G D56I S57W S59V V76L Q109R S116D T127V S144P A147H S167L G175D | 2.12 |
| T1I S13Y T22P S27L S39P S42G D56I S57W S59V V76L Q109R S116D T127V S144P A147K S167L G175D | 1.49 |
| T1I S13Y T22P S27L S39P S42G D56I S57W S59V V76L Q109R S116D T127V S144P A147R S167L G175D | 1.82 |
| T1I S13Y T22P S27L S39P S42G D56I S57Y S59V V76L Q109R S116D T127V S144P A147H S167L G175D | 2.12 |
| T1I S13Y T22P S27L S39P S42G D56L S57W S59V V76L Q109R S116D T127V S144P A147H S167L G175D | 1.88 |
| T1I S13Y T22P S27L S39P S42H D56I S57W S59V V76L Q109R S116D T127V S144P A147H S167L G175D | 1.46 |
| T1I S13Y T22P S27R S39P S42G D56I S57W S59V V76L Q109R S116D T127V S144P A147H S167L G175D | 2.22 |
| T1I S13Y T22P S27V S39P S42G D56I S57W S59V V76L Q109R S116D T127V S144P A147H S167L G175D | 2.09 |
| T1V S13Y T22P S27L S39P S42G D56I S57W S59V V76L Q109R S116D T127V S144P A147H S167L G175D | 1.42 |

TABLE 2-continued

| Mutations relative to *B. cibi* (SEQ ID NO: 1) | RAR Detergent (Assay C) |
|---|---|
| T1I K8R S13Y T22P S27L S39P S42G D56I S57W S59V V76L Q109R S116D T127V S144P A147H S167L G175D | 1.42 |
| T1I S13Y T22P S25P S27L S39P S42G D56I S57W S59V V76L Q109R S116D T127V S144P A147H S167L G175D | 1.73 |
| T1I S13Y T22P S25P S27L S39P S42G S57W S59V S68V V76L T77Y Q109R S116D T127V S144P A147H S167L | 1.18 |
| T1I S13Y T22P S25P S27L S39P S42G S57W S59V V76L T77Y Q109R S116D T127V S144P A147H S167L G175D | 1.41 |
| T1I S13Y T22P S25P S27R S39P S42G D56I S57W S59V V76L Q109R S116D T127V S144P A147H S167L G175D | 1.63 |
| T1I S13Y T22P S27K S39P S42G D56I S57W S59V V76L Q109R S116D T127V S144P A147H G162D S167L G175D | 2.60 |
| T1I S13Y T22P S27K S39P S42G D56I S57W S59V V76L S106L Q109R S116D T127V S144P A147H S167L G175D | 2.84 |
| T1I S13Y T22P S27K S39P S42G D56L S57W S59V T65L V76L Q109R S116D T127V S144P A147H S167L G175D | 2.05 |
| T1I S13Y T22P S27K S39P S42G D56L S57W S59V T65V V76L Q109R S116D T127V S144P A147H S167L G175D | 1.92 |
| T1I S13Y T22P S27K S39P S42G D56L S57W S59V V76L Q109R S116D T127V S130A S144P A147H S167L G175D | 1.94 |
| T1I S13Y T22P S27L L33K S39P S42G D56I S57W S59V V76L Q109R S116D T127V S144P A147H S167L G175D | 1.96 |
| T1I S13Y T22P S27L S39P S42G D56I S57W S59V S66Y V76L Q109R S116D T127V S144P A147H S167L G175D | 1.90 |
| T1I S13Y T22P S27L S39P S42G D56I S57W S59V S68V V76L Q109R S116D T127V S144P A147H S167L G175D | 1.15 |
| T1I S13Y T22P S27L S39P S42G D56I S57W S59V T65L V76L Q109R S116D T127V S144P A147H S167L G175D | 2.22 |
| T1I S13Y T22P S27L S39P S42G D56I S57W S59V T65V V76L Q109R S116D T127V S144P A147H S167L G175D | 2.00 |
| T1I S13Y T22P S27L S39P S42G D56I S57W S59V V76L Q109R S116D T127V S144P A147H G162D S167L G175D | 2.17 |
| T1I S13Y T22P S27L S39P S42G D56I S57W S59V V76L Q109R S116D T127V S144P A147H G162E S167L G175D | 2.32 |
| T1I S13Y T22P S27L S39P S42G D56I S57W S59V V76L Q109R S116D T127V T138D S144P A147H S167L G175D | 1.95 |
| T1I S13Y T22P S27L S39P S42G D56I S57W S59V V76L S106L Q109R S116D T127V S144P A147H S167L G175D | 2.30 |
| T1I S13Y T22P S27L S39P S42G D56I S57W S59V V76L T77Y Q109R S116D T127V S144P A147H S167L G175D | 1.75 |
| T1I S13Y T22P S27L S39P S42G D56L S57W S59V V76L Q109R S116D T127V S144P A147H G162D S167L G175D | 2.45 |
| T1I S13Y T22P S27R S39P S42G D56I S57W S59V T65V V76L Q109R S116D T127V S144P A147H S167L G175D | 1.88 |
| T1I S13Y T22P S27R S39P S42G D56L S57W S59V S66Y V76L Q109R S116D T127V S144P A147H S167L G175D | 1.19 |
| T1I S13Y T22P S27R S39P S42G D56L S57W S59V T65V V76L Q109R S116D T127V S144P A147H S167L G175D | 1.62 |
| T1I S13Y T22P S25P S27L S39P S42C S57W S59V S68V V76L T77Y Q109R S116D T127V S144P A147H S167L G175D | 1.31 |
| T1I S13Y T22P S25P S27L S39P S42G D56I S57W S59V T65L V76L Q109R S116D T127V S144P A147H S167L G175D | 1.70 |
| T1I S13Y T22P S25P S27L S39P S42G D56I S57W S59V T65V V76L Q109R S116D T127V S144P A147H S167L G175D | 1.74 |
| T1I S13Y T22P S25P S27L S39P S42G D56I S57W S59V V76L Q109R S116D T127V S144P A147H Q166D S167L G175D | 1.88 |
| T1I S13Y T22P S25P S27L S39P S42G S57W S59V S68V V76L T77Y Q109R S116D T127V S144P A147H S167L N178D | 1.26 |
| T1I S13Y T22P S25P S27R S39P S42G S57W S59V S66W V76L T77Y Q109R S116D T127V S144P A147H S167L G175D | 1.30 |
| T1I S13Y T22P S27K S39P S42G D56I S57W S59V T65V V76L Q109R S116D T127V S130A S144P A147H S167L G175D | 1.77 |
| T1I S13Y T22P S27K S39P S42G D56I S57W S59V T65V V76L S106L Q109R S116D T127V S144P A147H S167L G175D | 2.08 |
| T1I S13Y T22P S27K S39P S42G D56I S57W S59V V76L S106L Q109R S116D T127V S144P A147H G162D S167L G175D | 1.64 |
| T1I S13Y T22P S27L L33K S39P S42G D56I S57W S59V S66W V76L Q109R S116D T127V S144P A147H S167L G175D | 2.17 |
| T1I S13Y T22P S27L L33K S39P S42G D56I S57W S59V S66Y V76L Q109R S116D T127V S144P A147H S167L G175D | 1.98 |
| T1I S13Y T22P S27L L33K S39P S42G D56I S57W S59V T65L V76L Q109R S116D T127V S144P A147H S167L G175D | 2.25 |
| T1I S13Y T22P S27L L33K S39P S42G D56I S57W S59V T65V V76L Q109R S116D T127V S144P A147H S167L G175D | 2.73 |
| T1I S13Y T22P S27L S39P S42G D56I S57W S59V T65L S66W V76L Q109R S116D T127V S144P A147H S167L G175D | 2.12 |

TABLE 2-continued

| Mutations relative to *B. cibi* (SEQ ID NO: 1) | RAR Detergent (Assay C) |
|---|---|
| T1I S13Y T22P S27L S39P S42G D56I S57W S59V T65L V76L Q109R S116D T127V S144P A147H G162D S167L G175D | 2.31 |
| T1I S13Y T22P S27L S39P S42G D56I S57W S59V T65L V76L S106L Q109R S116D T127V S144P A147H S167L G175D | 1.56 |
| T1I S13Y T22P S27L S39P S42G D56I S57W S59V T65V V76L Q109R S116D T127V S144P A147H G162D S167L G175D | 2.90 |
| T1I S13Y T22P S27L S39P S42G D56I S57W S59V V76L S106L Q109R S116D T127V S144P A147H G162D S167L G175D | 3.46 |
| T1I S13Y T22P S27L S39P S42G D56L S57W S59V T65L V76L Q109R S116D T127V S130A S144P A147H S167L G175D | 1.13 |
| T1I S13Y T22P S27L S39P S42G D56L S57W S59V T65L V76L Q109R S116D T127V S144P A147H G162D S167L G175D | 2.03 |
| T1I S13Y T22P S27L S39P S42G D56L S57W S59V T65L V76L S106L Q109R S116D T127V S144P A147H S167L G175D | 1.77 |
| T1I S13Y T22P S27L S39P S42G D56L S57W S59V T65V V76L Q109R S116D T127V S144P A147H G162D S167L G175D | 2.29 |
| T1I S13Y T22P S27L S39P S42G D56L S57W S59V T65V V76L S106L Q109R S116D T127V S144P A147H S167L G175D | 2.07 |
| T1I S13Y T22P S27L S39P S42G D56L S57W S59V V76L Q109R S116D T127V S130A S144P A147H G162D S167L G175D | 1.80 |
| T1I S13Y T22P S27L S39P S42G D56L S57W S59V V76L S106L Q109R S116D T127V S144P A147H G162D S167L G175D | 1.81 |
| T1I S13Y T22P S27R S39P S42G D56I S57W S59V V76L S106L Q109R S116D T127V S144P A147H G162D S167L G175D | 1.75 |
| T1I S13Y T22P S27R S39P S42G D56L S57W S59V T65V V76L Q109R S116D T127V S144P A147H G162D S167L G175D | 2.21 |
| T1I S13Y T22P S25P S27L L33K S39P S42G D56I S57W S59V S66Y V76L Q109R S116D T127V S144P A147H S167L G175D | 2.14 |
| T1I S13Y T22P S25P S27L L33K S39P S42G S57W S59V S66W V76L T77Y Q109R S116D T127V S144P A147H S167L G175D | 2.45 |
| T1I S13Y T22P S25P S27L L33K S39P S42G S57W S59V S66Y V76L T77Y Q109R S116D T127V S144P A147H S167L G175D | 2.96 |
| T1I S13Y T22P S25P S27L L33K S39P S42G S57W S59V T65L V76L T77Y Q109R S116D T127V S144P A147H S167L G175D | 2.59 |
| T1I S13Y T22P S25P S27L L33K S39P S42G S57W S59V T65V V76L T77Y Q109R S116D T127V S144P A147H S167L G175D | 2.98 |
| T1I S13Y T22P S25P S27L S39P S42G S57W S59V S68V V76L T77Y Q109R S116D T127V S144P A147H S167L G175D N178E | 1.31 |
| T1I S13Y T22P S25P S27L S39P S42G S57W S59V T65L S66W V76L T77Y Q109R S116D T127V S144P A147H S167L G175D | 1.13 |
| T1I S13Y T22P S25P S27L S39P S42G S57W S59V T65L S66Y V76L T77Y Q109R S116D T127V S144P A147H S167L G175D | 2.15 |
| T1I S13Y T22P S25P S27L S39P S42G S57W S59V T65V S66Y V76L T77Y Q109R S116D T127V S144P A147H S167L G175D | 2.63 |
| T1I S13Y T22P S27K L33K S39P S42G S57W S59V T65V S66Y V76L T77Y Q109R S116D T127V S144P A147H S167L G175D | 1.76 |
| T1I S13Y T22P S27K S39P S42G S57W S59V T65V S66Y V76L T77Y Q109R S116D T127V S144P A147H G162D S167L G175D | 1.90 |
| T1I S13Y T22P S27K S39P S42G S57W S59V T65V S66Y V76L T77Y Q109R S116D T127V S144P A147H S167L G175D S181E | 1.72 |
| T1I S13Y T22P S27L S39P S42G D56I S57W S59V T65L V76L Q109R S116D T127V S130A S144P A147H G162D S167L G175D | 2.09 |
| T1I S13Y T22P S27L S39P S42G D56I S57W S59V T65L V76L S106L Q109R S116D T127V S130A S144P A147H S167L G175D | 1.77 |
| T1I S13Y T22P S27L S39P S42G D56I S57W S59V T65L V76L S106L Q109R S116D T127V S144P A147H G162D S167L G175D | 2.07 |
| T1I S13Y T22P S27L S39P S42G D56I S57W S59V T65V V76L Q109R S116D T127V S130A S144P A147H G162D S167L G175D | 2.03 |
| T1I S13Y T22P S27L S39P S42G D56I S57W S59V T65V V76L S106L Q109R S116D T127V S144P A147H G162D S167L G175D | 1.77 |
| T1I S13Y T22P S27L S39P S42G D56I S57W S59V V76L S106L Q109R S116D T127V S130A S144P A147H G162D S167L G175D | 1.88 |
| T1I S13Y T22P S27L S39P S42G D56L S57W S59V V76L S106L Q109R S116D T127V S130A S144P A147H G162D S167L G175D | 2.13 |
| T1I S13Y T22P S25P S27L S39P S42G S57W S59V T65V S66Y V76L T77Y Q109R S116D T127V S144P A147H G162D S167L G175D | 2.05 |
| T1I S13Y T22P S25P S27L S39P S42G S57W S59V T65V S66Y V76L T77Y Q109R S116D T127V S144P A147H S167L G175D S181E | 1.85 |
| T1I S13Y T22P S25P S27L S39P S42G S57W S59V T65V S66Y V76L T77Y S106L Q109R S116D T127V S144P A147H S167L G175D | 1.51 |
| T1I S13Y T22P S27K L33K S39P S42G D56I S57W S59V T65V S66Y V76L Q109R S116D T127V S144P A147H G162D S167L G175D | 3.04 |
| T1I S13Y T22P S27K L33K S39P S42G D56L S57W S59V T65L S66Y V76L Q109R S116D T127V S144P A147H G162D S167L G175D | 2.83 |
| T1I S13Y T22P S27K L33K S39P S42G D56L S57W S59V T65V S66Y V76L Q109R S116D T127V S144P A147H G162D S167L G175D | 2.23 |

TABLE 2-continued

| Mutations relative to *B. cibi* (SEQ ID NO: 1) | RAR Detergent (Assay C) |
|---|---|
| T1I S13Y T22P S27L L33K S39P S42G D56I S57W S59V T65L S66Y V76L Q109R S116D T127V S144P A147H G162D S167L G175D | 2.10 |
| T1I S13Y T22P S27L L33K S39P S42G D56I S57W S59V T65V S66Y V76L Q109R S116D T127V S144P A147H G162D S167L G175D | 3.01 |
| T1I S13Y T22P S27L L33K S39P S42G D56L S57W S59V T65L S66Y V76L Q109R S116D T127V S144P A147H G162D S167L G175D | 2.77 |
| T1I S13Y T22P S27L L33K S39P S42G D56L S57W S59V T65V S66Y V76L Q109R S116D T127V S144P A147H G162D S167L G175D | 1.98 |
| T1I S13Y T22P S25P S27L L33K S39P S42G S57W S59V T65V S66Y V76L T77Y Q109R S116D T127V S144P A147H G162D S167L G175D | 1.93 |
| T1I S13Y T22P S25P S27L L33K S39P S42G S57W S59V T65V S66Y V76L T77Y Q109R S116D T127V S144P A147H S167L G175D S181E | 1.79 |
| T1I S13Y T22P S25P S27L S39P S42G D56L S57W S59V T65V S66Y V76L T77Y Q109R S116D T127V S144P A147H G162D S167L G175D | 2.64 |
| T1I S13Y T22P S25P S27L S39P S42G D56L S57W S59V T65V S66Y V76L T77Y Q109R S116D T127V S144P A147H S167L G175D S181E | 1.37 |
| T1I S13Y T22P S25P S27L S39P S42G D56L S57W S59V T65V S66Y V76L T77Y S106L Q109R S116D T127V S144P A147H S167L G175D | 1.30 |
| T1I S13Y T22P S25P S27L S39P S42G S57W S59V T65V S66Y V76L T77Y Q109R S116D T127V S144P A147H G162D S167L G175D S181E | 1.88 |
| T1I S13Y T22P S25P S27L S39P S42G S57W S59V T65V S66Y V76L T77Y S106L Q109R S116D T127V S144P A147H G162D S167L G175D | 1.94 |
| T1I S13Y T22P S25P S27L S39P S42G S57W S59V T65V S66Y V76L T77Y S106L Q109R S116D T127V S144P A147H S167L G175D S181E | 1.44 |
| T1I S13Y T22P S27K L33K S39P S42G S57W S59V T65V S66Y V76L T77Y Q109R S116D T127V S144P A147H G162D S167L G175D S181E | 2.39 |
| T1I S13Y T22P S25P S27L L33K S39P S42G D56L S57W S59V T65V S66Y V76L T77Y Q109R S116D T127V S144P A147H G162E S167L G175D | 1.68 |

Example 4 Relative Activity Ratio of DNase Variants Relative to Reference Sample in Presence of Protease (Assay A)

Test conditions: DNase variants were stressed for 24 hours at 40° C. in a model detergent (Model detergent A) with 5% protease present. The variants were compared to the reference sample (SEQ ID NO: 28).

TABLE 3

| Mutations relative to *B. cibi* (SEQ ID NO: 1) | RAR protease Assay A |
|---|---|
| DNase variant (SEQ ID NO: 28) | 1.00 |
| T1I S13Y T22P S27K S42G S57W S59V V76L Q109R S116D T127V S144P A147H S167L G175D | 2.94 |
| T1I S13Y T22P S27R S42G S57W S59V V76L Q109R S116D T127V S144P A147H S167L G175D | 2.81 |
| T1I S13Y T22P S27L D32L S42G S57W S59V V76L Q109R S116D T127V S144P A147H S167L G175D | 1.32 |
| T1I S13Y T22P S27L D32R S42G S57W S59V V76L Q109R S116D T127V S144P A147H S167L G175D | 2.89 |
| T1I S13Y T22P S27L D32V S42G S57W S59V V76L Q109R S116D T127V S144P A147H S167L G175D | 1.24 |
| T1I S13Y T22P S27L L33R S42G S57W S59V V76L Q109R S116D T127V S144P A147H S167L G175D | 1.14 |
| T1I S13Y T22P S27L L33V S42G S57W S59V V76L Q109R S116D T127V S144P A147H S167L G175D | 1.18 |
| T1I S13Y T22P S27L L33Y S42G S57W S59V V76L Q109R S116D T127V S144P A147H S167L G175D | 1.25 |
| T1I S13Y T22P S27L S39C S42G S57W S59V V76L Q109R S116D T127V S144P A147H S167L G175D | 1.43 |
| T1I S13Y T22P S27L S42G D56L S57W S59V V76L Q109R S116D T127V S144P A147H S167L G175D | 1.24 |
| T1I S13Y T22P S27L S42G S57W S59V S66R V76L Q109R S116D T127V S144P A147H S167L G175D | 3.40 |
| T1I S13Y T22P S27L S42G S57W S59V S66W V76L Q109R S116D T127V S144P A147H S167L G175D | 1.16 |
| T1I S13Y T22P S27L S42G S57W S59V S66Y V76L Q109R S116D T127V S144P A147H S167L G175D | 3.34 |

TABLE 3-continued

| Mutations relative to *B. cibi* (SEQ ID NO: 1) | RAR protease Assay A |
|---|---|
| T1I S13Y T22P S27L S42G S57W S59V T65R V76L Q109R S116D T127V S144P A147H S167L G175D | 1.36 |
| T1I S13Y T22P S27L S42G S57W S59V V76L Q109R S116D T127V Q140G S144P A147H S167L G175D | 1.26 |
| T1I S13Y T22P S27L S42G S57W S59V V76L Q109R S116D T127V Q140V S144P A147H S167L G175D | 1.15 |
| T1I S13Y T22P S27L S42G S57W S59V V76L Q109R S116D T127V S130Y S144P A147H S167L G175D | 1.24 |
| T1I S13Y T22P S27L S42G S57W S59V V76L Q109R S116D T127V S144P A147H G162D S167L G175D | 1.17 |
| T1I S13Y T22P S27L S42G S57W S59V V76L Q109R S116D T127V S144P A147H K160V S167L G175D | 1.16 |
| T1I S13Y T22P S27L S42G S57W S59V V76L Q109R S116D T127V S144P A147H S167L G175D S179L | 1.64 |
| T1I S13Y T22P S27L S42G S57W S59V V76L Q109R S116D T127V S144P A147H S167L G175D S181E | 1.33 |
| T1I S13Y T22P S27L S42G S57W S59V V76L S101N Q109R S116D T127V S144P A147H S167L G175D | 2.47 |
| T1I S13Y T22P S27L S42G S57W S59V V76L S106L Q109R S116D T127V S144P A147H S167L G175D | 1.48 |
| T1I S13Y T22P S25P S27L S39P D56I S57W S59V V76L Q109R S116D T127V S144P A147H S167L G175D | 1.78 |
| T1I S13Y T22P S25P S27L S39P S42G D56I S57W S59V V76L Q109R T127V S144P A147H S167L G175D | 1.89 |
| T1I S13Y T22P S25P S27L S39P S42G S57W S59V S68V V76L Q109R S116D T127V S144P A147H S167L | 2.01 |
| T1I S13Y T22P S25P S27L S39P S42G S57W S59V S68V V76L Q109R T127V S144P A147H S167L G175D | 1.94 |
| T1I S13Y T22P S25P S27L S39P S42G S57W S59V V76L Q109R S116D T127V S144P A147H S167L G175D | 2.13 |
| T1I S13Y T22P S25P S27L S39P S57W S59V S68V V76L Q109R S116D T127V S144P A147H S167L G175D | 1.79 |
| T1I S13Y T22P S27K S39P S42G D56L S57W S59V V76L Q109R S116D T127V S144P A147H S167L G175D | 4.36 |
| T1I S13Y T22P S27L S39P S42G D56I S57W S59D V76L Q109R S116D T127V S144P A147H S167L G175D | 1.63 |
| T1I S13Y T22P S27L S39P S42G D56I S57W S59E V76L Q109R S116D T127V S144P A147H S167L G175D | 1.74 |
| T1I S13Y T22P S27L S39P S42G D56I S57W S59G V76L Q109R S116D T127V S144P A147H S167L G175D | 1.87 |
| T1I S13Y T22P S27L S39P S42G D56I S57W S59V V76L Q109R S116D T127V S144P A147H S167L G175D | 1.74 |
| T1I S13Y T22P S27L S39P S42G D56L S57W S59V V76L Q109R S116D T127V S144P A147H S167L G175D | 1.73 |
| T1I S13Y T22P S27R S39P S42G D56I S57W S59V V76L Q109R S116D T127V S144P A147H S167L G175D | 3.50 |
| T1I G4K S13Y T22P S27L S39P S42G D56I S57W S59V V76L Q109R S116D T127V S144P A147H S167L G175D | 1.83 |
| T1I K8R S13Y T22P S27L S39P S42G D56I S57W S59V V76L Q109R S116D T127V S144P A147H S167L G175D | 1.57 |
| T1I S13Y T22P S25P S27L S39P S42G D56I S57W S59V V76L Q109R S116D T127V S144P A147H S167L G175D | 2.39 |
| T1I S13Y T22P S25P S27L S39P S42G S57W S59V S68V V76L Q109R S116D T127V S144P A147H S167L G175D | 1.94 |
| T1I S13Y T22P S25P S27L S39P S42G S57W S59V S68V V76L Q109R S116D T127V S144P A147H S167L N178D | 2.34 |
| T1I S13Y T22P S25P S27L S39P S42G S57W S59V S68V V76L T77Y Q109R S116D T127V S144P A147H S167L | 1.84 |
| T1I S13Y T22P S25P S27L S39P S42G S57W S59V V76L T77Y Q109R S116D T127V S144P A147H S167L G175D | 2.10 |
| T1I S13Y T22P S25P S27R S39P S42G D56I S57W S59V V76L Q109R S116D T127V S144P A147H S167L G175D | 3.34 |
| T1I S13Y T22P S27K S39P S42G D56I S57W S59V V76L Q109R S116D T127V S144P A147H G162D S167L G175D | 4.29 |
| T1I S13Y T22P S27K S39P S42G D56I S57W S59V V76L S106L Q109R S116D T127V S144P A147H S167L G175D | 4.32 |
| T1I S13Y T22P S27K S39P S42G D56L S57W S59V T65L V76L Q109R S116D T127V S144P A147H S167L G175D | 4.51 |
| T1I S13Y T22P S27K S39P S42G D56L S57W S59V T65V V76L Q109R S116D T127V S144P A147H S167L G175D | 4.55 |
| T1I S13Y T22P S27K S39P S42G D56L S57W S59V V76L Q109R S116D T127V S130A S144P A147H S167L G175D | 4.67 |
| T1I S13Y T22P S27L L33K S39P S42G D56I S57W S59V V76L Q109R S116D T127V S144P A147H S167L G175D | 2.81 |
| T1I S13Y T22P S27L S39P S42G D56I S57W S59V S66Y V76L Q109R S116D T127V S144P A147H S167L G175D | 1.84 |

TABLE 3-continued

| Mutations relative to *B. cibi* (SEQ ID NO: 1) | RAR protease Assay A |
|---|---|
| T1I S13Y T22P S27L S39P S42G D56I S57W S59V T65L V76L Q109R S116D T127V S144P A147H S167L G175D | 1.48 |
| T1I S13Y T22P S27L S39P S42G D56I S57W S59V T65V V76L Q109R S116D T127V S144P A147H S167L G175D | 1.57 |
| T1I S13Y T22P S27L S39P S42G D56I S57W S59V V76L Q109R S116D T127V S144P A147H G162D S167L G175D | 1.95 |
| T1I S13Y T22P S27L S39P S42G D56I S57W S59V V76L Q109R S116D T127V S144P A147H G162E S167L G175D | 1.99 |
| T1I S13Y T22P S27L S39P S42G D56I S57W S59V V76L Q109R S116D T127V T138D S144P A147H S167L G175D | 2.62 |
| T1I S13Y T22P S27L S39P S42G D56I S57W S59V V76L S106L Q109R S116D T127V S144P A147H S167L G175D | 2.18 |
| T1I S13Y T22P S27L S39P S42G D56I S57W S59V V76L S106R Q109R S116D T127V S144P A147H S167L G175D | 3.55 |
| T1I S13Y T22P S27L S39P S42G D56L S57W S59V V76L Q109R S116D T127V S144P A147H G162D S167L G175D | 1.34 |
| T1I S13Y T22P S27L S42G S57W S59V V76L Q109R S116D T127V S144P A147H C148A S167L G175D S179L C180A | 1.34 |
| T1I S13Y T22P S27R S39P S42G D56I S57W S59V T65V V76L Q109R S116D T127V S144P A147H S167L G175D | 3.02 |
| T1I S13Y T22P S27R S39P S42G D56L S57W S59V S66Y V76L Q109R S116D T127V S144P A147H S167L G175D | 2.83 |
| T1I S13Y T22P S27R S39P S42G D56L S57W S59V T65L V76L Q109R S116D T127V S144P A147H S167L G175D | 4.41 |
| T1I S13Y T22P S27R S39P S42G D56L S57W S59V T65V V76L Q109R S116D T127V S144P A147H S167L G175D | 3.55 |
| T1I S7G S13Y T22P S27L S39P S42G D56I S57W S59V V76L Q109R S116D T127V S144P A147H S167L G175D | 1.86 |
| T1I S13Y T22P S25P S27L S3OP S39P S42G S57W S59V S68V V76L T77Y Q109R T127V S144P A147H S167L G175D | 1.79 |
| T1I S13Y T22P S25P S27L S39P S42C S57W S59V S68V V76L T77Y Q109R S116D T127V S144P A147H S167L G175D | 1.75 |
| T1I S13Y T22P S25P S27L S39P S42G D56I S57W S59V T65L V76L Q109R S116D T127V S144P A147H S167L G175D | 2.15 |
| T1I S13Y T22P S25P S27L S39P S42G D56I S57W S59V T65V V76L Q109R S116D T127V S144P A147H S167L G175D | 2.33 |
| T1I S13Y T22P S25P S27L S39P S42G S57W S59V S68V V76L Q109R S116D T127V S144P A147H S167L G175D N178D | 1.74 |
| T1I S13Y T22P S25P S27L S39P S42G S57W S59V S68V V76L Q109R S116D T127V S144P A147H S167L G175D N178E | 1.98 |
| T1I S13Y T22P S25P S27L S39P S42G S57W S59V S68V V76L T77Y Q109R S116D T127V S144P A147H S167L N178D | 1.95 |
| T1I S13Y T22P S25P S27R S39P S42G S57W S59V S66W V76L T77Y Q109R S116D T127V S144P A147H S167L G175D | 4.04 |
| T1I S13Y T22P S27K S39P S42G D56I S57W S59V T65L V76L Q109R S116D T127V S130A S144P A147H S167L G175D | 4.48 |
| T1I S13Y T22P S27K S39P S42G D56I S57W S59V T65V V76L Q109R S116D T127V S130A S144P A147H S167L G175D | 3.86 |
| T1I S13Y T22P S27K S39P S42G D56I S57W S59V T65V V76L S106L Q109R S116D T127V S144P A147H S167L G175D | 3.94 |
| T1I S13Y T22P S27K S39P S42G D56I S57W S59V V76L Q109R S116D T127V S130A S144P A147H G162D S167L G175D | 4.70 |
| T1I S13Y T22P S27K S39P S42G D56I S57W S59V V76L S106L Q109R S116D T127V S130A S144P A147H S167L G175D | 4.50 |
| T1I S13Y T22P S27K S39P S42G D56I S57W S59V V76L S106L Q109R S116D T127V S144P A147H G162D S167L G175D | 3.78 |
| T1I S13Y T22P S27L L33K S39P S42G D56I S57W S59V S66W V76L Q109R S116D T127V S144P A147H S167L G175D | 3.36 |
| T1I S13Y T22P S27L L33K S39P S42G D56I S57W S59V S66Y V76L Q109R S116D T127V S144P A147H S167L G175D | 2.90 |
| T1I S13Y T22P S27L L33K S39P S42G D56I S57W S59V T65L V76L Q109R S116D T127V S144P A147H S167L G175D | 3.43 |
| T1I S13Y T22P S27L L33K S39P S42G D56I S57W S59V T65V V76L Q109R S116D T127V S144P A147H S167L G175D | 3.59 |
| T1I S13Y T22P S27L S39P S42G D56I S57W S59V T65L S66W V76L Q109R S116D T127V S144P A147H S167L G175D | 2.73 |
| T1I S13Y T22P S27L S39P S42G D56I S57W S59V T65L V76L Q109R S116D T127V S144P A147H G162D S167L G175D | 1.91 |
| T1I S13Y T22P S27L S39P S42G D56I S57W S59V T65L V76L S106L Q109R S116D T127V S144P A147H S167L G175D | 2.08 |
| T1I S13Y T22P S27L S39P S42G D56I S57W S59V T65V V76L Q109R S116D T127V S144P A147H G162D S167L G175D | 1.79 |
| T1I S13Y T22P S27L S39P S42G D56I S57W S59V V76L S106L Q109R S116D T127V S144P A147H G162D S167L G175D | 2.17 |
| T1I S13Y T22P S27L S39P S42G D56L S57W S59V T65L V76L Q109R S116D T127V S144P A147H G162D S167L G175D | 1.50 |

TABLE 3-continued

| Mutations relative to *B. cibi* (SEQ ID NO: 1) | RAR protease Assay A |
|---|---|
| T1I S13Y T22P S27L S39P S42G D56L S57W S59V T65L V76L S106L Q109R S116D T127V S144P A147H S167L G175D | 2.37 |
| T1I S13Y T22P S27L S39P S42G D56L S57W S59V T65V V76L Q109R S116D T127V S130A S144P A147H S167L G175D | 1.48 |
| T1I S13Y T22P S27L S39P S42G D56L S57W S59V T65V V76L Q109R S116D T127V S144P A147H G162D S167L G175D | 1.86 |
| T1I S13Y T22P S27L S39P S42G D56L S57W S59V T65V V76L S106L Q109R S116D T127V S144P A147H S167L G175D | 2.28 |
| T1I S13Y T22P S27L S39P S42G D56L S57W S59V V76L Q109R S116D T127V S130A S144P A147H G162D S167L G175D | 1.90 |
| T1I S13Y T22P S27L S39P S42G D56L S57W S59V V76L S106L Q109R S116D T127V S130A S144P A147H S167L G175D | 1.13 |
| T1I S13Y T22P S27L S39P S42G D56L S57W S59V V76L S106L Q109R S116D T127V S144P A147H G162D S167L G175D | 2.26 |
| T1I S13Y T22P S27R S39P S42G D56I S57W S59V V76L Q109R S116D T127V S130A S144P A147H G162D S167L G175D | 4.29 |
| T1I S13Y T22P S27R S39P S42G D56I S57W S59V V76L S106L Q109R S116D T127V S130A S144P A147H S167L G175D | 2.25 |
| T1I S13Y T22P S27R S39P S42G D56I S57W S59V V76L S106L Q109R S116D T127V S144P A147H G162D S167L G175D | 4.23 |
| T1I S13Y T22P S27R S39P S42G D56L S57W S59V T65V V76L Q109R S116D T127V S144P A147H G162D S167L G175D | 4.40 |
| T1I S13Y T22P S25P S27L L33K S39P S42G D56I S57W S59V S66Y V76L Q109R S116D T127V S144P A147H S167L G175D | 3.56 |
| T1I S13Y T22P S25P S27L L33K S39P S42G S57W S59V S66W V76L T77Y Q109R S116D T127V S144P A147H S167L G175D | 3.90 |
| T1I S13Y T22P S25P S27L L33K S39P S42G S57W S59V S66Y V76L T77Y Q109R S116D T127V S144P A147H S167L G175D | 4.04 |
| T1I S13Y T22P S25P S27L L33K S39P S42G S57W S59V T65L V76L T77Y Q109R S116D T127V S144P A147H S167L G175D | 3.96 |
| T1I S13Y T22P S25P S27L L33K S39P S42G S57W S59V T65V V76L T77Y Q109R S116D T127V S144P A147H S167L G175D | 4.09 |
| T1I S13Y T22P S25P S27L S39P S42G S57W S59V S68V V76L T77Y Q109R S116D T127V S144P A147H Q166D S167L G175D | 1.66 |
| T1I S13Y T22P S25P S27L S39P S42G S57W S59V S68V V76L T77Y Q109R S116D T127V S144P A147H S167L G175D N178E | 2.22 |
| T1I S13Y T22P S25P S27L S39P S42G S57W S59V T65L S66W V76L T77Y Q109R S116D T127V S144P A147H S167L G175D | 1.17 |
| T1I S13Y T22P S25P S27L S39P S42G S57W S59V T65L S66Y V76L T77Y Q109R S116D T127V S144P A147H S167L G175D | 2.57 |
| T1I S13Y T22P S25P S27L S39P S42G S57W S59V T65V S66W V76L T77Y Q109R S116D T127V S144P A147H S167L G175D | 2.69 |
| T1I S13Y T22P S25P S27L S39P S42G S57W S59V T65V S66Y V76L T77Y Q109R S116D T127V S144P A147H S167L G175D | 2.70 |
| T1I S13Y T22P S25P S27R L33R S39P S42G S57W S59V S66Y V76L T77Y Q109R S116D T127V S144P A147H S167L G175D | 2.19 |
| T1I S13Y T22P S27K L33K S39P S42G S57W S59V T65V S66Y V76L T77Y Q109R S116D T127V S144P A147H S167L G175D | 3.55 |
| T1I S13Y T22P S27K S39P S42G S57W S59V T65V S66Y V76L T77Y Q109R S116D T127V S144P A147H G162D S167L G175D | 3.82 |
| T1I S13Y T22P S27K S39P S42G S57W S59V T65V S66Y V76L T77Y Q109R S116D T127V S144P A147H S167L G175D S181E | 3.82 |
| T1I S13Y T22P S27L S39P S42G D56I S57W S59V T65L V76L Q109R S116D T127V S130A S144P A147H G162D S167L G175D | 2.35 |
| T1I S13Y T22P S27L S39P S42G D56I S57W S59V T65L V76L S106L Q109R S116D T127V S130A S144P A147H S167L G175D | 2.12 |
| T1I S13Y T22P S27L S39P S42G D56I S57W S59V T65L V76L S106L Q109R S116D T127V S144P A147H G162D S167L G175D | 2.34 |
| T1I S13Y T22P S27L S39P S42G D56I S57W S59V T65V V76L Q109R S116D T127V S130A S144P A147H G162D S167L G175D | 1.82 |
| T1I S13Y T22P S27L S39P S42G D56I S57W S59V T65V V76L S106L Q109R S116D T127V S144P A147H G162D S167L G175D | 2.05 |
| T1I S13Y T22P S27L S39P S42G D56I S57W S59V V76L S106L Q109R S116D T127V S130A S144P A147H G162D S167L G175D | 2.61 |
| T1I S13Y T22P S27L S39P S42G D56L S57W S59V V76L S106L Q109R S116D T127V S130A S144P A147H G162D S167L G175D | 2.70 |
| T1I S13Y T22P S27R S39P S42G D56L S57W S59V V76L S106L Q109R S116D T127V S130A S144P A147H G162D S167L G175D | 4.38 |
| T1I S13Y T22P S25P S27L S39P S42G S57W S59V T65V S66Y V76L T77Y Q109R S116D T127V S144P A147H G162D S167L G175D | 2.39 |
| T1I S13Y T22P S25P S27L S39P S42G S57W S59V T65V S66Y V76L T77Y Q109R S116D T127V S144P A147H S167L G175D S181E | 2.46 |
| T1I S13Y T22P S25P S27L S39P S42G S57W S59V T65V S66Y V76L T77Y S106L Q109R S116D T127V S144P A147H S167L G175D | 2.69 |
| T1I S13Y T22P S27K L33K S39P S42G D56I S57W S59V T65V S66Y V76L Q109R S116D T127V S144P A147H G162D S167L G175D | 3.52 |

TABLE 3-continued

| Mutations relative to *B. cibi* (SEQ ID NO: 1) | RAR protease Assay A |
|---|---|
| T1I S13Y T22P S27K L33K S39P S42G D56L S57W S59V T65L S66Y V76L Q109R S116D T127V S144P A147H G162D S167L G175D | 3.63 |
| T1I S13Y T22P S27K L33K S39P S42G D56L S57W S59V T65V S66Y V76L Q109R S116D T127V S144P A147H G162D S167L G175D | 3.96 |
| T1I S13Y T22P S27L L33K S39P S42G D56I S57W S59V T65L S66Y V76L Q109R S116D T127V S144P A147H G162D S167L G175D | 4.56 |
| T1I S13Y T22P S27L L33K S39P S42G D56I S57W S59V T65V S66Y V76L Q109R S116D T127V S144P A147H G162D S167L G175D | 3.38 |
| T1I S13Y T22P S27L L33K S39P S42G D56L S57W S59V T65L S66Y V76L Q109R S116D T127V S144P A147H G162D S167L G175D | 3.43 |
| T1I S13Y T22P S27L L33K S39P S42G D56L S57W S59V T65V S66Y V76L Q109R S116D T127V S144P A147H G162D S167L G175D | 3.60 |
| T1I S13Y T22P S25P S27L L33K S39P S42G D56L S57W S59V T65V S66Y V76L T77Y Q109R S116D T127V S144P A147H S167L G175D | 4.34 |
| T1I S13Y T22P S25P S27L L33K S39P S42G S57W S59V T65V S66Y V76L T77Y Q109R S116D T127V S144P A147H G162D S167L G175D | 3.47 |
| T1I S13Y T22P S25P S27L L33K S39P S42G S57W S59V T65V S66Y V76L T77Y Q109R S116D T127V S144P A147H S167L G175D S181E | 3.71 |
| T1I S13Y T22P S25P S27L S39P S42G D56L S57W S59V T65V S66Y V76L T77Y Q109R S116D T127V S144P A147H G162D S167L G175D | 3.57 |
| T1I S13Y T22P S25P S27L S39P S42G D56L S57W S59V T65V S66Y V76L T77Y Q109R S116D T127V S144P A147H S167L G175D S181E | 2.68 |
| T1I S13Y T22P S25P S27L S39P S42G D56L S57W S59V T65V S66Y V76L T77Y S106L Q109R S116D T127V S144P A147H S167L G175D | 3.01 |
| T1I S13Y T22P S25P S27L S39P S42G S57W S59V T65V S66Y V76L T77Y Q109R S116D T127V S144P A147H G162D S167L G175D S181E | 2.34 |
| T1I S13Y T22P S25P S27L S39P S42G S57W S59V T65V S66Y V76L T77Y S106L Q109R S116D T127V S144P A147H G162D S167L G175D | 2.96 |
| T1I S13Y T22P S25P S27L S39P S42G S57W S59V T65V S66Y V76L T77Y S106L Q109R S116D T127V S144P A147H S167L G175D S181E | 2.77 |
| T1I S13Y T22P S27K L33K S39P S42G S57W S59V T65V S66Y V76L T77Y Q109R S116D T127V S144P A147H G162D S167L G175D S181E | 4.14 |
| T1I S13Y T22P S25P S27L L33K S39P S42G D56L S57W S59V T65V S66Y V76L T77Y Q109R S116D T127V S144P A147H G162E S167L G175D | 3.96 |

Example 5 Relative Activity Ratio of DNase Variants Relative to Reference Sample in Presence of Sulfite (Assay B)

Test conditions: The DNase variants were stressed for 1 hours at 60° C. in a model detergent containing 0.4% Sulfite (K2504). The variants were compared to the reference sample SEQ ID NO: 28.

TABLE 4

| Mutations relative to *B. cibi* (SEQ ID NO: 1) | RAR Sulfite Assay B |
|---|---|
| DNase variant (SEQ ID NO: 28) | 1.00 |
| T1I S13Y T22P S27K S42G S57W S59V V76L Q109R S116D T127V S144P A147H S167L G175D | 1.10 |
| T1I S13Y T22P S27R S42G S57W S59V V76L Q109R S116D T127V S144P A147H S167L G175D | 2.09 |
| T1I S13Y S27L S39P S42G D56I S57W S59V V76L Q109R S116D T127V S144P A147H S167L G175D | 1.98 |
| T1I S13Y T22P S27L L33H S42G S57W S59V V76L Q109R S116D T127V S144P A147H S167L G175D | 1.45 |
| T1I S13Y T22P S27L L33R S42G S57W S59V V76L Q109R S116D T127V S144P A147H S167L G175D | 4.02 |
| T1I S13Y T22P S27L L33V S42G S57W S59V V76L Q109R S116D T127V S144P A147H S167L G175D | 8.36 |
| T1I S13Y T22P S27L L33Y S42G S57W S59V V76L Q109R S116D T127V S144P A147H S167L G175D | 7.96 |
| T1I S13Y T22P S27L S39C S42G S57W S59V V76L Q109R S116D T127V S144P A147H S167L G175D | 2.30 |
| T1I S13Y T22P S27L S39P D56I S57W S59V V76L Q109R S116D T127V S144P A147H S167L G175D | 2.38 |
| T1I S13Y T22P S27L S39P S42G D56I S57W S59V Q109R S116D T127V S144P A147H S167L G175D | 2.40 |

TABLE 4-continued

| Mutations relative to *B. cibi* (SEQ ID NO: 1) | RAR Sulfite Assay B |
|---|---|
| T1I S13Y T22P S27L S39P S42G D56I S57W S59V V76L Q109R S116D S144P A147H S167L G175D | 2.39 |
| T1I S13Y T22P S27L S39P S42G D56I S57W S59V V76L Q109R S116D T127V A147H S167L G175D | 4.04 |
| T1I S13Y T22P S27L S39P S42G D56I S57W S59V V76L Q109R S116D T127V S144P A147H G175D | 3.64 |
| T1I S13Y T22P S27L S39P S42G D56I S57W S59V V76L Q109R S116D T127V S144P A147H S167L | 4.34 |
| T1I S13Y T22P S27L S39P S42G D56I S57W S59V V76L Q109R S116D T127V S144P S167L G175D | 2.15 |
| T1I S13Y T22P S27L S39P S42G D56I S57W S59V V76L Q109R T127V S144P A147H S167L G175D | 2.81 |
| T1I S13Y T22P S27L S39P S42G D56I S57W V76L Q109R S116D T127V S144P A147H S167L G175D | 3.97 |
| T1I S13Y T22P S27L S42G D56L S57W S59V V76L Q109R S116D T127V S144P A147H S167L G175D | 2.70 |
| T1I S13Y T22P S27L S42G S57W S59V S66W V76L Q109R S116D T127V S144P A147H S167L G175D | 3.95 |
| T1I S13Y T22P S27L S42G S57W S59V T65L V76L Q109R S116D T127V S144P A147H S167L G175D | 2.57 |
| T1I S13Y T22P S27L S42G S57W S59V T65M V76L Q109R S116D T127V S144P A147H S167L G175D | 3.52 |
| T1I S13Y T22P S27L S42G S57W S59V T65R V76L Q109R S116D T127V S144P A147H S167L G175D | 10.27 |
| T1I S13Y T22P S27L S42G S57W S59V V76L Q109R S116D T127V S144P A147H G162D S167L G175D | 1.33 |
| T1I S13Y T22P S27L S42G S57W S59V V76L Q109R S116D T127V S144P A147H W154Y S167L G175D | 1.22 |
| T1I S13Y T22P S39P S42G D56I S57W S59V V76L Q109R S116D T127V S144P A147H S167L G175D | 4.06 |
| T1I S9I S13Y T22P S27L S42G S57W S59V V76L Q109R S116D T127V S144P A147H S167L G175D | 2.41 |
| T1I T22P S27L S39P S42G D56I S57W S59V V76L Q109R S116D T127V S144P A147H S167L G175D | 4.45 |
| T1I S13Y T22P E23G S27L S42G S57W S59V V76L Q109R S116D T127V D133N S144P A147H S167L G175D | 1.21 |
| T1I S13Y T22P S25P S27L S39P D56I S57W S59V V76L Q109R S116D T127V S144P A147H S167L G175D | 1.42 |
| T1I S13Y T22P S25P S27L S39P S42G D56I S57W S59V V76L Q109R T127V S144P A147H S167L G175D | 1.46 |
| T1I S13Y T22P S25P S27L S39P S42G S57W S59V S68V V76L Q109R S116D T127V S144P A147H S167L | 1.21 |
| T1I S13Y T22P S25P S27L S39P S42G S57W S59V V76L Q109R S116D T127V S144P A147H S167L G175D | 1.61 |
| T1I S13Y T22P S27L S39P S42G D56I S57W S59D V76L Q109R S116D T127V S144P A147H S167L G175D | 2.96 |
| T1I S13Y T22P S27L S39P S42G D56I S57W S59E V76L Q109R S116D T127V S144P A147H S167L G175D | 4.93 |
| T1I S13Y T22P S27L S39P S42G D56I S57W S59G V76L Q109R S116D T127V S144P A147H S167L G175D | 2.37 |
| T1I S13Y T22P S27L S39P S42G D56I S57W S59V V76L Q109R S116D T127V S144P A147H S167L G175D | 3.17 |
| T1I S13Y T22P S27L S39P S42G D56I S57W S59V V76L Q109R S116D T127V S144P A147K S167L G175D | 2.80 |
| T1I S13Y T22P S27L S39P S42G D56I S57W S59V V76L Q109R S116D T127V S144P A147R S167L G175D | 3.81 |
| T1I S13Y T22P S27L S39P S42G D56I S57Y S59V V76L Q109R S116D T127V S144P A147H S167L G175D | 3.46 |
| T1I S13Y T22P S27L S39P S42G D56L S57W S59V V76L Q109R S116D T127V S144P A147H S167L G175D | 3.29 |
| T1I S13Y T22P S27L S39P S42H D56I S57W S59V V76L Q109R S116D T127V S144P A147H S167L G175D | 2.78 |
| T1I S13Y T22P S27R S39P S42G D56I S57W S59V V76L Q109R S116D T127V S144P A147H S167L G175D | 2.85 |
| T1I S13Y T22P S27V S39P S42G D56I S57W S59V V76L Q109R S116D T127V S144P A147H S167L G175D | 4.58 |
| T1V S13Y T22P S27L S39P S42G D56I S57W S59V V76L Q109R S116D T127V S144P A147H S167L G175D | 3.37 |
| T1I G4K S13Y T22P S27L S39P S42G D56I S57W S59V V76L Q109R S116D T127V S144P A147H S167L G175D | 2.15 |
| T1I K8R S13Y T22P S27L S39P S42G D56I S57W S59V V76L Q109R S116D T127V S144P A147H S167L G175D | 2.28 |
| T1I S13Y T22P S25P S27L S39P S42G D56I S57W S59V V76L Q109R S116D T127V S144P A147H S167L G175D | 2.83 |
| T1I S13Y T22P S25P S27L S39P S42G S57W S59V S68V V76L Q109R S116D T127V S144P A147H S167L N178D | 1.25 |

TABLE 4-continued

| Mutations relative to *B. cibi* (SEQ ID NO: 1) | RAR Sulfite Assay B |
|---|---|
| T1I S13Y T22P S25P S27L S39P S42G S57W S59V S68V V76L T77Y Q109R S116D T127V S144P A147H S167L | 1.49 |
| T1I S13Y T22P S25P S27L S39P S42G S57W S59V V76L T77Y Q109R S116D T127V S144P A147H S167L G175D | 1.99 |
| T1I S13Y T22P S25P S27R S39P S42G D56I S57W S59V V76L Q109R S116D T127V S144P A147H S167L G175D | 3.53 |
| T1I S13Y T22P S27K S39P S42G D56I S57W S59V V76L Q109R S116D T127V S144P A147H G162D S167L G175D | 3.90 |
| T1I S13Y T22P S27K S39P S42G D56L S57W S59V T65L V76L Q109R S116D T127V S144P A147H S167L G175D | 5.30 |
| T1I S13Y T22P S27K S39P S42G D56L S57W S59V T65V V76L Q109R S116D T127V S144P A147H S167L G175D | 5.62 |
| T1I S13Y T22P S27K S39P S42G D56L S57W S59V V76L Q109R S116D T127V S130A S144P A147H S167L G175D | 4.97 |
| T1I S13Y T22P S27L L33K S39P S42G D56I S57W S59V V76L Q109R S116D T127V S144P A147H S167L G175D | 3.74 |
| T1I S13Y T22P S27L S39P S42G D56I S57W S59V S66Y V76L Q109R S116D T127V S144P A147H S167L G175D | 4.25 |
| T1I S13Y T22P S27L S39P S42G D56I S57W S59V S68V V76L Q109R S116D T127V S144P A147H S167L G175D | 2.23 |
| T1I S13Y T22P S27L S39P S42G D56I S57W S59V T65L V76L Q109R S116D T127V S144P A147H S167L G175D | 2.92 |
| T1I S13Y T22P S27L S39P S42G D56I S57W S59V T65V V76L Q109R S116D T127V S144P A147H S167L G175D | 3.76 |
| T1I S13Y T22P S27L S39P S42G D56I S57W S59V V76L Q109R S116D T127V S144P A147H G162D S167L G175D | 4.85 |
| T1I S13Y T22P S27L S39P S42G D56I S57W S59V V76L Q109R S116D T127V S144P A147H G162E S167L G175D | 5.52 |
| T1I S13Y T22P S27L S39P S42G D56I S57W S59V V76L Q109R S116D T127V T138D S144P A147H S167L G175D | 5.64 |
| T1I S13Y T22P S27L S39P S42G D56I S57W S59V V76L S106L Q109R S116D T127V S144P A147H S167L G175D | 3.94 |
| T1I S13Y T22P S27L S39P S42G D56I S57W S59V V76L T77Y Q109R S116D T127V S144P A147H S167L G175D | 5.19 |
| T1I S13Y T22P S27L S39P S42G D56L S57W S59V V76L Q109R S116D T127V S144P A147H G162D S167L G175D | 2.16 |
| T1I S13Y T22P S27R S39P S42G D56I S57W S59V T65V V76L Q109R S116D T127V S144P A147H S167L G175D | 4.60 |
| T1I S13Y T22P S27R S39P S42G D56L S57W S59V S66Y V76L Q109R S116D T127V S144P A147H S167L G175D | 3.86 |
| T1I S13Y T22P S27R S39P S42G D56L S57W S59V T65L V76L Q109R S116D T127V S144P A147H S167L G175D | 2.69 |
| T1I S13Y T22P S27R S39P S42G D56L S57W S59V T65V V76L Q109R S116D T127V S144P A147H S167L G175D | 3.52 |
| T1I S7G S13Y T22P S27L S39P S42G D56I S57W S59V V76L Q109R S116D T127V S144P A147H S167L G175D | 2.75 |
| T1I S13Y T22P S25P S27L S39P S42C S57W S59V S68V V76L T77Y Q109R S116D T127V S144P A147H S167L G175D | 1.46 |
| T1I S13Y T22P S25P S27L S39P S42G D56I S57W S59V S68V V76L Q109R S116D T127V S144P A147H S167L G175D | 4.13 |
| T1I S13Y T22P S25P S27L S39P S42G D56I S57W S59V T65L V76L Q109R S116D T127V S144P A147H S167L G175D | 3.81 |
| T1I S13Y T22P S25P S27L S39P S42G D56I S57W S59V T65V V76L Q109R S116D T127V S144P A147H S167L G175D | 3.84 |
| T1I S13Y T22P S25P S27L S39P S42G D56I S57W S59V V76L Q109R S116D T127V S144P A147H Q166D S167L G175D | 3.53 |
| T1I S13Y T22P S25P S27L S39P S42G D56I S57W S59V V76L T77Y Q109R S116D T127V S144P A147H S167L G175D | 5.23 |
| T1I S13Y T22P S25P S27L S39P S42G S57W S59V S68V V76L T77Y Q109R S116D T127V S144P A147H S167L N178D | 1.39 |
| T1I S13Y T22P S25P S27R S39P S42G S57W S59V S66W V76L T77Y Q109R S116D T127V S144P A147H S167L G175D | 1.61 |
| T1I S13Y T22P S27K S39P S42G D56I S57W S59V T65L V76L Q109R S116D T127V S130A S144P A147H S167L G175D | 2.65 |
| T1I S13Y T22P S27K S39P S42G D56I S57W S59V T65V V76L Q109R S116D T127V S130A S144P A147H S167L G175D | 4.29 |
| T1I S13Y T22P S27K S39P S42G D56I S57W S59V T65V V76L S106L Q109R S116D T127V S144P A147H S167L G175D | 4.03 |
| T1I S13Y T22P S27K S39P S42G D56I S57W S59V V76L Q109R S116D T127V S130A S144P A147H G162D S167L G175D | 1.91 |
| T1I S13Y T22P S27K S39P S42G D56I S57W S59V V76L S106L Q109R S116D T127V S130A S144P A147H S167L G175D | 2.40 |
| T1I S13Y T22P S27K S39P S42G D56I S57W S59V V76L S106L Q109R S116D T127V S144P A147H G162D S167L G175D | 3.61 |
| T1I S13Y T22P S27L L33K S39P S42G D56I S57W S59V S66W V76L Q109R S116D T127V S144P A147H S167L G175D | 4.79 |

TABLE 4-continued

| Mutations relative to *B. cibi* (SEQ ID NO: 1) | RAR Sulfite Assay B |
|---|---|
| T1I S13Y T22P S27L L33K S39P S42G D56I S57W S59V S66Y V76L Q109R S116D T127V S144P A147H S167L G175D | 4.96 |
| T1I S13Y T22P S27L L33K S39P S42G D56I S57W S59V T65L V76L Q109R S116D T127V S144P A147H S167L G175D | 3.88 |
| T1I S13Y T22P S27L L33K S39P S42G D56I S57W S59V T65V V76L Q109R S116D T127V S144P A147H S167L G175D | 3.89 |
| T1I S13Y T22P S27L S39P S42G D56I S57W S59V T65L S66W V76L Q109R S116D T127V S144P A147H S167L G175D | 5.21 |
| T1I S13Y T22P S27L S39P S42G D56I S57W S59V T65L V76L Q109R S116D T127V S144P A147H G162D S167L G175D | 5.80 |
| T1I S13Y T22P S27L S39P S42G D56I S57W S59V T65L V76L S106L Q109R S116D T127V S144P A147H S167L G175D | 4.00 |
| T1I S13Y T22P S27L S39P S42G D56I S57W S59V T65V V76L Q109R S116D T127V S130A S144P A147H S167L G175D | 1.25 |
| T1I S13Y T22P S27L S39P S42G D56I S57W S59V T65V V76L Q109R S116D T127V S144P A147H G162D S167L G175D | 3.91 |
| T1I S13Y T22P S27L S39P S42G D56I S57W S59V V76L T77Y Q109R S116D T127V S144P A147H Q166D S167L G175D | 4.39 |
| T1I S13Y T22P S27L S39P S42G D56L S57W S59V T65L V76L Q109R S116D T127V S130A S144P A147H S167L G175D | 2.39 |
| T1I S13Y T22P S27L S39P S42G D56L S57W S59V T65L V76L Q109R S116D T127V S144P A147H G162D S167L G175D | 4.40 |
| T1I S13Y T22P S27L S39P S42G D56L S57W S59V T65L V76L S106L Q109R S116D T127V S144P A147H S167L G175D | 5.34 |
| T1I S13Y T22P S27L S39P S42G D56L S57W S59V T65V V76L Q109R S116D T127V S130A S144P A147H S167L G175D | 2.05 |
| T1I S13Y T22P S27L S39P S42G D56L S57W S59V T65V V76L Q109R S116D T127V S144P A147H G162D S167L G175D | 6.42 |
| T1I S13Y T22P S27L S39P S42G D56L S57W S59V T65V V76L S106L Q109R S116D T127V S144P A147H S167L G175D | 4.75 |
| T1I S13Y T22P S27L S39P S42G D56L S57W S59V V76L Q109R S116D T127V S130A S144P A147H G162D S167L G175D | 3.76 |
| T1I S13Y T22P S27L S39P S42G D56L S57W S59V V76L S106L Q109R S116D T127V S130A S144P A147H S167L G175D | 1.80 |
| T1I S13Y T22P S27L S39P S42G D56L S57W S59V V76L S106L Q109R S116D T127V S144P A147H G162D S167L G175D | 4.37 |
| T1I S13Y T22P S27R S39P S42G D56I S57W S59V V76L Q109R S116D T127V S130A S144P A147H G162D S167L G175D | 2.16 |
| T1I S13Y T22P S27R S39P S42G D56I S57W S59V V76L S106L Q109R S116D T127V S130A S144P A147H S167L G175D | 2.58 |
| T1I S13Y T22P S27R S39P S42G D56I S57W S59V V76L S106L Q109R S116D T127V S144P A147H G162D S167L G175D | 4.12 |
| T1I S13Y T22P S27R S39P S42G D56L S57W S59V T65V V76L Q109R S116D T127V S144P A147H G162D S167L G175D | 6.04 |
| T1I S13Y T22P S25P S27L L33K S39P S42G D56I S57W S59V S66Y V76L Q109R S116D T127V S144P A147H S167L G175D | 4.85 |
| T1I S13Y T22P S25P S27L L33K S39P S42G S57W S59V S66W V76L T77Y Q109R S116D T127V S144P A147H S167L G175D | 2.61 |
| T1I S13Y T22P S25P S27L L33K S39P S42G S57W S59V S66Y V76L T77Y Q109R S116D T127V S144P A147H S167L G175D | 2.28 |
| T1I S13Y T22P S25P S27L L33K S39P S42G S57W S59V T65L V76L T77Y Q109R S116D T127V S144P A147H S167L G175D | 2.13 |
| T1I S13Y T22P S25P S27L L33K S39P S42G S57W S59V T65VV76L T77Y Q109R S116D T127V S144P A147H S167L G175D | 2.04 |
| T1I S13Y T22P S25P S27L S39P S42G S57W S59V S68V V76L T77Y Q109R S116D T127V S144P A147H Q166D S167L G175D | 1.22 |
| T1I S13Y T22P S25P S27L S39P S42G S57W S59V S68V V76L T77Y Q109R S116D T127V S144P A147H S167L G175D N178E | 1.31 |
| T1I S13Y T22P S25P S27L S39P S42G S57W S59V T65L S66W V76L T77Y Q109R S116D T127V S144P A147H S167L G175D | 1.56 |
| T1I S13Y T22P S25P S27L S39P S42G S57W S59V T65L S66Y V76L T77Y Q109R S116D T127V S144P A147H S167L G175D | 2.52 |
| T1I S13Y T22P S25P S27L S39P S42G S57W S59V T65V S66W V76L T77Y Q109R S116D T127V S144P A147H S167L G175D | 1.26 |
| T1I S13Y T22P S25P S27L S39P S42G S57W S59V T65V S66Y V76L T77Y Q109R S116D T127V S144P A147H S167L G175D | 2.14 |
| T1I S13Y T22P S27K L33K S39P S42G S57W S59V T65V S66Y V76L T77Y Q109R S116D T127V S144P A147H S167L G175D | 3.19 |
| T1I S13Y T22P S27K S39P S42G S57W S59V T65V S66Y V76L T77Y Q109R S116D T127V S144P A147H G162D S167L G175D | 2.65 |
| T1I S13Y T22P S27K S39P S42G S57W S59V T65V S66Y V76L T77Y Q109R S116D T127V S144P A147H S167L G175D S181E | 2.56 |
| T1I S13Y T22P S27L S39P S42G D56I S57W S59V T65L V76L Q109R S116D T127V S130A S144P A147H G162D S167L G175D | 5.79 |
| T1I S13Y T22P S27L S39P S42G D56I S57W S59V T65L V76L S106L Q109R S116D T127V S130A S144P A147H S167L G175D | 4.69 |

TABLE 4-continued

| Mutations relative to *B. cibi* (SEQ ID NO: 1) | RAR Sulfite Assay B |
|---|---|
| T1I S13Y T22P S27L S39P S42G D56I S57W S59V T65L V76L S106L Q109R S116D T127V S144P A147H G162D S167L G175D | 4.93 |
| T1I S13Y T22P S27L S39P S42G D56I S57W S59V T65V V76L Q109R S116D T127V S130A S144P A147H G162D S167L G175D | 4.92 |
| T1I S13Y T22P S27L S39P S42G D56I S57W S59V T65V V76L S106L Q109R S116D T127V S144P A147H G162D S167L G175D | 4.51 |
| T1I S13Y T22P S27L S39P S42G D56I S57W S59V V76L S106L Q109R S116D T127V S130A S144P A147H G162D S167L G175D | 5.80 |
| T1I S13Y T22P S27L S39P S42G D56L S57W S59V V76L S106L Q109R S116D T127V S130A S144P A147H G162D S167L G175D | 5.59 |
| T1I S13Y T22P S27R S39P S42G D56L S57W S59V V76L S106L Q109R S116D T127V S130A S144P A147H G162D S167L G175D | 2.24 |
| T1I S13Y T22P S25P S27L S39P S42G S57W S59V T65V S66Y V76L T77Y Q109R S116D T127V S144P A147H G162D S167L G175D | 2.47 |
| T1I S13Y T22P S25P S27L S39P S42G S57W S59V T65V S66Y V76L T77Y Q109R S116D T127V S144P A147H S167L G175D S181E | 2.74 |
| T1I S13Y T22P S25P S27L S39P S42G S57W S59V T65V S66Y V76L T77Y S106L Q109R S116D T127V S144P A147H S167L G175D | 2.42 |
| T1I S13Y T22P S27K L33K S39P S42G D56I S57W S59V T65V S66Y V76L Q109R S116D T127V S144P A147H G162D S167L G175D | 3.20 |
| T1I S13Y T22P S27K L33K S39P S42G D56L S57W S59V T65L S66Y V76L Q109R S116D T127V S144P A147H G162D S167L G175D | 3.29 |
| T1I S13Y T22P S27K L33K S39P S42G D56L S57W S59V T65V s66Y V76L Q109R S116D T127V S144P A147H G162D S167L G175D | 2.92 |
| T1I S13Y T22P S27L L33K S39P S42G D56I S57W S59V T65L S66Y V76L Q109R S116D T127V S144P A147H G162D S167L G175D | 2.22 |
| T1I S13Y T22P S27L L33K S39P S42G D56I S57W S59V T65V S66Y V76L Q109R S116D T127V S144P A147H G162D S167L G175D | 3.33 |
| T1I S13Y T22P S27L L33K S39P S42G D56L S57W S59V T65L S66Y V76L Q109R S116D T127V S144P A147H G162D S167L G175D | 3.39 |
| T1I S13Y T22P S27L L33K S39P S42G D56L S57W S59V T65V S66Y V76L Q109R S116D T127V S144P A147H G162D S167L G175D | 3.46 |
| T1I S13Y T22P S25P S27L L33K S39P S42G D56L S57W S59V T65V S66Y V76L T77Y Q109R S116D T127V S144P A147H S167L G175D | 2.75 |
| T1I S13Y T22P S25P S27L L33K S39P S42G S57W S59V T65V S66Y V76L T77Y Q109R S116D T127V S144P A147H G162D S167L G175D | 2.76 |
| T1I S13Y T22P S25P S27L L33K S39P S42G S57W S59V T65V S66Y V76L T77Y Q109R S116D T127V S144P A147H S167L G175D S181E | 3.39 |
| T1I S13Y T22P S25P S27L S39P S42G D56L S57W S59V T65V S66Y V76L T77Y Q109R S116D T127V S144P A147H G162D S167L G175D | 2.82 |
| T1I S13Y T22P S25P S27L S39P S42G D56L S57W S59V T65V S66Y V76L T77Y Q109R S116D T127V S144P A147H S167L G175D S181E | 2.23 |
| T1I S13Y T22P S25P S27L S39P S42G D56L S57W S59V T65V S66Y V76L T77Y S106L Q109R S116D T127V S144P A147H S167L G175D | 2.60 |
| T1I S13Y T22P S25P S27L S39P S42G S57W S59V T65V S66Y V76L T77Y Q109R S116D T127V S144P A147H G162D S167L G175D S181E | 2.60 |
| T1I S13Y T22P S25P S27L S39P S42G S57W S59V T65V S66Y V76L T77Y S106L Q109R S116D T127V S144P A147H G162D S167L G175D | 2.82 |
| T1I S13Y T22P S25P S27L S39P S42G S57W S59V T65V S66Y V76L T77Y S106L Q109R S116D T127V S144P A147H S167L G175D S181E | 2.60 |
| T1I S13Y T22P S27K L33K S39P S42G S57W S59V T65V S66Y V76L T77Y Q109R S116D T127V S144P A147H G162D S167L G175D S181E | 3.26 |
| T1I S13Y T22P S25P S27L L33K S39P S42G D56L S57W S59V T65V S66Y V76L T77Y Q109R S116D T127V S144P A147H G162E S167L G175D | 3.04 |

Example 6: Testing DNase Variants for Stability

Each supernatant sample were split into two identical samples by transferring 10 ul supernatant to two 96-well standard microtiter plates each containing 240 ul Model A. After shaking for five minutes at 7500 rpm in a microtiter plate shaker, one microtiter plate was incubated at room temperature (21° C.=reference condition) for 20 min and the other microtiter plate was incubated in a 96-well PCR block at the stress conditions (stress setup 1. 49° C.-1140 min and stress setup 2. 60° C.-90 min). Sample sets (the reference condition and the stressed condition) were diluted 100-fold in dilution buffer (50 mM Tris, HCl, pH 7.5) before assaying the activity by usage of the DNAseAlert Substrate™ solution (Integrated DNA Technologies/Belgium, part #11-04-02-04, www.idtdna.com/pages/products/reagents/nuclease-detection-products).

DNase Activity Assay

For the DNase activity measurement, 10 ul 100-fold diluted reference DNase sample and stress DNase sample were transferred to a new 384-well microtiter plate and 40 ul DNAseAlert assay solution was added (50 mM TrisHCl, pH. 7.5, 5 mM MnCl2, 6 nM DNAseAlert Substrate™). The fluorescence (excitation 536 nm and emission 556 nm) was read each 90 seconds for a total of 30 minutes. From the kinetic curves, the slope of the reference sample (activity under reference conditions) and the corresponding stress sample (activity under stress conditions) was determined by linear regression. The residual activity (RA) for each DNase variant and the reference DNase (SEQ ID NO: 1) was calculated as: slope (stress sample)/slope(reference sample.

Half-Life Improvement Factor

The Half-life Improvement Factor ($T_{1/2}$ in minutes) for the DNase variants and the DNase reference (SEQ ID NO: 1) was calculated as: minutes×LN(0.5)/LN(RA). The Half-life Improvement Factor (HIF) for the variants was calculated as $T_{1/2variant}/T_{1/2reference}$. Improved variants were identified as variants having a Half-life Improvement Factor HIF larger than 1.0 (HIF reference (SEQ ID NO: 1)=1.0).

TABLE 5

Half-life improvement factor for *Bacillus cibi* (SEQ ID NO: 1) DNase variants

| Mutations | Stress cond. 1 | Stress cond. 2 |
|---|---|---|
| SEQ ID NO: 1 | 1.0 | 1.0 |
| T1I + K21E + T22P + S25P + S39P + S57W + V76L + T127V + A147H + S167L + G175D | 1.6 | |
| T1I + K21E + T22P + S57W + V76L + K107E + T127V + A147H + S167L + G175D | 1.7 | |
| T1I + K21E + T22P + S57W + V76L + S116D + T127V + A147H + S167L + G175D | 1.7 | |
| T1I + S57W + A147Q | 1.8 | |
| T1I + T22P + D45E + D56I + S57W + V76L + A112E + S116D + T127V + A147H + S167L + G175D | 1.8 | |
| T1I + T22P + D56I + S57W + N61E + V76L + A93G + A147H + S167L + G175D | 1.8 | |
| T1I + T22P + D56I + S57W + S68V + V76L + A147H + S167L + G175N + N178D | 1.9 | |
| T1I + T22P + D56I + S57W + S68V + V76L + A147H + S167L + T171D + G175D | 1.9 | |
| T1I + T22P + D56I + S57W + S68V + V76L + K107E + Q109R + A147H + S167L + G175D | 1.9 | |
| T1I + T22P + D56I + S57W + S68V + V76L + Q109R + A147H + S167L + G175D | 1.9 | |
| T1I + T22P + D56I + S57W + V76L + A93G + A147H + S167L + G175D | 2.0 | 1.5 |
| T1I + T22P + D56I + S57W + V76L + K107E + S116D + A147H + S167L + G175D | 2.1 | |
| T1I + T22P + D56I + S57W + V76L + K107E + T127V + A147H + S167L + G175D | 2.2 | |
| T1I + T22P + D56I + S57W + V76L + Q109K + S116D + T127V + A147H + S167L + G175D | 2.2 | |
| T1I + T22P + D56I + S57W + V76L + Q109R + S116D + A147H + G162S + S167L + G175D | 2.2 | |
| T1I + T22P + D56I + S57W + V76L + Q109R + S116D + A147H + S167L + G175D | 2.3 | |
| T1I + T22P + D56I + S57W + V76L + S116D + A147H + Q166D + S167L + G175D | 2.3 | |
| T1I + T22P + D56I + S57W + V76L + T127V + A147H + G162S + S167L + G175D | 2.3 | |
| T1I + T22P + D56I + S57Y + S68V + V76L + A147H + S167L + G175D | 2.4 | |
| T1I + T22P + S25P + D56I + S57W + V76L + T127V + A147H + S167L + G175D | 2.6 | |
| T1I + T22P + S25P + S57W + V76L + S116D + T127V + A147H + S167L + G175D | 2.6 | |
| T1I + T22P + S39A + S57W + N61E + V76L + A147H + S167L + T171D + G175D | 2.7 | |
| T1I + T22P + S39A + S57W + N61E + V76L + Q109R + A147H + S167L + G175D | 2.8 | |
| T1I + T22P + S39A + S57W + V76L + A147H + Q166D + S167L + G175D | 2.8 | |
| T1I + T22P + S39A + S57W + V76L + A147H + S167L + T171D + G175D | 2.9 | |
| T1I + T22P + S39A + S57W + V76L + Q109R + A147H + Q166D + S167L + G175D | 3.0 | |
| T1I + T22P + S39P + D56I + S57W + V76L + A147H + G162S + S167L + G175D | 3.1 | |
| T1I + T22P + S39P + D56I + S57W + V76L + K107E + A147H + S167L + G175D | 3.3 | |
| T1I + T22P + S39P + D56I + S57W + V76L + T127V + A147H + S167L + G175D | 3.6 | |
| T1I + T22P + S39P + S57W + V76L + S116D + A147H + G162S + S167L + G175D | 3.6 | |
| T1I + T22P + S39P + S57W + V76L + S116D + A147H + Q166D + S167L + G175D | 3.9 | |
| T1I + T22P + S39P + S57W + V76L + T127V + A147H + Q166D + S167L + G175D | 3.9 | |
| T1I + T22P + S39P + S57W + V76L + T127V + A147H + S167L + G175D | 4.2 | |
| T1I + T22P + S57W + A147H + S167L + G175D | 4.2 | |
| T1I + T22P + S57W + N61E + S68V + V76L + A147H + G162Q + S167L + G175D | 4.7 | |
| T1I + T22P + S57W + N61E + V76L + Q109R + A147H + Q166D + S167L + G175D | 4.9 | |
| T1I + T22P + S57W + N61E + V76L + Q109R + A147H + S167L + T171D + G175D | 5.0 | |
| T1I + T22P + S57W + V76K + T104A + T127P + A147H + G162Q + S167L + G175D | 5.1 | |
| T1I + T22P + S57W + V76L + A147H + S167F + G175D | 5.3 | |
| T1I + T22P + S57W + V76L + A147H + S167L | 5.4 | |
| T1I + T22P + S57W + V76L + A147H + S167L + G175D | 6.1 | |
| T1I + T22P + S57W + V76L + A147H + S167L + G175E | 6.7 | |
| T1I + T22P + S57W + V76L + A147H + S167L + T171D + G175D | 7.4 | |
| T1I + T22P + S57W + V76L + A93G + A147H + G162Q + S167L + G175D | 8.0 | |
| T1I + T22P + S57W + V76L + A93G + A147H + Q166D + S167L + G175D | 9.6 | |
| T1I + T22P + S57W + V76L + A93G + A147H + S167L + G175D | 9.9 | |
| T1I + T22P + S57W + V76L + K107E + S116D + T127V + A147H + S167L + G175D | 10.2 | |
| T1I + T22P + S57W + V76L + Q109R + A147H + Q166D + S167L + T171D + G175D | 11.1 | |
| T1I + T22P + S57W + V76L + Q109R + A147H + S167L + T171D + G175D | 12.2 | |
| T1L + N16G + T22P + D56I + S57Y + S68V + V76L + A147R | 14.0 | |
| T1L + N16G + T22P + S57Y + S68V + V76L + A93G + A147R + S167M | 18.8 | |
| T1L + T22P + D56I + S57Y + A147R + S167M | | 3.7 |
| T1L + T22P + D56I + S57Y + N61E + S68V + V76L + A147R | | 4.1 |
| T1L + T22P + D56I + S57Y + N61E + S68V + V76L + A147R + G175E | | 5.7 |
| T1L + T22P + D56I + S57Y + N61E + S68V + V76L + A147R + S167M | | 5.1 |
| T1L + T22P + D56I + S57Y + S68V + V76L + A147R | | 3.2 |
| T1L + T22P + D56I + S57Y + S68V + V76L + A147R + G162Q | | 5.3 |
| T1L + T22P + D56I + S57Y + S68V + V76L + A147R + G162Q + G175D | | 3.8 |
| T1L + T22P + D56I + S57Y + S68V + V76L + A147R + G162Q + G175E | | 4.1 |
| T1L + T22P + D56I + S57Y + S68V + V76L + A147R + G162Q + S167M | | 5.2 |
| T1L + T22P + D56I + S57Y + S68V + V76L + A147R + G175D | | 6.8 |
| T1L + T22P + D56I + S57Y + S68V + V76L + A147R + S167M + G175E | | 5.6 |
| T1L + T22P + D56I + S57Y + S68V + V76L + A147R + T171D | | 4.0 |
| T1L + T22P + D56I + S57Y + S68V + V76L + A93G + A147R | | 4.4 |
| T1L + T22P + D56I + S57Y + S68V + V76L + A93G + A147R + S167M | | 5.9 |
| T1L + T22P + D56I + S57Y + S68V + V76L + F78L + A147R | | 3.8 |
| T1L + T22P + D56I + S57Y + S68V + V76L + P91L + Q109R + A147R + G175E | | 3.2 |
| T1L + T22P + D56I + S57Y + S68V + V76L + Q109R + A147R | | 4.5 |
| T1L + T22P + D56I + S57Y + S68V + V76L + Q109R + A147R + G175D | | 4.5 |
| T1L + T22P + S39A + D56I + S57Y + S68V + V76L + A147R | | 4.7 |

TABLE 5-continued

| Half-life improvement factor for *Bacillus cibi* (SEQ ID NO: 1) DNase variants | | |
|---|---|---|
| Mutations | Stress cond. 1 | Stress cond. 2 |
| T1L + T22P + S39A + D56I + S57Y + S68V + V76L + A147R + G175E | | 6.0 |
| T1L + T22P + S57W + S68V + V76K + A147R | | 4.0 |
| T1L + T22P + S57Y + S68V + V76L + A147R + G162Q + S167M + G175D | | 3.8 |
| T1L + T22P + S57Y + S68V + V76L + A93G + A147R + S167M | | 3.0 |
| T1L + T22P + S57Y + S68V + V76L + A93G + A147R + S167M + G175E | | 2.7 |
| T1L + T22P + S57Y + S68V + V76L + Q109R + A147R + S167T | | 4.0 |

The invention claimed is:

1. A DNase variant, which comprises two or more substitutions selected from the group consisting of: T1I, T1L, T1V, S13Y, T22P, S25P, S27L, S39P, S42G, S42A, S42T, S57W, S57Y, S57F, S59V, S59I, S59L, V76L, V76I, Q109R, S116D, S116E, T127V, T127I, T127L, S144P, A147H, S167L, S167I, S167V, G175D and G175E, wherein the positions correspond to the positions of SEQ ID NO: 1 (numbering according to SEQ ID NO: 1), the variant has a sequence identity to the polypeptide shown in SEQ ID NO: 1 or the polypeptide shown in SEQ ID NO: 28 of at least 90%, and the variant has DNase activity.

2. The DNase variant of claim 1, wherein the variant has a sequence identity to the polypeptide shown in SEQ ID NO: 1 or the polypeptide shown in SEQ ID NO: 28 of at least 95%, and the variant has DNase activity.

3. The DNase variant according to claim 1 wherein the variant comprises one or more of the substitution sets selected from the group consisting of: T1I+S13Y, T1I+T22P, T1I+S25P, T1I+S27L, T1I+S39P, T1I+S42G, T1I+S42A, T1I+S42T, T1I+S57W, T1I+S57Y, T1I+S57F, T1I+S59V, T1I+S59I, T1I+S59L, T1I+V76L, T1I+V76I, T1I+Q109R, T1I+S116D, T1I+S116E, T1I+T127V, T1I+T127I, T1I+T127L, T1I+S144P, T1I+A147H, T1I+S167L, T1I+S167I, T1I+S167V, T1I+G175D, T1I+G175E, T1L+S13Y, T1L+T22P, T1L+S25P, T1L+S27L, T1L+S39P, T1L+S42G, T1L+S42A, T1L+S42T, T1L+S57W, T1L+S57Y, T1L+S57F, T1L+S59V, T1L+S59I, T1L+S59L, T1L+V76L, T1L+V76I, T1L+Q109R, T1L+S116D, T1L+S116E, T1L+T127V, T1L+T127I, T1L+T127L, T1L+S144P, T1L+A147H, T1L+S167L, T1L+5167I, T1L+S167V, T1L+G175D, T1L+G175E, T1V+S13Y, T1V+T22P, T1V+S25P, T1V+S27L, T1V+S39P, T1V+S42G, T1V+S42A, T1V+S42T, T1V+S57W, T1V+S57Y, T1V+S57F, T1V+S59V, T1V+559I, T1V+S59L, T1V+V76L, T1V+V76I, T1V+Q109R, T1V+S116D, T1V+S116E, T1V+T127V, T1V+T127I, T1V+T127L, T1V+S144P, T1V+A147H, T1V+S167L, T1V+5167I, T1V+S167V, T1V+G175D, T1V+G175E, S13Y+T22P, S13Y+S25P, S13Y+S27L, S13Y+S39P, S13Y+S42G, S13Y+S42A, S13Y+S42T, S13Y+S57W, S13Y+S57Y, S13Y+S57F, S13Y+S59V, S13Y+559I, S13Y+S59L, S13Y+V76L, S13Y+V76I, S13Y+Q109R, S13Y+S116D, S13Y+S116E, S13Y+T127V, S13Y+T127I, S13Y+T127L, S13Y+S144P, S13Y+A147H, S13Y+S167L, S13Y+5167I, S13Y+S167V, S13Y+G175D, S13Y+G175E, T22P+S25P, T22P+S27L, T22P+S39P, T22P+S42G, T22P+S42A, T22P+S42T, T22P+S57W, T22P+S57Y, T22P+S57F, T22P+S59V, T22P+S59I, T22P+S59L, T22P+V76L, T22P+V76I, T22P+Q109R, T22P+S116D, T22P+S116E, T22P+T127V, T22P+T127I, T22P+T127L, T22P+S144P, T22P+A147H, T22P+S167L, T22P+S167I, T22P+S167V, T22P+G175D, T22P+G175E, S25P+S27L, S25P+S39P, S25P+S42G, S25P+S42A, S25P+S42T, S25P+S57W, S25P+S57Y, S25P+S57F, S25P+S59V, S25P+S59I, S25P+S59L, S25P+V76L, S25P+V76I, S25P+Q109R, S25P+S116D, S25P+S116E, S25P+T127V, S25P+T127I, S25P+T127L, S25P+S144P, S25P+A147H, S25P+S167L, S25P+S167I, S25P+S167V, S25P+G175D, S25P+G175E, S27L+S39P, S27L+S42G, S27L+S42A, S27L+S42T, S27L+S57W, S27L+S57Y, S27L+S57F, S27L+S59V, S27L+S59I, S27L+S59L, S27L+V76L, S27L+V76I, S27L+Q109R, S27L+S116D, S27L+S116E, S27L+T127V, S27L+T127I, S27L+T127L, S27L+S144P, S27L+A147H, S27L+S167L, S27L+S167I, S27L+S167V, S27L+G175D, S27L+G175E, S39P+S42G, S39P+S42A, S39P+S42T, S39P+S57W, S39P+S57Y, S39P+S57F, S39P+S59V, S39P+S59I, S39P+S59L, S39P+V76L, S39P+V76I, S39P+Q109R, S39P+S116D, S39P+S116E, S39P+T127V, S39P+T127I, S39P+T127L, S39P+S144P, S39P+A147H, S39P+S167L, S39P+S167I, S39P+S167V, S39P+G175D, S39P+G175E, S42G+S57W, S42G+S57Y, S42G+S57F, S42G+S59V, S42G+S59I, S42G+S59L, S42G+V76L, S42G+V76I, S42G+Q109R, S42G+S116D, S42G+S116E, S42G+T127V, S42G+T127I, S42G+T127L, S42G+S144P, S42G+A147H, S42G+S167L, S42G+S167I, S42G+S167V, S42G+G175D, S42G+G175E, S42A+S57W, S42A+S57Y, S42A+S57F, S42A+S59V, S42A+S59I, S42A+S59L, S42A+V76L, S42A+V76I, S42A+Q109R, S42A+S116D, S42A+S116E, S42A+T127V, S42A+T127I, S42A+T127L, S42A+S144P, S42A+A147H, S42A+S167L, S42A+S167I, S42A+S167V, S42A+G175D, S42A+G175E, S42T+S57W, S42T+S57Y, S42T+S57F, S42T+S59V, S42T+S59I, S42T+S59L, S42T+V76L, S42T+V76I, S42T+Q109R, S42T+S116D, S42T+S116E, S42T+T127V, S42T+T127I, S42T+T127L, S42T+S144P, S42T+A147H, S42T+S167L, S42T+S167I, S42T+S167V, S42T+G175D, S42T+G175E, S57W+S59V, S57W+S59I, S57W+S59L, S57W+V76L, S57W+V76I, S57W+Q109R, S57W+S116D, S57W+S116E, S57W+T127V, S57W+T127I, S57W+T127L, S57W+S144P, S57W+A147H, S57W+S167L, S57W+S167I, S57W+S167V, S57W+G175D, S57W+G175E, S57Y+S59V, S57Y+S59I, S57Y+S59L, S57Y+V76L, S57Y+V76I, S57Y+Q109R, S57Y+S116D, S57Y+S116E, S57Y+T127V, S57Y+T127I, S57Y+T127L, S57Y+S144P, S57Y+A147H, S57Y+S167L, S57Y+S167I, S57Y+S167V, S57Y+G175D, S57Y+G175E, S57F+S59V, S57F+S59I, S57F+S59L, S57F+V76L, S57F+V76I, S57F+Q109R, S57F+S116D, S57F+S116E, S57F+T127V, S57F+T127I, S57F+T127L, S57F+S144P, S57F+A147H, S57F+S167L, S57F+S167I, S57F+S167V, S57F+G175D, S57F+G175E, S59V+V76L, S59V+V76I, S59V+Q109R, S59V+S116D, S59V+S116E, S59V+T127V, S59V+T127I, S59V+T127L, S59V+S144P, S59V+A147H, S59V+S167L, S59V+S167I, S59V+S167V, S59V+G175D, S59V+G175E, S59I+V76L, S59I+V76I, S59I+Q109R, S59I+S116D, S59I+S116E, S59I+T127V, S59I+T127I, S59I+T127L, S59I+S144P, S59I+A147H, S59I+S167L, S59I+S167I, S59I+S167V, S59I+G175D, S59I+G175E, S59L+V76L, S59L+V76I, S59L+Q109R, S59L+S116D, S59L+S116E, S59L+T127V, S59L+T127I, S59L+T127L, S59L+S144P, S59L+A147H, S59L+S167L, S59L+S167I, S59L+S167V, S59L+G175D, S59L+G175E, V76L+Q109R, V76L+S116D, V76L+S116E, V76L+T127V, V76L+T127I, V76L+T127L, V76L+S144P, V76L+A147H, V76L+S167L, V76L+S167I, V76L+S167V, V76L+G175D, V76L+G175E, V76I+Q109R, V76I+S116D, V76I+S116E, V76I+T127V, V76I+T127I, V76I+T127L, V76I+S144P, V76I+A147H, V76I+S167L, V76I+S167I, V76I+S167V, V76I+G175D, V76I+G175E, Q109R+S116D, Q109R+S116E, Q109R+T127V, Q109R+T127I, Q109R+T127L, Q109R+S144P, Q109R+A147H, Q109R+S167L, Q109R+S167I, Q109R+S167V, Q109R+G175D, Q109R+G175E, S116D+T127V, S116D+T127I, S116D+T127L, S116D+S144P, S116D+A147H, S116D+S167L, S116D+S167I, S116D+S167V, S116D+G175D, S116D+G175E, S116E+T127V, S116E+T127I, S116E+T127L, S116E+S144P, S116E+A147H, S116E+S167L, S116E+5167I, S116E+S167V, S116E+G175D, S116E+G175E, T127V+S144P, T127V+A147H, T127V+S167L, T127V+S167I, T127V+S167V, T127V+G175D, T127V+G175E, T127I+S144P, T127I+A147H, T127I+S167L, T127I+51671, T127I+S167V, T127I+G175D, T127I+G175E, T127L+S144P, T127L+A147H, T127L+S167L, T127L+S167I, T127L+S167V, T127L+G175D, T127L+G175E, S144P+A147H, S144P+S167L, S144P+S167I, S144P+S167V, S144P+G175D, S144P+G175E, A147H+S167L, A147H+S167I, A147H+S167V, A147H+G175D, A147H+G175E, S167L+G175D, S167L+G175E, 5167I+G175D, 5167I+G175E, S167V+G175D and S167V+G175E.

4. The DNase variant according to claim 1, wherein the two or more mutations are selected from the group consisting of T1I, S13Y, T22P, S25P, S27L, S39P, S42G, S57W, S59V, V76L, Q109R, S116D, T127V, S144P, A147H, S167L and G175D.

5. The DNase variant according to claim 1, wherein the variant comprises at least three substitutions selected from the group consisting of: T1I, T22P, S57W, V76L, A147H, S167L and G175D.

6. The DNase variant according to claim 5, wherein the DNase variant is selected from the group consisting of:

a) T1I+T22P+S57W+V76L+A147H+S167L,
b) T1I+T22P+S57W+V76L+A147H+G175D,
c) T1I+T22P+S57W+V76L+S167L+G175D,
d) T1I+T22P+S57W+A147H+S167L+G175D,
e) T1I+T22P+V76L+A147H+S167L+G175D,
f) T1I+S57W+V76L+A147H+S167L+G175D,
g) T22P+S57W+V76L+A147H+S167L+G175D, and
h) T1I+T22P+S57W+V76L+A147H+S167L+G175D.

7. The DNase variant according to claim 1, wherein the variant comprises 3, 4, 5, 6, 7, 8, 9, 10, 11, 12, 13, 14, 15, 16 or all of the mutations selected from the group consisting of: T1I, S13Y, T22P, S25P, S27L, S39P, S42G, S57W, S59V, V76L, Q109R, S116D, T127V, S144P, A147H, S167L and G175D.

8. The DNase variant of claim 1, wherein the variant further comprises one or more of the substitutions selected from the group consisting of: G4N, T5F, T5C, P6V, P6G, S7D, S7T, K8V, S9K, S9Q, S9V, S9L, S9F, S9P, S9R, A10D, A10M, A10I, A10Q, A10V, A10L, A10K, Q12S, Q12V, Q12E, Q14M, Q14R, N16S, A17C, A17V, A17E, A17T, T19K, T19L, T19S, T191, T19V, K21E, K21M, G24Y, S27R, G28L, Y29W, S30K, S30D, S30H, S30T, D32Q, L33K, 138V, 138M, Q40V, V49R, L511, K521, K52H, A55S, D56I, D56L, D56T, Y58A, Y58T, N61D, P63A, T65L, T651, T65V, T65R, T65K, S66W, S66Y, S68V, S681, S68W, S68Y, S68H, S68C, S68T, S68L, T77N, T77Y, T77W, T77R, F781, F78H, F78Y, F78C, T79G, T79R, N80K, S82L, S82E, S82K, S82R, S82H, D83C, D83F, D83L, L92T, A93G, E94N, G99S, S101D, S101A, S102M, S102L, S102V, S102A, S102K, S102T, S102R, T104P, T104A, T105V, T1051, S106L K107L, K107C, K107R, K107H, K107S, K107M, K107E, K107A, K107D, A112S, A125K, S1261, S126E, S126A, S126C, S130A S130E, G132R, D135R, T138Q, W139R, R143E, R143K, G145V, G145E, G145D, G145A, G149S, K152H, K152R, S156C, S156G, S156K, S156R, S156T, S156A, T157S, Y159F, K160V, W161L, W161Y, G162Q, G162D, G162M, G162R, G162A, G162S, G162E, G162L, G162K, G162V, G162H, S164R, S164T, Q166D, S168V, S168E, S168D, S168L, K170S, K170L, K170F, K170R, T171D, T171E, T171A, T171C, A172G, A172S, L173T, L173A, L173V, Q174L, M176H, L1771, N178D, N178E, N178T, N178S, N178A, S179E, S181R, S181E, S181D, S181F, S181H, S181W, S181L, S181M, S181Y, S181Q, S181G, S181A, Y182M, Y182C, Y182K, Y182G, Y182A, Y182S, Y182V, Y182D, Y182Q, Y182F, Y182L, Y182N, Y1821, Y182E, Y182T and Y182W.

9. The DNase variant according to claim 8, wherein the DNase variant is selected from the group consisting of:

a) T1I+S13Y+T22P+S25P+S27L+S39P+S42G+S57W+S59V+V76L+S144P+A147H+S167L+G175D;
b) T1I+S13Y+T22P+S27L+S42G+S57W+S59V+V76L+Q109R+S116D+T127V+S144P+A147H+S167L+G175D;
c) T1I+S13Y+T22P+S25P+S27L+S39P+S42G+S57W+S59V+V76L+Q109R+S116D+T127V+S144P+A147H+S167L+G175D;
d) T1I+S13Y+T22P+S25P+S27L+S39P+S42G+S57W+S59V+V76L+T77Y+Q109R+S116D+T127V+S144P+A147H+S167L+G175D;
e) T1I+T22P+D56I+S57W+V76L+Q109R+S116D+A147H+G162S+S167L+G175N;
f) T1I+S13Y+T22P+S27L+S39P+S42G+D56I+S57W+S59V+V76L+Q109R+S116D+T127V+S144P+A147H+S167L+G175D;

g) T1I+T22P+S25P+S27L+S42G+D56I+S57Y+S59V+V76L+T77Y+Q109R+S116D+T127V+S144P+A147H+Q166D+S167L+G175D+S181L;

h) T1I+S13Y+T22P+S25P+S27L+S39P+S42G+D56I+S57W+S59V+V76L+Q109R+S116D+T127V+S144P+A147H+S167L+G175D;

i) T1I+S13Y+T22P+S25P+S27L+S39P+S42G+D56I+S57W+S59V+V76L+Q109R+S116D+T127V+S144P+A147H+Q166D+S167L+G175D;

j) T1I+S13Y+T22P+S27R+S39P+S42G+D56I+S57W+S59V+V76L+Q109R+S116D+T127V+S144P+A147H+S167L+G175D;

k) T1I+S13Y+T22P+S27L+S39P+S42G+D56I+S57W+S59V+T65L+V76L+Q109R+S116D+T127V+S144P+A147H+S167L+G175D;

l) T1I+S13Y+T22P+S27L+L33K+S39P+S42G+D56I+S57W+S59V+T65V+V76L+Q109R+S116D+T127V+S144P+A147H+S167L+G175D;

m) T1I+S13Y+T22P+S25P+S27R+S39P+S42G+S57W+S59V+S66W+V76L+T77Y+Q109R+S116D+T127V+S144P+A147H+S167L+G175D;

n) T1I+S13Y+T22P+S25P+S27L+L33K+S39P+S42G+S57W+S59V+T65V+V76L+T77Y+Q109R+S116D+T127V+S144P+A147H+S167L+G175D;

o) T1I+S13Y+T22P+S25P+S27L+L33K+S39P+S42G+S57W+S59V+S66Y+V76L+T77Y+Q109R+S116D+T127V+S144P+A147H+S167L+G175D;

p) T1I+S13Y+T22P+S25P+S27L+S39P+S42G+S57W+S59V+T65V+S66Y+V76L+T77Y+Q109R+S116D+T127V+S144P+A147H+S167L+G175D;

q) T1I+S13Y+T22P+S27L+S39P+S42G+D56L+S57W+S59V+T65V+V76L+Q109R+S116D+T127V+S144P+A147H+G162D+S167L+G175D;

r) T1I+S13Y+T22P+S27R+S39P+S42G+D56L+S57W+S59V+T65V+V76L+Q109R+S116D+T127V+S144P+A147H+S167L+G175D;

s) T1I+S13Y+T22P+S27R+S39P+S42G+D56L+S57W+S59V+T65V+V76L+Q109R+S116D+T127V+S144P+A147H+G162D+S167L+G175D;

t) T1I+S13Y+T22P+S27K+S39P+S42G+D56I+S57W+S59V+T65V+V76L+S106L+Q109R+S116D+T127V+S144P+A147H+S167L+G175D;

u) T1I+S13Y+T22P+S27K+S39P+S42G+D56I+S57W+S59V+T65V+V76L+Q109R+S116D+T127V+S130A+S144P+A147H+S167L+G175D;

v) T1I+S13Y+T22P+S27L+S39P+S42G+D56L+S57W+S59V+T65L+V76L+Q109R+S116D+T127V+S130A+S144P+A147H+S167L+G175D; and w) T1I+S13Y+T22P+S27L+S39P+S42G+D56I+S57W+S59V+T65V+V76L+Q109R+S116D+T127V+S144P+A147H+G162D+S167L+G175.

10. The DNase variant according to claim 1, wherein the variant comprises one or both motifs [D/M/L][S/T]GYSR[D/N] (SEQ ID NO: 25) or ASXNRSKG (SEQ ID NO: 26).

* * * * *

UNITED STATES PATENT AND TRADEMARK OFFICE

CERTIFICATE OF CORRECTION

PATENT NO. : 11,441,136 B2
APPLICATION NO. : 16/757557
DATED : September 13, 2022
INVENTOR(S) : Oestergaard et al.

It is certified that error appears in the above-identified patent and that said Letters Patent is hereby corrected as shown below:

In the Claims

Please amend Claim 3 at Column 201, Line 44 – Column 203, Line 58 as follows:
3. The DNase variant according to claim 1 wherein the variant comprises one or more of the substitution sets selected from the group consisting of: T1I+S13Y, T1I+T22P, T1I+S25P, T1I+S27L, T1I+S39P, T1I+S42G, T1I+S42A, T1I+S42T, T1I+S57W, T1I+S57Y, T1I+S57F, T1I+S59V, T1I+S59I, T1I+S59L, T1I+V76L, T1I+V76I, T1I+Q109R, T1I+S116D, T1I+S116E, T1I+T127V, T1I+T127I, T1I+T127L, T1I+S144P, T1I+A147H, T1I+S167L, T1I+S167I, T1I+S167V, T1I+G175D, T1I+G175E, T1L+S13Y, T1L+T22P, T1L+S25P, T1L+S27L, T1L+S39P, T1L+S42G, T1L+S42A, T1L+S42T, T1L+S57W, T1L+S57Y, T1L+S57F, T1L+S59V, T1L+S59I, T1L+S59L, T1L+V76L, T1L+V76I, T1L+Q109R, T1L+S116D, T1L+S116E, T1L+T127V, T1L+T127I, T1L+T127L, T1L+S144P, T1L+A147H, T1L+S167L, T1L+S167I, T1L+S167V, T1L+G175D, T1L+G175E, T1V+S13Y, T1V+T22P, T1V+S25P, T1V+S27L, T1V+S39P, T1V+S42G, T1V+S42A, T1V+S42T, T1V+S57W, T1V+S57Y, T1V+S57F, T1V+S59V, T1V+S59I, T1V+S59L, T1V+V76L, T1V+V76I, T1V+Q109R, T1V+S116D, T1V+S116E, T1V+T127V, T1V+T127I, T1V+T127L, T1V+S144P, T1V+A147H, T1V+S167L, T1V+S167I, T1V+S167V, T1V+G175D, T1V+G175E, S13Y+T22P, S13Y+S25P, S13Y+S27L, S13Y+S39P, S13Y+S42G, S13Y+S42A, S13Y+S42T, S13Y+S57W, S13Y+S57Y, S13Y+S57F, S13Y+S59V, S13Y+S59I, S13Y+S59L, S13Y+V76L, S13Y+V76I, S13Y+Q109R, S13Y+S116D, S13Y+S116E, S13Y+T127V, S13Y+T127I, S13Y+T127L, S13Y+S144P, S13Y+A147H, S13Y+S167L, S13Y+S167I, S13Y+S167V, S13Y+G175D, S13Y+G175E, T22P+S25P, T22P+S27L, T22P+S39P, T22P+S42G, T22P+S42A, T22P+S42T, T22P+S57W, T22P+S57Y, T22P+S57F, T22P+S59V, T22P+S59I, T22P+S59L, T22P+V76L, T22P+V76I, T22P+Q109R, T22P+S116D, T22P+S116E, T22P+T127V, T22P+T127I, T22P+T127L, T22P+S144P, T22P+A147H, T22P+S167L, T22P+S167I, T22P+S167V, T22P+G175D, T22P+G175E, S25P+S27L, S25P+S39P, S25P+S42G, S25P+S42A, S25P+S42T, S25P+S57W, S25P+S57Y, S25P+S57F, S25P+S59V, S25P+S59I, S25P+S59L, S25P+V76L, S25P+V76I, S25P+Q109R, S25P+S116D, S25P+S116E, S25P+T127V, S25P+T127I, S25P+T127L, S25P+S144P, S25P+A147H, S25P+S167L, S25P+S167I, S25P+S167V, S25P+G175D, S25P+G175E, S27L+S39P, S27L+S42G, S27L+S42A, S27L+S42T, S27L+S57W, S27L+S57Y, S27L+S57F, S27L+S59V, S27L+S59I, S27L+S59L, S27L+V76L, S27L+V76I, S27L+Q109R, S27L+S116D, Signed and Sealed this
Seventh Day of March, 2023

Katherine Kelly Vidal

Katherine Kelly Vidal
*Director of the United States Patent and Trademark Office*

S27L+S116E, S27L+T127V, S27L+T127I, S27L+T127L, S27L+S144P, S27L+A147H, S27L+S167L, S27L+S167I, S27L+S167V, S27L+G175D, S27L+G175E, S39P+S42G, S39P+S42A, S39P+S42T, S39P+S57W, S39P+S57Y, S39P+S57F, S39P+S59V, S39P+S59I, S39P+S59L, S39P+V76L, S39P+V76I, S39P+Q109R, S39P+S116D, S39P+S116E, S39P+T127V, S39P+T127I, S39P+T127L, S39P+S144P, S39P+A147H, S39P+S167L, S39P+S167I, S39P+S167V, S39P+G175D, S39P+G175E, S42G+S57W, S42G+S57Y, S42G+S57F, S42G+S59V, S42G+S59I, S42G+S59L, S42G+V76L, S42G+V76I, S42G+Q109R, S42G+S116D, S42G+S116E, S42G+T127V. S42G+T127I. S42G+T127L, S42G+S144P, S42G+A147H, S42G+S167L, S42G+S167I, S42G+S167V, S42G+G175D, S42G+G175E, S42A+S57W, S42A+S57Y, S42A+S57F, S42A+S59V, S42A+S59I, S42A+S59L, S42A+V76L, S42A+V76I, S42A+Q109R, S42A+S116D, S42A+S116E, S42A+T127V, S42A+T127I, S42A+T127L, S42A+S144P, S42A+A147H, S42A+S167L, S42A+S167I, S42A+S167V, S42A+G175D, S42A+G175E, S42T+S57W, S42T+S57Y, S42T+S57F, S42T+S59V, S42T+S59I, S42T+S59L, S42T+V76L, S42T+V76I, S42T+Q109R, S42T+S116D, S42T+S116E, S42T+T127V, S42T+T127I, S42T+T127L, S42T+S144P, S42T+A147H, S42T+S167L, S42T+S167I, S42T+S167V, S42T+G175D, S42T+G175E, S57W+S59V, S57W+S59I, S57W+S59L, S57W+V76L, S57W+V76I, S57W+Q109R, S57W+S116D, S57W+S116E, S57W+T127V, S57W+T127I, S57W+T127L, S57W+S144P, S57W+A147H, S57W+S167L, S57W+S167I, S57W+S167V, S57W+G175D, S57W+G175E, S57Y+S59V, S57Y+S59I, S57Y+S59L, S57Y+V76L, S57Y+V76I, S57Y+Q109R, S57Y+S116D, S57Y+S116E, S57Y+T127V, S57Y+T127I, S57Y+T127L, S57Y+S144P, S57Y+A147H, S57Y+S167L, S57Y+S167I, S57Y+S167V, S57Y+G175D, S57Y+G175E, S57F+S59V, S57F+S59I, S57F+S59L, S57F+V76L, S57F+V76I, S57F+Q109R, S57F+S116D, S57F+S116E, S57F+T127V, S57F+T127I, S57F+T127L, S57F+S144P, S57F+A147H, S57F+S167L, S57F+S167I, S57F+S167V, S57F+G175D, S57F+G175E, S59V+V76L, S59V+V76I, S59V+Q109R, S59V+S116D, S59V+S116E, S59V+T127V, S59V+T127I, S59V+T127L, S59V+S144P, S59V+A147H, S59V+S167L, S59V+S167I, S59V+S167V, S59V+G175D, S59V+G175E, S59I+V76L, S59I+V76I, S59I+Q109R, S59I+S116D, S59I+S116E, S59I+T127V, S59I+T127I, S59I+T127L, S59I+S144P, S59I+A147H, S59I+S167L, S59I+S167I, S59I+S167V, S59I+G175D, S59I+G175E, S59L+V76L, S59L+V76I, S59L+Q109R, S59L+S116D, S59L+S116E, S59L+T127V, S59L+T127I, S59L+T127L, S59L+S144P, S59L+A147H, S59L+S167L, S59L+S167I, S59L+S167V, S59L+G175D, S59L+G175E, V76L+Q109R, V76L+S116D, V76L+S116E, V76L+T127V, V76L+T127I, V76L+T127L, V76L+S144P, V76L+A147H, V76L+S167L, V76L+S167I, V76L+S167V, V76L+G175D, V76L+G175E, V76I+Q109R, V76I+S116D, V76I+S116E, V76I+T127V, V76I+T127I, V76I+T127L, V76I+S144P, V76I+A147H, V76I+S167L, V76I+S167I, V76I+S167V, V76I+G175D, V76I+G175E, Q109R+S116D, Q109R+S116E, Q109R+T127V, Q109R+T127I, Q109R+T127L, Q109R+S144P, Q109R+A147H, Q109R+S167L, Q109R+S167I, Q109R+S167V, Q109R+G175D, Q109R+G175E, S116D+T127V, S116D+T127I, S116D+T127L, S116D+S144P, S116D+A147H, S116D+S167L, S116D+S167I, S116D+S167V, S116D+G175D, S116D+G175E, S116E+T127V, S116E+T127I, S116E+T127L, S116E+S144P, S116E+A147H, S116E+S167L. S116E+S167I, S116E+S167V. S116E+G175D, S116E+G175E, T127V+S144P, T127V+A147H, T127V+S167L, T127V+S167I, T127V+S167V, T127V+G175D, T127V+G175E, T127I+S144P, T127I+A147H, T127I+S167L, T127I+S167I, T127I+S167V, T127I+G175D, T127I+G175E, T127L+S144P, T127L+A147H, T127L+S167L, T127L+S167I, T127L+S167V, T127L+G175D, T127L+G175E, S144P+A147H, S144P+S167L, S144P+S167I, S144P+S167V, S144P+G175D, S144P+G175E, A147H+S167L, A147H+S167I, A147H+S167V, A147H+G175D, A147H+G175E, S167L+G175D, S167L+G175E, S167I+G175D, S167I+G175E, S167V+G175D and S167V+G175E.

Please amend Claim 8 at Column 204, Lines 17-49 as follows:
8. The DNase variant of claim 1, wherein the variant further comprises one or more of the substitutions selected from the group consisting of: G4N, T5F, T5C, P6V, P6G, S7D, S7T, K8V, S9K, S9Q, S9V, S9L, S9F, S9P, S9R, MOD, A10M, A10I, A10Q, A10V, A10L, A10K, Q12S, Q12V, Q12E, Q14M, Q14R, N16S, A17C, A17V, A17E, A17T, T19K, T19L, T19S, T19I, T19V, K21E, K21M, G24Y, S27R,_G28L, Y29W, S30K, S30D, S30H, S30T, D32Q, L33K, I38V, I38M, Q40V, V49R, L51I, K52I, K52H, A55S, D56I, D56L, D56T, Y58A, Y58T, N61D, P63A, T65L, T65V, T65R, T65K, S66W, S66Y, S68V, S68I, S68W, S68Y, S68H, S68C, S68T, S68L, T77N, T77Y, T77W, T77R, F78I, F78H, F78Y, F78C, T79G, T79R, N80K, S82L, S82E, S82K, S82R, S82H, D83C, D83F, D83L, L92T, A93G, E94N, G99S, S101D, S101A, S102M, S102L, S102V, S102A, S102K, S102T, S102R, T104P, T104A, T105V, T105I, S106L, K107L, K107C, K107R, K107H, K107S, K107M, K107E, K107A, K107D, A112S, A125K, S126I, S126E. S126A, S126C, S130A, S130E, G132R, D135R, T138Q, W139R, R143E, R143K, G145V, G145E, G145D, G145A, G149S, K152H, K152R, S156C, S156G, S156K, S156R, S156T, S156A, T157S, Y159F, K160V, W161L, W161Y, G162Q, G162D, G162M, G162R, G162A, G162S, G162E, G162L, G162K, G162V, G162H, S164R, S164T, Q166D, S168V, S168E, S168D, S168L, K170S, K170L, K170F, K170R, T171D, T171E, T171A, T171C, A172G, A172S, L173T, L173A, L173V, Q174L, M176H, L177I, N178D, N178E, N178T, N178S, N178A, S179E, S181R, S181E, S181D, S181F, S181H, S181W, S181L, S181M, S181Y, S181Q, S181G, S181A, Y182M, Y182C, Y182K, Y182G, Y182A, Y182S, Y182V, Y182D, Y182Q, Y182F, Y182L, Y182N, Y182I,_Y182E, Y182T and Y182W.